US012655438B2

(12) United States Patent     (10) Patent No.:   US 12,655,438 B2

Voytas et al.     (45) Date of Patent:    Jun. 16, 2026

(54) AUGMENTED sgRNAS AND METHODS FOR THEIR USE TO ENHANCE SOMATIC AND GERMLINE PLANT GENOME ENGINEERING

(71) Applicant: Regents of the University of Minnesota, Minneapolis, MN (US)

(72) Inventors: Daniel F. Voytas, Falcon Heights, MN (US); Evan Ellison, Elbow Lake, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 503 days.

(21) Appl. No.: 17/634,147

(22) PCT Filed: Aug. 7, 2020

(86) PCT No.: PCT/US2020/045397

§ 371 (c)(1),
(2) Date: Feb. 9, 2022

(87) PCT Pub. No.: WO2021/041001

PCT Pub. Date: Mar. 4, 2021

(65) Prior Publication Data

US 2022/0315938 A1     Oct. 6, 2022

Related U.S. Application Data

(60) Provisional application No. 62/885,009, filed on Aug. 9, 2019.

(51) Int. Cl.
*C12N 15/82*     (2006.01)
*C12N 9/22*     (2006.01)
*C12N 15/11*     (2006.01)

(52) U.S. Cl.
CPC ........... *C12N 15/8213* (2013.01); *C12N 9/22* (2013.01); *C12N 15/111* (2013.01); *C12N 15/8203* (2013.01); *C12N 15/825* (2013.01); *C12N 2310/20* (2017.05)

(58) Field of Classification Search
CPC .................................................. C12N 15/8213
See application file for complete search history.

(56) References Cited

U.S. PATENT DOCUMENTS

| | | | | |
|---|---|---|---|---|
| 11,306,309 | B2 * | 4/2022 | Porteus ................ | C12N 15/907 |
| 2013/0081151 | A1 | 3/2013 | Hong et al. | |
| 2016/0237451 | A1 | 8/2016 | Voytas et al. | |
| 2017/0114351 | A1 | 4/2017 | Mahfouz et al. | |
| 2017/0121693 | A1 | 5/2017 | Liu et al. | |
| 2017/0342427 | A1 * | 11/2017 | Kragler ................ | C12N 15/102 |
| 2020/0224221 | A1 * | 7/2020 | Gao .......................... | C12N 9/22 |

FOREIGN PATENT DOCUMENTS

WO     WO-2014186686 A2 *   11/2014    .......... C12N 15/102

OTHER PUBLICATIONS

Ali et al., "Efficient Virus-Mediated Genome Editing in Plants Using the CRISPR/Cas9 System," Mol. Plant, 8(8):1288-1291, Mar. 6, 2015.

Ali et al., "Pea early-browning virus-mediated genome editing via the CRISPR/Cas9 system in Nicotiana benthamiana and *Arabidopsis*," Virus Research, 244:333-337, Oct. 16, 2017.

Altpeter et al., "Advancing Crop Transformation in the Era of Genome Editing," Plant Cell, 28(7):1510-1520, Jul. 2016.

Altschul et al., "Gapped BLAST and PSI-BLAST: a new generation of protein database search programs," Nucleic Acids Research, 25(17):3389-3402, Sep. 1, 1997.

Anzalone et al., "Search-and-replace genome editing without double-strand breaks or donor DNA," Nature, 576(7785):149-157, Oct. 21, 2019.

Baltes et al., "Conferring resistance to geminiviruses with the CRISPR-Cas prokaryotic immune system," Nat. Plants, 1(10):15145, Sep. 28, 2015.

Banerjee et al., "Dynamics of a Mobile RNA of Potato Involved in a Long-Distance Signaling Pathway," Plant Cell, 18(12):3443-3457, Dec. 22, 2006.

Bhowmik et al., "Targeted mutagenesis in wheat microspores using CRISPR/Cas9," Sci. Reports, 8:6502, Apr. 25, 2018, 10 pages.

Burch-Smith et al., "Applications and advantages of virus-induced gene silencing for gene function studies in plants," Plant Journal, 39(5):734-746, Sep. 2004.

Busch et al., "Functional analysis of the early steps of carotenoid biosynthesis in tobacco," Plant Physiology, 128(2):439-453, Feb. 2002.

Čermák et al., "A Multipurpose Toolkit to Enable Advanced Genome Engineering in Plants," Plant Cell, 29(6):1196-1217, May 18, 2017.

Clough et al., "Floral dip: a simplified method for Agrobacterium-mediated transformation of *Arabidopsis thaliana*," Plant Journal, 16(6):735-743, Dec. 1998.

Cody et al., "Multiplexed gene editing and protein overexpression using a tobacco mosaic virus viral vector," Plant Physiology, 175(1):23-35, Jun. 29, 2017.

Cong et al., "Multiplex Genome Engineering Using CRISPR/Cas Systems," Science, 339(6121):819-823, Jan. 3, 2013.

Corbesier et al., "FT Protein Movement Contributes to Long-Distance Signaling in Floral Induction of *Arabidopsis*," Science, 316(5827):1030-1033, Apr. 19, 2007.

Deltcheva et al., "CRISPR RNA maturation by trans-encoded small RNA and host factor RNase III," Nature, 471(7340):602-607, Mar. 31, 2011.

Dinesh-Kumar et al., "Virus-Induced Gene Silencing," Methods Mol. Biology: Plant Functional Genomics, 236:287-294, 2003.

Ellison et al., "Multiplexed heritable gene editing using RNA viruses and mobile single guide RNAs," Nat. Plants, 6:620-624, Jun. 1, 2020.

(Continued)

*Primary Examiner* — David H Kruse

(74) *Attorney, Agent, or Firm* — Fish & Richardson P.C.

(57) ABSTRACT

Methods and materials for increasing somatic and germline genome editing are provided herein. For example, provided herein are methods and materials for using augmented sgRNAs to increase somatic and germline genome editing.

17 Claims, 16 Drawing Sheets

Specification includes a Sequence Listing.

(56) References Cited

OTHER PUBLICATIONS

Ferretti et al., "Complete genome sequence of an M1 strain of *Streptococcus pyogenes*," Proc. Natl. Acad. Sci. USA, 98(8):4658-4663, Apr. 10, 2001.

Gao et al., "Rescue of a plant cytorhabdovirus as versatile expression platforms for planthopper and cereal genomic studies," New Phytology, 223(4):2120-2133, Jun. 10, 2019.

Gao, "The future of CRISPR technologies in agriculture," Nat. Rev. Mol. Cell Biology, 19:275-276, Jan. 31, 2018.

Gaudelli et al., "Programmable base editing of A•T to G•C in genomic DNA without DNA cleavage," Nature, 551(7681):464-471, Oct. 25, 2017.

Gelvin, "Agrobacterium-mediated plant transformation: the biology behind the "gene-jockeying" tool," Microbiol. Mol. Biol. Reviews, 67(1):16-37, Mar. 2003.

Hamada et al., "An in planta biolistic method for stable wheat transformation," Sci. Reports, 7:11443, Sep. 13, 2017, 8 pages.

Haywood et al., "Phloem long-distance trafficking of Gibberellic Acid-Insensitive RNA regulates leaf development," Plant Journal, 42(1):49-68, Apr. 2005.

Hsiau et al., "Inference of CRISPR Edits from Sanger Trace Data," BioRxiv, 251082, Aug. 10, 2019, 17 pages.

Jackson et al., "Systemic movement of FT mRNA and a possible role in floral induction," Front. Plant Science, 3:127, Jun. 2012, 4 pages.

Jinek et al., "A programmable dual-RNA-guided DNA endonuclease in adaptive bacterial immunity," Science, 337(6096):816-821, Jun. 28, 2012.

Kim et al., "Developmental changes due to long-distance movement of a homeobox fusion transcript in tomato," Science, 293(5528):287-289, Jul. 13, 2001.

Knott et al., "CRISPR-Cas guides the future of genetic engineering," Science, 361(6405):866-869, Aug. 31, 2018.

Komor et al., "Programmable editing of a target base in genomic DNA without double-stranded DNA cleavage," Nature, 533(7603):420-424, Apr. 20, 2016.

Kumagai et al., "Cytoplasmic inhibition of carotenoid biosynthesis with virus-derived RNA," Proc. Natl Acad. Sci. USA, 92(5):1679-1683, Feb. 28, 1995.

Laufer et al., "Fluorescent labelling of beet necrotic yellow vein virus and beet soil-borne mosaic virus for co-and superinfection experiments in Nicotiana benthamiana," J. Gen. Virology, 99:1321-1330, Jul. 30, 2018.

Li et al., "A cis element within flowering locus T mRNA determines its mobility and facilitates trafficking of heterologous viral RNA," J. Virology, 83(8):3540-3548, Feb. 4, 2009.

Li et al., "Precise gene replacement in rice by RNA transcript-templated homologous recombination," Nat. Biotechnology, 37:445-450, Mar. 18, 2019.

Liang et al., "Efficient DNA-free genome editing of bread wheat using CRISPR/Cas9 ribonucleoprotein complexes," Nat. Communications, 8:14261, Jan. 18, 2017, 5 pages.

Liang et al., "Genome editing of bread wheat using biolistic delivery of CRISPR/Cas9 in vitro transcripts or ribonucleoproteins," Nat. Protocols, 13(3):413-430, Feb. 1, 2018.

Liu et al., "Virus-induced gene silencing in tomato," Plant Journal, 31(6):777-786, Sep. 2002.

Lowder et al., "A CRISPR/Cas9 Toolbox for Multiplexed Plant Genome Editing and Transcriptional Regulation," Plant Physiology, 169(2):971-985, Aug. 21, 2015.

Lowe et al., "Morphogenic Regulators Baby boom and Wuschel Improve Monocot Transformation," Plant Cell, 28(9):1998-2015, Sep. 6, 2016.

Luo et al., "Selective targeting of mobile mRNAs to plasmodesmata for cell-to-cell movement," Plant Physiology, 177(2):604-614, Mar. 26, 2018.

Marton et al., "Nontransgenic Genome Modification in Plant Cells," Plant Physiology, 154(3):1079-1087, Sep. 27, 2010.

Mei et al., "A Foxtail mosaic virus Vector for Virus-Induced Gene Silencing in Maize," Plant Physiology, 171(2):760-772, Apr. 28, 2016.

Notaguchi et al., "Identification of mRNAs that Move Over Long Distances Using an RNA-Seq Analysis of *Arabidopsis*/Nicotiana benthamiana Heterografts," Plant Cell Physiology, 56(2):311-321, Dec. 19, 2014.

Papikian et al., "Site-specific manipulation of *Arabidopsis* loci using CRISPR-Cas9 SunTag systems," Nat. Communications, 10(1):729, Feb. 13, 2019, 11 pages.

Park et al., "Cas-analyzer: an online tool for assessing genome editing results using NGS data," Bioinformatics, 33(2):286-288, Jan. 15, 2017.

Pasin et al., "Harnessed viruses in the age of metagenomics and synthetic biology: an update on infectious clone assembly and biotechnologies of plant viruses," Plant Biotechnol. Journal, 17(6):1010-1026, Jan. 24, 2019.

PCT International Preliminary Report on Patentability in International Appln. No. PCT/US2020/045397, dated Feb. 8, 2022, 9 pages.

PCT International Search Report and Written Opinion in International Appln. No. PCT/US2020/045397, dated Apr. 2, 2021, 14 pages.

Sharma et al., "Targets of the StBEL5 Transcription Factor Include the FT Ortholog StSP6A," Plant Physiology, 170(1):310-324, Nov. 9, 2015.

Shen et al., "High rates of virus-induced gene silencing by tobacco rattle virus in Populus," Tree Physiology, 35(9):1016-1029, Jul. 23, 2015.

Sparkes et al., "Rapid, transient expression of fluorescent fusion proteins in tobacco plants and generation of stably transformed plants," Nat. Protocols, 1(4):2019-2025, Nov. 30, 2006.

Svitashev et al., "Genome editing in maize directed by CRISPR-Cas9 ribonucleoprotein complexes," Nat. Communications, 7:13274, Nov. 16, 2016, 7 pages.

Xie et al., "Boosting CRISPR/Cas9 multiplex editing capability with the endogenous tRNA-processing system," Proc. Natl Acad. Sci. USA, 112(11):3570-3575, Mar. 2, 2015.

Zhang et al., "tRNA-Related Sequences Trigger Systemic mRNA Transport in Plants," Plant Cell, 28(6):1237-1249, Jun. 7, 2016.

* cited by examiner

FIG. 1

RNA Virus | Augmented sgRNA | RNA Virus

RNA Viral Vector

RNA Viral Vectors with augmented sgRNAs are used to infect Cas9 overexpressing plant lines Viral vectors spread throughout the plant, with gene editing by the augmented sgRNA becoming more prominent as the plant develops Plants are grown to maturity and seeds are collected High percentages of seedlings contain the desired modification fixed in the germline

FIG. 2B

Target-PDS1 sgRNA
Augmentation-None
Replicate Number-Plant 2

| Indel Type | Genotype | Frequency |
|---|---|---|
| WT Reference | TTTGGTAGTAGCGACTCCCATGGGGC | |
| +C | TTTGGTAGTAGCGACTCCCATGGGGC | 19.5% |
| -1bp | TTTGGTAGTAGCGACTC-ATGGGGC | 18.2% |
| -3bp | TTTGGTAGTAGCGA---CATGGGGC | 15.9% |
| -6bp | TTTGGTAGTAG------CATGGGGC | 4.5% |

FIG. 2C

Target-PDS1 sgRNA
Augmentation-FT
Replicate Number-Plant 2

| Indel Type | Genotype | Frequency |
|---|---|---|
| WT Reference | TTTGGTAGTAGCGACTCCCATGGGGC | |
| -1bp | TTTGGTAGTAGCGACT-CATGGGGC | 19.7% |
| +C | TTTGGTAGTAGCGACTCCCATGGGGC | 16.3% |
| -3bp | TTTGGTAGTAGCGA---CATGGGGC | 16.0% |
| -6bp | TTTGGTAGTAG------CATGGGGC | 5.6% |

FIG. 2A

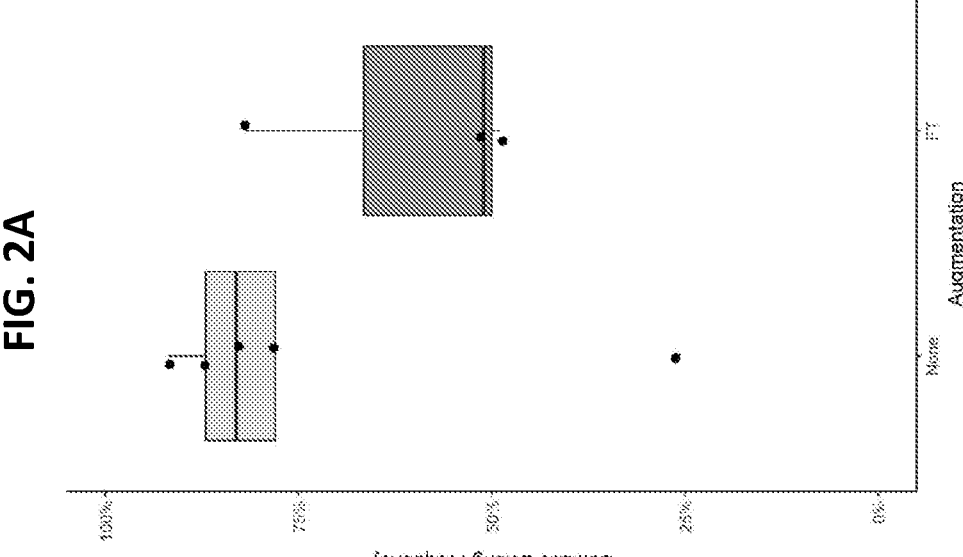

FIG. 4B

Target-PDS1 sgRNA, 8th Systemic Leaf
Augmentation-None
Replicate Number-Plant 2

| Indel Type | Genotype | Frequency |
|---|---|---|
| WT Reference | TTTGGTAGTAGCGACTCCATGGGGC | |
| -1bp | TTTGGTAGTAGCGACT-CATGGGGC | 16.9% |
| +C | TTTGGTAGTAGCGACTCCCATGGGGC | 11.1% |
| -4bp | TTTGGTAGTAGCGA----ATGGGGC | 6.2% |
| -6bp | TTTGGTAGTAG------CATGGGGC | 4.3% |

FIG. 4C

Target-PDS1 sgRNA, 8th Systemic Leaf
Augmentation-FT
Replicate Number-Plant 1

| Indel Type | Genotype | Frequency |
|---|---|---|
| WT Reference | TTTGGTAGTAGCGACTCCATGGGGC | |
| -3bp | TTTGGTAGTAGCGA---CATGGGGC | 22.0% |
| -1bp | TTTGGTAGTAGCGACT-CATGGGGC | 18.8% |
| +C | TTTGGTAGTAGCGACTCCCATGGGGC | 7.4% |
| -4bp | TTTGGTAGTAGCGA----ATGGGGC | 7.2% |

FIG. 4A

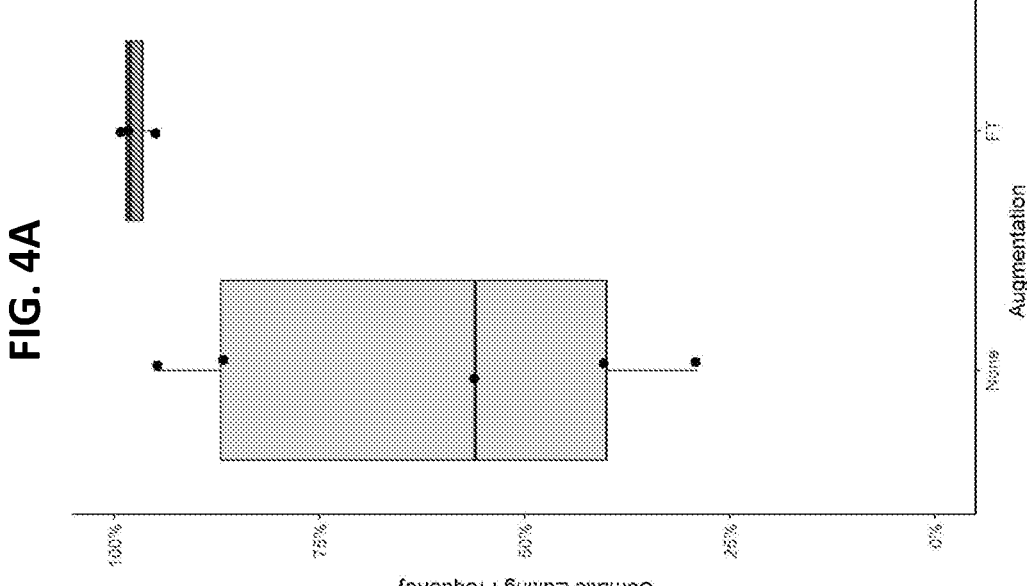

Somatic Editing Frequency

Augmentation

FIG. 5B

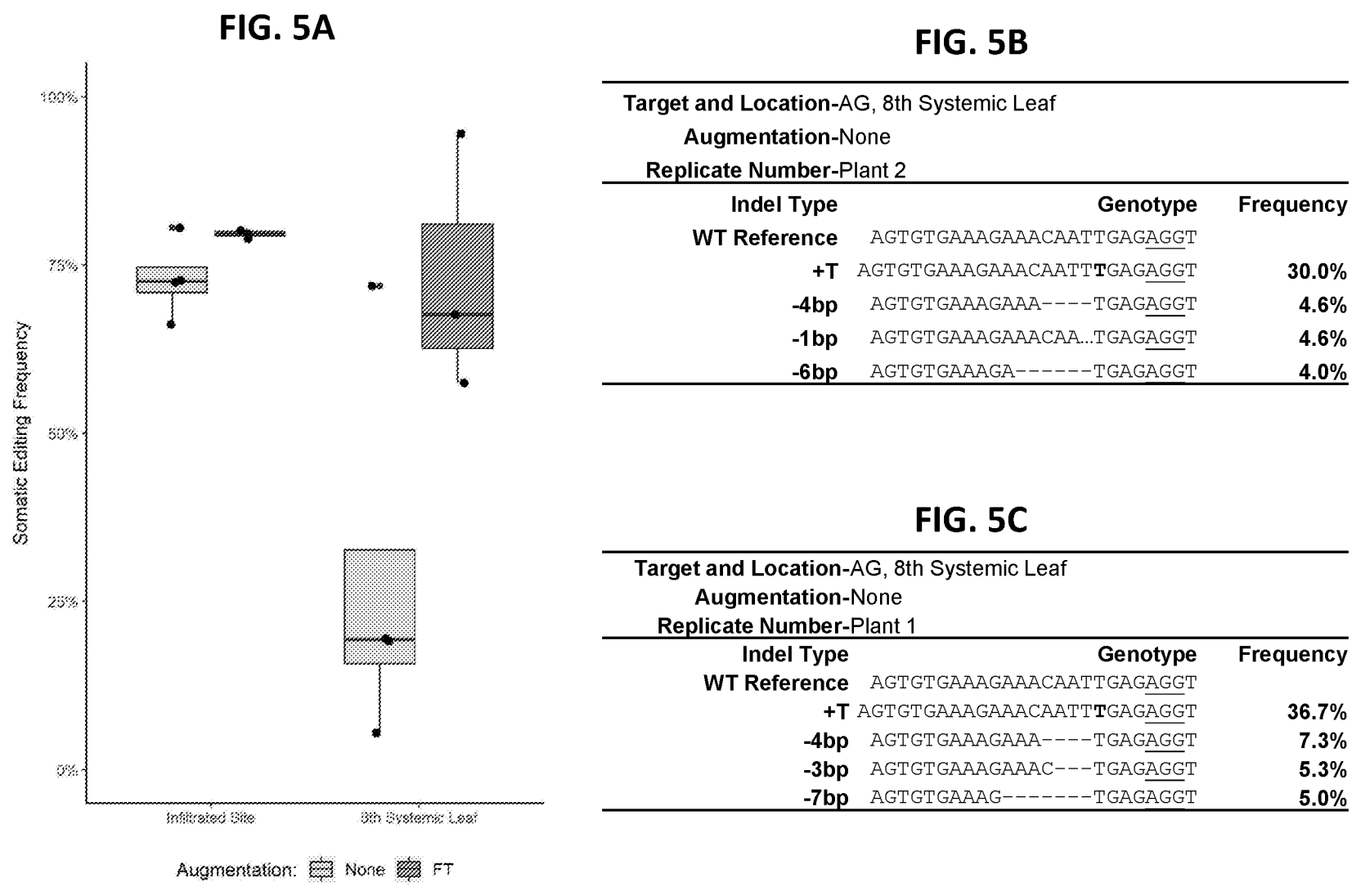

Target and Location-AG, 8th Systemic Leaf
Augmentation-None
Replicate Number-Plant 2

| Indel Type | Genotype | Frequency |
|---|---|---|
| WT Reference | AGTGTGAAAGAAACAATTGAGAGGT | |
| +T | AGTGTGAAAGAAACAATTTGAGAGGT | 30.0% |
| -4bp | AGTGTGAAAGAAA-----TGAGAGGT | 4.6% |
| -1bp | AGTGTGAAAGAAACAA...TGAGAGGT | 4.6% |
| -6bp | AGTGTGAAAGA-------TGAGAGGT | 4.0% |

FIG. 5C

Target and Location-AG, 8th Systemic Leaf
Augmentation-None
Replicate Number-Plant 1

| Indel Type | Genotype | Frequency |
|---|---|---|
| WT Reference | AGTGTGAAAGAAACAATTGAGAGGT | |
| +T | AGTGTGAAAGAAACAATTTGAGAGGT | 36.7% |
| -4bp | AGTGTGAAAGAAA-----TGAGAGGT | 7.3% |
| -3bp | AGTGTGAAAGAAAC---TGAGAGGT | 5.3% |
| -7bp | AGTGTGAAAG-------TGAGAGGT | 5.0% |

Target-PDS1 sgRNA
Augmentation-None
Parent Replicate Number-Plant 1

| Seedling Number | Allele 1 Genotype | Estimated Frequency | Allele 2 Genotype | Estimated Frequency | Conclusion |
|---|---|---|---|---|---|
| WT Reference | TTTGGTAGTAGCGACTCCATGGGGC | | TTTGGTAGTAGCGACTCCATGGGGC | | |
| 1 | TTTGGTAGTAGCGACTCCATGGGGC | | TTTGGTAGTAGCGACTCCATGGGGC | 100% | Wild Type |
| 2 | TTTGGTAGTAGCGACTCCATGGGGC | | TTTGGTAGTAGCGACTCCATGGGGC | 100% | Wild Type |
| 3 | TTTGGTAGTAGCGACTCCCATGGGGC | 41.00% | TTTGGTAGTAGCGA----ATGGGGC | 40.50% | Bi-allelic +C/-4bp |
| 7 | TTTGGTAGTAGCGACTCCATGGGGC | | TTTGGTAGTAGCGACTCCATGGGGC | 100% | Wild Type |
| 8 | TTTGGTAGTAGCGACTCCATGGGGC | | TTTGGTAGTAGCGACTCCATGGGGC | 100% | Wild Type |

FIG. 6C

Target-PDS1 sgRNA
Augmentation-FT
Parent Replicate Number-Plant 1

| Seedling Number | Allele 1 Genotype | Estimated Frequency | Allele 2 Genotype | Estimated Frequency | Conclusion |
|---|---|---|---|---|---|
| WT Reference | TTTGGTAGTAGCGACTCCATGGGGC | | TTTGGTAGTAGCGACTCCATGGGGC | | |
| 13 | TTTGGTAGTAGCGACTCCATGGGGC | | TTTGGTAGTAGCGACTCCATGGGGC | 100% | Wild Type |
| 15 | TTTGGTAGTAGCGACTCCATGGGGC | 48% | TTTGGTAGTAGCGACT--ATGGGGC | 46.9% | Heterozygous WT/-2bp |
| 16 | TTTGGTAGTAGCGACTCCATGGGGC | | TTTGGTAGTAGCGACTCCATGGGGC | 100% | Wild Type |
| 21 | TTTGGTAGTAGCGACTC-ATGGGGC | | TTTGGTAGTAGCGACTC-ATGGGGC | 98% | Bi-allelic -1bp/-1bp |
| 24 | TTTGGTAGTAGCGACTC-ATGGGGC | 45.1% | TTTGGTAGTAGCG-----TGGGGC | 39.9% | Bi-allelic -1bp/-6bp |

FIG. 8B

Target-AG sgRNA
Augmentation-None
Parent Replicate Number-Plant 2

| Seedling Number | Allele 1 Genotype | Estimated Frequency | Allele 2 Genotype | Estimated Frequency | Conclusion |
|---|---|---|---|---|---|
| WT Reference | AGTGTGAAAGAAACAATTGAGAGGT | | AGTGTGAAAGAAACAATTGAGAGGT | | |
| 1 | AGTGTGAAAGAAACAATTGAGAGGT | | AGTGTGAAAGAAACAATTGAGAGGT | 100% | Wild Type |
| 4 | AGTGTGAAAGAAACAATTGAGAGGT | 47.1% | AGTGTGAAAGAAACAATTGAGAGGT | 48.6% | Heterozygous WT/+T |
| 6 | AGTGTGAAAGAAACAATTGAGAGGT | | AGTGTGAAAGAAACAATTGAGAGGT | 100% | Wild Type |
| 8 | AGTGTGAAAGAAACAATTGAGAGGT | | AGTGTGAAAGAAACAATTGAGAGGT | 100% | Wild Type |
| 9 | AGTGTGAAAGAAACAATTGAGAGGT | | AGTGTGAAAGAAACAATTGAGAGGT | 100% | Wild Type |

FIG. 8C

Target-AG sgRNA
Augmentation-FT
Parent Replicate Number-Plant 1

| Seedling Number | Allele 1 Genotype | Estimated Frequency | Allele 2 Genotype | Estimated Frequency | Conclusion |
|---|---|---|---|---|---|
| WT Reference | AGTGTGAAAGAAACAATTGAGAGGT | | AGTGTGAAAGAAACAATTGAGAGGT | | |
| 1 | AGTGTGAAAGAAACAATTGAGAGGT | 45.8% | AGTGTGAAAGAAACAATTGAGAGGT | 44.1% | Heterozygous WT/+T |
| 2 | AGTGTGAAAGAAACAATTTGAGAGGT | 48% | AGTGTGAAAGAAACAAT-GAGAGGT | 43.3% | Bi-allelic +T/-1bp |
| 4 | AGTGTGAAAGAAACAATTGAGAGGT | | AGTGTGAAAGAAACAATTGAGAGGT | 100% | Wild Type |
| 5 | AGTGTGAAAGAAACAATTTGAGAGGT | | AGTGTGAAAGAAACAATTTGAGAGGT | 97.1% | Bi-allelic +T/+T |
| 6 | AGTGTGAAAGAAACAATTTGAGAGGT | | AGTGTGAAAGAAACAATTTGAGAGGT | 97.3% | Bi-allelic +T/+T |

FIG. 9B

Target and Location-AG sgRNA, 8th Systemic Leaf
Augmentation-mFT
Replicate Number-Plant 1

| Indel Type | Genotype | Frequency |
|---|---|---|
| WT Reference | AGTGTGAAAGAAACAATTGAGAGGT | |
| +T | AGTGTGAAAGAAACAATTTGAGAGGT | 41.4% |
| -6bp | AGTGTGAAAGA------TGAGAGGT | 4.2% |
| -5bp | AGTGTGAAAGAA-----TGAGAGGT | 4.0% |
| +A | AGTGTGAAAGAAACAATTAGAGAGGT | 3.9% |

FIG. 9C

Target and Location-AG sgRNA, 8th Systemic Leaf
Augmentation-102mFT
Replicate Number-Plant 1

| Indel Type | Genotype | Frequency |
|---|---|---|
| WT Reference | AGTGTGAAAGAAACAATTGAGAGGT | |
| +T | AGTGTGAAAGAAACAATTTGAGAGGT | 28.4% |
| -1bp | AGTGTGAAAGAAACAA-TGAGAGGT | 5.8% |
| -6bp | AGTGTGAAAGA------TGAGAGGT | 5.0% |
| -6bp | AGTGTGAAAGAA------GAGAGGT | 3.8% |

FIG. 9A

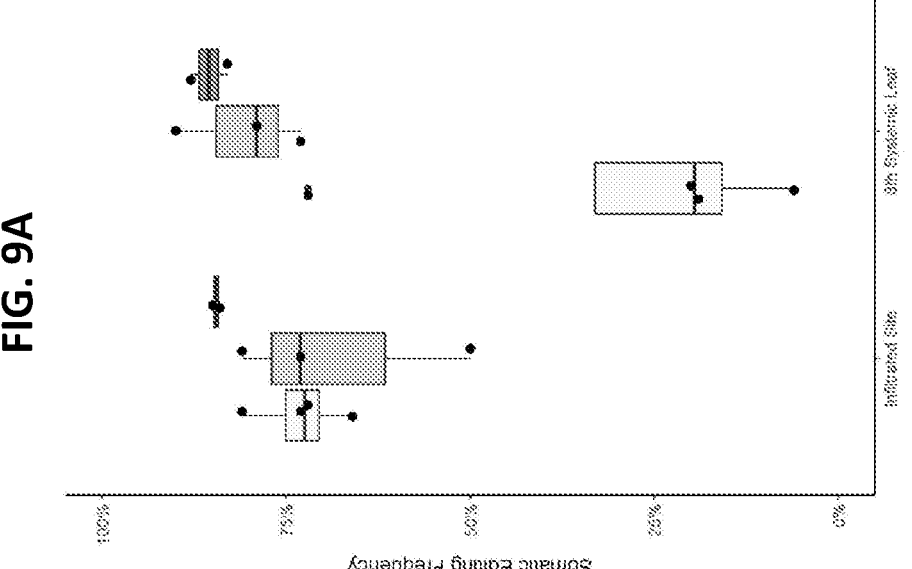

Augmentation: None mFT 102mFT

FIG. 10B

Target-AG sgRNA
Augmentation-mFT
Parent Replicate Number-Plant 1

| Seedling Number | Allele 1 Genotype | Estimated Frequency | Allele 2 Genotype | Estimated Frequency | Conclusion |
|---|---|---|---|---|---|
| WT Reference | AGTGTGAAAGAGAAACAATTGAGAGGT | | AGTGTGAAAGAGAAACAATTGAGAGGT | | |
| 1 | AGTGTGAAAGAGAAACAATTGAGAGGT | 44.8% | AGTGTGAAAGAGAAACAATTGAGAGGT | 41.7% | Heterozygous WT/+T |
| 2 | AGTGTGAAAGAAACAAT-GAGAGGT | 35.9% | AGTGTGAAAGAA--------GAGGT | 40.2% | Bi-allelic -1bp/-12bp |
| 3 | AGTGTGAAAGAAACAATTGAGAGGT | | AGTGTGAAAGAAACAATTGAGAGGT | 97.3% | Bi-allelic +T/+T |
| 4 | AGTGTGAAAGAAACAATTGAGAGGT | | AGTGTGAAAGAAACAATTGAGAGGT | 97.4% | Bi-allelic +T/+T |
| 5 | AGTGTGAAAGAGAAACAATTGAGAGGT | 43.7% | AGTGTGAAAGAGAAACAATTGAGAGGT | 44.7% | Heterozygous WT/+T |

FIG. 10C

Target-AG sgRNA
Augmentation-102mFT
Parent Replicate Number-Plant 2

| Seedling Number | Allele 1 Genotype | Estimated Frequency | Allele 2 Genotype | Estimated Frequency | Conclusion |
|---|---|---|---|---|---|
| WT Reference | AGTGTGAAAGAGAAACAATTGAGAGGT | | AGTGTGAAAGAGAAACAATTGAGAGGT | | |
| 5 | AGTGTGAAAGAGAAACAATTGAGAGGT | 47.2% | AGTGTGAAAGAAAC-----GAGAGGT | 44.7% | Heterozygous WT/-4bp |
| 6 | AGTGTGAAAGAAACAATTGAGAGGT | | AGTGTGAAAGAAACAATTGAGAGGT | 97.3% | Bi-allelic +T/+T |
| 9 | AGTGTGAAAGAAACAATTGAGAGGT | | AGTGTGAAAGAAACAATTGAGAGGT | 97.3% | Bi-allelic +T/+T |
| 10 | AGTGTGAAAGAGAAACAATTGAGAGGT | | AGTGTGAAAGAGAAACAATTGAGAGGT | 100% | Wild Type |
| 15 | AGTGT-------GAGAGGT | 39.5% | AGTGTGAAAGAA-------GAGAGGT | 35.6% | Bi-allelic -6bp/-13bp |

FIG. 11A

AG-102mFT-1-1 Genotype

Target-AG sgRNA
Augmentation-102mFT
Parent Replicate Number-Plant 1

| Plant Number | Allele 1 Genotype | Estimated Frequency | Allele 2 Genotype | Estimated Frequency | Conclusion |
|---|---|---|---|---|---|
| Wild Type Reference | AGTGTGAAAGAAACAATTGAGAGGT | | AGTGTGAAAGAAACAATTGAGAGGT | | |
| 1 | AGTGTGAAAGAAACAATTTGAGAGGT | | AGTGTGAAAGAAACAATTTGAGAGGT | 97% | Bi-allelic +T/+T |

FIG. 11B

AG-102mFT-1-1 Progeny

| Genotype | Frequency |
|---|---|
| Wild Type | 0% |
| Heterozygous | 0% |
| +T/+T | 100% |

FIG. 11C

AG-102mFT-1-5 Genotype

Target-AG sgRNA
Augmentation-102mFT
Parent Replicate Number-Plant 1

| Plant Number | Allele 1 Genotype | Estimated Frequency | Allele 2 Genotype | Estimated Frequency | Conclusion |
|---|---|---|---|---|---|
| Wild Type Reference | AGTGTGAAAGAAACAATTGAGAGGT | | AGTGTGAAAGAAACAATTGAGAGGT | | |
| 5 | AGTGTGAAAGAAACAATTTGAGAGGT | 41.5% | AGTGTGAAAGA-------GAGAGGT | 39.8% | Bi-allelic +T/-7bp |

FIG. 11D

AG-102mFT-1-5 Progeny

| Genotype | Frequency |
|---|---|
| Wild Type | 0% |
| +T/+T | 16% |
| -7bp/-7bp | 37% |
| +T/-7bp | 47% |

AUGMENTED sgRNAS AND METHODS FOR THEIR USE TO ENHANCE SOMATIC AND GERMLINE PLANT GENOME ENGINEERING

CROSS-REFERENCE TO RELATED APPLICATIONS

This application is a National Stage application under 35 U.S.C. § 371 of International Application No. PCT/US2020/045397, having an International Filing Date of Aug. 7, 2020, which claims benefit of priority from U.S. Provisional Application Ser. No. 61/885,009, filed on Aug. 9, 2019.

STATEMENT AS TO FEDERALLY SPONSORED RESEARCH

This invention was made with government support under Grant No. HR0011-17-2-0053 awarded by the Department of Defense/Defense Advanced Research Projects Agency (DARPA) and DE-SC0018277 awarded by the Department of Energy. The government has certain rights in the invention.

SEQUENCE LISTING

This application contains a Sequence Listing that has been submitted electronically as an ASCII text file named 09531_0439WO1_ST25.txt. The ASCII text file, created on Aug. 6, 2020, is 272 kilobytes in size. The material in the ASCII text file is hereby incorporated by reference in its entirety.

TECHNICAL FIELD

This document relates to methods and materials for increasing somatic and germline genome editing, and more particularly to methods and materials for using augmented sgRNAs to increase somatic and germline genome editing.

BACKGROUND

The advent of sequence-specific nuclease technology has made it possible to precisely introduce DNA sequence alterations into plant genomes. This has been particularly true since the advent of RNA guided sequence-specific nucleases, such as CRISPR/Cas9 genomes (Knott and Doudna, 2018, *Science,* 361(6405), 866-869, doi.org/10.1126/SCIENCE.AAT5011). With CRISPR/Cas9, researchers only need to change short sequences of RNA to direct an endonuclease to new genomic targets of interest. RNA guided endonucleases allow for diverse types of sequence modifications to be created, including deletions, insertions, and nucleotide substitutions. Recently, additional RNA guided reagents have been developed that allow for targeted base alterations through deamination (Gaudelli et al., 2017, *Nature,* 551(7681), 464-471, doi.org/10.1038/nature24644), transcriptional activation and repression (Lowder et al., 2015, *Plant Physiol,* 169(2), 971-985, doi.org/10.1104/pp. 15.00636) and epigenetic alterations (Papikian et al., 2019, *Nature Communications,* 10(1), 729, doi.org/10.1038/s41467-019-08736-7). Despite remarkably rapid advances in the development of CRISPR/Cas technology and its many applications, it is still a challenge to perform genome engineering in plants (Altpeter et al., 2016, *Plant Cell,* 28(7), 1510-1520, doi.org/10.1105/tpc.16.00196), primarily because delivery of the reagents to plant cells remains a major limitation in the widespread deployment of this technology.

Gene editing reagents generally are delivered to somatic plant cells via transformation, which typically involves delivering DNA that encodes gene editing reagents (e.g., CRISPR/Cas9, guide RNAs, donor templates) to plant cells using *Agrobacterium*-mediated T-DNA delivery (Gelvin, 2003, *Microbiol Mol Biol Rev: MMBR,* 67(1), 16-37, doi.org/10.1128/mmbr.67.1.16-37.2003) or physical means such as particle bombardment (Liang et al., 2017, *Nature Commun,* 8, 14261; doi.org/10.1038/ncomms14261). Upon delivery, editing can occur in the recipient somatic cells, which are then regenerated to whole plants. The process of regeneration usually begins by de-differentiating the cells into callus and then applying various hormone regimes (e.g., auxin and cytokinin) to induce differentiation—namely, the formation of shoots and roots (Altpeter et al., 2016, supra). For many plant species, protocols for regenerating plants from somatic cells are not available, and even in those species with established protocols, success often is genotype dependent. In addition to being technically challenging, the whole process can be very time consuming; it can take from several months to a year to generate an edited plant from the somatic cells that receive the editing reagents.

In some cases, virus vectors can be used to deliver gene editing reagents to plants. For example, RNA viruses have been used to deliver small single-guide RNAs (sgRNAs) for RNA-guided genome engineering (Ali et al., 2015, *Molecular Plant,* 8(8), 1288-1291, doi.org/10.1016/j.molp.2015.02.011; and U.S. Publication No. 2017/0114351). The frequency of germline mutations recovered from the resulting plants was extremely low, however, making this approach too inefficient as a useful means for creating genetic variation in plants. For such viruses to have real utility as vectors for genome engineering, the virus should infect germline cells so that mutant seed could be harvested from infected plants.

SUMMARY

This document is based, at least in part, on the discovery that higher frequencies of germline editing in infected plants can be achieved by modifying sgRNAs to be mobile, such that they can move from cell to cell and ultimately into the meristem, where editing can take place in cells that give rise to the germline. In addition, this document is based, at least in part, on the discovery that a virus can be used to deliver sgRNAs (e.g., augmented sgRNAs) to the germline in order to recover heritable gene edits at high frequency. A schematic illustrating an exemplary method as provided herein is shown in FIG. 1. Thus, this document provides materials and methods for gene editing, particularly in plants, using an RNA guided endonuclease and an enhanced sgRNA. In some cases, the enhanced sgRNA can be delivered via a viral vector.

In a first aspect, this document features a method for generating a plant having a specific genomic DNA sequence modification. The method can include delivering an augmented sgRNA to a transgenic plant that expresses an RNA guided gene editing reagent, where the augmented sgRNA contains (i) a sequence targeted to the specific genomic DNA sequence and (ii) a mobile RNA sequence; and recovering, from the plant to which the augmented sgRNA was delivered, tissue with a genetic modification induced at the specific genomic DNA sequence by the RNA-guided gene editing reagent, wherein the tissue is capable of transmitting the genetic modification to a next generation plant. The RNA guided gene editing reagent can be an RNA guided endonuclease (e.g., Cas9). The RNA guided gene editing reagent can be an RNA guided base editor (e.g., BE3). The RNA guided gene editing reagent can be an RNA guided epigenetic modifier. The mobile RNA sequence can be derived from Flowering Time (FT). The mobile RNA sequence can be at least 95% identical to the sequence set forth in SEQ ID NO:4, or at least 95% identical to a fragment of SEQ ID NO:4. The augmented sgRNA can include a sequence derived from BELS, GAI, tRNA-like motif, or LeT6. The method can include delivering the augmented sgRNA by RNA virus or by DNA virus, or by *Agrobacterium* (e.g., *Agrobacterium tumefaciens* or *Agrobacterium rhizogenes*). The method can include delivering the augmented sgRNA by biolistics, nanoparticles, or electroporation. The plant can be a dicot or a monocot. The plant can give rise to pollen and egg cells, where the genetic modification is transmitted to the next generation plant. The plant can contain edited cells that are regenerated through tissue culture into an edited plant that transmits the genetic modification to the next generation plant. The method can include delivering more than one augmented sgRNA to the plant, to create more than one sequence-specific genetic modification in the plant. The sgRNA can include an RNA sequence that serves as a repair template to incorporate a specific sequence change at or near the specific genomic DNA sequence. The sgRNA can include an RNA sequence that serves as a template for reverse transcription to create a repair template to incorporate a specific sequence change at or near the specific genomic DNA sequence. The method can include co-delivering the sgRNA with a DNA that serves as a repair template to incorporate a specific sequence change at or near the specific genomic DNA sequence.

In another aspect, this document features a method for generating a plant having a specific genomic DNA sequence modification. The method can include delivering (a) an augmented sgRNA and (b) a sequence encoding an RNA guided gene editing reagent to a plant, where the augmented sgRNA contains (i) a sequence targeted to the specific genomic DNA sequence and (ii) a first mobile RNA sequence, and where the sequence encoding the RNA guided gene editing reagent includes a second mobile RNA sequence; and recovering, from the plant to which the augmented sgRNA was delivered, tissue with a genetic modification induced at the specific genomic DNA sequence by the RNA-guided gene editing reagent, wherein the tissue is capable of transmitting the genetic modification to a next generation plant. The RNA guided gene editing reagent can be an RNA guided endonuclease (e.g., Cas9). The RNA guided gene editing reagent can be an RNA guided base editor (e.g., BE3). The RNA guided gene editing reagent can be an RNA guided epigenetic modifier.

The RNA guided gene editing reagent can be an RNA guided reverse transcriptase (e.g., a prime editor). The first mobile RNA sequence, the second mobile RNA sequence, or both mobile RNA sequences can be derived from FT. The first mobile RNA sequence, the second mobile RNA sequence, or both mobile RNA sequences can be at least 95% identical to the sequence set forth in SEQ ID NO:4, or at least 95% identical to a fragment of SEQ ID NO:4. The augmented sgRNA can contain a sequence derived from BELS, GAI, tRNA-like motif, or LeT6. The method can include delivering the augmented sgRNA by RNA virus, by DNA virus, or by *Agrobacterium* (e.g., *Agrobacterium tumefaciens* or *Agrobacterium rhizogenes*). The method can include delivering the augmented sgRNA by biolistics, nanoparticles, or electroporation. The plant can be a dicot or a monocot. The plant can give rise to pollen and egg cells, where the genetic modification is transmitted to the next generation plant. The plant can contain edited cells that are regenerated through tissue culture into an edited plant that transmits the genetic modification to the next generation plant. The method can include delivering more than one augmented sgRNA to the plant, to create more than one sequence-specific genetic modification in the plant. The sgRNA can include an RNA sequence that serves as a repair template to incorporate a specific sequence change at or near the specific genomic DNA sequence. The sgRNA can include an RNA sequence that serves as a template for reverse transcription to create a repair template to incorporate a specific sequence change at or near the specific genomic DNA sequence. The method can include co-delivering the sgRNA with a DNA that serves as a repair template to incorporate a specific sequence change at or near the specific genomic DNA sequence.

In another aspect, this document features an augmented sgRNA containing (i) a sequence targeted to a genomic sequence in a plant cell, and (ii) a mobile RNA sequence. The mobile RNA sequence can be derived from FT. The mobile RNA sequence can be at least 95% identical to the sequence set forth in SEQ ID NO:4, or at least 95% identical to a fragment of SEQ ID NO:4. The augmented sgRNA can include a sequence derived from BELS, GAI, tRNA-like motif, or LeT6.

In still another aspect, this document features a vector containing (i) a plant virus sequence and (ii) a sequence encoding an augmented sgRNA that contains a mobile RNA sequence and a sequence targeted to a genomic sequence in a plant cell. The mobile RNA sequence can be derived from FT. The mobile RNA sequence can be at least 95% identical to the sequence set forth in SEQ ID NO:4, or at least 95% identical to a fragment of SEQ ID NO:4. The augmented sgRNA can include a sequence derived from BELS, GAI, tRNA-like motif, or LeT6. The virus can be a Tobacco Rattle Virus.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic illustrating a method for generating heritable mutations in plants using RNA Viral Vectors. In general, an RNA Viral Vector (selected depending on the species of interest) is modified to express a sub-genomic RNA consisting of a sgRNA directly fused to a mobility sequence (referred to as an augmented sgRNA). The augmented sgRNA Viral Vectors can be delivered to Cas9-overexpressing plant lines. The Viral Vectors then can systemically infect and spread throughout the plant, continually expressing the augmented sgRNA. The augmented sgRNA can interact with the genome-encoded Cas9 for gene editing. Gene editing occurs with high efficiency in the leaf to which reagents are delivered. As the virus moves from the site of delivery, a lower efficiency of gene editing is observed in the first systemically infected leaves. Higher editing efficiencies are observed in later systemically infected leaves. Plants can mature and produce seed containing mutations caused by Cas9 and the virus-encoded augmented sgRNA. The seeds can be collected and planted, and a high percentage of the progeny will contain the desired mutation. Dashed lines indicate sectors of the plant where the genome is mutated by the augmented sgRNA. Solid lines indicate locations with fixed mutations in the germline. The absence of dashed and solid lines indicates plants with no targeted mutations.

FIGS. 2A-2C show insertion/deletion (indel) mutations occurring at the *N. benthamiana* PDS1 locus from TRV Vectors expressing augmented sgRNAs at the infiltrated site. FIG. 2A is a graph plotting average indel frequencies created by TRV Vectors that expressed non-augmented or Flowering Time (FT) augmented sgRNAs at the infiltrated site in Cas9-overexpressing *N. benthamiana* plants. The sgRNAs targeted the PDS1 locus (SEQ ID NO:9), and mutagenesis was assessed using Illumina based amplicon sequencing. The number of sequencing reads with indel mutations was quantified using CRISPR RGEN Tools. A wide variance in frequencies was observed at the infiltrated site, likely due to different delivery efficiencies. The non-augmented PDS1 sgRNA mutagenesis efficiency was assessed across five plant replicates. The augmented PDS1 sgRNA mutagenesis efficiency was assessed across three plant replicates. Dots indicate editing frequency from each plant replicate. FIG. 2B is a table displaying wild type sequence and the four most common indels (from top to bottom, SEQ ID NOS:73, 75, 76, 77, and 78) for plant replicate 2 when the non-augmented PDS1 sgRNA TRV Vectors were delivered. FIG. 2C is a table displaying wild type sequence and the four most common indels (from top to bottom, SEQ ID NOS:73, 78, 74, 76, and 77) for plant replicate 2 when the FT augmented PDS1 sgRNA TRV Vectors were delivered. All indels occurred at the expected Cas9 target site. For FIGS. 2B and 2C, added bases are indicated in bold letters, and deleted bases are indicated by dotted lines. WT=Wild Type. The Protospacer Adjacent Motif (PAM) site is underlined, and the gRNA target site is the 20 base pairs directly 5' of the PAM. Frequency was determined by dividing the number of reads with the indicated indel by the total number of reads.

FIG. 3A is an image showing an *N. benthamiana* plant after infection with a TRV that expressed an FT-augmented sgRNA targeting PDS1. The image was taken about 3 weeks after infiltration. Knockout of PDS1 resulted in loss of synthesis of photoprotective carotenoids, which in their absence, led to chlorophyll photobleaching and the observed white spots. The phenotype first emerged in the lower leaves and became more prominent in the newly developing upper leaves. FIG. 3B is an image showing mature *N. benthamiana* plants. On the left is a non-infected plant that did not display any photobleaching. On the right is a plant about two months after infection with TRV that expressed an FT-augmented sgRNA targeting PDS1, where the upper portion is almost completely photobleached.

FIGS. 4A-4C show indels occurring at the *N. benthamiana* PDS 1 locus in the 8th systemic leaf due to infection with TRV Vectors expressing augmented sgRNAs. FIG. 4A is a graph plotting average indel frequencies created in the 8th systemically infected leaf by TRV Vectors expressing non-augmented or FT-augmented sgRNAs in Cas9-overexpressing *N. benthamiana* plants. The sgRNAs targeted the PDS1 locus, and mutagenesis was assessed using Illumina based amplicon sequencing and quantified using CRISPR RGEN Tools. A wide variance in frequencies was observed when using non-augmented sgRNA vectors, whereas TRV Vectors expressing augmented sgRNAs produced consistently high editing efficiencies. The non-augmented PDS1 sgRNA mutagenesis efficiency was assessed across five plant replicates. The augmented PDS1 sgRNA mutagenesis efficiency was assessed across three plant replicates. Dots indicate editing frequency from each plant replicate. FIG. 4B is a table displaying wild type sequence and the four most common indels (from top to bottom, SEQ ID NOS:73, 78, 74, 79, and 77) for plant replicate 2 when the non-augmented PDS1 sgRNA TRV Vectors were delivered. FIG. 4C is a table displaying wild type sequence and the four most common indels (from top to bottom, SEQ ID NOS:73, 76, 78, 74, and 79) for plant replicate 1 when the FT-augmented PDS1 sgRNA TRV Vectors were delivered. All indels occurred at the expected Cas9 target site. For FIGS. 4B and 4C, added bases are indicated in bold letters. Deleted bases are indicated by dotted lines. WT=Wild Type. The PAM site is underlined, and the gRNA target site is the 20 base pairs directly 5' of the PAM. Frequency was determined by dividing the number of reads with the indicated indel by the total number of reads.

FIGS. 5A-5C show indels occurring at the *N. benthamiana* AG locus due to TRV Vectors expressing augmented sgRNAs. FIG. 5A is a graph plotting indel frequencies at the infiltrated site for the 8th systemically infected leaf by TRV Vectors expressing non-augmented or FT-augmented sgRNAs. The sgRNAs targeted the AG locus (SEQ ID NO:10), and mutagenesis was assessed using Illumina based amplicon sequencing and quantified using CRISPR RGEN Tools. Both non-augmented and augmented vectors resulted in high editing efficiencies at the infiltrated site, whereas the augmented vectors had higher editing efficiencies at the 8th systemic leaf. The non-augmented AG sgRNA mutagenesis efficiency was assessed across four plant replicates. The augmented AG sgRNA mutagenesis efficiency was assessed across three plant replicates. Dots indicate editing frequency from each plant replicate. FIG. 5B is a table displaying wild type and the four most common indels (from top to bottom, SEQ ID NOS:80, 81, 82, 83, and 84) for plant replicate 2 when the non-augmented AG sgRNA TRV Vectors were delivered. FIG. 5C is a table displaying wild type and the four most common indels (from top to bottom, SEQ ID NOS:80, 81, 82, 85, and 86) for plant replicate 1 when the FT-augmented AG sgRNA TRV Vectors were delivered. All indels occurred at the expected Cas9 target site. For both FIGS. 5B and 5C, added bases are indicated in bold letters. Deleted bases are indicated by dotted lines. WT=Wild Type. The PAM site is underlined, and the gRNA target site is the 20 base pairs directly 5' of the PAM. Frequency was determined by dividing the number of reads with the indicated indel by the total number of reads.

FIGS. 6A-6C show heritable mutations generated in plants infected with TRV Vectors expressing augmented sgRNAs targeting the *N. benthamiana* PDS1 locus (SEQ ID NO:9). FIG. 6A is a graph plotting the number of seedlings that contained indel mutations in at least one PDS1 allele. All three parental plants infected with TRV expressing an augmented PDS1 sgRNA produced a higher number of seedlings with indel mutations when compared to parental plants infected with TRV expressing a non-augmented PDS1 sgRNA. Between 13 and 28 seedlings were genotyped for each parent plant. FIG. 6B is a table displaying wild type sequence and the genotypes for each allele (allele 1 from top to bottom, SEQ ID NOS:73, 73, 73, 74, 73, and 73; allele 2 from top to bottom, SEQ ID NOS:73, 73, 73, 79, 73, and 73) of five representative seedlings from parental plant 1 infected with TRV expressing a non-augmented PDS1 sgRNA. FIG. 6C is a table displaying wild type sequence and the genotypes for each allele (allele 1 from top to bottom, SEQ ID NOS:73, 73, 73, 73, 75, and 75; allele 2 from top to bottom, SEQ ID NOS:73, 73, 87, 73, 75, and 88) of five representative seedlings from parental plant 1 infected with TRV expressing an augmented PDS1 sgRNA. The seedling number represents the seedling genotyped from that parent plant. Allele 1 and allele 2 genotypes show the observed indel at each allele. For both FIGS. 6B and 6C, added bases are indicated in bold letters. Deleted bases are indicated by dotted lines. WT=Wild Type. The PAM site is underlined, and the gRNA target site is the 20 base pairs directly 5' of the PAM. Frequency was determined by dividing the number of reads with the indicated indel by the total number of reads. When a seedling was determined to be Wild Type or to have identical indels at both loci, estimated frequency is only shown after allele 2. All data showing total heritable indel frequency was determined by Sanger sequencing of the PDS1 locus, followed by ICE analysis. There is an inherent amount of noise when using ICE analysis, as the assay is an estimation of the indel frequency using Sanger traces. Conclusions were made as follows: below 10% estimated indels=Wild-Type, 35%-65%=Heterozygous, 85%-100%=Bi-allelic. FIG. 11 verifies that frequencies not equal to 50 or 100% are due to noise.

FIGS. 8A-8C show heritable indel mutations from parental plants infected with TRV Vectors expressing augmented sgRNAs targeting the *N. benthamiana* AG locus (SEQ ID NO:10). FIG. 8A is a graph plotting the number of seedlings that contained indel mutations in at least one AG allele. All three parent plant replicates infected with TRV expressing an augmented AG sgRNA produced a higher number of seedlings with indel mutations as compared to parent plants infected with TRV expressing a non-augmented AG sgRNA. Every seedling genotyped from augmented guide plant 3 contained an indel in the AG locus. Between 11 and 20 seedlings were genotyped for each parent plant. FIG. 8B is a table displaying wild type sequence and the genotypes for each allele (allele 1, all SEQ ID NO: 80; and allele 2 from top to bottom, SEQ ID NOS:80, 80, 81, 80, 80, and 80) of five representative seedlings with edits from parent plant 2 infected with TRV expressing a non-augmented AG sgRNA.

FIG. 8C is a table displaying wild type sequence and the genotypes for each allele (allele 1 from top to bottom, SEQ ID NOS:80, 81, 81, 80, 81, and 81; allele 2 from top to bottom, SEQ ID NOS:80, 80, 89, 80, 81, and 81) of five representative seedlings with edits from parent plant 1 infected with TRV expressing an augmented AG sgRNA.

The seedling number represents the seedling genotyped from that parent plant. Allele 1 and allele 2 genotypes show the observed indel at each allele. For both FIGS. 8B and 8C, added bases are indicated in bold letters. Deleted bases are indicated by dotted lines. WT=Wild Type. The PAM site is underlined, and the gRNA target site is the 20 base pairs directly 5' of the PAM. Frequency was determined by dividing the number of reads with the indicated indel by the total number of reads. When a seedling was concluded to be Wild Type or to have identical indels at both loci, the estimated frequency is only shown after allele 2. All data showing the total heritable indel frequency were determined by Sanger sequencing the AG locus followed by ICE analysis.

FIGS. 9A-9C show indel mutations occurring at the *N. benthamiana* AG locus due to TRV Vectors expressing alternative FT-augmented sgRNAs. FIG. 9A is a graph plotting average indel frequencies at the infiltrated site or at the 8th systemic leaf created by TRV Vectors expressing non-augmented, mFT augmented, or 102mFT augmented sgRNAs in Cas9-overexpressing *N. benthamiana* plants. All sgRNAs targeted the AG locus, and mutagenesis was assessed using Illumina based amplicon sequencing and quantified using CRISPR RGEN Tools. Both non-augmented and augmented vectors resulted in high editing efficiencies at the infiltrated site, whereas both types of augmented sgRNAs had higher editing efficiencies at the 8th systemic leaf than the non-augmented sgRNA. The non-augmented AG sgRNA mutagenesis efficiency was assessed across four plant replicates. The mFT augmented AG sgRNA mutagenesis efficiency was assessed across three plant replicates. The 102mFT augmented AG sgRNA mutagenesis efficiency was assessed across two plant replicates. Dots indicate editing frequency from each plant replicate. FIG. 9B is a table displaying wild type sequence and the four most common indels (from top to bottom, SEQ ID NOS:80, 81, 84, 90, and 91) at the 8th systemic leaf for plant replicate 1 when the mFT-augmented AG sgRNA TRV Vectors were delivered. FIG. 9C is a table displaying wild type and the four most common indels (from top to bottom, SEQ ID NOS:80, 81, 83, 84, and 92) at the 8th systemic leaf for plant replicate 1 when the 102mFT-augmented AG sgRNA TRV Vectors were delivered. All indels occurred at the expected Cas9 target site. For both FIGS. 9B and 9C, added bases are indicated in bold letters. Deleted bases are indicated by dotted lines. WT=Wild Type. The PAM site is underlined, and the gRNA target site is the 20 base pairs directly 5' of the PAM. Frequency was determined by dividing the number of reads with the indicated indel by the total number of reads.

Figure 10A:
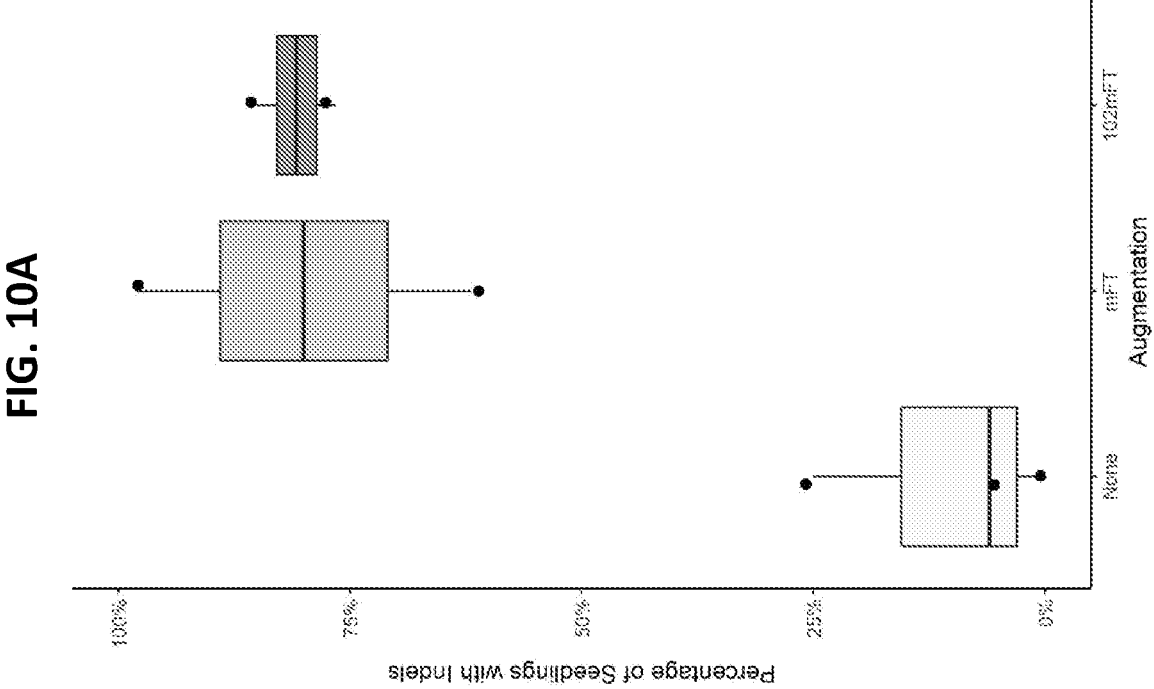

FIGS. 10A-10C show heritable indel mutations from parents infected with TRV Vectors expressing alternative FT-augmented sgRNAs targeting the *N. benthamiana* AG locus. FIG. 10A is a graph plotting the number of seedlings that to contained indels in at least one AG allele. Both parent plant replicates infected with TRV expressing either the mFT or the 102mFT augmented AG sgRNA produced a higher number of seedlings with indel mutations compared to parent plants infected with TRV expressing a non-augmented AG sgRNA. Every seedling genotyped from mFT augmented guide plant 1 contained an indel at the AG locus. Between 13 and 21 seedlings were genotyped for each parent plant. FIG. 10B is a table displaying wild type sequence and the genotypes for each allele (allele 1 from top to bottom, SEQ ID NOS:80, 80, 89, 81, 81, and 80; allele 2 from top to bottom, SEQ ID NOS:80, 81, 93, 81, 81, and 81) of five representative seedlings with edits from parent plant 1 infected with TRV expressing an mFT-augmented AG sgRNA. FIG. 10C is a table displaying wild type sequence and the genotypes for each allele (allele 1 from top to bottom, SEQ ID NOS:80, 80, 81, 81, 80, and 92; allele 2 from top to bottom, SEQ ID NOS:80, 94, 81, 81, 80, and 95) of five representative seedlings with edits from parent plant 2 infected with TRV expressing a 102mFT-augmented AG sgRNA. The seedling number represents the seedling geno-typed from that parent plant. Allele 1 and allele 2 genotypes show the observed indel at each allele. For both FIGS. 10B and 10C, added bases are indicated in bold letters. Deleted bases are indicated by dotted lines. WT=Wild Type. The PAM site is underlined, and the gRNA target site is the 20 base pairs directly 5' of the PAM. When a seedling was concluded to be Wild Type or to have identical indels at both loci, the estimated frequency is only shown after allele 2. All data showing the total heritable indel frequency were deter-mined by Sanger sequencing the AG locus followed by ICE analysis.

FIGS. 11A-11D show fixed heritable indel mutations two generations after parental plants were infected with TRV Vectors expressing 102mFT-augmented sgRNAs targeting the N. benthamiana AG locus. FIG. 11A is a table displaying wild type sequence and the genotype for each allele (allele 1 from to top bottom, SEQ ID NOS:80 and 81; allele 2 from top to bottom, SEQ ID NOS:80 and 81) of one seedling from a parental plant infected with a TRV Vector expressing the 102mFT-augmented sgRNA targeting the AG locus. The plant number represents the plant genotyped from that parent plant. Allele 1 and allele 2 genotypes show the observed indel mutation at each allele. This plant was concluded to have a homozygous+T insertion in both alleles. FIG. 11B is a table displaying the resulting genotypes of seedlings from the plant from FIG. 11A. Nineteen seedlings were genotyped, and all had the +T insertion in both alleles, indicating the indel was fixed in the genome. FIG. 11C is a table displaying wild type sequence and the genotype for each allele (allele 1 from top to bottom, SEQ ID NOS:80 and 81; allele 2 from top to bottom, SEQ ID NOS:80 and 96) of one seedling from another parental plant infected with a TRV Vector expressing the 102mFT-augmented sgRNA targeting the AG locus. The plant number represents the plant genotyped from that parent plant. Allele 1 and allele 2 genotypes show the observed indel at each allele. This plant was concluded to have a +T insertion in one allele and a −7 bp deletion in the other. FIG. 11D is a table displaying the resulting genotypes of seedlings from the plant from FIG. 11C. Nineteen seedlings were genotyped, and all had the indel mutations. The indels were as expected from selfing, with a portion being the same genotype as the parent (+T/−7 bp), and the rest being homozygous for either mutation (either +T or −7 bp). This indicated that the indels were fixed in the genome. Conclusions were determined by Sanger sequencing of the AG locus followed by ICE analysis.

Figure 12:
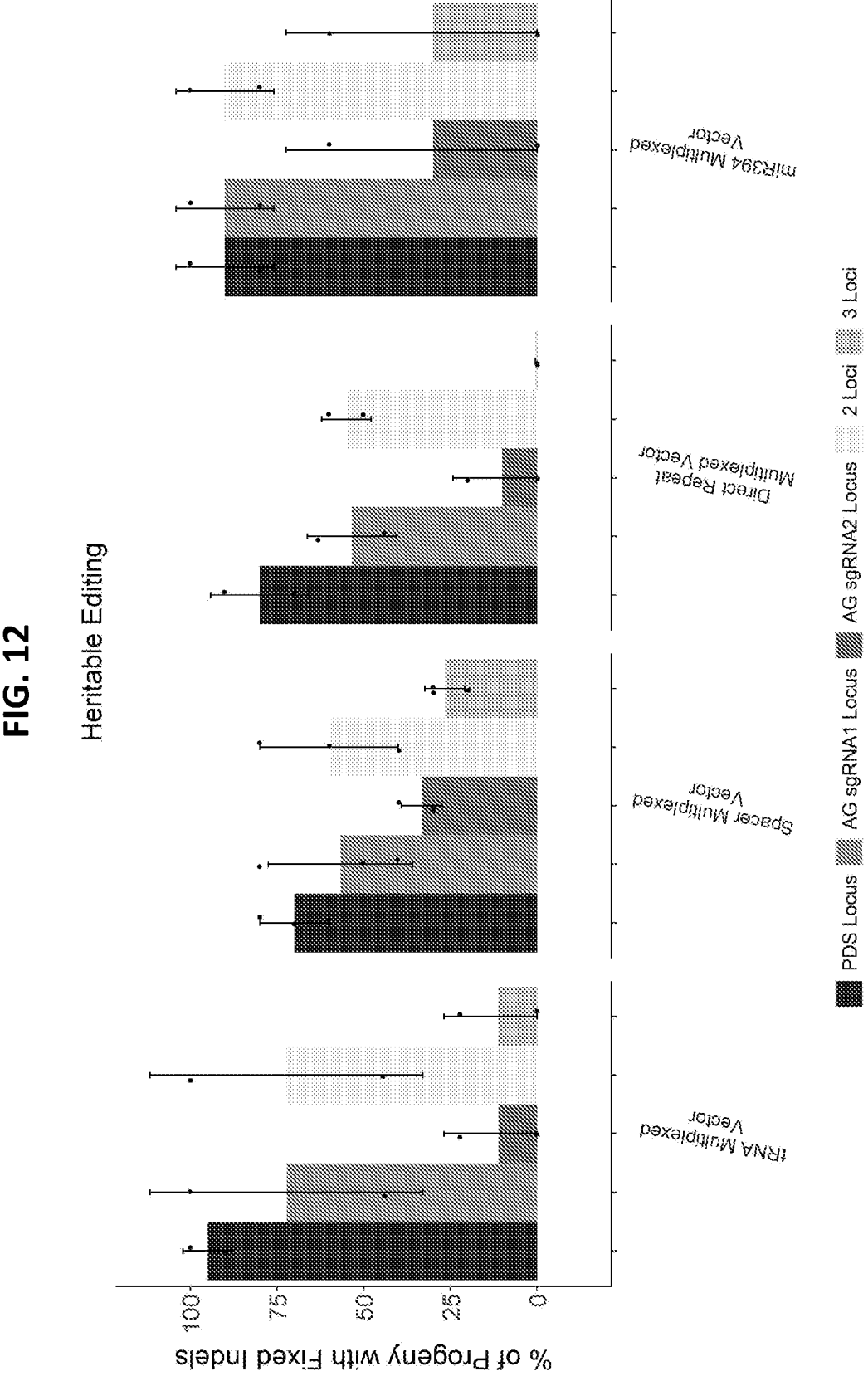

FIG. 12 is a series of graphs plotting the percentage of seedlings that contained indel mutations in one of three targeted alleles, in at least two out of three targeted alleles, or in all three targeted alleles obtained from parents infected with TRV vectors expressing multiplexed augmented sgR-NAs targeted to the N. benthamiana PDS1 locus (SEQ ID NO:9) and two sites in the AG locus (SEQ ID NO:10). Vectors were multiplexed by expressing each augmented sgRNA in tandem separated by either a self-cleaving tRNA sequence, a four nucleotide direct repeat cloning site, a short spacer sequence, or a miR394 target site. All four vector architectures produced a high number of seedlings with indel mutations in the individual loci as well as in multiple loci.

Figure 13:
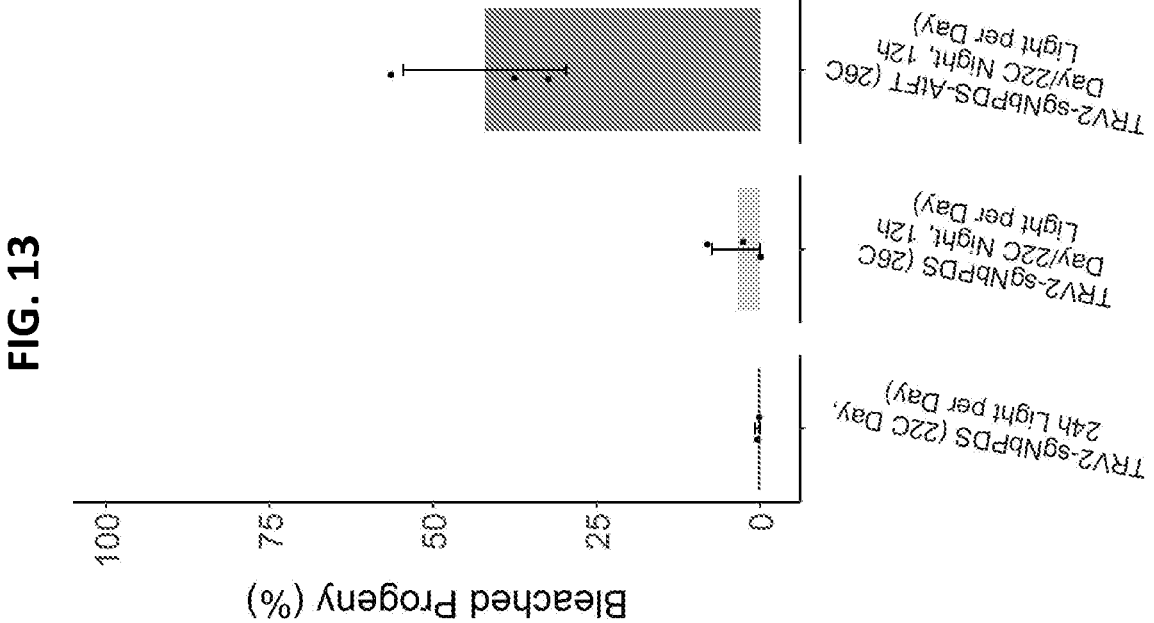

FIG. 13 is a graph plotting the ratio of seedlings that contained bi-allelic indels in the N. benthamiana PDS1 locus compared to the total number of seedlings assessed, where heritable indel mutations were obtained from parents infected with TRV vectors expressing non-augmented or augmented sgRNAs targeting the N. benthamiana PDS1 locus from plants grown under different environmental conditions. Plants infected with non-augmented sgRNAs were grown at either at 26° C. day/22° C. night temperatures with 12 hours of light per day or at 22° C. day temperatures with 24 hours of light per day. 0.37% of seedlings from parents grown at 22° C. day temperatures with 24 hours of light per day were photo-bleached, whereas 3.39% of seed-lings from parents grown at 26° C. day/22° C. night tem-peratures with 12 hours of light per day were photo-bleached. 42.14% of seedlings from parents infected with vectors expressing FT augmented sgRNAs grown at 26° C. day/22° C. night temperatures with 12 hours of light per day were photo-bleached. Thus, frequencies of somatic and germline mutations generated from RNA Viral Vectors were influenced by the environmental conditions.

DETAILED DESCRIPTION

This document is based, at least in part, on the discovery that higher frequencies of germline editing in infected plants can be achieved by using sgRNAs that have been modified to be mobile (e.g., by adding a mobile RNA element), such that they can move from cell to cell and ultimately into the meristem, where editing can take place in cells that give rise to the germline. In addition, this document is based, at least in part, on the discovery that a virus can be used to deliver sgRNAs (e.g., augmented sgRNAs) to plants in order to recover heritable gene edits at high frequency. As illustrated in FIG. 1, for example, an RNA Viral Vector (selected depending on the species of interest) can be modified to express a sub-genomic RNA consisting of a sgRNA directly fused to a mobility sequence (referred to as an augmented sgRNA). The augmented sgRNA Viral Vectors can be deliv-ered to Cas9-overexpressing plant lines, and the Viral Vec-tors can then systemically infect and spread throughout the plant, continually expressing the augmented sgRNA. The augmented sgRNA can interact with the genome-encoded Cas9 for gene editing. Gene editing occurs with high effi-ciency in the leaf to which reagents are delivered. As the virus moves from the site of delivery, a lower efficiency of gene editing is observed in the first systemically infected leaves. Higher editing efficiencies are observed in later systemically infected leaves. Plants can mature and produce seed containing mutations caused by Cas9 and the virus-encoded augmented sgRNA. The seeds can be collected and planted, and a high percentage of the progeny will contain the desired mutation.

Thus, this document provides materials and methods for gene editing, particularly in plants, using RNA guided endonucleases and augmented sgRNAs, and methods for using viral vectors to deliver sgRNAs (e.g., augmented sgRNAs) to plants in order to achieve somatic cell and germ line gene editing without the need for regeneration and tissue culture. For example, this document provides methods for enabling non-cell autonomous movement of sgRNAs from the CRISPR/Cas RNA guided endonuclease system, through the use of plant mobile RNA sequences to enhance RNA guided endonuclease editing efficacy, and through the use of viral mobile RNA sequences to enhance RNA guided endonuclease editing efficacy. Also as described herein, viruses engineered to express augmented sgRNAs can be used to infect transgenic Cas9 plants, which can allow editing to occur in all infected tissue.

Further, movement of the augmented sgRNAs to the meristem can allow for then editing in the germline, and DNA variation can be transmitted to the next generation. Modified sgRNAs can be used with Cas9 or any other appropriate RNA-guided engineering reagent, including base editors, transcriptional regulators, epigenetic modifiers, and prime editors, to create diverse types of alterations in plant genomes.

The methods disclosed herein for using modified sgRNA sequences to increase somatic cell gene editing can allow for more efficient uses of current gene editing and plant regeneration methods (e.g., gene specific knockouts, genomic structural modifications, and single base pair changes). For example, the augmented sgRNAs disclosed herein can be used with targeted cytosine or adenosine deaminases, such as apolipoprotein B mRNA editing enzyme, catalytic polypeptide-like (APOBEC)-CRISPR/Cas fusions (e.g., BE3 and ABE). The methods disclosed herein for using modified sgRNA sequences in combination with RNA Viral Vectors to achieve enhanced whole plant somatic cell gene editing also can allow for more efficient use of current gene editing and plant regeneration methods (e.g., systemic, gene specific knockouts, genomic structural modifications, and single base pair changes).

In addition, the use of modified sgRNA sequences in combination with RNA Viral Vectors as disclosed herein can be used for RNA guided transcriptional regulation studies in somatic cells (e.g., via RNA guided transcriptional regulators, such as deactivated Cas enzymes fused to activator or repressor motifs, in whole plant somatic cells), and for germline genetic modifications, which can lead to the generation of progeny with fixed, desired modifications.

The methods and materials disclosed herein can be used with any appropriate monocot or dicot plant species. In some cases, the methods and materials provided herein can be used with monocotyledonous plants, including banana, grasses such as *Brachypodium distachyon* and *Setaria viridis*, wheat (e.g., *Triticum aestivum*), oats, barley, maize (e.g., *Zea maize*), *Haynaldia villosa*, millet, palms, orchids, onions, pineapple, rice (e.g., *Oryza sativa*), rye, sorghum, bamboo, and sugarcane. In some cases, the methods and materials provided herein can be used with dicotyledonous plants, including alfalfa, amaranth, *Arabidopsis* (e.g., *Arabidopsis thaliana*), beans, Brassica, carnations, chrysanthemums, citrus plants, coffee, cotton, eucalyptus, grape, impatiens, melons, peanuts, peas, peppers, Petunia, poplars, potatoes, rapeseed, roses, safflower, soybeans, squash, strawberry, sugar beets, sunflower, tobacco (e.g., *Nicotiana benthamiana*), tomatoes (e.g., *Solanum lysopersicum*), and woody tree species.

In addition, the methods provided herein can be used for RNA template mediated homologous recombination. For example, an augmented sgRNA sequence in combination with an RNA viral vector can be combined with an RNA template for RNA template mediated homologous recombination, or with an RNA template that is reverse transcribed to make a DNA template for homologous recombination (prime editing), or with a DNA template for homologous recombination (Li et al., 2019, *Nature Biotechnol*, 37(4), 445-450, doi.org/10.1038/s41587-019-0065-7, Anzalone et al., 2019, *Nature*, 576, 149-157, doi.org/10.1038/s41586-019-1711-4). The delivery of specific sequences to be inserted in the genome by an RNA viral vector can greatly expanding the scope and capabilities of this technology.

This document also provides augmented sgRNA molecules. The augmented sgRNAs include an sgRNA sequence, as well as a moveable RNA element.

sgRNAs are specific RNA sequences that can be designed to recognize a target DNA region of interest, such as a particular sequence in a plant genome, and can direct an RNA guided endonuclease (e.g., a Cas nuclease, such as Cas9) to the targeted sequence for editing. sgRNAs include two main parts. The first is a Clustered Regularly-Interspaced Short Palindromic Repeats (crispr) RNA (crRNA), which is a sequence that is complementary to the target DNA and can be, in some cases, about 17 to 20 nucleotides in length. The second is a trans-activating RNA (tracrRNA), which serves as a binding scaffold for the Cas nuclease (Cong et al., 2013, *Science*, 339(6121), 819-823, doi.org/10.1126/science.1231143), SEQ ID NO:12). Cas9 is one type of Cas nuclease. crRNA sequence complementarity to the target DNA allows Cas9 to bind the target DNA. Cas9 recognizes a short protospacer adjacent motif (PAM), which is adjacent to the region of complementarity to the crRNA and aids in distinguishing self from non-self. Cas9 orthologs have been described in species such as *S. pyogenes* and *S. thermophiles*, and useful Cas9 nuclease sequences and structures include, for example, those known in the art (see, e.g., Ferretti et al., 2011, *Proc Natl Acad Sci USA* 98, 4658-4663, 2001; Deltcheva et al., 2011, *Nature* 471, 602-607, 2011; and Jinek, 2012, *Science* 337, 816-821).

The homology region within the crRNA sequence (the sequence that targets the crRNA to a desired DNA sequence) can be, for example, between about 10 and about 40 (e.g., 10 to 15, 15 to 18, 17 to 20, 18 to 21, 19 to 22, 20 to 23, 22 to 25, 25 to 30, 30 35, or 35 to 40) nucleotides in length. The tracrRNA hybridizing region within each RNA sequence can be between about 8 and about 20 (e.g., 8 to 10, 9 to 11, 10 to 12, 11 to 13, 12 to 14, 13 to 15, 14 to 16, 15 to 17, 16 to 18, 17 to 19, or 18 to 20) nucleotides in length.

Any appropriate sgRNA sequence can be included in the augmented sgRNA molecules provided herein. Methods for selecting sgRNA target sequences are described elsewhere (see, e.g., Cermak et al., 2017, *The Plant Cell* 29, 1196-1217, doi.org/10.1105/tpc.16.00922), and include online programs.

In addition to an sgRNA sequence, the augmented sgRNAs provided herein (and used in the methods provided herein) also include an RNA sequence that promotes mobility in plants. These mobile RNAs act as non-cell autonomous signals in plants, where they are transcribed in in one cell type and then translated in a second cell type after movement. Mobile RNAs often are used as developmental signals, controlling the timing of organ differentiation (Jackson et al., supra; Li et al., 2009, *J Virol*, 83(8), 3540-3548, doi.org/10.1128/JVI.02346-08; and Sharma et al., 2016, *Plant Physiol*, 170(1), 310-324, doi.org/10.1104/pp.15.01314). Mobile RNA sequences also can be used to engineer mobility to a reporter molecule such as GFP (Luo et al., 2018, *Plant Physiol*, 177, 604-614, doi.org/10.1104/pp. 18.00107; and Zhang et al., supra).

Any appropriate mobile RNA sequence can be used in the augmented sgRNAs provided herein. Non-limiting examples of RNA sequences that can promote intercellular mobility include FT and the other elements listed in TABLE 1 (see, also, Notaguchi et al., 2015, *Plant Cell Physiol*, 56(2), 311-321, doi.org/10.1093/pcp/pcu210; Banerjee et al., 2006, *Plant Cell*, 18(12), doi.org/10.1105/tpc.106.042473; Haywood et al., 2005, *The Plant J: For Cell*

*and Molecular Biology*, 42(1), 49-68, doi.org/10.1111/j.1365-313X.2005.02351.x; Zhang et al., 2016, *The Plant Cell*, 28(6), 1237-1249, doi.org/10.1105/tpc.15.01056; Kim et al., 2001, *Science*, 293(5528), 287-289, doi.org/10.1126/science.1059805; and Jackson and Hong, 2012, Front *Plant Sci*, 3, 127, doi.org/10.3389/fpls.2012.00127). FT has been implicated in promoting the initiation of flowering at the shoot apical meristem (Jackson et al., supra). FT is transcribed in leaf vascular tissue and moves through the vasculature to the apical meristem (Corbesier et al., 2007, *Science*, 316(5827), 1030-1033, science.sciencemag.org/content/316/5827/1030.full).

TABLE 1

RNA sequences that promote mobility in plants.

| Mobile Sequence | RNA Molecule | Movement | Species |
|---|---|---|---|
| BEL5 | mRNA | Systemic | *Solanum tuberosum* |
| GAI | mRNA | Systemic | *Arabidopsis thaliana*, *Cucurbita maxima*, monocot homologs |
| tRNA-like motif | tRNA | Systemic | *Arabidopsis thaliana*, *Cucurbita pepo*, viral homologs |
| LeT6 | mRNA | Systemic and directed to the meristem | *Solanum lycopersicum* |
| FT | mRNA | Systemic and directed to the meristem | *Arabidopsis thaliana*, *Nicotiana tabacum*, homologs identified in many other species |

The "RNA Molecule" column indicates whether each molecule functions as messenger RNA (mRNA) or transfer RNA (tRNA).
"Movement" describes whether there is experimental evidence of systemic movement through the phloem or if this movement is directed to the shoot apical meristem cells.
"Species" indicates which species each mobile element is from, or the species in which movement was validated.

As described herein, mobile RNA sequences can be added to sgRNA sequences to generate "augmented sgRNAs" that have enhanced effectiveness and increased mobility. For example, an FT sequence can be added directly to the 3' end of an sgRNA sequence, as described in the examples herein. It is noted, however, that a mobile RNA sequence can be located 5' of an sgRNA sequence, and can be any appropriate distance away from the sgRNA sequence within an augmented sgRNA molecule. For example, the 5' or 3' end of a mobile RNA element can be adjacent to the 5' or 3' end of an sgRNA, or a spacer of about 2 to about 10,000 nucleotides (e.g., about 2 to 10, about 10 to 50, about 50 to 100, about 100 to 200, about 200 to 500, about 500 to 1000, or about 1000 to 5000 nucleotides) can be present between the sgRNA portion and the mobile RNA portion of an augmented sgRNA as provided herein.

An exemplary FT sequence is set forth in SEQ ID NO:4. In some cases, a mobile RNA element can have at least 90% (e.g., at least 91%, at least 92%, at least 93%, at least 94%, at least 95%, at least 96%, at least 97%, at least 98%, at least 99%, or 100%) sequence identity to the sequence set forth in SEQ ID NO:4.

The terms "percent identity" or "identity" in the context of two or more nucleic acid sequences refer to two or more sequences that are the same or have a specified percentage of nucleotides or amino acid residues that are the same. The percent identity can be measured using sequence comparison software or algorithms or by visual inspection.

In general, percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. With regard to mobile RNA sequences, the total number of aligned nucleotides refers to the minimum number of mobile RNA nucleotides that are necessary to align the second sequence, and does not include alignment (e.g., forced alignment) with non-mobile RNA sequences. The total number of aligned nucleotides may correspond to the entire mobile RNA sequence or may correspond to fragments of a full-length mobile RNA sequence.

Sequences can be aligned using the algorithm described by Altschul et al. (1997, *Nucleic Acids Res*, 25, 3389-3402) as incorporated into BLAST (basic local alignment search tool) programs, available at ncbi.nlm.nih.gov on the World Wide Web. BLAST searches or alignments can be performed to determine percent sequence identity between a mobile RNA sequence and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a mobile RNA sequence and another sequence, the default parameters of the respective programs are used.

In some cases, a fragment of a full-length mobile RNA sequence can be used. A fragment can lack, for example, about 1% to about 50% (e.g., about 1 to about 5%, about 5 to about 10%, about 10 to about 20%, about 20 to about 30%, about 30 to about 40%, or about 40 to about 50%) of the full length sequence. In some cases, a fragment of a mobile RNA can be a truncated version that lacks the 5' portion of the full-length sequence, or a truncated version that lacks the 3' portion of the full-length sequence. A non-limiting example of a truncated mobile RNA that can be used in the augmented sgRNAs provided herein is the 102mFT element described herein (SEQ ID NO:6), which only includes 102 nucleotides from the 5' end of the full-length mFT molecule (SEQ ID NO:5).

In some embodiments, the augmented sgRNAs provided herein can be incorporated into viral vectors, which can be introduced into plants. Viruses that have been harnessed for use as vectors are described elsewhere (see, e.g., Pasin et al., 2019, *Plant Biotechnol J* 17, 1010-1026, onlinelibrary.wiley.com/doi/10.1111/pbi.13084). Among these, viruses such as Tobacco Rattle Virus (TRV) and Foxtail Mosaic Virus (FoMV) can be efficient vectors for virus-induced gene silencing, facilitating functional genomics in diverse plant species (Dinesh-Kumar et al., 2003, "Virus-Induced Gene Silencing," In *Plant Functional Genomics*, pp. 287-294, New Jersey: Humana Press, doi.org/10.1385/1-59259-413-1:287; and Mei et al., 2016, *Plant* Physiol, 171(2), 760-772, doi.org/10.1104/pp. 16.00172). TRV has a bipartite genome, consisting of two positive-sense single-stranded RNAs designated TRV1 and TRV2. The TRV2 genome can be modified to carry gene fragments for post-transcriptional gene silencing (Dinesh-Kumar et al., supra). TRV has been widely used for gene silencing in dicots, and also has been used as a vector for genome engineering. For example, when TRV2 was replaced with an RNA for the Zif268:FokI ZFN, targeted genome modifications were recovered in somatic tobacco and *petunia* cells at an integrated reporter gene (Marton et al., 2010, *Plant Physiol*, 154(3), 1079-1087, doi.org/10.1104/pp. 110.164806). A disadvantage of RNA viruses is that they tend to have limited cargo capacity (Dinesh-Kumar et al., supra). Most RNA viruses cannot replicate much more than 1 kb, and therefore they have little utility for delivering anything much larger than a ZFN monomer. The augmented sgRNA molecules provided herein, however, can more readily be delivered by virus vectors.

In addition to being introduced via viral vectors, the augmented sgRNAs provided herein can be delivered to a plant by any other suitable method, including by *Agrobacterium*, by direct injection, electroporation, biolistics, nanoparticle delivery, particle bombardment, chemical transfection, or any other useful method that can result in delivery to plant cells and expression of the delivered augmented sgRNA. It is to be understood that when sgRNAs are used or delivered as RNA, their sequences will contain uracil in place of thymine in the corresponding DNA sequences (e.g., the FT sequences described herein).

After delivery of an augmented sgRNA to a plant (e.g., a Cas9 expressing transgenic plant), any appropriate methods can be used to determine whether cells of the plant, and/or progeny of the plant, contain mutations at the targeted sequence. Such methods include those disclosed in the working Examples herein, for example. It is to be noted that in some cases, rather than using a Cas9-expressing transgenic plant, a sequence encoding a Cas endonuclease can be co-delivered to the plant along with the augmented sgRNA. Representative DNA and polypeptide sequences for Cas9 are set forth in SEQ ID NOS:97 and 98, respectively. In some cases, a Cas9 nucleotide sequence that is at least 90% identical (e.g., at least 91%, at least 92%, at least 93%, at least 94%, at least 95%, at least 96%, at least 97%, at least 98%, or at least 99% identical) to the sequence set forth in SEQ ID NO:97, or that encodes a polypeptide having a sequence that is at least 90% identical (e.g., at least 91%, at least 92%, at least 93%, at least 94%, at least 95%, at least 96%, at least 97%, at least 98%, or at least 99% identical) to the amino acid sequence of SEQ ID NO:98 can be used. When Cas9 is delivered with an augmented sgRNA, they can be delivered simultaneously, on the same vector (e.g., the same virus vector) or on separate vectors (e.g., separate virus vectors), or they can be delivered separately. It is noted that a sequence encoding Cas9 can be augmented by linking it to a mobile RNA, in the same manner by which sgRNAs are disclosed herein to be linked to mobile RNAs.

Moreover, in some embodiments, the methods provided herein can include introducing a donor RNA template with an augmented sgRNA, in order to promote template dependent homologous recombination at the targeted site. When a donor RNA template is delivered with an augmented sgRNA, they can be delivered simultaneously, on the same vector (e.g., the same virus vector) or on separate vectors (e.g., separate virus vectors), or they can be delivered separately. It is noted that a donor RNA template can be augmented by linking it to a mobile RNA, in the same manner by which sgRNAs are disclosed herein to be linked to mobile RNAs.

The invention will be further described in the following examples, which do not limit the scope of the invention described in the claims.

EXAMPLES

Example 1: Cloning of Augmented sgRNAs

In an attempt to increase the mobility of sgRNAs in plants, the sgRNAs were coupled to sequences from FT that promote mobility to the apical meristem. First, FT was cloned by obtaining the DNA sequence for the expressed FT mRNA from *Arabidopsis* (SEQ ID NO:4). To accomplish this, frozen leaf tissue of the *Arabidopsis* ecotype Columbia was ground into a fine powder using metallic beads and a paint shaker. The tissue was resuspended in 500 μL TRIZOL™ reagent and incubated at room temperature for 5 minutes. Chloroform was added (0.1 mL), and the solution was incubated at room temperature for 3 minutes before being centrifuged for 15 minutes at 12,000 relative centrifugal force (rcf) at 4° C. The aqueous phase was transferred to a fresh tube and mixed with 0.5 mL isopropanol. This mixture was incubated for 10 minutes at 4° C. and then centrifuged for 10 minutes at 12,000 rcf at 4° C. The supernatant from this reaction was discarded and the pellet was resuspended in 0.5 mL 75% ethanol before being vortexed and centrifuged for 5 minutes at 7,500 rcf at 4° C. All ethanol was discarded, and the pellet was resuspended in 30 μL distilled $H_2O$ ($dH_2O$), quantified using a NANODROP™ spectrophotometer, and stored at −80° C.

The FT mRNA sequence was amplified from the purified RNA using a reverse transcriptase polymerase chain reaction (RT-PCR) reaction and primers PP331 (SEQ ID NO:13) and PP332 (SEQ ID NO:14). The RT-PCR reaction was performed in a 12.5 μL QIAGEN® RT-PCR mix composed of 2.5 μL 5× QIAGEN® OneStep RT-PCR Buffer, 1 μL dNTP Mix, 1 μL Primer 1 (PP331), 1 μL Primer 2 (PP332), 1 μL *Arabidopsis* template RNA (50 ng), 0.5 μL QIAGEN® OneStep RT-PCR Enzyme Mix, and 6 μL $dH_2O$. The PCR conditions were 50° C./30 minutes+95° C./15 minutes+43× (94° C./40 seconds+55° C./40 seconds+72° C./1 minute)+72° C./10 minutes.

sgRNA sequences were augmented by directly fusing the FT complementary DNA (cDNA) to the 3' end of the sgRNA. This was accomplished by PCR-amplifying the sgRNA (compatible with SpCas9; Cong et al., supra) using Primer 1 oEE562 (SEQ ID NO:16) and Primer 2 oEE267 (SEQ ID NO:15), both of which contained AarI restriction enzyme recognition sites. The FT cDNA was amplified in a similar manner using Primer 1 oEE271 (SEQ ID NO:17) and Primer 2 oEE272 (SEQ ID NO:18), which also contained AarI recognition sites and complimentary overhangs to oEE267 (sgRNA rev). Both of these PCR reactions used 0.25 μL Q5 DNA Polymerase, 0.5 μL dNTPs, 5 μL Q5 DNA Polymerase, 1.25 μL Primer 1, 1.25 μL Primer 2, 0.5 μL DNA Template, and 16.25 μL $dH_2O$ and ran under the conditions 98° C./1 minute+10×(98° C./10 seconds+46° C./15 seconds+72° C./20 seconds)+25×(98° C./10 seconds+72° C./35 seconds)+72° C./2 minutes. The resulting PCR products were then cloned into the pEE081 cloning vector (SEQ ID NO:34) by adding 0.5 μL of each PCR product into a mixture of 1 μL pEE081 (50 ng), 0.5 μL AarI restriction enzyme, 0.4 μL AarI oligonucleotide, 1 μL T4 DNA Ligase, 2 μL T4 DNA Ligase Buffer, and 14.1 μL $dH_2O$. The reaction mixture was then cycled at 10×(37° C./5 minutes+16° C./10 minutes)+37° C./10 minutes+80° C./5 minutes to create pEE081-sgRNA-FT (SEQ ID NO:35). Upon completion of the cycle, *Escherichia coli* strain DH5α was transformed with 5 μL of the reaction. Transformed *E. coli* were selected on Lysogeny Broth (LB) agarose plates with 50 ng/μL kanamycin at 37° C. overnight. Surviving colonies of *E. coli* were individually selected and placed in 4 mL LB liquid medium with 50 ng/μL kanamycin and grown at 37° C. overnight. DNA was prepared from liquid cultures using a QIAGEN® miniprep kit according to the manufacturer's protocol. This initial version of a sgRNA augmented with FT sequences (SEQ ID NO:35) was used as a template for downstream cloning reactions described in the Examples below.

Example 2: Delivery of Augmented sgRNAs to Plants Cells for Genome Editing

The forward primer used to amplify the sgRNA for the initial vector contained a target site for the phytoene desaturase (PDS1) locus (Niben101Scf14708g00023.1) of *Nicotiana benthamiana* (5'-TTGGTAGTAGCGACTCCATG-3'; SEQ ID NO:7). With the fully assembled PDS1 sgRNA in this vector, it was hypothesized that the FT sequence augmentation would not interfere with Cas9 binding to the sgRNA or with its ability to target PDS1, thereby allowing for plant gene editing. To test this, the augmented sgRNA was PCR amplified using Primer 1 oEE561 (SEQ ID NO:19) and Primer 2 oEE435 (SEQ ID NO:20) with 50 ng of pEE081-sgRNA-FT (SEQ ID NO:35) used as a template. The PCR was performed using the Q5 DNA polymerase reaction mixture and conditions described in Example 1. The PCR product was then cloned into vector pEE160 (SEQ ID NO:36) by adding 0.5 µL of the PCR product into a mixture of 1 µL pEE160 (50 ng), 0.5 µL Esp3I restriction enzyme, 1 µL T4 DNA Ligase, 2 µL T4 DNA Ligase Buffer, and 15 µL dH$_2$O. The reaction mixture was cycled at 10×(37° C./5 minutes+16° C./10 minutes)+80° C./5 minutes to generate pEE429 (SEQ ID NO:37).

In vector pEE429, the augmented sgRNA targeting PDS1 was located 3' of a it) Nos promoter (SEQ ID NO:3). The sgRNA also contained AarI restriction enzyme recognition sites and appropriate overhang sequences so that it was compatible with Transfer (T)-DNA vectors (see, Cermak et al., supra). pEE429 was cloned into pTRANS_200, which contained T-DNA left and right borders and *Agrobacterium* origins of replication. This reaction took place by mixing 150 ng (1 µL) of pEE429, 150 ng (1 µL) of pMOD A0101, 150 ng (1 µL) of pMOD_B0000, 75 ng (1 µL) of pTRANS_200, 0.5 µL AarI restriction enzyme, 0.4 µL AarI oligonucleotide, 1 µL T4 DNA Ligase, 2 µL T4 DNA Ligase Buffer, and 12.1 µL dH$_2$O. The reaction mixture was then PCR-amplified, *E. coli* was transformed with the reaction mixture, and DNA was prepared in the same manner described in Example 1 to generate pEE478 (SEQ ID NO:38).

*Agrobacterium tumefaciens* strain GV3101 was transformed with 500 ng of pEE478 (SEQ ID NO:38). Transformed cells were selected on LB+kanamycin 50 ng/4+ gentamicin 50 ng/4 plates at 28° C. for 48 hours. One colony was selected for growth in 4 mL LB liquid medium+ kanamycin 50 ng/4+gentamicin 50 ng/4 at 28° C. for 24 hours. Liquid cultures were placed in a centrifuge for 10 minutes at 2500 rcf. The LB+antibiotic medium was discarded and the pellet of *Agrobacterium* cells were resuspended in 4 mL of Agroinfiltration Buffer (10 mM MgCl$_2$, 10 mM 2-(N-morpholino) ethanesufonic acid (MES), pH5.6). This suspension was again placed in a centrifuge for 10 minutes at 2500 rcf and the Agroinfiltration Buffer was discarded. The pelleted cells were resuspended in Agroinfiltration Buffer to OD600=1.0 and incubated at room temperature for 3 hours. After incubation, the resuspended cells were infiltrated into 6 week *N. benthamiana* plants at the underside of the 5th true leaf using a needless syringe (Sparkes et al., 2006, *Nature Protocols,* 1(4), 2019-2025, doi.org/10.1038/nprot.2006.286). *N. benthamiana* plants were grown in a growth chamber maintained at 26.5° C. Day/22° C. Night with a 12 hour day/night light cycle at 50% humidity. These growing conditions were used for all subsequent Examples To test the effectiveness of the augmented sgRNA to cleave genomic DNA at the PDS1 locus, DNA was extracted from the pEE478 (SEQ ID NO:38) infiltration site of *N. benthamiana* leaves two weeks after infiltration. To isolate genomic DNA, an 8 mm leaf punch was frozen in liquid nitrogen and ground to a fine powder using metallic beads and a paint shaker. 500 µL of CTAB buffer (2.0 g hexadecyl trimethyl-ammonium bromide (CTAB)), 10 mL 1M Tris pH 8.0, 4 mL 0.5M ethylenediaminetetraacetic acid di-sodium salt (EDTA), 8.1 g NaCl, 1 g Polyvinylpyrrolidone K30 (PVP), dH$_2$O up to 100 mL, pH adjusted to 5.0 per 100 mL of solution) and 10 µL 2-Mercaptoethanol was added and the samples were incubated at 65° C. for 30 minutes. Chloroform (400 µL) and Isoamyl-alcohol (16 µL) were added and the samples were incubated for 5 minutes at 4° C. Samples were then centrifuged for 5 minutes at 16,000 rcf and the supernatants were transferred to clean microfuge tubes. Ice-cold Isopropanol (350 µL) was added and the samples were incubated at 4° C. for 10 minutes and then centrifuged for 10 minutes at 16,000 rcf. The supernatants were discarded and the genomic DNA pellets were washed once in 75% ethanol. Samples were centrifuged for 5 minutes at 7,500 rcf and the supernatants were removed. The genomic DNA in the pellets was resuspended in 50 µl of dH$_2$O.

Genomic DNA from the infiltrated site is used as a template for a PCR reaction at this locus. The PCR reaction is performed using Primer 1 oEE552 (SEQ ID NO:21) and Primer 2 oEE504_R (SEQ ID NO:22). A reaction mixture consists of 1 µL primer 1, 1 µL primer 2, 7 µL dH$_2$O, and 10 µL PHIRE® Master Mix, and is run under the following conditions: 98° C./5 minutes+35×(98° C./5 seconds+62° C./5 seconds+72° C./35 seconds)+72° C./1 minute. The PCR reactions are purified using a QIAGEN® PCR Purification Kit following the manufacturer's protocol. Reactions are sent for Sanger sequencing using the primer oEE504_R (SEQ ID NO:22). After Sanger sequencing is performed, indel frequency is estimated using ICE™ software (Hsiau et al. 2019, *BioRxiv,* 251082, doi.org/10.1101/251082).

Example 3: Cloning of Augmented sgRNAs into a TRV Vector cDNA of the TRV1 and TRV2 genomes have been cloned into separate transformation vectors for efficient delivery to plant cells (Ali et al., supra). These vectors contain *Agrobacterium* origins of replication, T-DNA left and right borders, and the TRV1 or TRV2 cDNA sequences expressed from a 5' 35S promoter (SEQ ID NO:1). TRV2 can be modified to express heterologous sequences, including sgRNA sequences from the Pea Early Browning Virus (PeBV) sub-genomic promoter (SEQ ID NO:2) (see, Ali et al., supra).

Augmented sgRNAs were cloned into TRV2 by PCR amplification of the augmented sgRNA with the fused FT cDNA sequence described in Example 1. This was accomplished using Primer 1 oEE562 (SEQ ID NO:16) and Primer 2 oEE272 (SEQ ID NO:18) using pEE081-sgRNA-FT (SEQ ID NO:35) as a template and the Q5 PCR protocol described in Example 1. These primers contained AarI restriction enzyme recognition sites and compatible overhangs with cloning vector pEE083 (SEQ ID NO:39). The PCR amplicon was cloned into pEE083 in the same manner as described for the assembly of pEE081-sgRNA-FT in Example 1 to create pEE391 (SEQ ID NO:40).

Control (non-augmented) sgRNAs were cloned into TRV2 vectors in the same manner as described above, except that oEE282 (SEQ ID NO:25) was used instead of oEE272 (SEQ ID NO:18) to PCR amplify the control sgRNA vector. This assembly into pEE083 created control vector pEE390 (SEQ ID NO:41).

Example 4: Editing of Plant Genomic DNA Using Augmented sgRNAs and TRV

The forward primer used to amplify the augmented sgRNA in vector pEE391 contained the same PDS1 target sequence described in Example 2. Studies were conducted to determine whether the augmented PDS1 sgRNA in the TRV2 vector, pEE391, would be functional in creating double stranded breaks at PDS1 locus in *N. benthamiana* plants that overexpress SpCas9 (SEQ ID NO:11), which were generated as described elsewhere (Baltes et al., 2015, *Nature Plants* 2015 1:10, 1(10), 15145, doi.org/10.1038/nplants.2015.145). TRV1 (pNJB069, SEQ ID NO:42) and pEE391 (SEQ ID NO:40) contain the *Agrobacterium* origin of replication and T-DNA left and right borders and thus can be introduced into *N. benthamiana* cells through Agroinfiltration.

*Agrobacterium* strain GV3101 was separately transformed with vectors pEE390 (non-augmented, SEQ ID NO:41), pEE391 (augmented, SEQ ID NO:40), or pNJB069 (TRV1, SEQ ID NO:42). Cultures were grown and cells were resuspended in Agroinfiltration buffer as described in Example 2, except the final OD600 was 0.6 instead of 1.0. At this point, equal volumes of *Agrobacterium* cultures with pNJB069 to and pEE390 or pNJB069 and pEE391 were mixed together and incubated at room temperature for 3 hours. After incubation, the cells were infiltrated into 6 week old *N. benthamiana* plants that overexpress SpCas9 (SEQ ID NO:11) at the underside of the 5th true leaf using a needless syringe (Sparkes et al., supra).

To test the effectiveness of augmented sgRNAs expressed from TRV vectors to cleave genomic DNA at PDS, DNA was extracted from two 8 mm leaf punches at the site of infiltration, using the CTAB DNA Extraction protocol described in Example 2. The leaf punches were derived from SpCas9-overexpressing *N. benthamiana* tissues two weeks after being infiltrated with pEE390/pNJB069 or pEE391/pNJB069. A PCR reaction was performed using this genomic DNA as a template, Primer 1 oRN468 (SEQ ID NO:23) and Primer 2 oRN473 (SEQ ID NO:24), and the PHIRE PCR reaction mixture and cycle conditions described in Example 2. The resulting amplicons were purified using a QIAGEN® Gel Purification Kit and sent for ILLUMINA® based Next Generation Sequencing (NGS) using GENEWIZ® amplicon sequencing. Paired-end .fastq files resulting from NGS sequencing were analyzed using CRISPR RGEN Tools (Park et al. 2017, *Bioinformatics* 33, 286-288, doi.org/10.1093/bioinformatics/btw561) with a 40 bp comparison range to determine the indel frequency. Indels were found to occur at an average of 73% across five biological replicates for pEE390/pNJB069 infiltrated plants and 61% across three biological replicates for pEE391/pNJB069 infiltrated plants (FIG. 2A), indicating TRV vectors expressing augmented sgRNAs are able very efficiently edit the genomes of plant cells. The augmented and non-augmented PDS1 sgRNA mutagenesis efficiency was assessed across several plant replicates. Wild type sequence and the sequences of the four most common indels (from top to bottom, SEQ ID NOS:73, 74, 75, 76, and 77) when the non-augmented PDS1 sgRNA TRV Vectors were delivered are shown in FIG. 2B, and wild type sequence and the sequences for the four most common indels (from top to bottom, SEQ ID NOS:73, 78, 74, 76, and 77) when the FT augmented PDS1 sgRNA TRV Vectors were delivered are shown in FIG. 2C.

Example 5: Gene Editing in Plants Systemically Infected by TRV Expressing Augmented sgRNAs When both TRV1 and TRV2 are introduced into *N. benthamiana* cells, they are able to move cell-to-cell and through the phloem, resulting in systemic infection. The PDS1 locus targeted in this and previous Examples are involved in carotenoid biosynthesis, and complete loss of PDS function results in a white phenotype due to the lack of photo-protective carotenoids (Busch et al., 2002, *Plant Physiol*, 128(2), 439-453, doi.org/10.1104/pp. 010573). To test the effectiveness of augmented sgRNAs in TRV vectors to target DNA at the PDS1 locus in systemically infected tissue, 6 week old *N. benthamiana* plants that overexpress SpCas9 (SEQ ID NO:11) were leaf infiltrated with pEE390 (non-augmented)/pNJB069 or pEE391 (augmented)/pNJB069 in the same manner as described in Example 4.

Figure 3B:
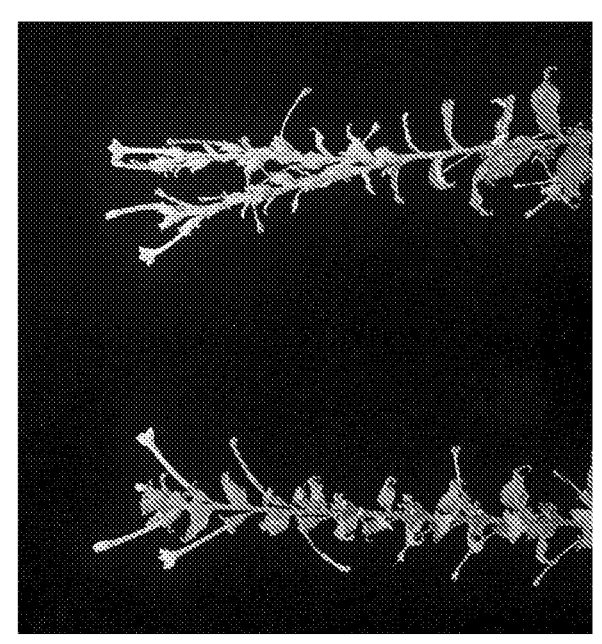
FIGS. 3A and 3B are images showing *N. benthamiana* plants displaying a phenotype caused by the knockout of PDS1.
Figure 3A:

About 2.5 weeks after infiltration, bleaching phenotypes typical of plants with biallelic PDS knockout mutations were observed (FIG. 3A). This phenotype became more prominent as the plant grew older (FIG. 3B). To confirm that the phenotype was caused by CRISPR/Cas9 mediated gene editing at PDS1, the 8th leaf up from the infiltrated leaf was analyzed for the presence of indel mutations caused by targeted double stranded breaks. DNA was extracted from two 8 mm leaf punches located at the base of the 8th systemic leaf four weeks after infiltration.

PCR was performed using the prepared genomic DNA as a template, Primer 1 oRN468 (SEQ ID NO:23), and Primer 2 oRN473 (SEQ ID NO:24), and the PHIRE PCR reaction mixture and amplification parameters as described in Example 2. The resulting amplicons were purified using a QIAGEN® Gel Purification Kit and sent for ILLUMINA® Next Generation Sequencing (NGS) using GENEWIZ® amplicon sequencing. The frequency of indel mutations was, on average, 61% (with wide variance) across five biological replicates for pEE390/pNJB069, which expressed a standard sgRNA. Virus vectors expressing augmented sgRNAs (pEE391/pNJB069) resulted in an average indel frequency of 97% across three biological replicates (FIG. 4A), indicating that TRV vectors expressing augmented sgRNAs are highly efficient at editing the genomes of systemically infected plant cells. Editing frequencies in all cases were determined using CRISPR RGEN Tools (Park et al., supra) on the paired-end .fastq files with a 40 bp comparison range. The augmented and non-augmented PDS1 sgRNA mutagenesis efficiency was assessed across several plant replicates. Wild type sequence and sequences of the four most common indels (from top to bottom, SEQ ID NOS:73, 78, 74, 79, and 77) when the non-augmented PDS1 sgRNA TRV Vectors were delivered are shown in FIG. 4B, and wild type sequence and the sequences for the four most common indels (from top to bottom, SEQ ID NOS:73, 76, 78, 74, and 79) when the FT augmented PDS1 sgRNA TRV Vectors were delivered are shown in FIG. 4C.

To assess the effectiveness of augmented sgRNAs to edit other locations in the genome, we assembled TRV clones expressing a sgRNA that targets the AGAMOUS (AG) locus in *N. benthamiana* (5'-GTGTGAAAGAAACAATTGAG-3'; SEQ ID NO:8). Augmented sgRNA and control vectors were assembled in the same manner as described in Example 3, except that primer oEE659 (SEQ ID NO:26) was used instead of oEE562 (SEQ ID NO:16). PCR amplification of augmented and control vectors and assembly into pEE083 (SEQ ID NO:39) resulted in the creation of pEE386 (control, SEQ ID NO:43) and pEE387 (augmented, SEQ ID NO:44) TRV2 vectors. *Agrobacterium* strain GV3101 was transformed with one of these two vectors, combined with pNJB069, and infiltrated into 6 week old *N. benthamiana* plants that overexpress SpCas9 (SEQ ID NO:11) as described in Example 4.

Tissue was harvested and DNA was extracted from the infiltrated site and systemic leaf 8 as described in Example 2. This genomic DNA was used as a template for a PHIRE PCR reaction as described in Example 2, using primers oEE693 (SEQ ID NO:27) and oEE697 (SEQ ID NO:28). The resulting amplicons were purified using a QIAGEN® Gel Purification Kit and sent for ILLUMINA® Next Generation Sequencing (NGS) using GENEWIZ® amplicon sequencing. Indels were determined to be present in, on average, 73% of the sequence reads derived from DNA at the infiltrated site and 29% of the reads derived from DNA at the 8th systemic leaf; wide variance was observed across four biological replicates for the pEE386/pNJB069 control vectors. Augmented guide vectors pEE387/pNJB069 resulted in an average indel frequency of 80% at the infiltrated site and 73% at the 8th systemic leaf across three biological replicates (FIG. 5A), indicating that TRV vectors expressing augmented sgRNAs are capable of efficiently editing systemically infected plant cells at multiple loci, exemplified by PDS1 and AG. Wild type sequence and sequences of the four most common indels (from top to bottom, SEQ ID NOS:80, 81, 82, 83, and 84) for plant replicate 2 when the non-augmented AG sgRNA TRV Vectors were delivered are shown in FIG. 5B, while wild type sequence and sequences for the four most common indels (from top to bottom, SEQ ID NOS:80, 81, 82, 85, and 86) for plant replicate 1 when the FT-augmented AG sgRNA TRV Vectors were delivered are shown in FIG. 5C.

Example 6: Editing of Germline Cells Using Augmented sgRNAs and TRV

To test the ability of augmented sgRNAs to improve heritable gene editing in plant species, 6 week old *N. benthamiana* plants that overexpress SpCas9 (SEQ ID NO:11) were leaf infiltrated with pEE390/pNJB069 or pEE391/pNJB069 in the same manner as described in Example 4. After a period of about 2 months, or when at least three seed pods had developed and opened, seed was collected from infected plants and all pods per plant were pooled together.

Figure 6A:
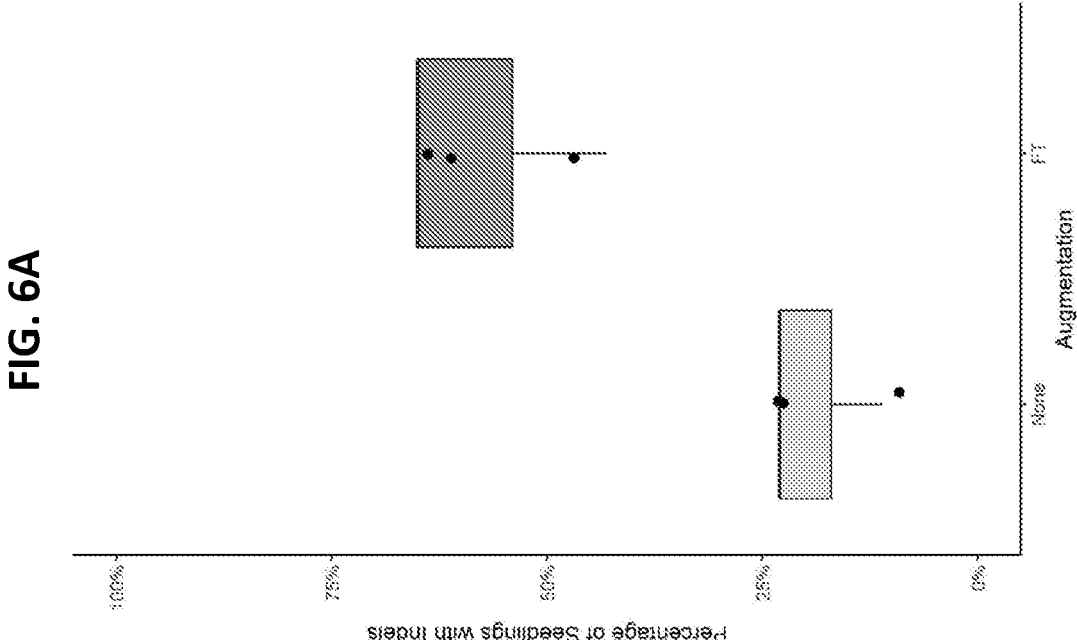
Figure 7:
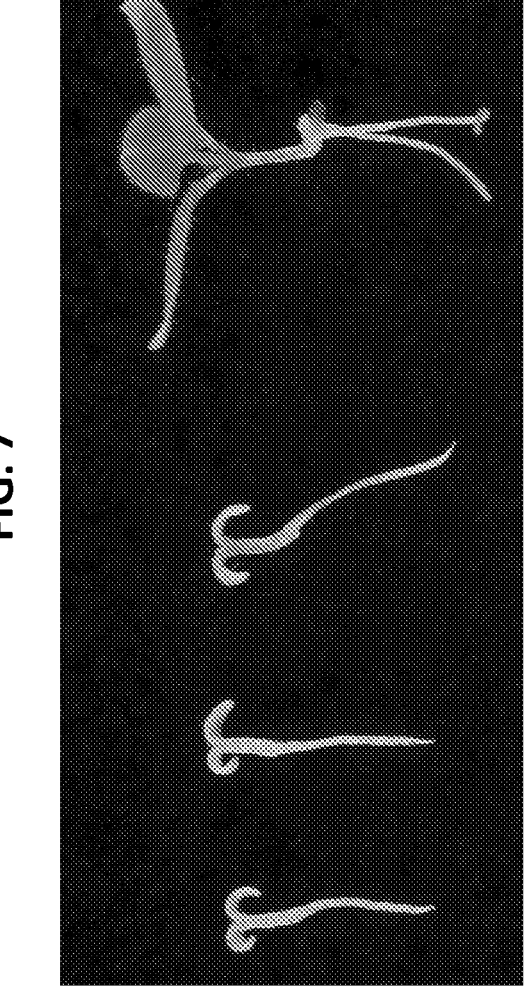
FIG. 7 is an image showing *N. benthamiana* seedlings displaying the photobleached phenotype caused by the knockout of PDS1. Seeds from a parent plant infected with TRV expressing an FT-augmented sgRNA targeting PDS1 were collected and planted. Some of the seedlings were photobleached white (left) compared to the phenotypically normal green seedlings (right). The bleached seedlings never grew larger than the image shown, whereas the green seedlings developed normally. Several of the white seedlings were genotyped and confirmed to contain indel mutations in the PDS1 locus.

Seeds from plants infected with pEE390/pNJB069 or pEE391/pNJB069 were sterilized in 50% bleach for 20 minutes, followed by 4 washes with dH2O. These seeds were placed on ½ MS+50 ng/4 kanamycin plates kept at 25° C. with a 16 hour day/8 hour night light cycle. After germination and growth until the 4-6 leaf stage, the seedlings were transferred to soil. At this point, one leaf was removed from a subset of seedlings and DNA was extracted according to the CTAB protocol described in Example 2. Each purified DNA sample, representing one seedling, was used as a template for a PHIRE PCR reaction as described in Example 2 using Primer 1 oEE552 (SEQ ID NO:21) and Primer 2 oEE504_R (SEQ ID NO:22). The PCR reactions were purified using a QIAGEN® PCR Purification Kit and sent for Sanger sequencing using the primer oEE504_R (SEQ ID NO:22). Indel frequency was then estimated using ICE™ software (Hsiau et al., supra). Results indicated that pEE390/pNJB069 (non-augmented control) was able to generate heritable indels at a frequency between 11% to 23%, whereas pEE391/pNJB069 (augmented sgRNA) was able to generate heritable indels at a frequency between 43% to 65% (FIG. 6A). Between 13 and 28 seedlings were genotyped for each parent plant. Wild type sequence and the genotypes for each allele (allele 1 from top to bottom, SEQ ID NOS:73, 73, 73, 74, 73, and 73; allele 2 from top to bottom, SEQ ID NOS:73, 73, 73, 79, 73, and 73) of five representative seedlings from parental plant 1 infected with TRV expressing a non-augmented PDS1 sgRNA are shown in FIG. 6B, while wild type sequence and the genotypes for each allele (allele 1 from top to bottom, SEQ ID NOS:73, 73, 73, 73, 75, and 75; allele 2 from top to bottom, SEQ ID NOS:73, 73, 87, 73, 75, and 88) of five representative seedlings from parental plant 1 infected with TRV expressing an augmented PDS1 sgRNA are shown in FIG. 6C. Furthermore, all homologs of PDS were knocked out using this method, resulting in several bleached white seedlings (FIG. 7).

Figure 8A:
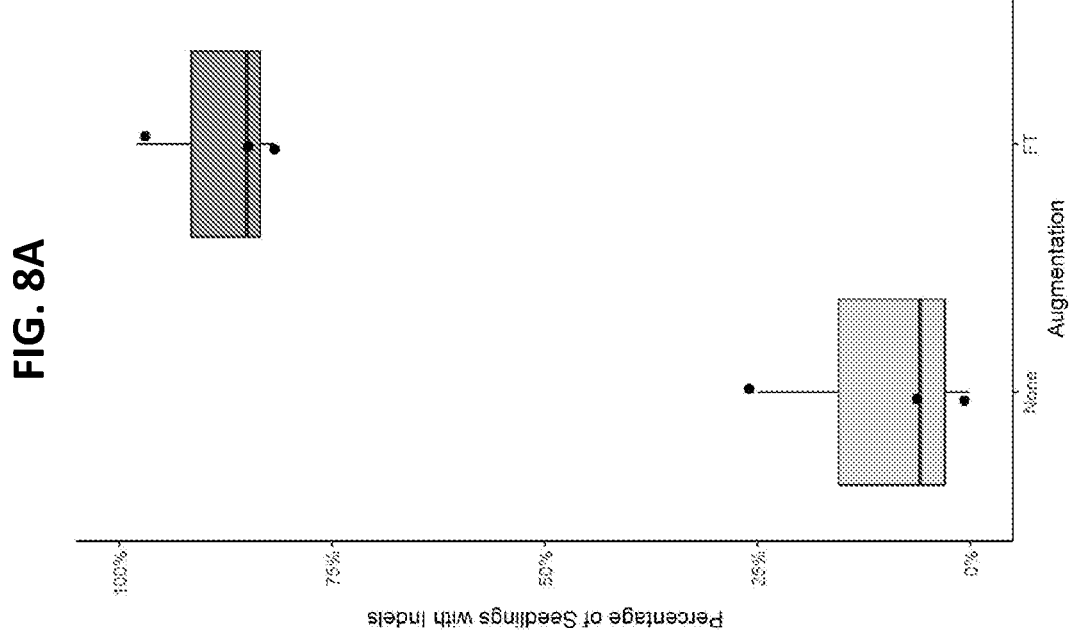

To test the ability of augmented sgRNAs to generate heritable indels at other loci, the experiment above was repeated using the pEE386/pNJB069 or pEE387/pNJB069 vectors described in Example 5. All experimental conditions were performed as indicated above except that Primer 1 oEE653 (SEQ ID NO:29) and Primer 2 oEE655 (SEQ ID NO:30) were used to PCR amplify the AG locus. Using ICE™ software, heritable editing for the non-augmented control vector pEE386/pNJB069 was determined to be between 0% and 25%, and heritable editing for the augmented sgRNA vectors pEE387/pNJB069 was determined to be between 82% and 100% (FIG. 8A). These results demonstrated the feasibility of augmented sgRNAs to generate heritable indels across multiple loci in plant genomes. Between 11 and 20 seedlings were genotyped for each parent plant. Wild type sequence and the genotypes for each allele (allele 1, all SEQ ID NO:80; and allele 2 from top to bottom, SEQ ID NOS:80, 80, 81, 80, 80, and 80) of five representative seedlings with edits from parent plant 2 infected with TRV expressing a non-augmented AG sgRNA are shown in FIG. 8B. Wild type sequence and the genotypes for each allele (allele 1 from top to bottom, SEQ ID NOS:80, 81, 81, 80, 81, and 81; allele 2 from top to bottom, SEQ ID NOS:80, 80, 89, 80, 81 and 81) of five representative seedlings with edits from parent plant 1 infected with TRV expressing an augmented AG sgRNA are shown in FIG. 8C.

Example 7: Editing of Systemic and Germline Cells Using Alternative FT sgRNA Augmentations and TRV Studies were conducted to test whether alternative augmentations or different variants of mobile RNA motifs would enable efficient somatic and germline editing. Specifically, two modified versions of the *Arabidopsis* FT sequence were tested for editing efficiency in *N. benthamiana*. Given the possibility that the full coding sequence of FT (SEQ ID NO:4) is not required to enable movement (Li et al, supra), a mutated version without a start codon (mFT, SEQ ID NO:5) and a truncated version lacking 102 nucleotides (102mFT, SEQ ID NO:6) were tested for their ability to enable movement.

Augmented sgRNAs were constructed with mFT or 102mFT by amplifying the sgRNA sequence with Primer 1 oEE659 (SEQ ID NO:26) and Primer 2 oEE267 (SEQ ID NO:15). The FT sequences were amplified with Primer 1 oEE273 (SEQ ID NO:31) and Primer 2 oEE272 (SEQ ID NO:18) for mFT, or Primer 1 oEE273 (SEQ ID NO:31) and Primer 2 oEE274 (SEQ ID NO:32) for 102mFT. All ampli-fications used pEE081-sgRNA-FT (SEQ ID NO:35) as a template. PCR amplifications were performed using the same Q5 amplification protocol as described in Example 1. The sgRNA amplicon was combined with the mFT amplicon for assembly into pEE083 (SEQ ID NO:39) to create pEE388 (SEQ ID NO:45) using the AarI assembly protocol described in Example 1. Similarly, the sgRNA amplicon was combined with the 102mFT amplicon for assembly into pEE083 to create pEE389 (SEQ ID NO:46). Both vectors pEE388 and pEE389 expressed augmented guides that tar-geted the AG locus described in Example 5. *Agrobacterium* strains with these vectors and pNJB069 were prepared for leaf infiltration and infiltrated into 6 week old *N. benthami-ana* plants that overexpress SpCas9 (SEQ ID NO:11) in the same manner as described in Example 4. Tissue was col-lected from the infiltrated site and the 8th leaf up from the infiltrated leaf. DNA was extracted, submitted for NGS sequencing, and analyzed in the same manner as described in Example 4. Indel frequency at the infiltrated site was determined to be an average of 68% for pEE388/pNJB069 infiltrated plants and 85% for pEE389/pNJB069 infiltrated plants. Indel frequency at the 8th systemic leaf averaged 81% for pEE388/pNJB069 infiltrated plants and 85% for pEE389/pNJB069 infiltrated plants (FIG. 9A). This indi-cated that alternative augmentations of the sgRNA still enabled highly efficient viral-mediated systemic gene edit-ing. Wild type sequence and the four most common indels (from top to bottom, SEQ ID NOS:80, 81, 84, 90, and 91) at the 8th systemic leaf for plant replicate 1 when the mFT-augmented AG sgRNA TRV Vectors were delivered are shown in FIG. 9B. The four most common indels (from top to bottom, SEQ ID NOS:80, 81, 83, 84, and 92) at the 8th systemic leaf for plant replicate 1 when the 102mFT-augmented AG sgRNA TRV Vectors were delivered are shown in FIG. 9C.

After about 2 months, or when three or more seed pods had developed, seed was collected from plants infected with pEE388/pNJB069 or pEE389/pNJB069. Seed was steril-ized, germinated, and screened for the presence of indels at the target of interest in the same manner as described in Example 6. Heritable indels in seedlings were observed at a frequency of 62% to 100% for pEE388/pNJB069 parent plants and 76% to 85% for pEE389/pNJB069 parent plants (FIG. 10A). These data indicated that different augmenta-tions still enable sgRNAs expressed from RNA Viral Vectors to perform high frequency systemic and germline editing. Between 13 and 21 seedlings were genotyped for each parent plant. Wild type sequence and the genotypes for each allele (allele 1 from top to bottom, SEQ ID NOS:80, 80, 89, 81, 81, and 80; allele 2 from top to bottom, SEQ ID NOS:80, 81, 93, 81, 81, and 81) of five representative seedlings with edits from parent plant 1 infected with TRV expressing an mFT-augmented AG sgRNA are shown in FIG. 10B, and wild type sequence and the genotypes for each allele (allele 1 from top to bottom, SEQ ID NOS:80, 80, 81, 81, 80, and 92; allele 2 from top to bottom, SEQ ID NOS:80, 94, 81, 81, 80, and 95) of five representative seedlings with edits from parent plant 2 infected with TRV expressing a 102mFT-augmented AG sgRNA are shown in FIG. 10C.

To validate that these mutations were transmitted to the germline, two plants that were concluded to have either homozygous or bi-allelic edits in the AG locus were main-tained until they were able to produce seed. Seed from these plants was sterilized and germinated as described above. DNA was extracted from several seedlings, the AG locus was PCR amplified, and Sanger sequencing was performed as described above. ICE™ software indicated that these progeny plants had only the expected indels (FIGS. 11A-11D), confirming that the augmented sgRNAs are able to generate heritable germline mutations.

Example 8: Editing of Systemic and Germline Cells Using Alternative sgRNA Augmentations and TRV The types of sgRNA augmentations that enable high efficiency, heritable plant gene editing can include RNA sequences other than those derived from FT. For example, a tRNA-like motif is added to the 3' end of sgRNAs in the same manner as described in Example 1. This augmented sgRNA is then assembled into an RNA Viral Vector, such as TRV, to enable systemic gene editing. The TRV2 vectors express sgRNAs augmented with tRNA-like sequences that target genomic sequences, such as those in the *N. bentha-miana* genome. The TRV2 vectors are then introduced into *Agrobacterium* and infiltrated into leaves of *N. benthamiana* plants that overexpress SpCas9 (SEQ ID NO:11) along with a TRV1 vector. After sufficient time for the virus to spread, tissue is extracted from infiltrated and systemically infected leaves to confirm high efficiency gene editing. After seed develops from the infected plant, the seed is planted and progeny are screened for the presence of heritable gene edits. Through genome sequencing, the frequency of heri-table gene editing is quantified in the screened seedlings. This demonstrates that different RNA sequences (e.g., those listed in TABLE 1) can promote sgRNA mobility and give rise to high frequency, heritable gene edits.

Example 9: Multiplexed Gene Editing of Germline Cells Using Augmented sgRNAs and TRV Vectors A powerful application of CRISPR mediated gene editing is the ability to easily multiplex—that is, to target multiple loci simultaneously for mutagenesis. To test the ability of RNA Viral Vectors with augmented sgRNAs to carry out multiplexed gene editing and yield heritable editing at multiple loci from one infection, plants were infected with viral vectors expressing multiple different sgRNAs. The previously used PDS1 and AG targets were used, along with an additional target (5'-TTGATTGTCTTCTCAAGCAG-3'; SEQ ID NO:47) in the AG locus (SEQ ID NO:48). This second AG target (SEQ ID NO:47) is several hundred base pairs 5' of the AG target site described above (SEQ ID NO:8). Four vectors were created that each contain these three 102mFT augmented sgRNAs separated by either a tRNA that is excised by endogenous tRNA-processing enzymes (Xie et al., *Proc. Natl Acad. Sci. USA*, 2015, 112, 3570-3575, doi.org/10.1073/pnas.1420294112) (SEQ ID NO:49), or a four nucleotide direct repeat cloning linker, or a 23 nucleotide spacer sequence (SEQ ID NO:50), or a 24 nucleotide miR394 target site (SEQ ID NO:51). The tRNA sgRNA vector, which utilizes a tRNA sequence that is excised from the mRNA (Xie et al., supra), was assembled by amplifying the sgRNA with Primer 1 oEE659 (SEQ ID NO:26) and Primer 2 oEE733 (SEQ ID NO:52) with pEE081-sgRNA-FT (SEQ ID NO:35) as a template, and amplifying the tRNA with Primer 1 oEE734 (SEQ ID NO:53) and Primer 2 oEE735 (SEQ ID NO:54) with pMOD_B2303 (Cermak et al., supra) as a template. The augmented sgRNA amplicon was combined with the tRNA amplicon for assembly into pEE083 (SEQ ID NO:39) to create a tRNA intermediate vector. This tRNA intermediate vector was then used as a template for PCR amplification of each sgRNA using oEE659 (SEQ ID NO:26) and oEE736 (SEQ ID NO:55), oEE884 (SEQ ID NO:56) and oEE738 (SEQ ID NO:57), and oEE885 (SEQ ID NO:58) and oEE274 (SEQ ID NO:32). Each amplicon was combined for assembly into pEE083 to create pEE491 (SEQ ID NO:59). Spacer multiplexed vectors were assembled by PCR amplification from the pEE081-sgRNA-FT template using forward primers oEE659 (SEQ ID NO:26), oEE884 (SEQ ID NO:56), or oEE885 (SEQ ID NO:58) and reverse primers oEE866 (SEQ ID NO:60), oEE867 (SEQ ID NO:61), oEE274 (SEQ ID NO:32), respectively. Direct repeat multiplexed vectors were assembled by PCR amplification from the pEE081-sgRNA-FT template using forward primers oEE659 (SEQ ID NO:26), oEE884 (SEQ ID NO:56), or oEE885 (SEQ ID NO:58) and reverse primers oEE765 (SEQ ID NO:62), oEE766 (SEQ ID NO:63), oEE274 (SEQ ID NO:32), respectively. Multiplexed vectors with the miR394 spacer were assembled by PCR amplification from the pEE081-sgRNA-FT template using forward primers oEE659 (SEQ ID NO:26), oEE884 (SEQ ID NO:56), or oEE885 (SEQ ID NO:58) and reverse primers oEE752 (SEQ ID NO:64), oEE755 (SEQ ID NO:65), oEE274 (SEQ ID NO:32), respectively. The three augmented sgRNA amplicons for each vector were assembled into pEE083 to create pEE531 (spacer)(SEQ ID NO:66), pEE495 (direct repeat) (SEQ ID NO:67), or pEE493 (miR394)(SEQ ID NO:68).

*Agrobacterium* strain GV3101 transformed with these vectors and pNJB069 were prepared for leaf infiltration and infiltrated into 6 week old *N. benthamiana* plants that overexpress SpCas9 (SEQ ID NO:11) in the same manner as described in Example 4. Beginning around 2.5 weeks after infection, the PDS knockout phenotype (FIG. 3A) was observed for all vectors, suggesting that every vector (tRNA, direct repeat, spacer, and miR394) was able to move through infection and edit systemic tissue.

After about 2 months, or when three or more seed pods had developed, seed was collected from plants infected with pEE491/pNJB069, pEE531/pNJB069, pEE495/pNJB069, or pEE493/pNJB069. Seed was sterilized, germinated, and screened for the presence of indels at the target of interest in the same manner as described in Example 6. Heritable indels in seedlings were observed at frequencies of 90% to 100% (PDS1), 44% to 100% (AG sgRNA1), 0% to 22% (AG sgRNA2), 44% to 100% (two loci targeted), and 0% to 22% (three loci targeted) for pEE491/pNJB069 parent plants. 60% to 70% (PDS1), 40% to 80% (AG sgRNA1), 30% to 40% (AG sgRNA2), 40% to 80% (two loci targeted), and 20% to 30% (three loci targeted) for pEE531/pNJB069 parent plants. 70% to 90% (PDS1), 44% to 63% (AG sgRNA1), 0% to 20% (AG sgRNA2), 50% to 60% (two loci targeted), and 0% to 30% (three loci targeted) for pEE495/pNJB069 parent plants. 80% to 100% (PDS1), 80% to 100% (AG sgRNA1), 0% to 60% (AG sgRNA2), 80% to 100% (two loci targeted), and 0% to 60% (three loci targeted) for pEE493/pNJB069 parent plants (FIG. 12). The identification of indels at all three target loci for pEE491/pNJB069, pEE531/pNJB069, pEE495/pNJB069, and pEE494/pNJB069 parent plants indicated that RNA Viral Vectors with augmented sgRNAs can be infected into plants to perform multiplexed germline gene editing.

Another means of multiplexing augmented sgRNAs using RNA Viral Vectors is co-infection of multiple viral vectors, each expressing one or more sgRNAs. Each vector expressing one or more guides is assembled as described in Example 7 or Example 9. Vectors are designed with individual sgRNAs targeting PDS (SEQ ID NO:7), AG sgRNA1 (SEQ ID NO:8), or AG sgRNA2 (SEQ ID NO:47). *Agro-*

*bacterium* strain GV3101 is transformed with these three vectors, along with TRV1 vector pNJB069 and prepared for Agroinfiltration as described in Example 4. The four vectors are then mixed 3:1:1:1; that is, 3 parts pNJB069: 1 part RNA Viral Vector with augmented sgRNA targeting PDS: 1 part RNA Viral Vector with augmented sgRNA targeting AG sgRNA1:1 part RNA Viral Vector with augmented sgRNA targeting AG sgRNA2. The combined Agroinfiltration mixture is then infiltrated into six week old *N. benthamiana* plants that overexpress SpCas9 (SEQ ID NO:11) as described in Example 4. Observation of the PDS knockout phenotype (FIG. 3A) beginning around 2.5 weeks after infection suggests efficient somatic cell editing. After about 2 months, or when three or more seeds pods have developed, seed is collected. Seed is sterilized, germinated, and screened for the presence of indels in all three targets in the same manner as described in Example 6. The presence of progeny with indels in more than one locus indicates the capability of co-infection of RNA Viral Vectors with augmented sgRNAs into plants for multiplexed germline gene editing.

Example 10: Base Editing of Somatic and Germline Cells Using Augmented sgRNAs and TRV Vectors Augmented sgRNAs can be used to enhance efficiency other forms of gene editing, such as base editing. To test whether augmented sgRNAs can more efficiently achieve gene editing, transgenic *N. benthamiana* plants that express base editor 3 (BE3; SEQ ID NO:71) were generated (Komor et al., 2016, *Nature*, 533(7603), 420-424, doi.org/10.1038/nature17946) using a transformation protocol described elsewhere (Sparkes et al., supra). A sgRNA sequence was designed (5'-GGACCTCATGATTCAGATCC-3'; SEQ ID NO:69) that targets the VEN-6 locus (SEQ ID NO:70) of *N. benthamiana*. This sequence contains a cytosine 15 base pairs 5' of the TGG PAM site, which is within the target window for effective cytosine deamination by BE3 (Komor et al., supra). This sgRNA was augmented by amplifying the sgRNA and mFT sequence using Primer 1 oEE769 (SEQ ID NO:33) and Primer 2 oEE272 (SEQ ID NO:18) with pEE388 (SEQ ID NO:45) as a template. PCR amplifications were performed using the Q5 amplification protocol described in Example 1. The sgRNA amplicon was combined with the mFT amplicon for assembly into pEE083 to create pEE499 (SEQ ID NO:72) using the AarI assembly protocol described in Example 1. *Agrobacterium* strain GV101 was transformed with this vector, along with TRV1 vector pNJB069 (SEQ ID NO:42) and prepared for Agroinfiltration as described in Example 4. This mixture was infiltrated into 6 week old BE3-overexpressing *N. benthamiana* plants.

Quantification of base editing efficiency in infiltrated and systemic tissue is performed using the same methods described in Examples 4 and 5, respectively. Approximately 4 weeks after infiltration, leaf punches are taken and DNA is extracted from the infiltrated site and the 8th systemically infected leaf. The genomic DNA is used as a template for PCR amplification of the VEN-6 locus around the sgRNA target site. The PCR amplicon is then purified and submitted for NGS to quantify the base editing frequency; that is, the frequency at which cytosines are converted to guanines (or the inverse). Detection of base editing validates the use of RNA Viral Vectors for introducing specific nucleotide sequence changes in plants.

The use of RNA Viral Vectors to achieve heritable base editing is then demonstrated. Progeny of BE3-overexpressing plants, which have been infected with RNA Viral Vectors with augmented sgRNAs, are assessed for heritable base editing. Seed is collected from plants infected with pEE499/pNJB069, sterilized, germinated, and screened for the presence of base edits, indicated by either homozygous or heterozygous single base substitutions in the VEN-6 locus. The presence of single base substitutions at the target site indicates RNA Viral Vectors expressing augmented sgRNAs can be used to perform heritable, site-specific, base editing in transgenic plants that express base editors. This also demonstrates that augmented sgRNAs are compatible with other forms of CRISPR-mediated gene editing, such as base editing.

Example 11: Template Dependent Homologous Recombination Using Augmented sgRNAs and RNA Viral Vectors Another powerful application of CRISPR-mediated gene editing is the ability to make highly precise, targeted DNA sequence changes through template-dependent homologous recombination. This typically is achieved using a DNA template to repair a targeted DNA double strand break. Recent reports indicate that RNA also can be used as a template to repair DNA breaks, and that sequences from the RNA can be copied into the genome at the break site (see, e.g., Li et al. 2019, supra).

Using an RNA template with homology to the target of interest and augmented sgRNAs, RNA Viral Vectors are used for template-mediated repair of double strand breaks. This makes it possible to create specific DNA sequence changes in plant genomes. For example, a FoMV is modified to express an augmented sgRNA targeting the ALS2 locus of maize. Fused directly to the augmented sgRNA are sequences with homology to the ALS2 locus, including homology arms both 5' and 3' of the sgRNA target site. The RNA template also contains two single nucleotide polymorphisms (SNPs) that change a proline codon to a serine codon, along with several SNPs that prevent the augmented sgRNA from continuing to cut the target site. The proline to serine substitution confers resistance to the herbicide chlorsulfuron (Svitashev et al., 2016, *Nature Communications*, 7, 13274, doi.org/10.1038/ncomms13274). *Agrobacterium* strain GV101 is transformed with this vector, and cultures are prepared for Agroinfiltration and infiltrated into 6 week old *N. benthamiana* plants as described in Example 4. Two weeks after infiltration, the infiltrated leaf is ground in phosphate buffer (3.57 g sodium phosphate dibasic heptahydrate, 0.92 g sodium phosphate monobasic monohydrate, up to 1 L dH$_2$O, pH 7.2). Sap from the infiltrated leaf is then rub inoculated onto Cas9-overexpressing 2-leaf maize seedlings.

Four weeks after infection, tissue is harvested from infiltrated and systemic leaves, and DNA is extracted using the methods described in Example 4. The genomic DNA is used as a template for PCR amplification of the ALS2 locus around the sgRNA target site. The PCR amplicon is then purified and submitted for NGS in order to quantify the frequency of RNA-templated homology-directed repair—the frequency at which specific bases are inserted that convert the proline codon to a serine codon and that mutate the sgRNA target site. Detection of these specific base pair substitutions validates the use of RNA Viral Vectors for site specific RNA template-mediated homology-directed repair.

To validate the use of RNA Viral Vectors for heritable RNA template-mediated homology-directed repair, the progeny of Cas9-overexpressing maize plants infected with RNA Viral Vectors expressing augmented sgRNAs and the RNA template need to be assessed. Seed is collected from plants infected with this vector, sterilized, and germinated on chlorosulfuron, because RNA template-mediated repair should provide resistance to this herbicide (Svitashev et al., supra). Surviving seedlings are screened for the presence of the specific base pair substitutions present in the RNA template in the ALS2 locus as described in Example 6. Detection of these specific base pair substitutions in progeny validates the use of RNA Viral Vectors for creating heritable mutations through site specific RNA template-mediated homology-directed repair.

Another means of creating targeted DNA sequence changes through template-dependent homologous recombination and augmented sgRNAs is through prime editing (Anzalone et al., supra), which utilizes a reverse transcriptase to create a DNA template. The reverse transcriptase copies an RNA template that extends from the sgRNA, resulting in a cDNA template that is used for homologous recombination at the targeted site. As in the previous example, fused directly to the augmented sgRNA is the RNA template that contains the modification of interest to be incorporated into the genome. Also included is a primer binding site for reverse transcription. The FoMV vectors are introduced into prime editor-overexpressing maize seedlings as described above. Somatic infected tissue and progeny are assessed for the presence of precise mutations in the ALS2 locus as outlined above and in Examples 4 and 6.

Example 12: Optimization of Growth Conditions for Improved Heritable Genome Editing Using TRV Vectors Particular environmental conditions can be optimal for virus infection (Shen et al., 2015, *Tree Physiol*, 35(9), 1016-1029, doi.org/10.1093/treephys/tpv064), which could affect the frequency at which viral-mediated heritable mutations are recovered in SpCas9-overexpressing plants. Suboptimal environments may result in poor systemic infection, resulting in low frequencies of transmission of heritable mutations, whereas optimal environments may result in high frequencies of transmission of heritable mutations. To test this, *Agrobacterium* strain GV3101 was transformed with TRV vectors containing non-augmented and augmented sgRNAs (pEE390, SEQ ID NO:41, pEE391, SEQ ID NO:40) as described in Example 3. Cultures were prepared and infiltrated into *N. benthamiana* plants that overexpress SpCas9 (SEQ ID NO:11) in the same manner as described in Example 4. A subset of the pEE390 infiltrated plants were kept in an environment maintained at 26° C. day/22° C. night with 12 hour of light per day, while another subset of the infiltrated plants are kept in an environment at 22° C. day with 24 hour days. The plants matured and produced seed. Seeds were then collected, sterilized, germinated, and screened for the presence of bi-allelic mutations at PDS, visualized by the presence of fully bleached seedlings (FIG. 7). Quantification of bleached seedlings, compared to green seedlings, indicated a difference in the frequency at which heritable edits were generated when then parents were grown at 26° C. day/22° C. night with 12 hour of light per day versus 22° C. with 24 hour days (FIG. 13). This result indicated that there are optimal environmental conditions for generating high frequencies of heritable mutations when using RNA Viral Vectors, including those that express non-augmented sgRNAs.

Example 13: Augmented sgRNAs with Augmented Cas9 Vectors Improve Non-RNA Viral Mediated Gene Editing Efficiencies Studies are conducted to add sequences that promote the mobility of both the sgRNA and Cas9. This may increase the frequency of gene editing, since even untransformed cells may receive both reagents from transformed neighboring cells. For example, SpCas9 is augmented by fusing the FT sequence directly 3' of the coding sequence in the same manner as Example 1. The augmented SpCas9 is assembled along with augmented sgRNAs described in Example 2 into a vector that can be delivered to plants cells. The augmented SpCas9 and augmented sgRNA vector is cloned into a vector with T-DNA borders and appropriate *Agrobacterium* origins of replication. *Agrobacterium* is transformed with this vector for delivery to plant cells. For example, the plant cells can be callus generated from leaf tissue, followed by regeneration of transformed cells into whole plants (Sparkes et al., supra). Each regenerated plant is genotyped in the same manner described in Example 6. Quantification of the number of plants with mutations in the desired locus reveals a higher portion of plants with indels when compared to plants transformed with vectors containing non-augmented gRNAs and non-augmented SpCas9. This indicates that augmentation is not limited to improving the effectiveness of sgRNAs, but also can allow mobility of other RNA sequences and can be utilized to enhance other approaches to gene editing.

Example 14: Augmented sgRNAs Improve DNA-Template Homology-Directed Repair

Further work is conducted to add sequences that promote the mobility of the sgRNA in order to improve the efficiency of DNA-templated homology-directed repair. Homology-directed repair by DNA-templates is improved by the presence of double-stranded DNA breaks, and the high gene editing efficiency of augmented sgRNAs may enhance this repair. For example, sgRNA sequences targeting a locus in the *N. benthamiana* genome are augmented with the FT sequence as described in Example 1. The augmented sgRNAs are then delivered to *N. benthamiana* cells along with vectors encoding SpCas9 and carrying a DNA repair template. Allowing sufficient time for double-stranded break formation and repair by the DNA-template, DNA is extracted from transformed tissue. The target locus is PCR amplified and submitted for NGS in order to quantify the frequency of DNA-templated homology-directed repair (the frequency at which specific bases encoded by the DNA-template are inserted). A higher frequency of template incorporation compared to vectors with non-augmented sgRNAs demonstrates the use of augmented sgRNAs for improving DNA-templated homology-directed repair.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating a plant comprising a specific genomic DNA sequence modification, the method comprising:

delivering an augmented sgRNA to a transgenic plant that expresses an RNA guided gene editing reagent, wherein the augmented sgRNA comprises (i) a sequence targeted to the specific genomic DNA sequence and (ii) a mobile RNA sequence; and recovering, from the plant to which the augmented sgRNA comprising the mobile RNA sequence was delivered, tissue with a genetic modification induced at the specific genomic DNA sequence by the RNA-guided gene editing reagent, wherein the tissue is capable of transmitting the genetic modification to a next generation plant.

2. The method of claim 1, wherein the RNA guided gene editing reagent is an RNA guided endonuclease, an RNA guided base editor, or an RNA guided epigenetic modifier.

3. The method of claim 1, wherein the mobile RNA sequence is derived from Flowering Time (FT).

4. The method of claim 1, wherein the mobile RNA sequence is derived from BEL5, GAI, a tRNA-like motif, or LeT6.

5. The method of claim 1, comprising delivering the augmented sgRNA by RNA virus or DNA virus.

6. The method of claim 1, comprising delivering the augmented sgRNA by *Agrobacterium*, biolistics, nanoparticles, or electroporation.

7. The method of claim 1, wherein the plant gives rise to pollen and egg cells, and wherein the genetic modification is transmitted to the next generation plant, or wherein the plant comprises edited cells that are regenerated through tissue culture into an edited plant that transmits the genetic modification to the next generation plant.

8. The method of claim 1, wherein the sgRNA comprises an RNA sequence that serves as a template for reverse transcription to create a repair template to incorporate a specific sequence change at or near the specific genomic DNA sequence, or wherein the method comprises co-delivering the sgRNA with a DNA that serves as a repair template to incorporate a specific sequence change at or near the specific genomic DNA sequence.

9. A method for generating a plant comprising a specific genomic DNA sequence modification, the method comprising:

delivering (a) an augmented sgRNA and (b) a sequence encoding an RNA guided gene editing reagent to a plant, wherein the augmented sgRNA comprises (i) a sequence targeted to the specific genomic DNA sequence and (ii) a first mobile RNA sequence, and wherein the sequence encoding the RNA guided gene editing reagent comprises a second mobile RNA sequence; and recovering, from the plant to which the augmented sgRNA comprising the mobile RNA sequence was delivered, tissue with a genetic modification induced at the specific genomic DNA sequence by the RNA-guided gene editing reagent, wherein the tissue is capable of transmitting the genetic modification to a next generation plant.

10. The method of claim 9, wherein the RNA guided gene editing reagent is an RNA guided endonuclease.

11. The method of claim 9, wherein the RNA guided gene editing reagent is an RNA guided base editor, an RNA guided epigenetic modifier, or an RNA guided reverse transcriptase.

12. The method of claim 9, wherein the first mobile RNA sequence, the second mobile RNA sequence, or both mobile RNA sequences are derived from FT.

13. The method of claim 9, wherein the augmented sgRNA comprises a sequence derived from BEL5, GAI, tRNA-like motif, or LeT6.

14. The method of claim 9, comprising delivering the augmented sgRNA by RNA virus or by DNA virus.

15. The method of claim 9, comprising delivering the augmented sgRNA by *Agrobacterium*, biolistics, nanoparticles, or electroporation.

16. The method of claim 9, wherein the plant gives rise to pollen and egg cells, and wherein the genetic modification is transmitted to the next generation plant, or wherein the plant comprises edited cells that are regenerated through tissue culture into an edited plant that transmits the genetic modification to the next generation plant.

17. The method of claim 9, wherein the sgRNA comprises an RNA sequence that serves as a repair template to incorporate a specific sequence change at or near the specific genomic DNA sequence, or wherein the sgRNA comprises an RNA sequence that serves as a template for reverse transcription to create a repair template to incorporate a specific sequence change at or near the specific genomic DNA sequence, or wherein the method comprises co-delivering the sgRNA with a DNA that serves as a repair template to incorporate a specific sequence change at or near the specific genomic DNA sequence.

* * * * *

SEQUENCE LISTING

<160> NUMBER OF SEQ ID NOS: 98

<210> SEQ ID NO 1
<211> LENGTH: 842
<212> TYPE: DNA
<213> ORGANISM: Cauliflower mosaic virus

<400> SEQUENCE: 1

```
agatttgcct tttcaatttc agaaagaatg ctaacccaca gatggttaga gaggcttacg      60
cagcaggtat catcaagacg atctacccga gcaataatct ccaggaaatc aaataccttc     120
ccaagaaggt taaagatgca gtcaaaagat tcaggactaa ctgcatcaag aacacagaga     180
aagatatatt tctcaagatc agaagtacta ttccagtatg gacgattcaa ggcttgcttc     240
acaaaccaag gcaagtaata gagattggag tctctaaaaa ggtagttccc actgaatcaa     300
aggccatgga gtcaaagatt caaatagagg acctaacaga actcgccgta aagactggcg     360
aacagttcat acagagtctc ttacgactca atgacaagaa gaaaatcttc gtcaacatgg     420
tggagcacga cacacttgtc tactccaaaa atatcaaaga tacagtctca gaagaccaaa     480
gggcaattga gactttcaa caaagggtaa tatccggaaa cctcctcgga ttccattgcc     540
cagctatctg tcactttatt gtgaagatag tggaaaagga aggtggctcc tacaaatgcc     600
atcattgcga taaaggaaag gccatcgttg aagatgcctc tgccgacagt ggtcccaaag     660
atggaccccc acccacgagg agcatcgtgg aaaaagaaga cgttccaacc acgtcttcaa     720
agcaagtgga ttgatgtgat atctccactg acgtaaggga tgacgcacaa tcccactatc     780
```

```
cttcgcaaga cccttcctct atataaggaa gttcatttca tttggagaga acacgggggga      840 ct                                                                       842

<210> SEQ ID NO 2
<211> LENGTH: 187
<212> TYPE: DNA
<213> ORGANISM: Pea early browning virus

<400> SEQUENCE: 2
gagcatcttg ttctgggggtt tcacactatc tttagagaaa gtgttaagtt aattaagtta       60
tcttaattaa gagcataatt atactgattt gtctctcgtt gatagagtct atcattctgt      120
tactaaaaat ttgacaactc ggtttgctga cctactggtt actgtatcac ttacccgagt      180
taacgag                                                                 187

<210> SEQ ID NO 3
<211> LENGTH: 299
<212> TYPE: DNA
<213> ORGANISM: Agrobacterium tumefasciens

<400> SEQUENCE: 3
gatcatgagc ggagaattaa gggagtcacg ttatgacccc cgccgatgac gcgggacaag       60 ccgtttttacg tttggaactg acagaaccgc aacgttgaag gagccactca gccgcgggtt      120
tctggagttt aatgagctaa gcacatacgt cagaaaccat tattgcgcgt tcaaaagtcg      180
cctaaggtca ctatcagcta gcaaatattt cttgtcaaaa atgctccact gacgttccat      240
aaattcccct cggtatccaa ttagagtctc atattcactc tcaatccaaa taatctgca       299

<210> SEQ ID NO 4
<211> LENGTH: 528
<212> TYPE: DNA
<213> ORGANISM: Arabidopsis thaliana

<400> SEQUENCE: 4
atgtctataa atataagaga ccctcttata gtaagcagag ttgttggaga cgttcttgat       60
ccgtttaata gatcaatcac tctaaaggtt acttatggcc aaagagaggt gactaatggc      120
ttggatctaa ggccttctca ggttcaaaac aagccaagag ttgagattgg tggagaagac      180
ctcaggaact tctatacttt ggttatggtg gatccagatg ttccaagtcc tagcaaccct      240
cacctccgag aatatctcca ttggttggtg actgatatcc ctgctacaac tggaacaacc      300
tttggcaatg agattgtgtg ttacgaaaat ccaagtccca ctgcaggaat tcatcgtgtc      360
gtgtttatat tgtttcgaca gcttggcagg caaacagtgt atgcaccagg gtggcgccag      420
aacttcaaca ctcgcgagtt tgctgagatc tacaatctcg gccttcccgt ggccgcagtt      480
ttctacaatt gtcagaggga gagtggctgc ggaggaagaa gactttag                   528

<210> SEQ ID NO 5
<211> LENGTH: 528
<212> TYPE: DNA
<213> ORGANISM: Artificial
<220> FEATURE:
<223> OTHER INFORMATION: synthetic oligonucleotide

<400> SEQUENCE: 5
tagtctataa atataagaga ccctcttata gtaagcagag ttgttggaga cgttcttgat       60
ccgtttaata gatcaatcac tctaaaggtt acttatggcc aaagagaggt gactaatggc      120
ttggatctaa ggccttctca ggttcaaaac aagccaagag ttgagattgg tggagaagac      180
```

-continued

```
ctcaggaact tctatacttt ggttatggtg gatccagatg ttccaagtcc tagcaaccct     240
cacctccgag aatatctcca ttggttggtg actgatatcc ctgctacaac tggaacaacc     300
tttggcaatg agattgtgtg ttacgaaaat ccaagtccca ctgcaggaat tcatcgtgtc     360
gtgtttatat tgtttcgaca gcttggcagg caaacagtgt atgcaccagg gtggcgccag     420
aacttcaaca ctcgcgagtt tgctgagatc tacaatctcg gccttcccgt ggccgcagtt     480
ttctacaatt gtcagaggga gagtggctgc ggaggaagaa gactttag                  528
```

```
<210> SEQ ID NO 6
<211> LENGTH: 102
<212> TYPE: DNA
<213> ORGANISM: Artificial
<220> FEATURE:
<223> OTHER INFORMATION: synthetic oligonucleotide

<400> SEQUENCE: 6
tagtctataa atataagaga ccctcttata gtaagcagag ttgttggaga cgttcttgat      60
ccgtttaata gatcaatcac tctaaaggtt acttatggcc aa                        102
```

```
<210> SEQ ID NO 7
<211> LENGTH: 20
<212> TYPE: DNA
<213> ORGANISM: Nicotiana benthamiana

<400> SEQUENCE: 7
ttggtagtag cgactccatg                                                  20
```

```
<210> SEQ ID NO 8
<211> LENGTH: 20
<212> TYPE: DNA
<213> ORGANISM: Nicotiana benthamiana

<400> SEQUENCE: 8
gtgtgaaaga aacaattgag                                                  20
```

```
<210> SEQ ID NO 9
<211> LENGTH: 683
<212> TYPE: DNA
<213> ORGANISM: Nicotiana benthamiana

<400> SEQUENCE: 9
catagtgcga gaacaagttt cgtatggact gtaaaagcta gaatcttttt tacttttgca      60
tataaatttg tgtaataaat gcttaagaac cagaatattg aaaaaacaaa ggaattctac     120
atagtattta ggttcacaag tgggacaatc ttcttacagt gaaatatctt tatgtcaggc     180
ttaatttact gctattttgt tcagtaaaat gccccaaatt ggacttgttt ctgccgttaa     240
tttgagagtc caaggtaatt cagcttatct ttggagctcg aggtcttctt tgggaactga     300
aagtcaagat ggtcgcttgc aaaggaattt gttatgtttt ggtagtagcg actccatggg     360
gcataagttt agaattcgta ctcccagtgc catgaccaga agattgacaa aggacttcaa     420
tcctttaaag gtttgttttg aatgcgaaag tgtgatgctg aatttatgat cacgagcata     480
tattctctaa aataagatat cttgccattc aggtagtctg cattgattat ccaagaccgg     540
agctagacaa tacagttaac tatttggagg cggcgttatc atcatcatca tttcgtactt     600
cctcacgccc aacaaaacca ttggagattg ttattgctgg tgcaggtgat tttttccagt     660
catctatatt tgtagtcttc att                                            683
```

```
<210> SEQ ID NO 10
<211> LENGTH: 1536
<212> TYPE: DNA
<213> ORGANISM: Nicotiana benthamiana

<400> SEQUENCE: 10
attctctttc atccgtcaat ggagggaaaa attacttttt tacaccaatt tcctttcttt        60
tttcttggtc aaaccaaacc aaacaagtaa atgcaaaatg ttggcatttt ctcttccttt       120
ttcgtcatcc aaagtacaaa caaggagtca gtctttctat ttcattggaa aaaatttcca       180
atgctttgtg caaatgtgct aagttctttt atctcttttc ctctcttttt ctttcccttc       240
gatttctgcc tttagaattc agatttagct ggcgtttgaa caaattctta actactgctt       300
tatctgcttt ggaaggtgtg tttttcattag atatttgtta ttatagccaa gttcaaccag       360
caagggttag gatggttgga atcctttcac cttaaccaaa agtcttgcat tcgtacttcg       420
gggatgattt ttttctttgg cactgagtat ttttacccct tagttgtcag ataaggcctg       480
aattcgaatt agtcgtgtca gtatggatat ggctaaacag aatcaaccat tgaagaatat       540
ttaaagagaa taggcttaac tattgctagg caggatagtg ctgtgaaaaa tgaaatttag       600
ggtacaaaaa atataaatta tataaagggt cttttttgctg tcctctctta aattttgatt       660
ttgacggcca tgagaatata atgaatcttg tgaatatcta aatggtcatc tttctagtta       720
tttagctcgg atatttgcgt gtaacggaaa tatctgatta tgtttgtcaa tagtatatgt       780
gattgaaaag agaactattc taacatttga atggtgcagt gtgaaagaaa caattgagag       840
gtacaagaaa gcttgttcag attcctcaaa cactgattca atttccgagg ctaatgctca       900
ggtatatagt aagtagtaaa taatttcaaa caatcctctc tcatctcatt tcaagtaagt       960
tagggtaaac ttcatgccta tactgttatg acaaattttg attatcagaa tagggtggtt      1020
ctcatatcat atgtaggaaa tgaacaagat attgcaacaa caaaaaaaaa ggacttctct      1080
cttcatactt tatataatat ttaaaagaaa agaggtagat tactgtttgg ttagttttcc      1140
tacttataaa ttgaaactta ttccaatgaa taataaaact tcattcttca ttcttccatc      1200
cagtttactt tgtttacttt gtttgtatta gtttgacttg gcataaagtt ttagtaaaaa      1260
aagaacttga gatttagtat ctgttggaag aggattgcta ttaatatttg gagggaggct      1320
tttaggctaa gggaattttg gaagagtaga aagattttgg agaagagaaa cttttattac      1380
tcaaacttgt ttttgattct tttggcttga tatgttgtgt gttgtgtgtt atacaaatgc      1440
caaatgccat cccatattta taggggaggc ttgccaagct ctagagtgtc tagagagttc      1500
taccatttcc tagctatgta catgtgctag aattct                                1536

<210> SEQ ID NO 11
<211> LENGTH: 4443
<212> TYPE: DNA
<213> ORGANISM: Artificial
<220> FEATURE:
<223> OTHER INFORMATION: synthetic oligonucleotide

<400> SEQUENCE: 11
atggattaca aggatgatga tgataaggat tacaaggatg atgatgataa gatggctcca        60
aagaagaaga gaaaggttgg aatccacgga gttccagctg ctgataagaa gtactctatc       120
ggacttgaca tcggaaccaa ctctgttgga tgggctgtta tcaccgatga gtacaaggtt       180
ccatctaaga agttcaaggt tcttggaaac accgatagac actctatcaa gaagaacctt       240
atcggtgctc ttcttttcga ttctggagag accgctgagg ctaccagatt gaagagaacc       300
```

-continued

```
gctagaagaa gatacaccag aagaaagaac agaatctgct accttcagga aatcttctct    360
aacgagatgg ctaaggttga tgattctttc ttccacagac ttgaggagtc tttccttgtt    420
gaggaggata agaagcacga gagacaccca atcttcggaa acatcgttga tgaggttgct    480
taccacgaga agtacccaac catctaccac cttagaaaga agttggttga ttctaccgat    540
aaggctgatc ttagacttat ctaccttgct cttgctcaca tgatcaagtt cagaggacac    600
ttccttatcg agggagacct taacccagat aactctgatg ttgataagtt gttcatccag    660
cttgttcaga cctacaacca gcttttcgag gagaacccaa tcaacgcttc tggagttgat    720
gctaaggcta tcctttctgc tagactttct aagtctcgta gacttgagaa ccttatcgct    780
cagcttccag gagagaagaa gaacggactt ttcggaaacc ttatcgctct ttctcttgga    840
cttaccccaa acttcaagtc taacttcgat cttgctgagg atgctaagtt gcagctttct    900
aaggatacct acgatgatga tcttgataac cttcttgctc agatcggaga tcagtacgct    960
gatcttttcc ttgctgctaa gaaccttttct gatgctatcc ttctttctga catccttaga   1020
gttaacaccg agatcaccaa ggctccactt tctgcttcta tgatcaagag atacgatgag   1080
caccaccagg atcttaccct tttgaaggct cttgttagac agcagcttcc agagaagtac   1140
aaggaaatct tcttcgatca gtctaagaac ggatacgctg gatacatcga tggaggagct   1200
tctcaggagg agttctacaa gttcatcaag ccaatccttg agaagatgga tggaaccgag   1260
gagcttcttg ttaagttgaa cagagaggat cttcttagaa agcagagaac cttcgataac   1320
ggatctatcc cacaccagat ccaccttgga gagcttcacg ctatccttcg tagacaggag   1380
gatttctacc cattcttgaa ggataacaga gagaagatcg agaagatcct taccttcaga   1440
atcccatact acgttggacc acttgctaga ggaaactctc gtttcgcttg gatgaccaga   1500
aagtctgagg agaccatcac cccttggaac ttcgaggagg taagtttctg cttctacctt   1560
tgatatatat ataataatta tcattaatta gtagtaatat aatatttcaa atatttttt    1620 caaaataaaa gaatgtagta tatagcaatt gcttttctgt agtttataag tgtgtatatt   1680
ttaatttata acttttctaa tatatgacca aaatttgttg atgtgcaggt tgttgataag   1740
ggagcttctg ctcagtcttt catcgagaga atgaccaact tcgataagaa ccttccaaac   1800
gagaaggttc ttccaaagca ctctcttctt tacgagtact tcaccgtta caacgagctt    1860 accaaggtta agtacgttac cgagggaatg agaaagccag cttttccttt ctggagagcag   1920 aagaaggcta tcgttgatct tctttttcaag accaacagaa aggttaccgt taagcagttg   1980
aaggaggatt acttcaagaa gatcgagtgc ttcgattctg ttgaaatctc tggagttgag   2040
gatagattca acgcttctct tggaacctac cacgatcttt tgaagatcat caaggataag   2100
gatttccttg ataacgagga gaacgaggac atccttgagg acatcgttct tacccttacc   2160
cttttcgagg atagagagat gatcgaggag agactcaaga cctacgctca ccttttcgat   2220
gataaggtta tgaagcagtt gaagagaaga agatacaccg gatggggtag actttctcgt   2280
aagttgatca acggaatcag agataagcag tctggaaaga ccatccttga tttcttgaag   2340
tctgatggat tcgctaacag aaacttcatg cagcttatcc acgatgattc tcttaccttc    2400
aaggaggaca tccagaaggc tcaggtttct ggacagggag attctcttca cgagcacatc   2460
gctaaccttg ctggatctcc agctatcaag aagggaatcc ttcagaccgt taaggttgtt   2520
gatgagcttg ttaaggttat gggtagacac aagccagaga acatcgttat cgagatggct    2580
agagagaacc agaccaccca gaagggacag aagaactctc gtgagagaat gaagagaatc   2640
```

-continued

```
gaggagggaa tcaaggagct tggatctcaa atcttgaagg agcacccagt tgagaacacc      2700
cagcttcaga acgagaagtt gtacctttac taccttcaga acggaagaga tatgtacgtt      2760
gatcaggagc ttgacatcaa cagactttct gattacgatg ttgatcacat cgttccacag      2820
tctttcttga aggatgattc tatcgataac aaggttctta cccgttctga taagaacaga      2880
ggaaagtctg ataacgttcc atctgaggag gttgttaaga agatgaagaa ctactggaga      2940
cagcttctta acgctaagtt gatcacccag agaaagttcg ataaccttac caaggctgag      3000
agaggaggac tttctgagct tgataaggct ggattcatca agagacagct tgttgagacc      3060
agacagatca ccaagcacgt tgctcagatc cttgattctc gtatgaacac caagtacgat      3120
gagaacgata agttgatcag agaggttaag gttatcacct tgaagtctaa gttggtttct      3180
gatttcagaa aggatttcca gttctacaag gttagagaga tcaacaacta ccaccacgct      3240
cacgatgctt accttaacgc tgttgttgga accgctctta tcaagaagta cccaaagttg      3300
gagtctgagt tcgtttacgg agattacaag gtttacgatg ttagaaagat gatcgctaag      3360
tctgagcagg agatcggaaa ggctaccgct aagtacttct tctactctaa catcatgaac      3420
ttcttcaaga ccgagatcac ccttgctaac ggagagatca gaaagagacc acttatcgag      3480
accaacggag agaccggaga gatcgtttgg gataagggaa gagatttcgc taccgttaga      3540
aaggttcttt ctatgccaca ggttaacatc gttaagaaaa ccgaggttca gaccggagga      3600
ttctctaagg agtctatcct tccaaagaga aactctgata agttgatcgc tagaaagaag      3660
gattgggacc caaagaagta cggaggattc gattctccaa ccgttgctta ctctgttctt      3720
gttgttgcta aggttgagaa gggaaagtct aagaagttga agtctgttaa ggagcttctt      3780
ggaatcacca tcatggagcg ttcttctttc gagaagaacc caatcgattt ccttgaggct      3840
aagggataca aggaggttaa gaaggatctt atcatcaagt tgccaaagta ctctcttttc      3900
gagcttgaga acggaagaaa gagaatgctt gcttctgctg gagagcttca gaagggaaac      3960
gagcttgctc ttccatctaa gtacgttaac ttcctttacc ttgcttctca ctacgagaag      4020
ttgaagggat ctccagagga taacgagcag aagcagcttt cgttgagca gcacaagcac      4080 taccttgatg agatcatcga gcaaatctct gagttctcta agagagttat ccttgctgat      4140
gctaaccttg ataaggttct ttctgcttac aacaagcaca gagataagcc aatcagagag      4200
caggctgaga acatcatcca ccttttcacc cttaccaacc ttggtgctcc agctgctttc      4260
aagtacttcg ataccaccat cgatagaaaa agatacacct ctaccaagga ggttcttgat      4320 gctacccta tccaccagtc tatcaccgga ctttacgaga ccagaatcga tctttctcag      4380
cttggaggag ataagagacc agctgctacc aagaaggctg acaggctaa gaagaagaag      4440 tga                                                                    4443
```

```
<210> SEQ ID NO 12
<211> LENGTH: 76
<212> TYPE: DNA
<213> ORGANISM: Artificial
<220> FEATURE:
<223> OTHER INFORMATION: synthetic oligonucleotide

<400> SEQUENCE: 12
gttttagagc tagaaatagc aagttaaaat aaggctagtc cgttatcaac ttgaaaaagt      60
ggcaccgagt cggtgc                                                       76

<210> SEQ ID NO 13
<211> LENGTH: 35
```

```
<212> TYPE: DNA
<213> ORGANISM: Artificial
<220> FEATURE:
<223> OTHER INFORMATION: synthetic oligonucleotide

<400> SEQUENCE: 13
aagatcatcg atgtctataa atataagaga ccctc                                    35

<210> SEQ ID NO 14
<211> LENGTH: 35
<212> TYPE: DNA
<213> ORGANISM: Artificial
<220> FEATURE:
<223> OTHER INFORMATION: synthetic oligonucleotide

<400> SEQUENCE: 14
agaagccggc cgaagtcttc ttcctccgca gccac                                    35

<210> SEQ ID NO 15
<211> LENGTH: 31
<212> TYPE: DNA
<213> ORGANISM: Artificial
<220> FEATURE:
<223> OTHER INFORMATION: synthetic oligonucleotide

<400> SEQUENCE: 15
tcacctgcta gtgggagcac cgactcggtg c                                        31

<210> SEQ ID NO 16
<211> LENGTH: 49
<212> TYPE: DNA
<213> ORGANISM: Artificial
<220> FEATURE:
<223> OTHER INFORMATION: synthetic oligonucleotide

<400> SEQUENCE: 16
acacctgcaa cgaaacttgg tagtagcgac tccatggttt tagagctag               49

<210> SEQ ID NO 17
<211> LENGTH: 45
<212> TYPE: DNA
<213> ORGANISM: Artificial
<220> FEATURE:
<223> OTHER INFORMATION: synthetic oligonucleotide)

<400> SEQUENCE: 17
acacctgcgc tctcccgcgg ccaccatgtc tataaatata agaga                    45

<210> SEQ ID NO 18
<211> LENGTH: 36
<212> TYPE: DNA
<213> ORGANISM: Artificial
<220> FEATURE:
<223> OTHER INFORMATION: synthetic oligonucleotide

<400> SEQUENCE: 18
tcacctgcta gtcactctaa agtcttcttc ctccgc                                  36

<210> SEQ ID NO 19
<211> LENGTH: 45
<212> TYPE: DNA
<213> ORGANISM: Artificial
<220> FEATURE:
<223> OTHER INFORMATION: synthetic oligonucleotide

<400> SEQUENCE: 19
```

```
acgtctcgca ggttggtagt agcgactcca tggtttttaga gctag                    45

<210> SEQ ID NO 20
<211> LENGTH: 34
<212> TYPE: DNA
<213> ORGANISM: Artificial
<220> FEATURE:
<223> OTHER INFORMATION: synthetic oligonucleotide

<400> SEQUENCE: 20
tcgtctctcg agctaaagtc ttcttcctcc gcag                                  34

<210> SEQ ID NO 21
<211> LENGTH: 23
<212> TYPE: DNA
<213> ORGANISM: Artificial
<220> FEATURE:
<223> OTHER INFORMATION: synthetic oligonucleotide

<400> SEQUENCE: 21
ggttcacaag tgggacaatc ttc                                              23

<210> SEQ ID NO 22
<211> LENGTH: 19
<212> TYPE: DNA
<213> ORGANISM: Artificial
<220> FEATURE:
<223> OTHER INFORMATION: synthetic oligonucleotide

<400> SEQUENCE: 22
tgtctagctc cggtcttgg                                                   19

<210> SEQ ID NO 23
<211> LENGTH: 57
<212> TYPE: DNA
<213> ORGANISM: Artificial
<220> FEATURE:
<223> OTHER INFORMATION: synthetic oligonucleotide

<400> SEQUENCE: 23
acactctttc cctacacgac gctcttccga tctcaattgc cgttaatttg agagtcc        57

<210> SEQ ID NO 24
<211> LENGTH: 56
<212> TYPE: DNA
<213> ORGANISM: Artificial
<220> FEATURE:
<223> OTHER INFORMATION: synthetic oligonucleotide

<400> SEQUENCE: 24
gactggagtt cagacgtgtg ctcttccgat cttgctatgc tcgtgatcat aaattc         56

<210> SEQ ID NO 25
<211> LENGTH: 31
<212> TYPE: DNA
<213> ORGANISM: Artificial
<220> FEATURE:
<223> OTHER INFORMATION: synthetic oligonucleotide

<400> SEQUENCE: 25
tcacctgcta gtcactgcac cgactcggtg c                                     31

<210> SEQ ID NO 26
<211> LENGTH: 49
<212> TYPE: DNA
<213> ORGANISM: Artificial
```

-continued

```
<220> FEATURE:
<223> OTHER INFORMATION: synthetic oligonucleotide

<400> SEQUENCE: 26
acacctgcaa cgaaacgtgt gaaagaaaca attgaggttt tagagctag              49

<210> SEQ ID NO 27
<211> LENGTH: 61
<212> TYPE: DNA
<213> ORGANISM: Artificial
<220> FEATURE:
<223> OTHER INFORMATION: synthetic oligonucleotide

<400> SEQUENCE: 27
acactctttc cctacacgac gctcttccga tctaaagacg gccatgagaa tataatgaat    60
c                                                                    61

<210> SEQ ID NO 28
<211> LENGTH: 58
<212> TYPE: DNA
<213> ORGANISM: Artificial
<220> FEATURE:
<223> OTHER INFORMATION: synthetic oligonucleotide

<400> SEQUENCE: 28
gactggagtt cagacgtgtg ctcttccgat ctgtggatat gagaaccacc ctattctg      58

<210> SEQ ID NO 29
<211> LENGTH: 21
<212> TYPE: DNA
<213> ORGANISM: Artificial
<220> FEATURE:
<223> OTHER INFORMATION: synthetic oligonucleotide

<400> SEQUENCE: 29
ctttcatccg tcaatggagg g                                              21

<210> SEQ ID NO 30
<211> LENGTH: 26
<212> TYPE: DNA
<213> ORGANISM: Artificial
<220> FEATURE:
<223> OTHER INFORMATION: synthetic oligonucleotide

<400> SEQUENCE: 30
gccaagtcaa actaatacaa acaaag                                         26

<210> SEQ ID NO 31
<211> LENGTH: 36
<212> TYPE: DNA
<213> ORGANISM: Artificial
<220> FEATURE:
<223> OTHER INFORMATION: synthetic oligonucleotide

<400> SEQUENCE: 31
acacctgcgc tctccctagt ctataaatat aagaga                              36

<210> SEQ ID NO 32
<211> LENGTH: 35
<212> TYPE: DNA
<213> ORGANISM: Artificial
<220> FEATURE:
<223> OTHER INFORMATION: synthetic oligonucleotide

<400> SEQUENCE: 32
```

-continued

```
tcacctgcta gtcactttgg ccataagtaa ccttt                                    35

<210> SEQ ID NO 33
<211> LENGTH: 49
<212> TYPE: DNA
<213> ORGANISM: Artificial
<220> FEATURE:
<223> OTHER INFORMATION: synthetic oligonucleotide

<400> SEQUENCE: 33
acacctgcaa cgaaacggac ctcatgattc agatccgttt tagagctag                     49

<210> SEQ ID NO 34
<211> LENGTH: 2791
<212> TYPE: DNA
<213> ORGANISM: Artificial
<220> FEATURE:
<223> OTHER INFORMATION: synthetic oligonucleotide

<400> SEQUENCE: 34
gccttgacgg caaaatccct taacgtgagt tttcgttcca ctgagcgtca gaccccgtag         60
aaaagatcaa aggatcttct tgagatcctt tttttctgcg cgtaatctgc tgcttgcaaa        120
caaaaaaacc accgctacca gcggtggttt gtttgccgga tcaagagcta ctaactcttt        180
ttccgaaggt aactggcttc agcagagcgc agataccaaa tactgttctt ctagtgtagc        240
cgtagttagg ccaccacttc aagaactctg tagcaccgcc tacatacctc gctctgctaa        300
tcctgttacc agtggctgct gccagtggcg ataagtcgtg tcttaccggg ttggactcaa        360
gacgatagtt accggataag gcgcagcggt cgggctgaac ggggggttcg tgctcacagc        420
ccagcttgga gcgaacgacc tacaccgaac tgagatacct acagcgtgag ctatgagaaa        480
gcgccacgct tcccgaaggg agaaaggcgg acaggtatcc ggtaagcggc agggtcggaa        540
caggagagcg cacgagggag cttccagggg gaaacgcctg gtatctttat agtcctgtcg        600
ggtttcgcca cctctgactt gagcgtcgat ttttgtgatg ctcgtcaggg gggcggagcc        660
tatggaaaaa cgccagcaac gcggcctttt tacggttcct ggccttttgc tggccttttg        720
ctcacatgtt ctttcctgcg ttatcccctg attctgtgga taaccgtatt accgcctttg        780
agtgagctga taccgctcgc cgcagccgaa cgaccgagcg cagcgagtca gtgagcgagg        840
aagcgggaga gcgcccagct cttcatgagg gtgttagggt aaccaacatc agtgaagaga        900
aacggcggca ggtgccatgg gttttagagc tagaaatagc aagttaaaat aaggctagtc        960
cgttatcaac ttgaaaaagt ggcaccgagt cggtgcgttt aaacaagcca gataacagta       1020
tgcgtatttg cgcgctgatt tttgcggtat aagaatatat actgatatgt atacccgaag       1080
tatgtcaaaa ggaggtatgc tatgaagcag cgtattacag tgacagttga cagcgacagc       1140
tatcagttgc tcaaggcata tatgatgtca atatctccgg tctggtaagc acaaccatgc       1200
agaatgaagc ccgtcgtctg cgtgccgaac gctggaaagc ggaaaatcag gaagggatgg       1260
ctgaggtcgc ccggtttatt gaaatgaacg gctcttttgc tgacgagaac aggggctggt       1320
gaaatgcagt ttaaggttta cacctataaa agagagagcc gttatcgtct gtttgtggat       1380
gtacagagtg atattattga cacgcccggg cgacggatgg tgatccccct ggccagtgca       1440
cgtctgctgt cagataaagt ctcccgtgaa ctttacccgg tggtgcatat cggggatgaa       1500
agctggcgca tgatgaccac cgatatggcc agtgtgccgg tttccgttat cggggaagaa       1560
gtggctgatc tcagccaccg cgaaaatgac atcaaaaacg ccattaacct gatgttctgg       1620
ggaatataac acctgcaacg agtggccaga gagcatgaa aagccttagg gtcaggtggc        1680
```

```
acttttcggg gaaatgtgcg atgaacccct atttgtttat ttttctaaat acattcaaat      1740
atgtatccgc taatgagaca ataaccctga taaatgcttc aattatattg aaaaaggaag      1800
agtatgagta tccaacattt ccgtgtcgcc cttattccct tttttgcggc cttctgcctt      1860
cctgtttttg ctcacccaga aacgctggtg aaagtaaaag atgctgaaga tcagttgggt      1920
gcccgagtgg gttacattga actggatctc aacagcggca aaatcttaga gagttttcgc      1980
cccgaagaac gcttcccaat gatgagcact ttcaaagttc tgctatgtgg cgcggtgtta      2040
tcccgtattg atgctgggca agagcaactc ggtcgccgca tacactattc tcagaatgac      2100
ttggttgagt attcaccagt cacagaaaag catcttacgg atggcatgac agtaagagaa      2160
ttatgtagtg ctgccataac catgagtgat aacactgcgg ccaacttact tctgacaacg      2220
attggaggac cgaaggagct aaccgctttt ttgcacaaca tgggggatca tgtaactcgc      2280
cttgatcgtt gggaaccgga gctgaatgaa gccataccaa acgacgagcg tgacaccacg      2340
atgcctgtag caatggcaac aactctccgc aaactattaa ctggcgaact acttactctt      2400
gcttcacgcc agcaactcat tgactggatg gaggcggaca agttgcagg accacttctg      2460 cgctcggcac ttccggctgg ctggtttatt gctgataaat ctggagccgg tgagcgtggc      2520
tctcgcggta tcattgcagc actggggcca gatggtaagc cctcccgtat cgtagttatc      2580
tacacgacgg ggagtcaggc aactatggat gaacgaaata gacagatcgc tgagataggt      2640
gcctcactga ttaagcattg gtaactgtca gacgaaggga aataaatagt agcccgcctg      2700
atgtgcgggc ttttttttgg tggtggttac cagtgtcgct tagctaccgt aggtcctctt      2760
aggcggtccg attagcgaca tagtcatcaa t                                     2791
```

```
<210> SEQ ID NO 35
<211> LENGTH: 2691
<212> TYPE: DNA
<213> ORGANISM: Artificial
<220> FEATURE:
<223> OTHER INFORMATION: synthetic oligonucleotide

<400> SEQUENCE: 35
```

```
gccttgacgg caaaatccct taacgtgagt tttcgttcca ctgagcgtca gaccccgtag        60
aaaagatcaa aggatcttct tgagatcctt tttttctgcg cgtaatctgc tgcttgcaaa       120
caaaaaaacc accgctacca gcggtggttt gtttgccgga tcaagagcta ctaactcttt       180
ttccgaaggt aactggcttc agcagagcgc agataccaaa tactgttctt ctagtgtagc       240
cgtagttagg ccaccacttc aagaactctg tagcaccgcc tacatacctc gctctgctaa       300
tcctgttacc agtggctgct gccagtggcg ataagtcgtg tcttaccggg ttggactcaa       360
gacgatagtt accggataag gcgcagcggt cgggctgaac ggggggttcg tgctcacagc       420
ccagcttgga gcgaacgacc tacaccgaac tgagatacct acagcgtgag ctatgagaaa       480
gcgccacgct tcccgaaggg agaaaggcgg acaggtatcc ggtaagcggc agggtcggaa       540
caggagagcg cacgagggag cttccagggg gaaacgcctg gtatctttat agtcctgtcg       600
ggtttcgcca cctctgactt gagcgtcgat ttttgtgatg ctcgtcaggg gggcggagcc       660
tatggaaaaa cgccagcaac gcggcctttt tacggttcct ggccttttgc tggccttttg       720
ctcacatgtt ctttcctgcg ttatccctg attctgtgga taaccgtatt accgcctttg        780
agtgagctga taccgctcgc cgcagccgaa cgaccgagcg cagcgagtca gtgagcgagg       840
aagcgggaga gcgcccagct cttcatgagg gtgttagggt aaccaacatc agtgaagaga       900
```

-continued

```
aacttggtag tagcgactcc atggtttag agctagaaat agcaagttaa aataaggcta      960
gtccgttatc aacttgaaaa agtggcaccg agtcggtgct cccgcggcca ccatgtctat     1020
aaatataaga gaccctctta tagtaagcag agttgttgga gacgttcttg atccgtttaa     1080
tagatcaatc actctaaagg ttacttatgg ccaaagagag gtgactaatg gcttggatct     1140
aaggccttct caggttcaaa acaagccaag agttgagatt ggtggagaag acctcaggaa     1200
cttctatact ttggttatgg tggatccaga tgttccaagt cctagcaacc ctcacctccg     1260
agaatatctc cattggttgg tgactgatat ccctgctaca actggaacaa cctttggcaa     1320
tgagattgtg tgttacgaaa atccaagtcc cactgcagga attcatcgtg tcgtgtttat     1380
attgtttcga cagcttggca ggcaaacagt gtatgcacca gggtggcgcc agaacttcaa     1440
cactcgcgag tttgctgaga tctacaatct cggccttccc gtggccgcag ttttctacaa     1500
ttgtcagagg gagagtggct gcggaggaag aagactttag agtggccaga agagcatgaa     1560
aagccttagg gtcaggtggc acttttcggg gaaatgtgcg atgaacccct atttgtttat     1620
ttttctaaat acattcaaat atgtatccgc taatgagaca ataaccctga taaatgcttc     1680
aattatattg aaaaaggaag agtatgagta tccaacattt ccgtgtcgcc cttattccct     1740
tttttgcggc cttctgcctt cctgtttttg ctcacccaga aacgctggtg aaagtaaaag     1800
atgctgaaga tcagttgggt gcccgagtgg gttacattga actggatctc aacagcggca     1860
aaatcttaga gagtttttcgc cccgaagaac gcttcccaat gatgagcact ttcaaagttc     1920
tgctatgtgg cgcggtgtta tcccgtattg atgctgggca agagcaactc ggtcgccgca     1980
tacactattc tcagaatgac ttggttgagt attcaccagt cacagaaaag catcttacgg     2040
atggcatgac agtaagagaa ttatgtagtg ctgccataac catgagtgat aacactgcgg     2100
ccaacttact tctgacaacg attggaggac cgaaggagct aaccgctttt ttgcacaaca     2160
tgggggatca tgtaactcgc cttgatcgtt gggaaccgga gctgaatgaa gccataccaa     2220
acgacgagcg tgacaccacg atgcctgtag caatggcaac aactctccgc aaactattaa     2280
ctggcgaact acttactctt gcttcacgcc agcaactcat tgactggatg gaggcggaca     2340
aagttgcagg accacttctg cgctcggcac ttccggctgg ctggtttatt gctgataaat     2400
ctggagccgg tgagcgtggc tctcgcggta tcattgcagc actggggcca gatggtaagc     2460
cctcccgtat cgtagttatc tacacgacgg ggagtcaggc aactatggat gaacgaaata     2520
gacagatcgc tgagataggt gcctcactga ttaagcattg gtaactgtca gacgaaggga     2580
aataaatagt agcccgcctg atgtgcgggc ttttttttgg tggtggttac cagtgtcgct     2640
tagctaccgt aggtcctctt aggcggtccg attagcgaca tagtcatcaa t              2691
```

<210> SEQ ID NO 36
<211> LENGTH: 3372
<212> TYPE: DNA
<213> ORGANISM: Artificial
<220> FEATURE:
<223> OTHER INFORMATION: synthetic oligonucleotide

<400> SEQUENCE: 36

```
gccttgacgg caaaatccct taacgtgagt tttcgttcca ctgagcgtca gaccccgtag      60
aaaagatcaa aggatcttct tgagatcctt tttttctgcg cgtaatctgc tgcttgcaaa     120
caaaaaaacc accgctacca gcggtggttt gtttgccgga tcaagagcta ctaactcttt     180
ttccgaaggt aactggcttc agcagagcgc agataccaaa tactgttctt ctagtgtagc     240
cgtagttagg ccaccacttc aagaactctg tagcaccgcc tacataccte gctctgctaa     300
```

```
tcctgttacc agtggctgct gccagtggcg ataagtcgtg tcttaccggg ttggactcaa      360
gacgatagtt accggataag gcgcagcggt cgggctgaac ggggggttcg tgctcacagc      420
ccagcttgga gcgaacgacc tacaccgaac tgagatacct acagcgtgag ctatgagaaa      480
gcgccacgct tcccgaaggg agaaaggcgg acaggtatcc ggtaagcggc agggtcggaa      540
caggagagcg cacgagggag cttccagggg gaaacgcctg gtatctttat agtcctgtcg      600
ggtttcgcca cctctgactt gagcgtcgat ttttgtgatg ctcgtcaggg gggcggagcc      660
tatggaaaaa cgccagcaac gcggcctttt tacggttcct ggccttttgc tggccttttg      720
ctcacatgtt ctttcctgcg ttatcccctg attctgtgga taaccgtatt accgcctttg      780
agtgagctga taccgctcgc cgcagccgaa cgaccgagcg cagcgagtca gtgagcgagg      840
aagcggaaga gcgcccacct gcaacgccgg cgtaatatgg cgcgccgatc atgagcggag      900
aattaaggga gtcacgttat gaccccgccc gatgacgcgg gacaagccgt tttacgtttg      960
gaactgacag aaccgcaacg ttgaaggagc cactcagccg cgggtttctg gagtttaatg     1020
agctaagcac atacgtcaga aaccattatt gcgcgttcaa aagtcgccta aggtcactat     1080
cagctagcaa atatttcttg tcaaaaatgc tccactgacg ttccataaat tcccctcggt     1140
atccaattag agtctcatat tcactctcaa tccaaataat ctgcaacctg caggggagac     1200
gaagccagat aacagtatgc gtatttgcgc gctgattttt gcggtataag aatatatact     1260
gatatgtata cccgaagtat gtcaaaagga ggtatgctat gaagcagcgt attacagtga     1320
cagttgacag cgacagctat cagttgctca aggcatatat gatgtcaata tctccggtct     1380
ggtaagcaca accatgcaga atgaagcccg tcgtctgcgt gccgaacgct ggaaagcgga     1440
aaatcaggaa gggatggctg aggtcgcccg gtttattgaa atgaacggct cttttgctga     1500
cgagaacagg ggctggtgaa atgcagttta aggtttacac ctataaaaga gagagccgtt     1560
atcgtctgtt tgtggatgta cagagtgata ttattgacac gcccgggcga cggatggtga     1620
tccccctggc cagtgcacgt ctgctgtcag ataaagtctc ccgtgaactt tacccggtgg     1680
tgcatatcgg ggatgaaagc tggcgcatga tgaccaccga tatggccagt gtgccggttt     1740
ccgttatcgg ggaagaagtg gctgatctca gccaccgcga aaatgacatc aaaaacgcca     1800
ttaacctgat gttctgggga atataacgtc tcactcgagg ttcgagtatt atggcattgg     1860
gaaaactgtt tttcttgtac catttgttgt gcttgtaatt tactgtgttt tttattcggt     1920
tttcgctatc gaactgtgaa atggaaatgg atggagaaga gttaatgaat gatatggtcc     1980
ttttgttcat tctcaaatta atattatttg tttttttctct tatttgttgt gtgttgaatt     2040
tgaaattata agagatatgc aaacattttg ttttgagtaa aaatgtgtca aatcgtggcc     2100
tctaatgacc gaagttaata tgaggagtaa aacacttgta gttgtgagct cgcgcgtagt     2160
cctcggtaat atcgcagaac aaaagtacct gatatcgagt gtacttcaag tcacaccggc     2220
gagtgactag caggtgatga aaagccttag ggtcaggtgg cacttttcgg ggaaatgtgc     2280
gatgaacccc tatttgttta ttttttctaaa tacattcaaa tatgtatccg ctaatgagac     2340
aataaccctg ataaatgctt caattatatt gaaaaaggaa gagtatgagt atccaacatt     2400
tccgtgtcgc ccttattccc ttttttgcgg ccttctgcct tcctgttttt gctcacccag     2460
aaacgctggt gaaagtaaaa gatgctgaag atcagttggg tgcccgagtg ggttacattg     2520
aactggatct caacagcggc aaaatcttag agagttttcg ccccgaagaa cgcttcccaa     2580
tgatgagcac tttcaaagtt ctgctatgtg gcgcggtgtt atcccgtatt gatgctgggc     2640
```

-continued

```
aagagcaact cggtcgccgc atacactatt ctcagaatga cttggttgag tattcaccag    2700
tcacagaaaa gcatcttacg gatggcatga cagtaagaga attatgtagt gctgccataa    2760
ccatgagtga taacactgcg gccaacttac ttctgacaac gattggagga ccgaaggagc    2820
taaccgcttt tttgcacaac atgggggatc atgtaactcg ccttgatcgt gggaaccgg     2880 agctgaatga agccatacca aacgacgagc gtgacaccac gatgcctgta gcaatggcaa    2940
caactctccg caaactatta actggcgaac tacttactct tgcttcacgc cagcaactca    3000
ttgactggat ggaggcggac aaagttgcag gaccacttct gcgctcggca cttccggctg    3060
gctggtttat tgctgataaa tctggagccg gtgagcgtgg gtctcgcggt atcattgcag    3120
cactggggcc agatggtaag ccctcccgta tcgtagttat ctacacgacg gggagtcagg    3180
caactatgga tgaacgaaat agacagatcg ctgagatagg tgcctcactg attaagcatt    3240
ggtaactgtc agacgaaggg aaataaatag tagcccgcct gatgtgcggg cttttttttg    3300
gtggtggtta ccagtgtcgc ttagctaccg taggtcctct taggcggtcc gattagcgac    3360
atagtcatca at                                                        3372
```

```
<210> SEQ ID NO 37
<211> LENGTH: 3370
<212> TYPE: DNA
<213> ORGANISM: Artificial
<220> FEATURE:
<223> OTHER INFORMATION: synthetic oligonucleotide

<400> SEQUENCE: 37
gccttgacgg caaaatccct taacgtgagt tttcgttcca ctgagcgtca gaccccgtag      60
aaaagatcaa aggatcttct tgagatcctt tttttctgcg cgtaatctgc tgcttgcaaa     120
caaaaaaacc accgctacca gcggtggttt gtttgccgga tcaagagcta ctaactcttt     180
ttccgaaggt aactggcttc agcagagcgc agataccaaa tactgttctt ctagtgtagc     240
cgtagttagg ccaccacttc aagaactctg tagcaccgcc tacatacctc gctctgctaa     300
tcctgttacc agtggctgct gccagtggcg ataagtcgtg tcttaccggg ttggactcaa     360
gacgatagtt accggataag gcgcagcggt cgggctgaac ggggggttcg tgctcacagc     420
ccagcttgga gcgaacgacc tacaccgaac tgagatacct acagcgtgag ctatgagaaa     480
gcgccacgct tcccgaaggg agaaaggcgg acaggtatcc ggtaagcggc agggtcggaa     540
caggagagcg cacgagggag cttccagggg gaaacgcctg gtatctttat agtcctgtcg     600
ggtttcgcca cctctgactt gagcgtcgat ttttgtgatg ctcgtcaggg gggcggagcc     660
tatggaaaaa cgccagcaac gcggcctttt tacggttcct ggccttttgc tggccttttg     720
ctcacatgtt ctttcctgcg ttatcccctg attctgtgga taaccgtatt accgcctttg     780
agtgagctga taccgctcgc cgcagccgaa cgaccgagcg cagcgagtca gtgagcgagg     840
aagcggaaga gcgcccacct gcaacgccgg cgtaatatgg cgcgccgatc atgagcggag     900
aattaaggga gtcacgttat gaccccgccg atgacgcgg gacaagccgt tttacgtttg      960
gaactgacag aaccgcaacg ttgaaggagc cactcagccg cgggtttctg gagtttaatg    1020
agctaagcac atacgtcaga aaccattatt gcgcgttcaa aagtcgccta aggtcactat    1080
cagctagcaa atatttcttg tcaaaaatgc tccactgacg ttccataaat tcccctcggt    1140
atccaattag agtctcatat tcactctcaa tccaaataat ctgcaacctg caggttggta    1200
gtagcgactc catggtttta gagctagaaa tagcaagtta aaataaggct agtccgttat    1260
caacttgaaa aagtggcacc gagtcggtgc tcccgcggcc accatgtcta taaatataag    1320
```

-continued

```
agaccctctt atagtaagca gagttgttgg agacgttctt gatccgttta atagatcaat      1380
cactctaaag gttacttatg gccaaagaga ggtgactaat ggcttggatc taaggccttc      1440
tcaggttcaa aacaagccaa gagttgagat tggtggagaa gacctcagga acttctatac      1500
tttggttatg gtggatccag atgttccaag tcctagcaac cctcacctcc gagaatatct      1560
ccattggttg gtgactgata tccctgctac aactggaaca acctttggca atgagattgt      1620
gtgttacgaa aatccaagtc ccactgcagg aattcatcgt gtcgtgttta tattgtttcg      1680
acagcttggc aggcaaacag tgtatgcacc agggtggcgc cagaacttca acactcgcga      1740
gtttgctgag atctacaatc tcggccttcc cgtggccgca gttttctaca attgtcagag      1800
ggagagtggc tgcggaggaa gaagacttta gctcgaggtt cgagtattat ggcattggga      1860
aaactgtttt tcttgtacca tttgttgtgc ttgtaattta ctgtgttttt tattcggttt      1920
tcgctatcga actgtgaaat ggaaatggat ggagaagagt taatgaatga tatggtcctt      1980
ttgttcattc tcaaattaat attatttgtt ttttctctta tttgttgtgt gttgaatttg      2040
aaattataag agatatgcaa acattttgtt ttgagtaaaa atgtgtcaaa tcgtggcctc      2100
taatgaccga agttaatatg aggagtaaaa cacttgtagt tgtgagctcg cgcgtagtcc      2160
tcggtaatat cgcagaacaa aagtacctga tatcgagtgt acttcaagtc acaccggcga      2220
gtgactagca ggtgatgaaa agccttaggg tcaggtggca cttttcgggg aaatgtgcga      2280
tgaaccccta tttgtttatt tttctaaata cattcaaata tgtatccgct aatgagacaa      2340
taaccctgat aaatgcttca attatattga aaaaggaaga gtatgagtat ccaacatttc      2400
cgtgtcgccc ttattccctt ttttgcggcc ttctgccttc ctgttttttgc tcacccagaa      2460 acgctggtga agtaaaaaga tgctgaagat cagttgggtg cccgagtggg ttacattgaa      2520
ctggatctca acagcggcaa aatcttagag agttttcgcc ccgaagaacg cttcccaatg      2580
atgagcactt tcaaagttct gctatgtggc gcggtgttat cccgtattga tgctgggcaa      2640
gagcaactcg gtcgccgcat acactattct cagaatgact tggttgagta ttcaccagtc      2700
acagaaaagc atcttacgga tggcatgaca gtaagagaat tatgtagtgc tgccataacc      2760
atgagtgata acactgcggc caacttactt ctgacaacga ttggaggacc gaaggagcta      2820
accgcttttt tgcacaacat gggggatcat gtaactcgcc ttgatcgttg ggaaccggag      2880
ctgaatgaag ccataccaaa cgacgagcgt gacaccacga tgcctgtagc aatggcaaca      2940
actctccgca aactattaac tggcgaacta cttactcttg cttcacgcca gcaactcatt      3000
gactggatgg aggcggacaa agttgcagga ccacttctgc gctcggcact ccggctggc      3060 tggtttattg ctgataaatc tggagccggt gagcgtgggt ctcgcggtat cattgcagca      3120
ctggggccag atggtaagcc ctcccgtatc gtagttatct acacgacggg gagtcaggca      3180
actatggatg aacgaaatag acagatcgct gagataggtg cctcactgat taagcattgg      3240
taactgtcag acgaagggaa ataaatagta gcccgcctga tgtgcgggct ttttttttggt      3300 ggtggttacc agtgtcgctt agctaccgta ggtcctctta ggcggtccga ttagcgacat      3360
agtcatcaat                                                             3370
```

<210> SEQ ID NO 38
<211> LENGTH: 13128
<212> TYPE: DNA
<213> ORGANISM: Artificial
<220> FEATURE:
<223> OTHER INFORMATION: synthetic oligonucleotide -continued

```
<400> SEQUENCE: 38
tcgcggacac agccaagtcc gccgcctggg gcgctccgtc gatcactacg aagtcgcgcc      60
ggccgatggc cttcacgtcg cggtcaatcg tcgggcggtc gatgccgaca acggttagcg     120
gttgatcttc ccgcacggcc gcccaatcgc gggcactgcc ctggggatcg gaatcgacta     180
acagaacatc ggccccggcg agttgcaggg cgcgggctag atgggttgcg atggtcgtct     240
tgcctgaccc gcctttctgg ttaagtacag cgataacctt catgcgttcc ccttgcgtat     300
ttgtttattt actcatcgca tcatatacgc agcgaccgca tgacgcaagc tgttttactc     360
aaatacacat caccttttta gacggcggcg ctcggtttct tcagcggcca agctggccgg     420
ccaggccgcc agcttggcat cagacaaacc ggccaggatt tcatgcagcc gcacggttga     480
gccgtgcgcg ggcggctcga acacgtaccg ggccgcgatc atctccgcct cgatctcttc     540
ggtaatgaaa aacggttcgt cctggccgtc ctggtgcggt ttcatgcttg ttcctcttgg     600
cgttcattct cggcggccgc cagggcgtcg gcctcggtca atgcgtcctc acggaaggca     660
ccgcgccgcc tggcctcggt gggcgtcact tcctcgctgc gctcaagtgc gcggtacagg     720
gtcgagcgat gcacgccaag cagtgcagcc gcctctttca cggtgcggcc ttcctggtcg     780
atcagctcgc gggcgtgcgc gatctgtgcc ggggtgaggg tagggcgggg gccaaacttc     840
acgcctcggg ccttggcggc ctcgcgcccg ctccgggtgc ggtcgatgat tagggaacgc     900
tcgaactcgg caatgccggc gaacacggtc aacaccatgc ggccggccgg cgtggtggtg     960
tcggcccacg gctctgccag gctacgcagg cccgcgccgg cctcctggat gcgctcggca    1020
atgtccagta ggtcgcgggt gctgcgggcc aggcggtcta gcctggtcac tgtcacaacg    1080
tcgccagggc gtaggtggtc aagcatcctg gccagctccg ggcggtcgcg cctggtgccg    1140
gtgatcttct cggaaaacag cttggtgcag ccggccgcgt gcagttcggc ccgttggttg    1200
gtcaagtcct ggtcgtcggt gctgacgcgg gcatagccca gcaggccagc ggcggcgctc    1260
ttgttcatgg cgtaatgtct ccggttctag tcgcaagtat tctactttat gcgactaaaa    1320
cacgcgacaa gaaaacgcca ggaaaagggc agggcggcag cctgtcgcgt aacttaggac    1380
ttgtgcgaca tgtcgttttc agaagacggc tgcactgaac gtcagaagcc gactgcacta    1440
tagcagcgga ggggttggat caaagtactt tgatcccgag gggaaccctg tggttggcat    1500
gcacatacaa atggacgaac ggataaacct ttttcacgccc tttttaaatat ccgttattct    1560 aataaacgct ctttttctctt aggtttaccc gccaatatat cctgtcaaac actgatagtt    1620
tttcgtacga ccctcggtac cgatcggcgc gccagatttg cctttttcaat ttcagaaaga    1680 atgctaaccc acagatggtt agagaggctt acgcagcagg tatcatcaag acgatctacc    1740
cgagcaataa tctccaggaa atcaaatacc ttcccaagaa ggttaaagat gcagtcaaaa    1800
gattcaggac taactgcatc aagaacacag agaaagatat atttctcaag atcagaagta    1860
ctattccagt atggacgatt caaggcttgc ttcacaaacc aaggcaagta atagagattg    1920
gagtctctaa aaaggtagtt cccactgaat caaaggccat ggagtcaaag attcaaatag    1980
aggacctaac agaactcgcc gtaaagactg gcgaacagtt catacagagt ctcttacgac    2040
tcaatgacaa gaagaaaatc ttcgtcaaca tggtggagca cgacacactt gtctactcca    2100
aaaatatcaa agatacagtc tcagaagacc aaagggcaat tgagactttt caacaaaggg    2160
taatatccgg aaacctcctc ggattccatt gcccagctat ctgtcacttt attgtgaaga    2220
tagtggaaaa ggaaggtggc tcctacaaat gccatcattg cgataaagga aaggccatcg    2280
ttgaagatgc ctctgccgac agtggtccca aagatggacc cccacccacg aggagcatcg    2340
```

```
tggaaaaaga agacgttcca accacgtctt caaagcaagt ggattgatgt gatatctcca      2400
ctgacgtaag ggatgacgca caatcccact atccttcgca agacccttcc tctatataag      2460
gaagttcatt tcatttggag agaacacggg ggactcctgc aggtagatcg ctcgtcgaca      2520
tggataagaa gtactctatc ggactcgata tcggaactaa ctctgtggga tgggctgtga      2580
tcaccgatga gtacaaggtg ccatctaaga agttcaaggt tctcggaaac accgataggc      2640
actctatcaa gaaaaacctt atcggtgctc tcctcttcga ttctggtgaa actgctgagg      2700
ctaccagact caagagaacc gctagaagaa ggtacaccag aagaaagaac aggatctgct      2760
acctccaaga gatcttctct aacgagatgg ctaaagtgga tgattcattc ttccacaggc      2820
tcgaagagtc attcctcgtg gaagaagata agaagcacga gaggcaccct atcttcggaa      2880
acatcgttga tgaggtggca taccacgaga agtaccctac tatctaccac ctcagaaaga      2940
agctcgttga ttctactgat aaggctgatc tcaggctcat ctacctcgct ctcgctcaca      3000
tgatcaagtt cagaggacac ttcctcatcg agggtgatct caaccctgat aactctgatg      3060
tggataagtt gttcatccag ctcgtgcaga cctacaacca gcttttcgaa gagaaccta      3120 tcaacgcttc aggtgtggat gctaaggcta tcctctctgc taggctctct aagtcaagaa      3180
ggcttgagaa cctcattgct cagctccctg gtgagaagaa gaacggactt ttcggaaact      3240
tgatcgctct ctctctcgga ctcacccta acttcaagtc taacttcgat ctcgctgagg      3300
atgcaaagct ccagctctca aaggatacct acgatgatga tctcgataac ctcctcgctc      3360
agatcggaga tcagtacgct gatttgttcc tcgctgctaa gaacctctct gatgctatcc      3420
tcctcagtga tatcctcaga gtgaacaccg agatcaccaa ggctccactc tcagcttcta      3480
tgatcaagag atacgatgag caccaccagg atctcacact tctcaaggct cttgttagac      3540
agcagctccc agagaagtac aaagagattt tcttcgatca gtctaagaac ggatacgctg      3600
gttacatcga tggtggtgca tctcaagaag agttctacaa gttcatcaag cctatcctcg      3660
agaagatgga tggaaccgag gaactcctcg tgaagctcaa tagagaggat cttctcagaa      3720
agcagaggac cttcgataac ggatctatcc ctcatcagat ccacctcgga gagttgcacg      3780
ctatccttag aaggcaagag gatttctacc cattcctcaa ggataacagg gaaaagattg      3840
agaagattct caccttcaga atcccttact acgtgggacc tctcgctaga ggaaactcaa      3900
gattcgcttg gatgaccaga aagtctgagg aaaccatcac cccttggaac ttcgaagagg      3960
tggtggataa gggtgctagt gctcagtctt tcatcgagag gatgaccaac ttcgataaga      4020
accttccaaa cgagaaggtg ctccctaagc actctttgct ctacgagtac ttcaccgtgt      4080
acaacgagtt gaccaaggtt aagtacgtga ccgagggaat gaggaagcct gctttttttgt      4140 caggtgagca aaagaaggct atcgttgatc tcttgttcaa gaccaacaga aaggtgaccg      4200
tgaagcagct caaagaggat tacttcaaga aaatcgagtg cttcgattca gttgagattt      4260
ctggtgttga ggataggttc aacgcatctc tcggaaccta ccacgatctc tcaagatca      4320 ttaaggataa ggatttcttg gataacgagg aaaacgagga tatcttggag gatatcgttc      4380
ttaccctcac cctctttgaa gatagagaga tgattgaaga aaggctcaag acctacgctc      4440
atctcttcga tgataaggtg atgaagcagt tgaagagaag aagatacact ggttggggaa      4500
ggctctcaag aaagctcatt aacggaatca gggataagca gtctggaaag acaatccttg      4560
atttcctcaa gtctgatgga ttcgctaaca gaaacttcat gcagctcatc cacgatgatt      4620
ctctcacctt taaagaggat atccagaagg ctcaggtttc aggacagggt gatagtctcc      4680
```

-continued

```
atgagcatat cgctaacctc gctggatctc ctgcaatcaa gaagggaatc ctccagactg   4740
tgaaggttgt ggatgagttg gtgaaggtga tgggaaggca taagcctgag aacatcgtga   4800
tcgaaatggc tagagagaac cagaccactc agaagggaca gaagaactct agggaaagga   4860
tgaagaggat cgaggaaggt atcaaagagc ttggatctca gatcctcaaa gagcaccctg   4920
ttgagaacac tcagctccag aatgagaagc tctacctcta ctacctccag aacggaaggg   4980
atatgtatgt ggatcaagag ttggatatca acaggctctc tgattacgat gttgatcata   5040
tcgtgccaca gtcattcttg aaggatgatt ctatcgataa caaggtgctc accaggtctg   5100
ataagaacag gggtaagagt gataacgtgc caagtgaaga ggttgtgaag aaaatgaaga   5160
actattggag gcagctcctc aacgctaagc tcatcactca gagaaagttc gataacttga   5220
ctaaggctga gaggggagga ctctctgaat tggataaggc aggattcatc aagaggcagc   5280
ttgtggaaac caggcagatc actaagcacg ttgcacagat cctcgattct aggatgaaca   5340
ccaagtacga tgagaacgat aagttgatca gggaagtgaa ggttatcacc ctcaagtcaa   5400
agctcgtgtc tgatttcaga aaggatttcc aattctacaa ggtgagggaa atcaacaact   5460
accaccacgc tcacgatgct taccttaacg ctgttgttgg aaccgctctc atcaagaagt   5520
atcctaagct cgagtcagag ttcgtgtacg gtgattacaa ggtgtacgat gtgaggaaga   5580
tgatcgctaa gtctgagcaa gagatcggaa aggctaccgc taagtatttc ttctactcta   5640
acatcatgaa tttcttcaag accgagatta ccctcgctaa cggtgagatc agaaagaggc   5700
cactcatcga gacaaacggt gaaacaggtg agatcgtgtg ggataaggga agggatttcg   5760
ctaccgttag aaaggtgctc tctatgccac aggtgaacat cgttaagaaa accgaggtgc   5820
agaccggtgg attctctaaa gagtctatcc tccctaagag gaactctgat aagctcattg   5880
ctaggaagaa ggattgggac cctaagaaat acggtggttt cgattctcct accgtggctt   5940
actctgttct cgttgtggct aaggttgaga agggaaagag taagaagctc aagtctgtta   6000
aggaacttct cggaatcact atcatggaaa ggtcatcttt cgagaagaac ccaatcgatt   6060
tcctcgaggc taagggatac aaagaggtta agaaggatct catcatcaag ctcccaaagt   6120
actcactctt cgaactcgag aacggtagaa agaggatgct cgcttctgct ggtgagcttc   6180
aaaagggaaa cgagcttgct ctcccatcta agtacgttaa ctttctttac ctcgcttctc   6240
actacgagaa gttgaaggga tctccagaag ataacgagca gaagcaactt ttcgttgagc   6300
agcacaagca ctacttggat gagatcatcg agcagatctc tgagttctct aaaagggtga   6360
tcctcgctga tgcaaacctc gataaggtgt gtctgcttta caacaagcac agagataagc   6420
ctatcaggga acaggcagag aacatcatcc atctcttcac ccttaccaac ctcggtgctc   6480
ctgctgcttt caagtacttc gatacaacca tcgataggaa gagatacacc tctaccaaag   6540
aagtgctcga tgctaccctc atccatcagt ctatcactgg actctacgag actaggatcg   6600
atctctcaca gctcggtggt gattcaaggg ctgatcctaa gaagaagagg aaggtttgac   6660
gtcgacgata tgaagatgaa gatgaaatat ttggtgtgtc aaataaaaag cttgtgtgct   6720
taagtttgtg ttttttttctt ggcttgttgt gttatgaatt tgtggctttt tctaatatta   6780
aatgaatgta agatcacatt ataatgaata aacaaatgtt tctataatcc attgtgaatg   6840
ttttgttgga tctcttctgc agcatataac tactgtatgt gctatggtat ggactatgga   6900
atatgattaa agataagcca gagctctggt gacggacggc gcgactagtt ttacgtacgt   6960
taattaaccc ggcgtaatat ggcgcgccga tcatgagcgg agaattaagg gagtcacgtt   7020
atgacccccg ccgatgacgc gggacaagcc gttttacgtt tggaactgac agaaccgcaa   7080
```

-continued

```
cgttgaagga gccactcagc cgcgggtttc tggagtttaa tgagctaagc acatacgtca    7140
gaaaccatta ttgcgcgttc aaaagtcgcc taaggtcact atcagctagc aaatatttct    7200
tgtcaaaaat gctccactga cgttccataa attccctcg gtatccaatt agagtctcat     7260
attcactctc aatccaaata atctgcaacc tgcaggttgg tagtagcgac tccatggttt    7320
tagagctaga aatagcaagt taaaataagg ctagtccgtt atcaacttga aaaagtggca    7380
ccgagtcggt gctcccgcgg ccaccatgtc tataaatata agagaccctc ttatagtaag    7440
cagagttgtt ggagacgttc ttgatccgtt aatagatca atcactctaa aggttactta     7500
tggccaaaga gaggtgacta atggcttgga tctaaggcct tctcaggttc aaaacaagcc    7560
aagagttgag attggtggag aagacctcag gaacttctat actttggtta tggtggatcc    7620
agatgttcca agtcctagca accctcacct ccgagaatat ctccattggt tggtgactga    7680
tatccctgct acaactggaa caacctttgg caatgagatt gtgtgttacg aaaatccaag    7740
tcccactgca ggaattcatc gtgtcgtgtt tatattgttt cgacagcttg gcaggcaaac    7800
agtgtatgca ccagggtggc gccagaactt caacactcgc gagtttgctg agatctacaa    7860
tctcggcctt cccgtggccg cagttttcta caattgtcag agggagagtg gctgcggagg    7920
aagaagactt tagctcgagg ttcgagtatt atggcattgg gaaaactgtt tttcttgtac    7980
catttgttgt gcttgtaatt tactgtgttt tttattcggt tttcgctatc gaactgtgaa    8040
atggaaatgg atggagaaga gttaatgaat gatatggtcc ttttgttcat tctcaaatta    8100
atattatttg tttttttctct tatttgttgt gtgttgaatt tgaaattata agagatatgc    8160
aaacattttg ttttgagtaa aaatgtgtca aatcgtggcc tctaatgacc gaagttaata    8220
tgaggagtaa aacacttgta gttgtgagct cgcgcgtagt cctcggtaat atcgcagaac    8280
aaaagtacct gatatcgagt gtacttcaag tcacaccggc gagtgtttga tcgccggcgg    8340
taccgagtgt acttcaagtc actcaattcg gcgttaattc agtacattaa aaacgtccgc    8400
aatgtgttat taagttgtct aagcgtcaat ttgtttacac cacaatatat cctgccacca    8460
gccagccaac agctccccga ccggcagctc ggcacaaaat caccactcga tacaggcagc    8520
ccatcagtcc gggacggcgt cagcgggaga ccgttgtaa ggcggcagac tttgctcatg     8580
ttaccgatgc tattcggaag aacggcaact aagctgccgg gtttgaaaca cggatgatct    8640
cgcggagggt agcatgttga ttgtaacgat gacagagcgt tgctgcctgt gatcaccgcg    8700
gtttcaaaat cggctccgtc gatactatgt tatacgccaa ctttgaaaac aactttgaaa    8760
aagctgtttt ctggtattta aggttttaga atgcaaggaa cagtgaattg gagttcgtct    8820
tgttataatt agcttcttgg ggtatcttta aatactgtag aaaagaggaa ggaaataata    8880
aatggctaaa atgagaatat caccggaatt gaaaaaactg atcgaaaaat accgctgcgt    8940
aaaagatacg gaaggaatgt ctcctgctaa ggtatataag ctggtgggag aaaatgaaaa    9000
cctatattta aaaatgacgg acagccggta taaagggacc acctatgatg tggaacggga    9060
aaaggacatg atgctatggc tggaaggaaa gctgcctgtt ccaaaggtcc tgcactttga    9120
acggcatgat ggctggagca atctgctcat gagtgaggcc gatggcgtcc tttgctcgga    9180
agagtatgaa gatgaacaaa gccctgaaaa gattatcgag ctgtatgcgg agtgcatcag    9240
gctctttcac tccatcgaca tatcggattg tccctatacg aatagcttag acagccgctt    9300
agccgaattg gattacttac tgaataacga tctggccgat gtggattgcg aaaactggga    9360
agaagacact ccatttaaag atccgcgcga gctgtatgat tttttaaaga cggaaaagcc    9420
```

```
cgaagaggaa cttgtctttt cccacggcga cctgggagac agcaacatct ttgtgaaaga    9480
tggcaaagta agtggcttta ttgatcttgg gagaagcggc agggcggaca agtggtatga    9540
cattgccttc tgcgtccggt cgatcaggga ggatatcggg gaagaacagt atgtcgagct    9600
attttttgac ttactgggga tcaagcctga ttgggagaaa ataaaatatt atattttact    9660
ggatgaattg ttttagtacc tagaatgcat gaccaaaatc ccttaacgtg agttttcgtt    9720
ccactgagcg tcagacccccg tagaaaagat caaaggatct tcttgagatc cttttttttct   9780 gcgcgtaatc tgctgcttgc aaacaaaaaa accaccgcta ccagcggtgg tttgtttgcc    9840
ggatcaagag ctaccaactc ttttttccgaa ggtaactggc ttcagcagag cgcagatacc   9900
aaatactgtc cttctagtgt agccgtagtt aggccaccac ttcaagaact ctgtagcacc    9960
gcctacatac ctcgctctgc taatcctgtt accagtggct gctgccagtg gcgataagtc    10020
gtgtcttacc gggttggact caagacgata gttaccggat aaggcgcagc ggtcgggctg    10080
aacggggggt tcgtgcacac agcccagctt ggagcgaacg acctacaccg aactgagata    10140
cctacagcgt gagctatgag aaagcgccac gcttcccgaa gggagaaagg cggacaggta    10200
tccggtaagc ggcagggtcg aacaggaga gcgcacgagg gagcttccag ggggaaacgc     10260
ctggtatctt tatagtcctg tcgggtttcg ccacctctga cttgagcgtc gattttttgtg   10320 atgctcgtca gggggggcgga gcctatggaa aaacgccagc aacgcggcct ttttacggtt   10380
cctggccttt tgctggcctt ttgctcacat gttctttcct gcgttatccc ctgattctgt    10440
ggataaccgt attaccgcct ttgagtgagc tgataccgct cgccgcagcc gaacgaccga    10500
gcgcagcgag tcagtgagcg aggaagcgga agagcgcctg atgcggtatt ttctccttac    10560
gcatctgtgc ggtatttcac accgcatatg gtgcactctc agtacaatct gctctgatgc    10620
cgcatagtta agccagtata cactccgcta tcgctacgtg actgggtcat ggctgcgccc    10680
cgacacccgc caacacccgc tgacgcgccc tgacgggctt gtctgctccc ggcatccgct    10740
tacagacaag ctgtgaccgt ttccgggagc tgcatgtgtc agaggttttc accgtcatca    10800
ccgaaacgcg cgaggcaggg tgccttgatg tgggcgccgg cggtcgagtg cgacggcgc     10860 ggcttgtccg cgccctggta gattgcctgg ccgtaggcca gccatttttg agcggccagc    10920
ggccgcgata ggccgacgcg aagcggcggg gcgtagggag cgcagcgacc gaagggtagg    10980
cgttttttgc agctcttcgg ctgtgcgctg gccagacagt tatgcacagg ccaggcgggt    11040
tttaagagtt ttaataagtt ttaaagagtt ttaggcggaa aaatcgcctt ttttctcttt    11100
tatatcagtc acttacatgt gtgaccggtt cccaatgtac ggctttgggt tcccaatgta    11160
cgggttccgg ttcccaatgt acggctttgg gttcccaatg tacgtgctat ccacaggaaa    11220
gaggcctttt cgaccttttt cccctgctag ggcaatttgc cctagcatct gctccgtaca    11280
ttaggaaccg gcggatgctt cgccctcgat caggttgcgg tagcgcatga ctaggatcgg    11340
gccagcctgc cccgcctcct ccttcaaatc gtactccggc aggtcatttg acccgatcag    11400
cttgcgcacg gtgaaacaga acttcttgaa ctctccggcg ctgccactgc gttcgtagat    11460
cgtcttgaac aaccatctgg cttctgcctt gcctgcggcg cggcgtgcca ggcggtagag    11520 aaaacgccg atgccgggat cgatcaaaaa gtaatcgggg tgaaccgtca gcacgtccgg     11580
gttcttgcct tctgtgatct cgcggtacat ccaatcagct agctcgatct cgatgtactc    11640
cggccgcccg gtttcgctct ttacgatctt gtagcggcta atcaaggctt caccctcgga   11700
taccgtcacc aggcggccgt tcttggcctt cttcgtacgc tgcatggcaa cgtgcgtggt    11760
gtttaaccga atgcaggttt ctaccaggtc gtctttctgc tttccgccat cggctcgccg   11820
```

```
gcagaacttg agtacgtccg caacgtgtgg acggaacacg cggccgggct tgtctccctt   11880
cccttcccgg tatcggttca tggattcggt tagatgggaa accgccatca gtaccaggtc   11940
gtaatcccac acactggcca tgccggccgg ccctgcggaa acctctacgt gcccgtctgg   12000
aagctcgtag cggatcacct cgccagctcg tcggtcacgc ttcgacagac ggaaaacggc   12060
cacgtccatg atgctgcgac tatcgcgggt gcccacgtca tagagcatcg gaacgaaaaa   12120
atctggttgc tcgtcgccct tgggcggctt cctaatcgac ggcgcaccgg ctgccggcgg   12180
ttgccgggat tctttgcgga ttcgatcagc ggccgcttgc cacgattcac cggggcgtgc   12240
ttctgcctcg atgcgttgcc gctgggcggc ctgcgcggcc ttcaacttct ccaccaggtc   12300
atcacccagc gccgcgccga tttgtaccgg gccggatggt ttgcgaccgt cacgccgatt   12360
cctcgggctt gggggttcca gtgccattgc agggccggca gacaacccag ccgcttacgc   12420
ctggccaacc gcccgttcct ccacacatgg ggcattccac ggcgtcggtg cctggttgtt   12480 cttgatttc catgccgcct cctttagccg ctaaaattca tctactcatt tattcatttg   12540
ctcatttact ctggtagctg cgcgatgtat tcagatagca gctcggtaat ggtcttgcct   12600
tggcgtaccg cgtacatctt cagcttggtg tgatcctccg ccggcaactg aaagttgacc   12660
cgcttcatgg ctggcgtgtc tgccaggctg gccaacgttg cagccttgct gctgcgtgcg   12720
ctcggacggc cggcacttag cgtgtttgtg cttttgctca ttttctcttt acctcattaa   12780
ctcaaatgag ttttgattta atttcagcgg ccagcgcctg gacctcgcgg gcagcgtcgc   12840
cctcgggttc tgattcaaga acggttgtgc cggcggcggc agtgcctggg tagctcacgc   12900
gctgcgtgat acgggactca agaatgggca gctcgtaccc ggccagcgcc tcggcaacct   12960
caccgccgat gcgcgtgcct ttgatcgccc gcgacacgac aaaggccgct tgtagccttc   13020
catccgtgac ctcaatgcgc tgcttaacca gctccaccag gtcggcggtg gcccatatgt   13080
cgtaagggct tggctgcacc ggaatcagca cgaagtcggc tgccttga            13128
```

```
<210> SEQ ID NO 39
<211> LENGTH: 10239
<212> TYPE: DNA
<213> ORGANISM: Artificial
<220> FEATURE:
<223> OTHER INFORMATION: synthetic oligonucleotide

<400> SEQUENCE: 39
ggggagctgt tggctggctg gtggcaggat atattgtggt gtaaacaaat tgacgcttag     60
acaacttaat aacacattgc ggacgttttt aatgtactga attaacgccg aattaattcc    120
taggccacca tgttgggccc ggcgcgccaa gcttgcatgc ctgcaggtca acatggtgga    180
gcacgacact ctcgtctact ccaagaatat caaagataca gtctcagaag accagagggc    240
tattgagact tttcaacaaa gggtaatatc gggaaacctc ctcggattcc attgcccagc    300
tatctgtcac ttcatcgaaa ggacagtaga aaaggaagat ggcttctaca aatgccatca    360
ttgcgataaa ggaaaggcta tcgttcaaga tgcctctacc gacagtggtc ccaaagatgg    420
acccccaccc acgaggaaca tcgtggaaaa agaagacgtt ccaaccacgt cttcaaagca    480
agtggattga tgtgatggtc aacatggtgg agcacgacac tctcgtctac tccaagaata    540
tcaaagatac agtctcagaa gaccagaggg ctattgagac ttttcaacaa agggtaatat    600
cgggaaacct cctcggattc cattgcccag ctatctgtca cttcatcgaa aggacagtag    660
aaaaggaaga tggcttctac aaatgccatc attgcgataa aggaaaggct atcgttcaag    720
```

-continued

```
atgcctctac cgacagtggt cccaaagatg gaccccccacc cacgaggaac atcgtggaaa    780
aagaagacgt tccaaccacg tcttcaaagc aagtggattg atgtgatatc tccactgacg    840
taagggatga cgcacaatcc cactatcctt cgcaagaccc ttcctctata taaggaagtt    900 catttcatt ggagaggata aaacattgca cctatggtgt tgccctggct ggggtatgtc    960
agtgatcgca gtagaatgta ctaattgaca agttggagaa tacggtagaa cgtccttatc    1020
caacacagcc tttatccctc tccctgacga ggttttttgtc agtgtaatat ttctttttga    1080
actatccagc ttagtaccgt acgggaaagt gactggtgtg cttatctttg aaatgttact    1140
ttgggtttcg gttctttagg ttagtaagaa agcacttgtc ttctcataca aaggaaaacc    1200
tgagacgtat cgcttacgaa agtagcaatg aaagaaaggt ggtggtttta atcgctaccg    1260
caaaaacgat ggggtcgttt taattaactt ctcctacgca agcgtctaaa cggacgttgg    1320
ggttttgcta gtttctttag agaaaactag ctaagtcttt aatgttatca ttagagatgg    1380
cataaatata atacttgtgt ctgctgataa gatcatttta atttggacga ttagacttgt    1440
tgaactacag gttactgaat cacttgcgct aatcaacatg ggagatatgt acgatgaatc    1500
atttgacaag tcgggcggtc ctgctgactt gatggacgat tcttgggtgg aatcagtttc    1560
gtggaaagat ctgttgaaga agttacacag cataaaattt gcactacagt ctggtagaga    1620
tgagatcact gggttactag cggcactgaa tagacagtgt ccttattcac catatgagca    1680
gtttccagat aagaaggtgt atttcctttt agactcacgg gctaacagtg ctcttggtgt    1740
gattcagaac gcttcagcgt tcaagagacg agctgatgag aagaatgcag tggcgggtgt    1800
tacaaatatt cctgcgaatc caaacacaac ggttacgacg aaccaaggga gtactactac    1860
taccaaggcg aacactggct cgactttgga agaagacttg tacacttatt acaaattcga    1920
tgatgcctct acagctttcc acaaatctct aacttcgtta gagaacatgg agttgaagag    1980
ttattaccga aggaactttg agaaagtatt cgggattaag tttggtggag cagctgctag    2040
ttcatctgca ccgcctccag cgagtggagg tccgatacgt cctaatccct agggatttaa    2100
ggacgtgaac tctgttgaga tctctgtgaa attcagaggg tgggtgatac catattcact    2160
gatgccatta gcgacatcta aatagggcta attgtgacta atttgaggga atttcctta    2220 ccattgacgt cagtgtcgtt ggtagcattt gagtttcgga gcatcttgtt ctggggtttc    2280
acactatctt tagagaaagt gttaagttaa ttaagttatc ttaattaaga gcataattat    2340
actgatttgt ctctcgttga tagagtctat cattctgtta ctaaaaattt gacaactcgg    2400
tttgctgacc tactggttac tgtatcactt acccgagtta acgagtctag aaacggcggc    2460
aggtgccatg ggttttagag ctagaaatag caagttaaaa taaggctagt ccgttatcaa    2520
cttgaaaaag tggcaccgag tcggtgcgtt taaacaagcc agataacagt atgcgtattt    2580
gcgcgctgat ttttgcggta taagaatata tactgatatg tatacccgaa gtatgtcaaa    2640
aggaggtatg ctatgaagca gcgtattaca gtgacagttg acagcgacag ctatcagttg    2700
ctcaaggcat atatgatgtc aatatctccg gtctggtaag cacaaccatg cagaatgaag    2760
cccgtcgtct gcgtgccgaa cgctggaaag cggaaaatca ggaagggatg gctgaggtcg    2820
cccggtttat tgaaatgaac ggctcttttg ctgacgagaa caggggctgg tgaaatgcag    2880
tttaaggttt acacctataa aagagagagc cgttatcgtc tgtttgtgga tgtacagagt    2940
gatattattg acacgcccgg cgacggatg gtgatccccc tggccagtgc acgtctgctg    3000
tcagataaag tctcccgtga actttacccg gtggtgcata tcgggatga aagctggcgc    3060 atgatgacca ccgatatggc cagtgtgccg gtttccgtta tcggggaaga agtggctgat    3120
```

-continued

```
ctcagccacc gcgaaaatga catcaaaaac gccattaacc tgatgttctg gggaatataa    3180
cacctgcgct cagtgccggg catgtcccga agacattaaa ctacggttct ttaagtagat    3240
ccgtgtctga agttttaggt tcaatttaaa cctacgagat tgacattctc gactgatctt    3300
gattgatcgg taagtctttt gtaatttaat tttctttttg attttatttt aaattgttat    3360
ctgtttctgt gtatagactg tttgagatcg gcgtttggcc gactcattgt cttaccatag    3420
gggaacggac tttgtttgtg ttgttatttt atttgtattt tattaaaatt ctcaacgatc    3480
tgaaaaagcc tcgcggctaa gagattgttg gggggtgagt aagtactttt aaagtgatga    3540
tggttacaaa ggcaaaaggg gtaaaacccc tcgcctacgt aagcgttatt acgcccgtct    3600
gtacttatat cagtacactg acgagtccct aaaggacgaa acgggagaac gctagccacc    3660
accaccacca ccacgtgtga attacaggtg accagctcga atttcccga tcgttcaaac    3720 atttggcaat aaagtttctt aagattgaat cctgttgccg gtcttgcgat gattatcata    3780
taatttctgt tgaattacgt taagcatgta ataattaaca tgtaatgcat gacgttattt    3840
atgagatggg tttttatgat tagagtcccg caattataca tttaatacgc gatagaaaac    3900
aaaatatagc gcgcaaacta ggataaatta tcgcgcgcgg tgtcatctat gttactagat    3960
cgggaattaa actatcagtg tttgacagga tatattggcg ggtaaaccta agagaaaaga    4020
gcgtttatta gaataacgga tatttaaaag ggcgtgaaaa ggtttatccg ttcgtccatt    4080
tgtatgtgca tgccaaccac agggttcccc tcgggatcaa agtactttga tccaacccct    4140
ccgctgctat agtgcagtcg gcttctgacg ttcagtgcag ccgtcttctg aaaacgacat    4200
gtcgcacaag tcctaagtta cgcgacaggc tgccgccctg ccctttttcct ggcgttttct    4260 tgtcgcgtgt tttagtcgca taaagtagaa tacttgcgac tagaaccgga gacattacgc    4320
catgaacaag agcgccgccg ctggcctgct gggctatgcc cgcgtcagca ccgacgacca    4380
ggacttgacc aaccaacggg ccgaactgca cgcggccggc tgcaccaagc tgtttttccga    4440 gaagatcacc ggcaccaggc gcgaccgccc ggagctggcc aggatgcttg accacctacg    4500
ccctggcgac gttgtgacag tgaccaggct agaccgcctg gcccgcagca cccgcgacct    4560
actggacatt gccgagcgca tccaggaggc cggcgcgggc ctgcgtagcc tggcagagcc    4620
gtgggccgac accaccacgc cggccggccg catggtgttg accgtgttcg ccggcattgc    4680
cgagttcgag cgttccctaa tcatcgaccg cacccggagc gggcgcgagg ccgccaaggc    4740
ccgaggcgtg aagtttggcc cccgccctac cctcacccccg gcacagatcg cgcacgcccg    4800
cgagctgatc gaccaggaag gccgcaccgt gaaagaggcg gctgcactgc ttggcgtgca    4860
tcgctcgacc ctgtaccgcg cacttgagcg cagcgaggaa gtgacgccca ccgaggccag    4920
gcggcgcggt gccttccgtg aggacgcatt gaccgaggcc gacgccctgg cggccgcga    4980 gaatgaacgc caagaggaac aagcatgaaa ccgcaccagg acggccagga cgaaccgttt    5040
ttcattaccg aagagatcga ggcggagatg atcgcggccg ggtacgtgtt cgagccgccc    5100
gcgcacgtct caaccgtgcg gctgcatgaa atcctggccg gtttgtctga tgccaagctg    5160
gcggcctggc cggccagctt ggccgctgaa gaaaccgagc gccgccgtct aaaaaggtga    5220
tgtgtatttg agtaaaacag cttgcgtcat gcggtcgctg cgtatatgat gcgatgagta    5280
aataaacaaa tacgcaaggg gaacgcatga aggttatcgc tgtacttaac cagaaaggcg    5340
ggtcaggcaa gacgaccatc gcaacccatc tagcccgcgc cctgcaactc gccggggccg    5400
atgttctgtt agtcgattcc gatccccagg gcagtgcccg cgattgggcg gccgtgcggg    5460
```

```
aagatcaacc gctaaccgtt gtcggcatcg accgcccgac gattgaccgc gacgtgaagg    5520
ccatcggccg gcgcgacttc gtagtgatcg acggagcgcc ccaggcggcg gacttggctg    5580
tgtccgcgat caaggcagcc gacttcgtgc tgattccggt gcagccaagc ccttacgaca    5640
tatgggccac cgccgacctg gtggagctgg ttaagcagcg cattgaggtc acggatggaa    5700
ggctacaagc ggcctttgtc gtgtcgcggg cgatcaaagg cacgcgcatc ggcggtgagg    5760
ttgccgaggc gctggccggg tacgagctgc ccattcttga gtcccgtatc acgcagcgcg    5820
tgagctaccc aggcactgcc gccgccggca caaccgttct tgaatcagaa cccgagggcg    5880
acgctgcccg cgaggtccag gcgctggccg ctgaaattaa atcaaaactc atttgagtta    5940
atgaggtaaa gagaaaatga gcaaaagcac aaacacgcta agtgccggcc gtccgagcgc    6000
acgcagcagc aaggctgcaa cgttggccag cctggcagac acgccagcca tgaagcgggt    6060
caactttcag ttgccggcgg aggatcacac caagctgaag atgtacgcgg tacgccaagg    6120
caagaccatt accgagctgc tatctgaata catcgcgcag ctaccagagt aaatgagcaa    6180
atgaataaat gagtagatga ttttagcgg ctaaaggagg cggcatggaa aatcaagaac    6240
aaccaggcac cgacgccgtg gaatgcccca tgtgtggagg aacgggcggt tggccaggcg    6300
taagcggctg ggttgtctgc cggccctgca atggcactgg aacccccaag cccgaggaat    6360
cggcgtgacg gtcgcaaacc atccggcccg gtacaaatcg cgcggcgct gggtgatgac    6420 ctggtggaga agttgaaggc cgcgcaggcc gcccagcggc aacgcatcga ggcagaagca    6480
cgccccggtg aatcgtggca agcggccgct gatcgaatcc gcaaagaatc cggcaaccg    6540 ccggcagccg gtgcgccgtc gattaggaag ccgcccaagg gcgacgagca accagatttt    6600
ttcgttccga tgctctatga cgtgggcacc cgcgatagtc gcagcatcat ggacgtggcc    6660
gttttccgtc tgtcgaagcg tgaccgacga gctggcgagg tgatccgcta cgagcttcca    6720
gacgggcacg tagaggtttc cgcagggccg gccggcatgg ccagtgtgtg ggattacgac    6780
ctggtactga tggcggtttc ccatctaacc gaatccatga accgataccg ggaagggaag    6840
ggagacaagc ccggccgcgt gttccgtcca cacgttgcgg acgtactcaa gttctgccgg    6900
cgagccgatg gcggaaagca gaaagacgac ctggtagaaa cctgcattcg gttaaacacc    6960
acgcacgttg ccatgcagcg tacgaagaag gccaagaacg gccgcctggt gacggtatcc    7020
gagggtgaag ccttgattag ccgctacaag atcgtaaaga gcgaaaccgg gcggccggag    7080
tacatcgaga tcgagctagc tgattggatg taccgcgaga tcacagaagg caagaacccg    7140
gacgtgctga cggttcaccc cgattacttt ttgatcgatc ccggcatcgg ccgttttctc    7200
taccgcctgg cacgccgcgc cgcaggcaag gcagaagcca gatggttgtt caagacgatc    7260
tacgaacgca gtggcagcgc cggagagttc aagaagttct gtttcaccgt gcgcaagctg    7320
atcgggtcaa atgacctgcc ggagtacgat ttgaaggagg aggcggggca ggctggcccg    7380
atcctagtca tgcgctaccg caacctgatc gagggcgaag catccgccgg ttcctaatgt    7440
acggagcaga tgctagggca aattgcccta gcagggaaa aaggtcgaaa aggtctcttt    7500
cctgtggata gcacgtacat tgggaaccca aagccgtaca ttgggaaccg gaacccgtac    7560
attgggaacc caaagccgta cattgggaac cggtcacaca tgtaagtgac tgatataaaa    7620
gagaaaaaag gcgatttttc cgcctaaaac tctttaaaac ttattaaaac tcttaaaacc    7680
cgcctggcct gtgcataact gtctggccag cgcacagccg aagagctgca aaaagcgcct    7740
acccttcggt cgctgcgctc cctacgcccc gccgcttcgc gtcggcctat cgcggccgct    7800
ggccgctcaa aaatggctgg cctacggcca ggcaatctac cagggcgcgg acaagccgcg    7860
```

```
ccgtcgccac tcgaccgccg gcgcccacat caaggcaccc tgcctcgcgc gtttcggtga    7920
tgacggtgaa aacctctgac acatgcagct cccggagacg gtcacagctt gtctgtaagc    7980
ggatgccggg agcagacaag cccgtcaggg cgcgtcagcg ggtgttggcg ggtgtcgggg    8040
cgcagccatg acccagtcac gtagcgatag cggagtgtat actggcttaa ctatgcggca    8100
tcagagcaga ttgtactgag agtgcaccat atgcggtgtg aaataccgca cagatgcgta    8160
aggagaaaat accgcatcag gcgctcttcc gcttcctcgc tcactgactc gctgcgctcg    8220
gtcgttcggc tgcggcgagc ggtatcagct cactcaaagg cggtaatacg gttatccaca    8280
gaatcagggg ataacgcagg aaagaacatg tgagcaaaag gccagcaaaa ggccaggaac    8340
cgtaaaaagg ccgcgttgct ggcgtttttc cataggctcc gcccccctga cgagcatcac    8400
aaaaatcgac gctcaagtca gaggtggcga aacccgacag gactataaag ataccaggcg    8460 tttcccctg gaagctccct cgtgcgctct cctgttccga ccctgccgct taccggatac    8520
ctgtccgcct ttctcccttc gggaagcgtg gcgctttctc atagctcacg ctgtaggtat    8580
ctcagttcgg tgtaggtcgt tcgctccaag ctgggctgtg tgcacgaacc ccccgttcag    8640
cccgaccgct gcgccttatc cggtaactat cgtcttgagt ccaacccggt aagacacgac    8700
ttatcgccac tggcagcagc cactggtaac aggattagca gagcgaggta tgtaggcggt    8760
gctacagagt tcttgaagtg gtggcctaac tacggctaca ctagaaggac agtatttggt    8820
atctgcgctc tgctgaagcc agttaccttc ggaaaaagag ttggtagctc ttgatccggc    8880
aaacaaacca ccgctggtag cggtggtttt tttgtttgca agcagcagat tacgcgcaga    8940
aaaaaaggat ctcaagaaga tcctttgatc ttttctacgg ggtctgacgc tcagtggaac    9000
gaaaactcac gttaagggat tttggtcatg cattctaggt actaaaacaa ttcatccagt    9060
aaaatataat attttatttt ctcccaatca ggcttgatcc ccagtaagtc aaaaaatagc    9120
tcgacatact gttcttcccc gatatcctcc ctgatcgacc ggacgcagaa ggcaatgtca    9180
taccacttgt ccgccctgcc gcttctccca agatcaataa agccacttac tttgccatct    9240
ttcacaaaga tgttgctgtc tcccaggtcg ccgtgggaaa agacaagttc ctcttcgggc    9300
ttttccgtct ttaaaaaatc atacagctcg cgcggatctt taaatggagt gtcttcttcc    9360
cagttttcgc aatccacatc ggccagatct ttattcagta agtaatccaa ttcggctaag    9420
cggctgtcta agctattcgt atagggacaa tccgatatgt cgatggagtg aaagagcctg    9480
atgcactccg catacagctc gataatcttt tcagggcttt gttcatcttc atactcttcc    9540
gagcaaagga cgccatcggc ctcactcatg agcagattgc tccagccatc atgccgttca    9600
aagtgcagga cctttggaac aggcagcttt ccttccagcc atagcatcat gtcctttttcc    9660 cgttccacat cataggtggt cccttttatac cggctgtccg tcattttaa atataggttt    9720 tcattttctc ccaccagctt atataccttta gcaggagaca ttccttccgt atcttttacg    9780
cagcggtatt tttcgatcag ttttttcaat tccggtgata ttctcatttt agccatttat    9840
tatttccttc ctcttttcta cagtatttaa agatacccca agaagctaat tataacaaga    9900
cgaactccaa ttcactgttc cttgcattct aaaaccttaa ataccagaaa acagctttt    9960 caaagttgtt ttcaaagttg gcgtataaca tagtatcgac ggagccgatt ttgaaaccgc    10020
ggtgatcaca ggcagcaacg ctctgtcatc gttacaatca acatgctacc ctccgcgaga    10080
tcatccgtgt ttcaaacccg gcagcttagt tgccgttctt ccgaatagca tcggtaacat    10140
gagcaaagtc tgccgcctta caacggctct cccgctgacg ccgtcccgga ctgatgggct    10200
```

-continued

```
gcctgtatcg agtggtgatt ttgtgccgag ctgccggtc                        10239

<210> SEQ ID NO 40
<211> LENGTH: 10139
<212> TYPE: DNA
<213> ORGANISM: Artificial
<220> FEATURE:
<223> OTHER INFORMATION: synthetic oligonucleotide

<400> SEQUENCE: 40
ataaaacatt gcacctatgg tgttgccctg gctggggtat gtcagtgatc gcagtagaat      60
gtactaattg acaagttgga gaatacggta gaacgtcctt atccaacaca gcctttatcc     120
ctctccctga cgaggttttt gtcagtgtaa tatttctttt tgaactatcc agcttagtac     180
cgtacgggaa agtgactggt gtgcttatct ttgaaatgtt actttgggtt tcggttcttt     240
aggttagtaa gaaagcactt gtcttctcat acaaaggaaa acctgagacg tatcgcttac     300
gaaagtagca atgaaagaaa ggtggtggtt ttaatcgcta ccgcaaaaac gatggggtcg     360
ttttaattaa cttctcctac gcaagcgtct aaacggacgt tggggttttg ctagtttctt     420
tagagaaaac tagctaagtc tttaatgtta tcattagaga tggcataaat ataatacttg     480
tgtctgctga taagatcatt ttaatttgga cgattagact tgttgaacta caggttactg     540
aatcacttgc gctaatcaac atgggagata tgtacgatga atcatttgac aagtcgggcg     600
gtcctgctga cttgatggac gattcttggg tggaatcagt ttcgtggaaa gatctgttga     660
agaagttaca cagcataaaa tttgcactac agtctggtag agatgagatc actgggttac     720
tagcggcact gaatagacag tgtccttatt caccatatga gcagtttcca gataagaagg     780
tgtatttcct tttagactca cgggctaaca gtgctcttgg tgtgattcag aacgcttcag     840
cgttcaagag acgagctgat gagaagaatg cagtggcggg tgttacaaat attcctgcga     900
atccaaacac aacggttacg acgaaccaag ggagtactac tactaccaag gcgaacactg     960
gctcgacttt ggaagaagac ttgtacactt attacaaatt cgatgatgcc tctacagctt    1020
tccacaaatc tctaacttcg ttagagaaca tggagttgaa gagttattac cgaaggaact    1080
ttgagaaagt attcgggatt aagtttggtg gagcagctgc tagttcatct gcaccgcctc    1140
cagcgagtgg aggtccgata cgtcctaatc cctagggatt taaggacgtg aactctgttg    1200
agatctctgt gaaattcaga gggtgggtga taccatattc actgatgcca ttagcgacat    1260
ctaaataggg ctaattgtga ctaatttgag ggaatttcct ttaccattga cgtcagtgtc    1320
gttggtagca tttgagtttc ggagcatctt gttctggggt ttcacactat ctttagagaa    1380
agtgttaagt taattaagtt atcttaatta agagcataat tatactgatt tgtctctcgt    1440
tgatagagtc tatcattctg ttactaaaaa tttgacaact cggtttgctg acctactggt    1500
tactgtatca cttacccgag ttaacgagtc tagaaacttg gtagtagcga ctccatggtt    1560
ttagagctag aaatagcaag ttaaaataag gctagtccgt tatcaacttg aaaaagtggc    1620
accgagtcgg tgctcccgcg gccaccatgt ctataaatat aagagaccct cttatagtaa    1680
gcagagttgt tggagacgtt cttgatccgt ttaatagatc aatcactcta aaggttactt    1740
atggccaaag agaggtgact aatggcttgg atctaaggcc ttctcaggtt caaaacaagc    1800
caagagttga gattggtgga gaagacctca ggaacttcta tactttggtt atggtggatc    1860
cagatgttcc aagtcctagc aaccctcacc tccgagaata tctccattgg ttggtgactg    1920
atatccctgc tacaactgga acaacctttg gcaatgagat gtgtgtgtac gaaaatccaa    1980
gtcccactgc aggaattcat cgtgtcgtgt ttatattgtt tcgacagctt ggcaggcaaa    2040
```

```
cagtgtatgc accagggtgg cgccagaact tcaacactcg cgagtttgct gagatctaca    2100
atctcggcct tcccgtggcc gcagttttct acaattgtca gagggagagt ggctgcggag    2160
gaagaagact ttagagtgcc gggcatgtcc cgaagacatt aaactacggt tctttaagta    2220
gatccgtgtc tgaagtttta ggttcaattt aaacctacga gattgacatt ctcgactgat    2280
cttgattgat cggtaagtct tttgtaattt aattttcttt ttgattttat tttaaattgt    2340
tatctgtttc tgtgtataga ctgtttgaga tcggcgtttg gccgactcat tgtcttacca    2400
taggggaacg gactttgttt gtgttgttat tttatttgta ttttattaaa attctcaacg    2460
atctgaaaaa gcctcgcggc taagagattg ttggggggtg agtaagtact tttaaagtga    2520
tgatggttac aaaggcaaaa ggggtaaaac ccctcgccta cgtaagcgtt attacgcccg    2580
tctgtactta tatcagtaca ctgacgagtc cctaaaggac gaaacgggag aacgctagcc    2640
accaccacca ccaccacgtg tgaattacag gtgaccagct cgaatttccc cgatcgttca    2700
aacatttggc aataaagttt cttaagattg aatcctgttg ccggtcttgc gatgattatc    2760
atataatttc tgttgaatta cgttaagcat gtaataatta acatgtaatg catgacgtta    2820
tttatgagat gggtttttat gattagagtc ccgcaattat acatttaata cgcgatagaa    2880
aacaaaatat agcgcgcaaa ctaggataaa ttatcgcgcg cggtgtcatc tatgttacta    2940
gatcgggaat taaactatca gtgtttgaca ggatatattg gcgggtaaac ctaagagaaa    3000
agagcgttta ttagaataac ggatatttaa aagggcgtga aaaggtttat ccgttcgtcc    3060
atttgtatgt gcatgccaac cacagggttc ccctcgggat caaagtactt tgatccaacc    3120
cctccgctgc tatagtgcag tcggcttctg acgttcagtg cagccgtctt ctgaaaacga    3180
catgtcgcac aagtcctaag ttacgcgaca ggctgccgcc ctgccctttt cctggcgttt    3240
tcttgtcgcg tgttttagtc gcataaagta gaatacttgc gactagaacc ggagacatta    3300
cgccatgaac aagagcgccg ccgctggcct gctgggctat gcccgcgtca gcaccgacga    3360
ccaggacttg accaaccaac gggccgaact gcacgcggcc ggctgcacca agctgttttc    3420
cgagaagatc accggcacca ggcgcgaccg cccggagctg gccaggatgc ttgaccacct    3480
acgccctggc gacgttgtga cagtgaccag gctagaccgc ctggcccgca gcacccgcga    3540
cctactggac attgccgagc gcatccagga ggccggcgcg ggcctgcgta gcctggcaga    3600
gccgtgggcc gacaccacca cgccggccgg ccgcatggtg ttgaccgtgt cgccggcat    3660 tgccgagttc gagcgttccc taatcatcga ccgcacccgg agcgggcgcg aggccgccaa    3720
ggcccgaggc gtgaagtttg gcccccgccc taccctcacc ccggcacaga tcgcgcacgc    3780
ccgcgagctg atcgaccagg aaggccgcac cgtgaaagag gcggctgcac tgcttggcgt    3840
gcatcgctcg accctgtacc gcgcacttga gcgcagcgag gaagtgacgc gccaccgaggc    3900 caggcggcgc ggtgccttcc gtgaggacgc attgaccgag gccgacgccc tggcggccgc    3960
cgagaatgaa cgccaagagg aacaagcatg aaaccgcacc aggacggcca ggacgaaccg    4020
tttttcatta ccgaagagat cgaggcggag atgatcgcgg ccgggtacgt gttcgagccg    4080
cccgcgcacg tctcaaccgt gcggctgcat gaaatcctgg ccggtttgtc tgatgccaag    4140
ctggcggcct ggccggccag cttggccgct gaagaaaccg agcgccgccg tctaaaaagg    4200
tgatgtgtat ttgagtaaaa cagcttgcgt catgcggtcg ctgcgtatat gatgcgatga    4260
gtaaataaac aaatacgcaa ggggaacgca tgaaggttat cgctgtactt aaccagaaag    4320
gcgggtcagg caagacgacc atcgcaaccc atctagcccg cgccctgcaa ctcgccgggg    4380
```

```
ccgatgttct gttagtcgat tccgatcccc agggcagtgc ccgcgattgg gcggccgtgc   4440
gggaagatca accgctaacc gttgtcggca tcgaccgccc gacgattgac cgcgacgtga   4500
aggccatcgg ccggcgcgac ttcgtagtga tcgacggagc gccccaggcg gcggacttgg   4560
ctgtgtccgc gatcaaggca gccgacttcg tgctgattcc ggtgcagcca agcccttacg   4620
acatatgggc caccgccgac ctggtggagc tggttaagca gcgcattgag gtcacggatg   4680
gaaggctaca agcggccttt gtcgtgtcgc gggcgatcaa aggcacgcgc atcgcggtg    4740 aggttgccga ggcgctggcc gggtacgagc tgcccattct tgagtcccgt atcacgcagc   4800
gcgtgagcta cccaggcact gccgccgccg gcacaaccgt tcttgaatca gaacccgagg   4860
gcgacgctgc ccgcgaggtc caggcgctgg ccgctgaaat taaatcaaaa ctcatttgag   4920
ttaatgaggt aaagagaaaa tgagcaaaag cacaaacacg ctaagtgccg gccgtccgag   4980
cgcacgcagc agcaaggctg caacgttggc cagcctggca gacacgccag ccatgaagcg   5040
ggtcaacttt cagttgccgg cggaggatca caccaagctg aagatgtacg cggtacgcca   5100
aggcaagacc attaccgagc tgctatctga atacatcgcg cagctaccag agtaaatgag   5160
caaatgaata aatgagtaga tgaattttag cggctaaagg aggcggcatg gaaaatcaag   5220
aacaaccagg caccgacgcc gtggaatgcc ccatgtgtgg aggaacgggc ggttggccag   5280
gcgtaagcgg ctgggttgtc tgccggccct gcaatggcac tggaaccccc aagcccgagg   5340
aatcggcgtg acggtcgcaa accatccggc ccggtacaaa tcggcgcggc gctgggtgat   5400
gacctggtgg agaagttgaa ggccgcgcag gccgcccagc ggcaacgcat cgaggcagaa   5460
gcacgccccg gtgaatcgtg gcaagcggcc gctgatcgaa tccgcaaaga atcccggcaa   5520
ccgccggcag ccggtgcgcc gtcgattagg aagccgccca agggcgacga gcaaccagat   5580
tttttcgttc cgatgctcta tgacgtgggc acccgcgata gtcgcagcat catggacgtg   5640
gccgttttcc gtctgtcgaa gcgtgaccga cgagctggcg aggtgatccg ctacgagctt   5700
ccagacgggc acgtagaggt ttccgcaggg ccggccggca tggccagtgt gtgggattac   5760
gacctggtac tgatggcggt ttcccatcta accgaatcca tgaaccgata ccgggaaggg   5820
aagggagaca gccccggccg cgtgttccgt ccacacgttg cggacgtact caagttctgc   5880
cggcgagccg atggcggaaa gcagaaagac gacctggtag aaacctgcat tcggttaaac   5940
accacgcacg ttgccatgca gcgtacgaag aaggccaaga acggccgcct ggtgacggta   6000
tccgagggtg aagccttgat tagccgctac aagatcgtaa agagcgaaac cgggcggccg   6060
gagtacatcg agatcgagct agctgattgg atgtaccgcg agatcacaga aggcaagaac   6120
ccggacgtgc tgacggttca ccccgattac tttttgatcg atcccggcat cggccgtttt   6180
ctctaccgcc tggcacgccg cgccgcaggc aaggcagaag ccagatggtt gttcaagacg   6240
atctacgaac gcagtggcag cgccggagag ttcaagaagt tctgtttcac cgtgcgcaag   6300
ctgatcgggt caaatgacct gccggagtac gatttgaagg aggaggcggg gcaggctggc   6360
ccgatcctag tcatgcgcta ccgcaacctg atcgagggcg aagcatccgc cggttcctaa   6420
tgtacggagc agatgctagg gcaaattgcc ctagcagggg aaaaaggtcg aaaaggtctc   6480
tttcctgtgg atagcacgta cattgggaac ccaaagccgt acattgggaa ccggaacccg   6540
tacattggga acccaaagcc gtacattggg aaccggtcac acatgtaagt gactgatata   6600
aaagagaaaa aaggcgattt ttccgcctaa aactctttaa aacttattaa aactcttaaa   6660
acccgcctgg cctgtgcata actgtctggc cagcgcacag ccgaagagct gcaaaaagcg   6720
cctacccttc ggtcgctgcg ctccctacgc cccgccgctt cgcgtcggcc tatcgcggcc   6780
```

```
gctggccgct caaaaatggc tggcctacgg ccaggcaatc taccagggcg cggacaagcc     6840
gcgccgtcgc cactcgaccg ccggcgccca catcaaggca ccctgcctcg cgcgtttcgg     6900
tgatgacggt gaaaacctct gacacatgca gctcccggag acggtcacag cttgtctgta     6960
agcggatgcc gggagcagac aagcccgtca gggcgcgtca gcgggtgttg gcgggtgtcg     7020
gggcgcagcc atgacccagt cacgtagcga tagcggagtg tatactggct taactatgcg     7080
gcatcagagc agattgtact gagagtgcac catatgcggt gtgaaatacc gcacagatgc     7140
gtaaggagaa aataccgcat caggcgctct ccgcttcct cgctcactga ctcgctgcgc     7200
tcggtcgttc ggctgcggcg agcggtatca gctcactcaa aggcggtaat acggttatcc     7260
acagaatcag gggataacgc aggaaagaac atgtgagcaa aaggccagca aaaggccagg     7320
aaccgtaaaa aggccgcgtt gctggcgttt ttccataggc tccgcccccc tgacgagcat     7380
cacaaaaatc gacgctcaag tcagaggtgg cgaaacccga caggactata aagataccag     7440
gcgtttcccc ctggaagctc cctcgtgcgc tctcctgttc cgaccctgcc gcttaccgga     7500
tacctgtccg cctttctccc ttcgggaagc gtggcgcttt ctcatagctc acgctgtagg     7560
tatctcagtt cggtgtaggt cgttcgctcc aagctgggct gtgtgcacga acccccgtt     7620 cagcccgacc gctgcgcctt atccggtaac tatcgtcttg agtccaaccc ggtaagacac     7680
gacttatcgc cactggcagc agccactggt aacaggatta gcagagcgag gtatgtaggc     7740
ggtgctacag agttcttgaa gtggtggcct aactacggct acactagaag gacagtattt     7800
ggtatctgcg ctctgctgaa gccagttacc ttcggaaaaa gagttggtag ctcttgatcc     7860
ggcaaacaaa ccaccgctgg tagcggtggt ttttttgttt gcaagcagca gattacgcgc     7920
agaaaaaaag gatctcaaga agatcctttg atcttttcta cggggtctga cgctcagtgg     7980
aacgaaaact cacgttaagg gattttggtc atgcattcta ggtactaaaa caattcatcc     8040
agtaaaatat aatattttat tttctcccaa tcaggcttga tccccagtaa gtcaaaaaat     8100
agctcgacat actgttcttc cccgatatcc tccctgatcg accggacgca gaaggcaatg     8160
tcataccact tgtccgccct gccgcttctc ccaagatcaa taaagccact tactttgcca     8220
tctttcacaa agatgttgct gtctcccagg tcgccgtggg aaaagacaag ttcctcttcg     8280 ggctttccg tctttaaaaa atcatacagc tcgcgcggat ctttaaatgg agtgtcttct     8340
tcccagtttt cgcaatccac atcggccaga tcgttattca gtaagtaatc caattcggct     8400
aagcggctgt ctaagctatt cgtataggga caatccgata tgtcgatgga gtgaaagagc     8460
ctgatgcact ccgcatacag ctcgataatc ttttcagggc tttgttcatc ttcatactct     8520
tccgagcaaa ggacgccatc ggcctcactc atgagcagat tgctccagcc atcatgccgt     8580
tcaaagtgca ggacctttgg aacaggcagc tttccttcca gccatagcat catgtccttt     8640
tcccgttcca catcataggt ggtccctta taccggctgt ccgtcatttt taaatatagg     8700
ttttcatttt ctcccaccag cttatatacc ttagcaggag acattccttc cgtatctttt     8760
acgcagcggt attttttcgat cagttttttc aattccggtg atattctcat tttagccatt     8820
tattatttcc ttcctctttt ctacagtatt taaagatacc ccaagaagct aattataaca     8880
agacgaactc caattcactg ttccttgcat tctaaaacct taaataccag aaaacagctt     8940
tttcaaagtt gttttcaaag ttggcgtata acatagtatc gacggagccg attttgaaac     9000
cgcggtgatc acaggcagca acgctctgtc atcgttacaa tcaacatgct accctccgcg     9060
agatcatccg tgtttcaaac ccggcagctt agttgccgtt cttccgaata gcatcggtaa     9120
```

```
catgagcaaa gtctgccgcc ttacaacggc tctcccgctg acgccgtccc ggactgatgg      9180
gctgcctgta tcgagtggtg attttgtgcc gagctgccgg tcggggagct gttggctggc      9240
tggtggcagg atatattgtg gtgtaaacaa attgacgctt agacaactta ataacacatt      9300
gcggacgttt ttaatgtact gaattaacgc cgaattaatt cctaggccac catgttgggc      9360
ccggcgcgcc aagcttgcat gcctgcaggt caacatggtg gagcacgaca ctctcgtcta      9420
ctccaagaat atcaaagata cagtctcaga agaccagagg gctattgaga cttttcaaca      9480
aagggtaata tcgggaaacc tcctcggatt ccattgccca gctatctgtc acttcatcga      9540
aaggacagta gaaaggaag atggcttcta caaatgccat cattgcgata aaggaaaggc      9600
tatcgttcaa gatgcctcta ccgacagtgg tcccaaagat ggacccccac ccacgaggaa      9660
catcgtggaa aaagaagacg ttccaaccac gtcttcaaag caagtggatt gatgtgatgg      9720
tcaacatggt ggagcacgac actctcgtct actccaagaa tatcaaagat acagtctcag      9780
aagaccagag ggctattgag acttttcaac aaagggtaat atcgggaaac ctcctcggat      9840
tccattgccc agctatctgt cacttcatcg aaaggacagt agaaaaggaa gatggcttct      9900
acaaatgcca tcattgcgat aaaggaaagg ctatcgttca agatgcctct accgacagtg      9960
gtcccaaaga tggaccccca cccacgagga acatcgtgga aaaagaagac gttccaacca    10020
cgtcttcaaa gcaagtggat tgatgtgata tctccactga cgtaagggat gacgcacaat    10080
cccactatcc ttcgcaagac ccttcctcta tataaggaag ttcatttcat ttggagagg     10139
```

```
<210> SEQ ID NO 41
<211> LENGTH: 9598
<212> TYPE: DNA
<213> ORGANISM: Artificial
<220> FEATURE:
<223> OTHER INFORMATION: synthetic oligonucleotide

<400> SEQUENCE: 41
ggggagctgt tggctggctg gtggcaggat atattgtggt gtaaacaaat tgacgcttag        60
acaacttaat aacacattgc ggacgttttt aatgtactga attaacgccg aattaattcc       120
taggccacca tgttgggccc ggcgcgccaa gcttgcatgc ctgcaggtca acatggtgga       180
gcacgacact ctcgtctact ccaagaatat caaagataca gtctcagaag accagagggc       240
tattgagact tttcaacaaa gggtaatatc gggaaacctc ctcggattcc attgcccagc       300
tatctgtcac ttcatcgaaa ggacagtaga aaaggaagat ggcttctaca atgccatca       360 ttgcgataaa ggaaaggcta tcgttcaaga tgcctctacc gacagtggtc ccaaagatgg       420
accccacccc acgaggaaca tcgtggaaaa agaagacgtt ccaaccacgt cttcaaagca       480
agtggattga tgtgatggtc aacatggtgg agcacgacac tctcgtctac tccaagaata       540
tcaaagatac agtctcagaa gaccagaggg ctattgagac ttttcaacaa agggtaatat       600
cgggaaacct cctcggattc cattgcccag ctatctgtca cttcatcgaa aggacagtag       660
aaaaggaaga tggcttctac aaatgccatc attgcgataa aggaaaggct atcgttcaag       720
atgcctctac cgacagtggt cccaaagatg accccccacc cacgaggaac atcgtggaaa       780
aagaagacgt tccaaccacg tcttcaaagc aagtggattg atgtgatatc tccactgacg       840
taagggatga cgcacaatcc cactatcctt cgcaagaccc ttcctctata taaggaagtt       900
catttcattt ggagaggata aaacattgca cctatggtgt tgccctggct ggggtatgtc       960
agtgatcgca gtagaatgta ctaattgaca agttggagaa tacggtagaa cgtccttatc      1020
caacacagcc tttatccctc tccctgacga ggtttttgtc agtgtaatat ttcttttga      1080
```

-continued

```
actatccagc ttagtaccgt acgggaaagt gactggtgtg cttatctttg aaatgttact    1140
ttgggtttcg gttctttagg ttagtaagaa agcacttgtc ttctcataca aaggaaaacc    1200
tgagacgtat cgcttacgaa agtagcaatg aaagaaaggt ggtggtttta atcgctaccg    1260
caaaaacgat ggggtcgttt taattaactt ctcctacgca agcgtctaaa cggacgttgg    1320
ggttttgcta gtttctttag agaaaactag ctaagtcttt aatgttatca ttagagatgg    1380
cataaatata atacttgtgt ctgctgataa gatcatttta atttggacga ttagacttgt    1440
tgaactacag gttactgaat cacttgcgct aatcaacatg ggagatatgt acgatgaatc    1500
atttgacaag tcgggcggtc ctgctgactt gatggacgat tcttgggtgg aatcagtttc    1560
gtggaaagat ctgttgaaga agttacacag cataaaattt gcactacagt ctggtagaga    1620
tgagatcact gggttactag cggcactgaa tagacagtc ccttattcac catatgagca      1680
gtttccagat aagaaggtgt atttcctttt agactcacgg gctaacagtg ctcttggtgt      1740
gattcagaac gcttcagcgt tcaagagacg agctgatgag aagaatgcag tggcgggtgt      1800
tacaaatatt cctgcgaatc caaacacaac ggttacgacg aaccaaggga gtactactac      1860
taccaaggcg aacactggct cgactttgga agaagacttg tacacttatt acaaattcga      1920
tgatgcctct acagctttcc acaaatctct aacttcgtta gagaacatgg agttgaagag      1980
ttattaccga aggaactttg agaaagtatt cgggattaag tttggtggag cagctgctag      2040
ttcatctgca ccgcctccag cgagtggagg tccgatacgt cctaatccct agggatttaa      2100
ggacgtgaac tctgttgaga tctctgtgaa attcagaggg tgggtgatac catattcact      2160
gatgccatta gcgacatcta aatagggcta attgtgacta atttgaggga atttccttta      2220
ccattgacgt cagtgtcgtt ggtagcattt gagtttcgga gcatcttgtt ctggggtttc      2280
acactatctt tagagaaagt gttaagttaa ttaagttatc ttaattaaga gcataattat      2340
actgatttgt ctctcgttga tagagtctat cattctgtta ctaaaaattt gacaactcgg      2400
tttgctgacc tactggttac tgtatcactt acccgagtta acgagtctag aaacttggta      2460
gtagcgactc catggtttta gagctagaaa tagcaagtta aaataaggct agtccgttat      2520
caacttgaaa aagtggcacc gagtcggtgc agtgccgggc atgtcccgaa gacattaaac      2580
tacggttctt taagtagatc cgtgtctgaa gttttaggtt caatttaaac ctacgagatt      2640
gacattctcg actgatcttg attgatcggt aagtcttttg taatttaatt ttctttttga      2700
ttttatttta aattgttatc tgtttctgtg tatagactgt ttgagatcgg cgtttggccg      2760
actcattgtc ttaccatagg ggaacggact ttgtttgtgt tgttatttta tttgtatttt      2820
attaaaattc tcaacgatct gaaaaagcct cgcggctaag agattgttgg ggggtgagta      2880
agtactttta aagtgatgat ggttacaaag gcaaaagggg taaaacccct cgcctacgta      2940
agcgttatta cgcccgtctg tacttatatc agtacactga cgagtcccta aaggacgaaa      3000
cgggagaacg ctagccacca ccaccaccac cacgtgtgaa ttacaggtga ccagctcgaa      3060
tttccccgat cgttcaaaca tttggcaata aagtttctta agattgaatc ctgttgccgg      3120
tcttgcgatg attatcatat aatttctgtt gaattacgtt aagcatgtaa taattaacat      3180
gtaatgcatg acgttatta tgagatgggt ttttatgatt agagtcccgc aattatacat        3240
ttaatacgcg atagaaaaca aaatatagcg cgcaaactag gataaattat cgcgcgcggt        3300
gtcatctatg ttactagatc gggaattaaa ctatcagtgt ttgacaggat atattggcgg        3360
gtaaacctaa gagaaaagag cgtttattag aataacggat atttaaaagg gcgtgaaaag        3420
```

-continued

```
gtttatccgt tcgtccattt gtatgtgcat gccaaccaca gggttcccct cgggatcaaa    3480
gtactttgat ccaacccctc cgctgctata gtgcagtcgg cttctgacgt tcagtgcagc    3540
cgtcttctga aaacgacatg tcgcacaagt cctaagttac gcgacaggct gccgccctgc    3600
ccttttcctg gcgtttttctt gtcgcgtgtt ttagtcgcat aaagtagaat acttgcgact    3660
agaaccggag acattacgcc atgaacaaga gcgccgccgc tggcctgctg ggctatgccc    3720
gcgtcagcac cgacgaccag gacttgacca accaacgggc cgaactgcac gcggccggct    3780
gcaccaagct gttttccgag aagatcaccg gcaccaggcg cgaccgcccg gagctggcca    3840
ggatgcttga ccacctacgc cctggcgacg ttgtgacagt gaccaggcta gaccgcctgg    3900
cccgcagcac ccgcgaccta ctggacattg ccgagcgcat ccaggaggcc ggcgcgggcc    3960
tgcgtagcct ggcagagccg tgggccgaca ccaccacgcc ggccggccgc atggtgttga    4020
ccgtgttcgc cggcattgcc gagttcgagc gttccctaat catcgaccgc acccggagcg    4080
ggcgcgaggc cgccaaggcc cgaggcgtga agtttggccc ccgccctacc ctcacccccgg    4140 cacagatcgc gcacgcccgc gagctgatcg accaggaagg ccgcaccgtg aaagaggcgg    4200
ctgcactgct tggcgtgcat cgctcgaccc tgtaccgcgc acttgagcgc agcgaggaag    4260
tgacgcccac cgaggccagg cggcgcgtg ccttccgtga ggacgcattg accgaggccg    4320
acgccctggc ggccgccgag aatgaacgcc aagaggaaca agcatgaaac cgcaccagga    4380
cggccaggac gaaccgtttt tcattaccga agagatcgag gcggagatga tcgcggccgg    4440
gtacgtgttc gagccgcccg cgcacgtctc aaccgtgcgg ctgcatgaaa tcctggccgg    4500
tttgtctgat gccaagctgg cggcctggcc ggccagcttg gccgctgaag aaaccgagcg    4560
ccgccgtcta aaaggtgat gtgtatttga gtaaacagc ttgcgtcatg cggtcgctgc    4620
gtatatgatg cgatgagtaa ataaacaaat acgcaagggg aacgcatgaa ggttatcgct    4680
gtacttaacc agaaaggcgg gtcaggcaag acgaccatcg caacccatct agcccgcgcc    4740
ctgcaactcg ccggggccga tgttctgtta gtcgattccg atccccaggg cagtgcccgc    4800
gattgggcgg ccgtgcggga agatcaaccg ctaaccgttg tcggcatcga ccgcccgacg    4860
attgaccgcg acgtgaaggc catcggccgg cgcgacttcg tagtgatcga cggagcgccc    4920
caggcggcgg acttggctgt gtccgcgatc aaggcagccg acttcgtgct gattccggtg    4980
cagccaagcc cttacgacat atgggccacc gccgacctgg tggagctggt taagcagcgc    5040
attgaggtca cggatggaag ctacaagcg gcctttgtcg tgtcgcgggc gatcaaaggc    5100
acgcgcatcg cggtgaggt tgccgaggcg ctggccgggt acgagctgcc cattcttgag    5160
tcccgtatca cgcagcgcgt gagctaccca ggcactgccg ccgccggcac aaccgttctt    5220
gaatcagaac ccgagggcga cgctgccccgc gaggtccagg cgctggccgc tgaaattaaa    5280
tcaaaactca tttgagttaa tgaggtaaag agaaaatgag caaaagcaca aacacgctaa    5340
gtgccggccg tccgagcgca cgcagcagca aggctgcaac gttggccagc ctggcagaca    5400
cgccagccat gaagcgggtc aactttcagt tgccggcgga ggatcacacc aagctgaaga    5460
tgtacgcggt acgccaaggc aagaccatta ccgagctgct atctgaatac atcgcgcagc    5520
taccagagta aatgagcaaa tgaataaatg agtagatgaa ttttagcggc taaaggaggc    5580
ggcatggaaa atcaagaaca accaggcacc gacgccgtgg aatgccccat gtgtggagga    5640
acgggcggtt ggccaggcgt aagcggctgg gttgtctgcc ggccctgcaa tggcactgga    5700
acccccaagc ccgaggaatc ggcgtgacgg tcgcaaacca tccggcccgg tacaaatcgg    5760
cgcggcgctg ggtgatgacc tggtggagaa gttgaaggcc gcgcaggccg cccagcggca    5820
```

-continued

```
acgcatcgag gcagaagcac gccccggtga atcgtggcaa gcggccgctg atcgaatccg    5880
caaagaatcc cggcaaccgc cggcagccgg tgcgccgtcg attaggaagc cgcccaaggg    5940
cgacgagcaa ccagattttt tcgttccgat gctctatgac gtgggcaccc gcgatagtcg    6000
cagcatcatg gacgtggccg tttccgtct  gtcgaagcgt gaccgacgag ctggcgaggt    6060
gatccgctac gagcttccag acgggcacgt agaggtttcc gcagggccgg ccggcatggc    6120
cagtgtgtgg gattacgacc tggtactgat ggcggtttcc catctaaccg aatccatgaa    6180
ccgataccgg gaagggaagg gagacaagcc cggccgcgtg ttccgtccac acgttgcgga    6240
cgtactcaag ttctgccggc gagccgatgg cggaaagcag aaagacgacc tggtagaaac    6300
ctgcattcgg ttaaacacca cgcacgttgc catgcagcgt acgaagaagg ccaagaacgg    6360
ccgcctggtg acggtatccg agggtgaagc cttgattagc cgctacaaga tcgtaaagag    6420
cgaaaccggg cggccggagt acatcgagat cgagctagct gattggatgt accgcgagat    6480
cacagaaggc aagaacccgg acgtgctgac ggttcacccc gattactttt tgatcgatcc    6540
cggcatcggc cgttttctct accgcctggc acgccgcgcc gcaggcaagg cagaagccag    6600
atggttgttc aagacgatct acgaacgcag tggcagcgcc ggagagttca agaagttctg    6660
tttcaccgtg cgcaagctga tcgggtcaaa tgacctgccg gagtacgatt tgaaggagga    6720
ggcggggcag gctggcccga tcctagtcat gcgctaccgc aacctgatcg agggcgaagc    6780
atccgccggt tcctaatgta cggagcagat gctagggcaa attgccctag caggggaaaa    6840
aggtcgaaaa ggtctctttc ctgtggatag cacgtacatt gggaacccaa agccgtacat    6900
tgggaaccgg aacccgtaca ttgggaaccc aaagccgtac attgggaacc ggtcacacat    6960
gtaagtgact gatataaaag agaaaaaagg cgatttttcc gcctaaaact ctttaaaact    7020
tattaaaact cttaaaaccc gcctggcctg tgcataactg tctggccagc gcacagccga    7080
agagctgcaa aaagcgccta cccttcggtc gctgcgctcc ctacgccccg ccgcttcgcg    7140
tcggcctatc gcggccgctg gccgctcaaa aatggctggc ctacggccag gcaatctacc    7200
agggcgcgga caagccgcgc cgtcgccact cgaccgccgg cgcccacatc aaggcaccct    7260
gcctcgcgcg tttcggtgat gacggtgaaa acctctgaca catgcagctc ccggagacgg    7320
tcacagcttg tctgtaagcg gatgccggga gcagacaagc ccgtcagggc gcgtcagcgg    7380
gtgttggcgg gtgtcggggc gcagccatga cccagtcacg tagcgatagc ggagtgtata    7440
ctggcttaac tatgcggcat cagagcagat tgtactgaga gtgcaccata tgcggtgtga    7500
aataccgcac agatgcgtaa ggagaaaata ccgcatcagg cgctcttccg cttcctcgct    7560
cactgactcg ctgcgctcgg tcgttcggct gcggcgagcg gtatcagctc actcaaaggc    7620
ggtaatacgg ttatccacag aatcaggggga taacgcagga agaacatgt  gagcaaaagg    7680 ccagcaaaag gccaggaacc gtaaaaaggc cgcgttgctg gcgttttttcc ataggctccg    7740 cccccctgac gagcatcaca aaaatcgacg ctcaagtcag aggtggcgaa acccgacagg    7800
actataaaga taccaggcgt ttccccctgg aagctccctc gtgcgctctc ctgttccgac    7860
cctgccgctt accggatacc tgtccgcctt tctcccttcg ggaagcgtgg cgctttctca    7920
tagctcacgc tgtaggtatc tcagttcggt gtaggtcgtt cgctccaagc tgggctgtgt    7980
gcacgaaccc cccgttcagc ccgaccgctg cgccttatcc ggtaactatc gtcttgagtc    8040
caacccggta agacacgact tatcgccact ggcagcagcc actggtaaca ggattagcag    8100
agcgaggtat gtaggcggtg ctacagagtt cttgaagtgg tggcctaact acggctacac    8160
```

-continued

```
tagaaggaca gtatttggta tctgcgctct gctgaagcca gttaccttcg gaaaaagagt    8220
tggtagctct tgatccggca aacaaaccac cgctggtagc ggtggttttt ttgtttgcaa    8280
gcagcagatt acgcgcagaa aaaaaggatc tcaagaagat cctttgatct tttctacggg    8340
gtctgacgct cagtggaacg aaaactcacg ttaagggatt ttggtcatgc attctaggta    8400
ctaaaacaat tcatccagta aaatataata ttttatttttc tcccaatcag gcttgatccc    8460
cagtaagtca aaaatagct cgacatactg ttcttccccg atatcctccc tgatcgaccg    8520
gacgcagaag gcaatgtcat accacttgtc cgccctgccg cttctcccaa gatcaataaa    8580
gccacttact ttgccatctt tcacaaagat gttgctgtct cccaggtcgc cgtgggaaaa    8640
gacaagttcc tcttcgggct tttccgtctt taaaaaatca tacagctcgc gcggatcttt    8700
aaatggagtg tcttcttccc agttttcgca atccacatcg gccagatcgt tattcagtaa    8760
gtaatccaat tcggctaagc ggctgtctaa gctattcgta tagggacaat ccgatatgtc    8820
gatggagtga agagcctga tgcactccgc atacagctcg ataatctttt cagggctttg    8880
ttcatcttca tactcttccg agcaaaggac gccatcggcc tcactcatga gcagattgct    8940
ccagccatca tgccgttcaa agtgcaggac ctttggaaca ggcagctttc cttccagcca    9000
tagcatcatg tccttttccc gttccacatc ataggtggtc cctttatacc ggctgtccgt    9060 cattttttaaa tataggtttt cattttctcc caccagctta tataccttag caggagacat    9120
tccttccgta tcttttacgc agcggtattt ttcgatcagt tttttcaatt ccggtgtatat    9180 tctcatttta gccatttatt atttccttcc tcttttctac agtatttaaa gatacccaa    9240 gaagctaatt ataacaagac gaactccaat tcactgttcc ttgcattcta aaaccttaaa    9300
taccagaaaa cagctttttc aaagttgttt tcaaagttgg cgtataacat agtatcgacg    9360
gagccgattt tgaaaccgcg gtgatcacag gcagcaacgc tctgtcatcg ttacaatcaa    9420
catgctaccc tccgcgagat catccgtgtt tcaaacccgg cagcttagtt gccgttcttc    9480
cgaatagcat cggtaacatg agcaaagtct gccgccttac aacggctctc ccgctgacgc    9540
cgtcccggac tgatgggctg cctgtatcga gtggtgattt tgtgccgagc tgccggtc      9598
```

```
<210> SEQ ID NO 42
<211> LENGTH: 14351
<212> TYPE: DNA
<213> ORGANISM: Artificial
<220> FEATURE:
<223> OTHER INFORMATION: synthetic oligonucleotide

<400> SEQUENCE: 42
```

```
ggggagctgt tggctggctg gtggcaggat atattgtggt gtaaacaaat tgacgcttag     60
acaacttaat aacacattgc ggacgttttt aatgtactga attaacgccg aattaattcc    120
taggccacca tgttgggccc ggcgcgccaa gcttgcatgc ctgcaggtca acatggtgga    180
gcacgacact ctcgtctact ccaagaatat caaagataca gtctcagaag accagagggc    240
tattgagact tttcaacaaa gggtaatatc gggaaacctc ctcggattcc attgcccagc    300
tatctgtcac ttcatcgaaa ggacagtaga aaggaagat ggcttctaca aatgccatca    360
ttgcgataaa ggaaaggcta tcgttcaaga tgcctctacc gacagtggtc ccaaagatgg    420
acccccaccc acgaggaaca tcgtggaaaa agaagacgtt ccaaccacgt cttcaaagca    480
agtggattga tgtgatggtc aacatggtgg agcacgacac tctcgtctac tccaagaata    540
tcaaagatac agtctcagaa gaccagaggg ctattgagac ttttcaacaa agggtaatat    600
cgggaaacct cctcggattc cattgcccag ctatctgtca cttcatcgaa aggacagtag    660
```

-continued

```
aaaaggaaga tggcttctac aaatgccatc attgcgataa aggaaaggct atcgttcaag      720
atgcctctac cgacagtggt cccaaagatg dacccccacc cacgaggaac atcgtggaaa      780
aagaagacgt tccaaccacg tcttcaaagc aagtggattg atgtgatatc tccactgacg      840
taagggatga cgcacaatcc cactatcctt cgcaagaccc ttcctctata taaggaagtt      900
catttcattt ggagaggata aaacatttca atcctttgaa cgcggtagaa cgtgctaatt      960
ggattttggt gagaacgcgg tagaacgtac ttatcaccta cagttttatt ttgttttttct     1020 ttttggttta atctatccag cttagtaccg agtgggggaa agtgactggt gtgcctaaaa     1080
ccttttcttt gatactttgt aaaaatacat acagatacaa tggcgaacgg taacttcaag     1140
ttgtctcaat tgctcaatgt ggacgagatg tctgctgagc agaggagtca tttctttgac     1200
ttgatgctga ctaaacctga ttgtgagatc gggcaaatga tgcaaagagt tgttgttgat     1260
aaagtcgatg acatgattag agaaagaaag actaaagatc cagtgattgt tcatgaagtt     1320
ctttctcaga aggaacagaa caagttaatg gaaatttatc ctgaattcaa tatcgtgttt     1380
aaagacgaca aaaacatggt tcatgggttt gcggctgctg agcgaaaact acaagcttta     1440
ttgcttttag atagagttcc tgctctgcaa gaggtggatg acatcggtgg tcaatggtcg     1500
ttttgggtaa ctagaggtga gaaaaggatt cattcctgtt gtccaaatct agatattcgg     1560
gatgatcaga gagaaatttc tcgacagata tttcttactg ctattggtga tcaagctaga     1620
agtggtaaga gacagatgtc ggagaatgag ctgtggatgt atgaccaatt tcgtaaaaat     1680 attgctcgc ctaacgcggt taggtgcaat aatacatatc acggttgtac atgtaggggt     1740
ttttctgatg gtaagaagaa aggcgcgcag tatgcgatag ctcttcacag cctgtatgac     1800
ttcaagttga aagacttgat ggctactatg gttgagaaga aaactaaagt gggtcatgct     1860
gctatgcttt ttgctcctga aagtatgtta gtggacgaag gtccattacc ttctgttgac     1920
ggttactaca tgaagaagaa cgggaagatc tatttcggtt ttgagaaaga tccttccttt     1980
tcttacattc atgactggga agagtacaag aagtatctac tggggaagcc agtgagttac     2040
caagggaatg tgttctactt cgaaccgtgg caggtgagag gagacacgat gcttttttcg     2100
atctacagga tagctggagt tccgaggagg tctctatcat cgcaagagta ctaccgaaga     2160
atatatatca gtagatggga aaacatggtt gttgtcccaa ttttcgatct ggtcgaatca     2220
acgcgagagt tggtcaagaa agacctgttt gtagagaaac aattcatgga caagtgtttg     2280
gattacatag ctaggttatc tgaccagcag ctgaccataa gcaatgttaa atcatatttg     2340
agttcaaata attgggtctt attcataaac ggggcggccg tgaagaacaa gcaaagtgta     2400
gattctcgag atttacagtt gttggctcaa actttgctag tgaaggaaca agtggcgaga     2460
cctgtcatga gggagttgcg tgaagcaatt ctgactgaga cgaaacctat cacgtcattg     2520
actgatgtgc tgggtttaat atcaagaaaa atgtggaagc agtttgctaa caagatcgca     2580
gtcggcggat cgttggcat ggttggtact ctaattggat tctatccaaa gaaggtacta     2640
acctgggcga aggacacacc aaatggtcca gaactatgtt acgagaactc gcacaaaacc     2700
aaggtgatag tatttctgag tgttgtgtat gccattggag gaatcacgct tatgcgtcga     2760
gacatccgag atggactggt gaaaaaacta tgtgatatgt ttgatatcaa acggggggcc     2820
catgtcttag acgttgagaa tccgtgccgc tattatgata tcaacgattt ctttagcagt     2880
ctgtattcgg catctgagtc cggtgagacc gtttttaccag atttatccga ggtaaaagcc     2940
aagtctgata agttattgca gcagaagaaa gaaatcgctg acgagtttct aagtgcaaaa     3000
```

-continued

```
ttctctaact attctggcag ttcggtgaga acttctccac catcggtggt cggttcatct    3060
cgaagcggac tgggtctgtt gttggaagac agtaacgtgc tgacccaagc tagagttgga    3120
gtttcaagaa aggtagccga tgaggagatc atggagcagt ttctgagtgg tcttattgac    3180
actgaagcag aaattgacga ggttgttcca gccttttcag ctgaatgtga aagaggggaa    3240
acaagcggta caaaggtgtt gtgtaacctt ttaacgccac caggatttga gaacgtgttg    3300
ccagctgtca aacctttggt cagcaaagga aaaacggtca aacgtgtcga ttacttccaa    3360
gtgatgggag gtgagagatt accaaaaagg ccggttgtca gtggagacga ttctgtggac    3420
gctagaagag agtttctgta ctacttagat gcggagagag tcgctcaaaa tgatgaaatt    3480
atgtctctgt atcgtgacta ttcgagagga gttattcgaa ctggaggtca gaattacccg    3540
cacggactgg gagtgtggga tgtgagatg aagaactggt gcatacgtcc agtggtcact    3600
gaacatgctt atgtgtccaa cccagacaaa cgtatggatg attggtcggg atacttagaa    3660
gtggctgttt gggaacgagg tatgttggtc aacgacttcg cggtcgaaag gatgagtgat    3720
tatgtcatag tttgcgatca gacgtatctt tgcaataaca ggttgatctt ggacaattta    3780
agtgccctgg atctaggacc agttaactgt tcttttgaat tagttgacgg tgtacctggt    3840
tgtggtaagt cgacaatgat tgtcaactca gctaatcctt gtgtcgatgt ggttctctct    3900
actgggagag cagcaaccga cgacttgatc gagagattcg cgagcaaagg ttttccatgc    3960
aaattgaaaa ggagagtgaa gacggttgat tcttttttga tgcattgtgt tgatggttct    4020
ttaaccggag acgtgttgca tttcgatgaa gctctcatgg cccatgctgg tatggtgtac    4080
ttttgcgctc agatagctgg tgctaaacga tgtatctgtc aaggagatca gaatcaaatt    4140
tctttcaagc ctagggtatc tcaagttgat ttgaggtttt ctagtctggt cggaaagttt    4200
gacattgtta cagaaaaaag agaaacttac agaagtccag cagatgtggc tgccgtattg    4260
aacaagtact atactggaga tgtcagaaca cataacgcga ctgctaattc gatgacggtg    4320
aggaagattg tgtctaaaga acaggtttct ttgaagcctg gtgctcagta cataactttc    4380
cttcagtctg agaagaagga gttggtaaat ttgttggcat tgaggaaagt ggcagctaaa    4440
gtgagtacag tacacgagtc gcaaggagag acattcaaag atgtagtcct agtcaggacg    4500
aaacctacgg atgactcaat cgctagaggt cgggagtact taatcgtggc gttgtcgcgt    4560
cacacacaat cacttgtgta tgaaactgtg aaagaggacg atgtaagcaa agagatcagg    4620
gaaagtgccg cgcttacgaa ggcggctttg gcaagatttt ttgttactga gaccgtctta    4680
tgacggtttc ggtctaggtt tgatgttttt agacatcatg aagggccttg cgccgttcca    4740
gattcaggta cgattacgga cttggagatg tggtacgacg ctttgtttcc gggaaattcg    4800
ttaagagact caagcctaga cgggtatttg gtggcaacga ctgattgcaa tttgcgatta    4860
gacaatgtta cgatcaaaag tggaaactgg aaagacaagt ttgctgaaaa agaaacgttt    4920
ctgaaaccgg ttattcgtac tgctatgcct gacaaaagga agactactca gttggagagt    4980
ttgttagcgt tgcagaaaag gaaccaagcg gcacccgatc tacaagaaaa tgtgcacgca    5040
acagttctaa tcgaagagac gatgaagaag ttgaaatctg ttgtctacga tgtgggaaaa    5100
attcgggctg atcctattgt caatagagct caaatggaga gatggtggag aaatcaaagc    5160
acagcggtac aggctaaggt agtagcagat gtgagagagt tacatgaaat agactattcg    5220
tcttacatgt ttatgatcaa atctgacgtg aaacctaaga ctgatttaac accgcaattt    5280
gaatactccg ctctacagac tgttgtgtat cacgagaagt tgatcaactc gttgttcggt    5340
ccaattttca aagaaattaa tgaacgcaag ttggatgcta tgcaaccaca ttttgtgttc    5400
```

-continued

```
aacacgagaa tgacatcgag tgatttaaac gatcgagtga agttcttaaa tacggaagcg      5460
gcttacgact ttgttgagat agacatgtct aaattcgaca agtcggcaaa tcgcttccat      5520
ttacaactgc agctggagat ttacaggtta tttgggctag atgagtgggc ggccttcctt      5580
tgggaggtgt cgcacactca aactactgtg agagatattc aaaatggtat gatggcgcat      5640
atttggtacc aacaaagag tggagatgct gatacttata atgcaaattc agatagaaca      5700
ctgtgtgcac tcttgtctga attaccattg gagaaagcag tcatggttac atatggagga      5760
gatgactcac tgattgcgtt tcctagagga acgcagtttg ttgatccgtg tccaaagttg      5820
gctactaagt ggaatttcga gtgcaagatt tttaagtacg atgtcccaat gttttgtggg      5880
aagttcttgc ttaagacgtc atcgtgttac gagttcgtgc cagatccggt aaaagttctg      5940
acgaagttgg ggaaaaagag tataaaggat gtgcaacatt tagccgagat ctacatctcg      6000
ctgaatgatt ccaatagagc tcttgggaac tacatggtgg tatccaaact gtccgagtct      6060
gtttcagacc ggtatttgta caaaggtgat tctgttcatg cgctttgtgc gctatggaag      6120
catattaaga gttttacagc tctgtgtaca ttattccgag acgaaaacga taaggaattg      6180
aacccggcta aggttgattg gaagaaggca cagagagctg tgtcaaactt ttacgactgg      6240
taatatggaa gacaagtcat tggtcacctt gaagaagaag actttcgaag tctcaaaatt      6300
ctcaaatcta ggggccattg aattgtttgt ggacggtagg aggaagagac cgaagtattt      6360
tcacagaaga agagaaactg tcctaaatca tgttggtggg aagaagagtg aacacaagtt      6420
agacgttttt gaccaaaggg attacaaaat gattaaatct tacgcgtttc taaagatagt      6480
aggtgtacaa ctagttgtaa catcacatct acctgcagat acgcctgggt tcattcaaat      6540
cgatctgttg gattcgagac ttactgagaa aagaaagaga ggaaagacta ttcagagatt      6600
caaagctcga gcttgcgata actgttcagt tgcgcagtac aaggttgaat acagtatttc      6660
cacacaggag aacgtacttg atgtctggaa ggtggggttgt atttctgagg gcgttccggt      6720
ctgtgacggt acatacccctt tcagtatcga agtgtcgcta atatgggttg ctactgattc      6780
gactaggcgc ctcaatgtgg aagaactgaa cagttcggat tacattgaag gcgatttttac      6840 cgatcaagag gtttttcggtg agttcatgtc tttgaaacaa gtggagatga agacgattga      6900
ggcgaagtac gatggtcctt acagaccagc tactactaga cctaagtcat tattgtcaag      6960
tgaagatgtt aagagagcgt ctaataagaa aaactcgtct taatgcataa agaaatttat      7020
tgtcaatatg acgtgtgtac tcaagggttg tgtgaatgaa gtcactgttc ttggtcacga      7080
gacgtgtagt atcggtcatg ctaacaaatt gcgaaagcaa gttgctgaca tggttggtgt      7140
cacacgtagg tgtgcggaaa ataattgtgg atggtttgtc tgtgttgtta tcaatgattt      7200
tacttttgat gtgtataatt gttgtggccg tagtcacctt gaaaagtgtc gtaaacgtgt      7260
tgaaacaaga aatcgagaaa tttggaaaca aattcgacga aatcaagctg aaaacatgtc      7320
tgcgacagct aaaaagtctc ataattcgaa gacctctaag aagaaattca agaggacag      7380 agaatttggg acaccaaaaa gattttttaag agatgatgtt cctttcggga ttgatcgttt      7440
gtttgctttt tgatttttatt ttatattgtt atctgtttct gtgtatagac tgtttgagat      7500
tggcgcttgg ccgactcatt gtcttaccat aggggaacgg actttgtttg tgttgttatt      7560
ttatttgtat tttattaaaa ttctcaatga tctgaaaagg cctcgaggct aagagattat      7620
tggggggtga gtaagtactt ttaaagtgat gatggttaca aaggcaaaag gggtaaaacc      7680
cctcgcctac gtaagcgtta ttacgcccgt ctgtacttat atcagtacac tgacgagtcc      7740
```

-continued

```
ctaaaggacg aaacgggaga acgctagcca ccaccaccac caccacgtgt gaattacagg    7800
tgaccagctc gaatttcccc gatcgttcaa acatttggca ataaagtttc ttaagattga    7860
atcctgttgc cggtcttgcg atgattatca tataatttct gttgaattac gttaagcatg    7920
taataattaa catgtaatgc atgacgttat ttatgagatg ggtttttatg attagagtcc    7980
cgcaattata catttaatac gcgatagaaa acaaaatata gcgcgcaaac taggataaat    8040
tatcgcgcgc ggtgtcatct atgttactag atcgggaatt aaactatcag tgtttgacag    8100
gatatattgg cgggtaaacc taagagaaaa gagcgtttat tagaataacg gatatttaaa    8160
agggcgtgaa aaggtttatc cgttcgtcca tttgtatgtg catgccaacc acagggttcc    8220
cctcgggatc aaagtacttt gatccaaccc ctccgctgct atagtgcagt cggcttctga    8280
cgttcagtgc agccgtcttc tgaaaacgac atgtcgcaca agtcctaagt tacgcgacag    8340
gctgccgccc tgcccttttc ctggcgtttt cttgtcgcgt gttttagtcg cataaagtag    8400
aatacttgcg actagaaccg gagacattac gccatgaaca agagcgccgc cgctggcctg    8460
ctgggctatg cccgcgtcag caccgacgac caggacttga ccaaccaacg ggccgaactg    8520
cacgcggccg gctgcaccaa gctgtttttcc gagaagatca ccggcaccag gcgcgaccgc    8580
ccggagctgg ccaggatgct tgaccaccta cgccctggcg acgttgtgac agtgaccagg    8640
ctagaccgcc tggcccgcag cacccgcgac ctactggaca ttgccgagcg catccaggag    8700
gccggcgcgg gcctgcgtag cctggcagag ccgtgggccg acaccaccac gccggccggc    8760
cgcatggtgt tgaccgtgtt cgccggcatt gccgagttcg agcgttccct aatcatcgac    8820
cgcacccgga gcgggcgcga ggccgccaag gcccgaggcg tgaagtttgg cccccgccct    8880
accctcaccc cggcacagat cgcgcacgcc cgcgagctga tcgaccagga aggccgcacc    8940
gtgaaagagg cggctgcact gcttggcgtg catcgctcga ccctgtaccg cgcacttgag    9000
cgcagcgagg aagtgacgcc caccgaggcc aggcggcgcg gtgccttccg tgaggacgca    9060
ttgaccgagg ccgacgccct ggcggccgcc gagaatgaac gccaagagga acaagcatga    9120
aaccgcacca ggacggccag gacgaaccgt ttttcattac cgaagagatc gaggcggaga    9180
tgatcgcggc cgggtacgtg ttcgagccgc ccgcgcacgt ctcaaccgtg cggctgcatg    9240
aaatcctggc cggtttgtct gatgccaagc tggcggcctg gccggccagc ttggccgctg    9300
aagaaaccga gcgccgccgt ctaaaaaggt gatgtgtatt tgagtaaaac agcttgcgtc    9360
atgcggtcgc tgcgtatatg atgcgatgag taaataaaca aatacgcaag gggaacgcat    9420
gaaggttatc gctgtactta accagaaagg cgggtcaggc aagacgacca tcgcaaccca    9480
tctagcccgc gccctgcaac tcgccggggc cgatgttctg ttagtcgatt ccgatcccca    9540
gggcagtgcc cgcgattggg cggccgtgcg ggaagatcaa ccgctaaccg ttgtcggcat    9600
cgaccgcccg acgattgacc gcgacgtgaa ggccatcggc cggcgcgact cgtagtgat    9660 cgacggagcg ccccaggcgg cggacttggc tgtgtccgcg atcaaggcag ccgacttcgt    9720
gctgattccg gtgcagccaa gcccttacga catatgggcc accgccgacc tggtggagct    9780
ggttaagcag cgcattgagg tcacggatgg aaggctacaa gcggcctttg tcgtgtcgcg    9840
ggcgatcaaa ggcacgcgca tcggcggtga ggttgccgag gcgctggccg ggtacgagct    9900
gcccattctt gagtcccgta tcacgcagcg cgtgagctac ccaggcactg ccgccgccgg    9960
cacaaccgtt cttgaatcag aacccgaggg cgacgctgcc cgcgaggtcc aggcgctggc    10020
cgctgaaatt aaatcaaaac tcatttgagt taatgaggta aagagaaaat gagcaaaagc    10080
acaaacacgc taagtgccgg ccgtccgagc gcacgcagca gcaaggctgc aacgttggcc    10140
```

```
agcctggcag acacgccagc catgaagcgg gtcaactttc agttgccggc ggaggatcac    10200
accaagctga agatgtacgc ggtacgccaa ggcaagacca ttaccgagct gctatctgaa    10260
tacatcgcgc agctaccaga gtaaatgagc aaatgaataa atgagtagat gaattttagc    10320
ggctaaagga ggcggcatgg aaaatcaaga acaaccaggc accgacgccg tggaatgccc    10380
catgtgtgga ggaacgggcg gttggccagg cgtaagcggc tgggttgtct gccggccctg    10440
caatggcact ggaacccca agcccgagga atcggcgtga cggtcgcaaa ccatccggcc    10500
cggtacaaat cggcgcggcg ctgggtgatg acctggtgga gaagttgaag gccgcgcagg    10560
ccgcccagcg gcaacgcatc gaggcagaag cacgcccgg tgaatcgtgg caagcggccg    10620
ctgatcgaat ccgcaaagaa tcccggcaac cgccggcagc cggtgcgccg tcgattagga    10680
agccgcccaa gggcgacgag caaccagatt ttttcgttcc gatgctctat gacgtgggca    10740
cccgcgatag tcgcagcatc atggacgtgg ccgtttccg tctgtcgaag cgtgaccgac    10800
gagctggcga ggtgatccgc tacgagcttc cagacgggca cgtagaggtt ccgcagggc    10860 cggccggcat ggccagtgtg tgggattacg acctggtact gatggcggtt tcccatctaa    10920
ccgaatccat gaaccgatac cgggaaggga agggagacaa gcccggccgc gtgttccgtc    10980
cacacgttgc ggacgtactc aagttctgcc ggcgagccga tggcggaaag cagaaagacg    11040
acctggtaga aacctgcatt cggttaaaca ccacgcacgt tgccatgcag cgtacgaaga    11100
aggccaagaa cggccgcctg gtgacggtat ccgagggtga agccttgatt agccgctaca    11160
agatcgtaaa gagcgaaacc gggcggccgg agtacatcga gatcgagcta gctgattgga    11220
tgtaccgcga gatcacagaa ggcaagaacc cggacgtgct gacggttcac cccgattact    11280
ttttgatcga tcccggcatc ggccgttttc tctaccgcct ggcacgccgc gccgcaggca    11340
aggcagaagc cagatggttg ttcaagacga tctacgaacg cagtggcagc gccggagagt    11400
tcaagaagtt ctgtttcacc gtgcgcaagc tgatcgggtc aaatgacctg ccggagtacg    11460
atttgaagga ggaggcgggg caggctggcc cgatcctagt catgcgctac cgcaacctga    11520
tcgagggcga agcatccgcc ggttcctaat gtacggagca gatgctaggg caaattgccc    11580 tagcaggggga aaaaggtcga aaaggtctct ttcctgtgga tagcacgtac attgggaacc    11640
caaagccgta cattgggaac cggaacccgt acattgggaa cccaaagccg tacattggga    11700
accggtcaca catgtaagtg actgatataa aagagaaaaa aggcgatttt ccgcctaaa    11760 actctttaaa acttattaaa actcttaaaa cccgcctggc ctgtgcataa ctgtctggcc    11820
agcgcacagc cgaagagctg caaaaagcgc ctacccttcg gtcgctgcgc tccctacgcc    11880
ccgccgcttc gcgtcggcct atcgcggccg ctggccgctc aaaaatggct ggcctacggc    11940
caggcaatct accagggcgc ggacaagccg cgccgtcgcc actcgaccgc cggcgcccac    12000
atcaaggcac cctgcctcgc gcgtttcggt gatgacggtg aaaacctctg acacatgcag    12060
ctcccggaga cggtcacagc ttgtctgtaa gcggatgccg ggagcagaca gcccgtcag    12120 ggcgcgtcag cgggtgttgg cgggtgtcgg ggcgcagcca tgacccagtc acgtagcgat    12180
agcggagtgt atactggctt aactatgcgg catcagagca gattgtactg agagtgcacc    12240
atatgcggtg tgaaataccg cacagatgcg taaggagaaa ataccgcatc aggcgctctt    12300
ccgcttcctc gctcactgac tcgctgcgct cggtcgttcg gctgcggcga gcggtatcag    12360
ctcactcaaa ggcggtaata cggttatcca cagaatcagg ggataacgca ggaaagaaca    12420
tgtgagcaaa aggccagcaa aaggccagga accgtaaaaa ggccgcgttg ctggcgtttt    12480
```

-continued

```
tccataggct ccgcccccct gacgagcatc acaaaaatcg acgctcaagt cagaggtggc      12540
gaaacccgac aggactataa agataccagg cgtttccccc tggaagctcc ctcgtgcgct      12600
ctcctgttcc gaccctgccg cttaccggat acctgtccgc ctttctccct tcgggaagcg      12660
tggcgctttc tcatagctca cgctgtaggt atctcagttc ggtgtaggtc gttcgctcca      12720
agctgggctg tgtgcacgaa ccccccgttc agcccgaccg ctgcgcctta tccggtaact      12780
atcgtcttga gtccaacccg gtaagacacg acttatcgcc actggcagca gccactggta      12840
acaggattag cagagcgagg tatgtaggcg gtgctacaga gttcttgaag tggtggccta      12900
actacggcta cactagaagg acagtatttg gtatctgcgc tctgctgaag ccagttacct      12960
tcggaaaaag agttggtagc tcttgatccg gcaaacaaac caccgctggt agcggtggtt      13020 ttttgtttg caagcagcag attacgcgca gaaaaaaagg atctcaagaa gatcctttga      13080
tcttttctac ggggtctgac gctcagtgga acgaaaactc acgttaaggg attttggtca      13140
tgcattctag gtactaaaac aattcatcca gtaaaatata atattttatt ttctcccaat      13200
caggcttgat ccccagtaag tcaaaaaata gctcgacata ctgttcttcc ccgatatcct      13260
ccctgatcga ccggacgcag aaggcaatgt cataccactt gtccgccctg ccgcttctcc      13320
caagatcaat aaagccactt actttgccat cttttcacaaa gatgttgctg tctcccaggt      13380
cgccgtggga aaagacaagt tcctcttcgg gctttttccgt ctttaaaaaa tcatacagct      13440
cgcgcggatc tttaaatgga gtgtcttctt cccagttttc gcaatccaca tcggccgat      13500 cgttattcag taagtaatcc aattcggcta agcggctgtc taagctattc gtatagggac      13560
aatccgatat gtcgatggag tgaaagagcc tgatgcactc cgcatacagc tcgataatct      13620
tttcagggct ttgttcatct tcatactctt ccgagcaaag gacgccatcg gcctcactca      13680
tgagcagatt gctccagcca tcatgccgtt caaagtgcag gacctttgga acaggcagct      13740
ttccttccag ccatagcatc atgtcctttt cccgttccac atcataggtg gtccctttat      13800
accggctgtc cgtcatttt aaatataggt tttcattttc tcccaccagc ttatatacct      13860
tagcaggaga cattccttcc gtatctttta cgcagcggta tttttcgatc agttttttca      13920
attccggtga tattctcatt ttagccattt attatttcct tcctctttttc tacagtattt      13980 aaagataccc caagaagcta attataacaa gacgaactcc aattcactgt tccttgcatt      14040
ctaaaacctt aaataccaga aaacagcttt ttcaaagttg ttttcaaagt tggcgtataa      14100
catagtatcg acggagccga ttttgaaacc gcggtgatca caggcagcaa cgctctgtca      14160
tcgttacaat caacatgcta ccctccgcga gatcatccgt gtttcaaacc cggcagctta      14220
gttgccgttc ttccgaatag catcggtaac atgagcaaag tctgccgcct tacaacggct      14280
ctcccgctga cgccgtcccg gactgatggg ctgcctgtat cgagtggtga ttttgtgccg      14340
agctgccggt c                                                          14351
```

```
<210> SEQ ID NO 43
<211> LENGTH: 9598
<212> TYPE: DNA
<213> ORGANISM: Artificial
<220> FEATURE:
<223> OTHER INFORMATION: synthetic oligonucleotide

<400> SEQUENCE: 43
ataaaacatt gcacctatgg tgttgccctg gctggggtat gtcagtgatc gcagtagaat        60
gtactaattg acaagttgga gaatacggta gaacgtcctt atccaacaca gcctttatcc       120
ctctccctga cgaggttttt gtcagtgtaa tatttctttt tgaactatcc agcttagtac       180
```

```
cgtacgggaa agtgactggt gtgcttatct ttgaaatgtt actttgggtt tcggttcttt      240
aggttagtaa gaaagcactt gtcttctcat acaaaggaaa acctgagacg tatcgcttac      300
gaaagtagca atgaaagaaa ggtggtggtt ttaatcgcta ccgcaaaaac gatggggtcg      360
ttttaattaa cttctcctac gcaagcgtct aaacggacgt tggggttttg ctagtttctt      420
tagagaaaac tagctaagtc tttaatgtta tcattagaga tggcataaat ataatacttg      480
tgtctgctga taagatcatt ttaatttgga cgattagact tgttgaacta caggttactg      540
aatcacttgc gctaatcaac atgggagata tgtacgatga atcatttgac aagtcgggcg      600
gtcctgctga cttgatggac gattcttggg tggaatcagt ttcgtggaaa gatctgttga      660
agaagttaca cagcataaaa tttgcactac agtctggtag agatgagatc actgggttac      720
tagcggcact gaatagacag tgtccttatt caccatatga gcagtttcca gataagaagg      780
tgtatttcct tttagactca cgggctaaca gtgctcttgg tgtgattcag aacgcttcag      840
cgttcaagag acgagctgat gagaagaatg cagtggcggg tgttacaaat attcctgcga      900
atccaaacac aacggttacg acgaaccaag ggagtactac tactaccaag gcgaacactg      960
gctcgacttt ggaagaagac ttgtacactt attacaaatt cgatgatgcc tctacagctt     1020
tccacaaatc tctaacttcg ttagagaaca tggagttgaa gagttattac cgaaggaact     1080
ttgagaaagt attcgggatt aagtttggtg gagcagctgc tagttcatct gcaccgcctc     1140
cagcgagtgg aggtccgata cgtcctaatc cctagggatt taaggacgtg aactctgttg     1200
agatctctgt gaaattcaga gggtgggtga taccatattc actgatgcca ttagcgacat     1260
ctaaataggg ctaattgtga ctaatttgag ggaatttcct ttaccattga cgtcagtgtc     1320
gttggtagca tttgagtttc ggagcatctt gttctggggt ttcacactat ctttagagaa     1380
agtgttaagt taattaagtt atcttaatta agagcataat tatactgatt tgtctctcgt     1440
tgatagagtc tatcattctg ttactaaaaa tttgacaact cggtttgctg acctactggt     1500
tactgtatca cttacccgag ttaacgagtc tagaaacgtg tgaaagaaac aattgaggtt     1560
ttagagctag aaatagcaag ttaaaataag gctagtccgt tatcaacttg aaaaagtggc     1620
accgagtcgg tgcagtgccg ggcatgtccc gaagacatta aactacggtt ctttaagtag     1680
atccgtgtct gaagttttag gttcaattta aacctacgag attgacattc tcgactgatc     1740
ttgattgatc ggtaagtctt ttgtaattta attttctttt tgattttatt ttaaattgtt     1800
atctgtttct gtgtatagac tgtttgagat cggcgtttgg ccgactcatt gtcttaccat     1860
aggggaacgg actttgtttg tgttgttatt ttatttgtat tttattaaaa ttctcaacga     1920
tctgaaaaag cctcgcggct aagagattgt tgggggtga gtaagtactt ttaaagtgat     1980
gatggttaca aaggcaaaag gggtaaaacc cctcgcctac gtaagcgtta ttacgcccgt     2040
ctgtacttat atcagtacac tgacgagtcc ctaaaggacg aaacgggaga acgctagcca     2100
ccaccaccac caccacgtgt gaattacagg tgaccagctc gaattcccc gatcgttcaa      2160 acatttggca ataaagtttc ttaagattga atcctgttgc cggtcttgcg atgattatca     2220
tataatttct gttgaattac gttaagcatg taataattaa catgtaatgc atgacgttat     2280
ttatgagatg ggtttttatg attagagtcc cgcaattata catttaatac gcgatagaaa     2340
acaaaatata gcgcgcaaac taggataaat tatcgcgcgc ggtgtcatct atgttactag     2400
atcgggaatt aaactatcag tgtttgacag gatatattgg cgggtaaacc taagagaaaa     2460
gagcgtttat tagaataacg gatatttaaa agggcgtgaa aaggtttatc cgttcgtcca     2520
```

-continued

```
tttgtatgtg catgccaacc acagggttcc cctcgggatc aaagtacttt gatccaaccc   2580
ctccgctgct atagtgcagt cggcttctga cgttcagtgc agccgtcttc tgaaaacgac   2640
atgtcgcaca agtcctaagt tacgcgacag gctgccgccc tgcccttttc ctggcgtttt   2700
cttgtcgcgt gttttagtcg cataaagtag aatacttgcg actagaaccg agacacattac  2760 gccatgaaca agagcgccgc cgctggcctg ctgggctatg cccgcgtcag caccgacgac   2820
caggacttga ccaaccaacg ggccgaactg cacgcggccg gctgcaccaa gctgttttcc   2880
gagaagatca ccggcaccag gcgcgaccgc ccggagctgg ccaggatgct tgaccaccta   2940
cgccctggcg acgttgtgac agtgaccagg ctagaccgcc tggcccgcag cacccgcgac   3000
ctactggaca ttgccgagcg catccaggag gccggcgcgg gcctgcgtag cctggcagag   3060
ccgtgggccg acaccaccac gccggccggc cgcatggtgt tgaccgtgtt cgccggcatt   3120
gccgagttcg agcgttccct aatcatcgac cgcacccgga gcgggcgcga ggccgccaag   3180
gcccgaggcg tgaagtttgg cccccgccct accctcaccc cggcacagat cgcgcacgcc   3240
cgcgagctga tcgaccagga aggccgcacc gtgaaagagg cggctgcact gcttggcgtg   3300
catcgctcga ccctgtaccg cgcacttgag cgcagcgagg aagtgacgcc caccgaggcc   3360
aggcggcgcg gtgccttccg tgaggacgca ttgaccgagg ccgacgccct ggcggccgcc   3420
gagaatgaac gccaagagga acaagcatga aaccgcacca ggacggccag gacgaaccgt   3480
ttttcattac cgaagagatc gaggcggaga tgatcgcggc cgggtacgtg ttcgagccgc   3540
ccgcgcacgt ctcaaccgtg cggctgcatg aaatcctggc cggtttgtct gatgccaagc   3600
tggcggcctg gccggccagc ttggccgctg aagaaaccga gcgccgccgt ctaaaaaggt   3660
gatgtgtatt tgagtaaaac agcttgcgtc atgcggtcgc tgcgtatatg atgcgatgag   3720
taaataaaca aatacgcaag gggaacgcat gaaggttatc gctgtactta accagaaagg   3780
cgggtcaggc aagacgacca tcgcaaccca tctagcccgc gccctgcaac tcgccggggc   3840
cgatgttctg ttagtcgatt ccgatcccca gggcagtgcc cgcgattggg cggccgtgcg   3900
ggaagatcaa ccgctaaccg ttgtcggcat cgaccgcccg acgattgacc gcgacgtgaa   3960
ggccatcggc cggcgcgact tcgtagtgat cgacggagcg ccccaggcgg cggacttggc   4020
tgtgtccgcg atcaaggcag ccgacttcgt gctgattccg gtgcagccaa gcccttacga   4080
catatgggcc accgccgacc tggtggagct ggttaagcag cgcattgagg tcacggatgg   4140
aaggctacaa gcggcctttg tcgtgtcgcg ggcgatcaaa ggcacgcgca tcggcggtga   4200
ggttgccgag gcgctggccg ggtacgagct gcccattctt gagtcccgta tcacgcagcg   4260
cgtgagctac ccaggcactg ccgccgccgg cacaaccgtt cttgaatcag aacccgaggg   4320
cgacgctgcc cgcgaggtcc aggcgctggc cgctgaaatt aaatcaaaac tcatttgagt   4380
taatgaggta aagagaaaat gagcaaaagc acaaacacgc taagtgccgg ccgtccgagc   4440
gcacgcagca gcaaggctgc aacgttggcc agcctggcag acacgccagc catgaagcgg   4500
gtcaactttc agttgccggc ggaggatcac accaagctga agatgtacgc ggtacgccaa   4560
ggcaagacca ttaccgagct gctatctgaa tacatcgcgc agctaccaga gtaaatgagc   4620
aaatgaataa atgagtagat gaattttagc ggctaaagga ggcggcatgg aaaatcaaga   4680
acaaccaggc accgacgccg tggaatgccc catgtgtgga ggaacgggcg gttggccagg   4740
cgtaagcggc tgggttgtct gccggccctg caatggcact ggaacccca agcccgagga   4800 atcgcgtga cggtcgcaaa ccatccggcc cggtacaaat cggcgcggcg ctgggtgatg   4860
acctggtgga gaagttgaag gccgcgcagg ccgcccagcg gcaacgcatc gaggcagaag   4920
```

-continued

```
cacgccccgg tgaatcgtgg caagcggccg ctgatcgaat ccgcaaagaa tcccggcaac      4980
cgccggcagc cggtgcgccg tcgattagga agccgcccaa gggcgacgag caaccagatt      5040
ttttcgttcc gatgctctat gacgtgggca cccgcgatag tcgcagcatc atggacgtgg      5100
ccgttttccg tctgtcgaag cgtgaccgac gagctggcga ggtgatccgc tacgagcttc      5160
cagacgggca cgtagaggtt tccgcagggc cggccggcat ggccagtgtg tgggattacg      5220
acctggtact gatggcggtt tcccatctaa ccgaatccat gaaccgatac cgggaaggga      5280
agggagacaa gcccggccgc gtgttccgtc cacacgttgc ggacgtactc aagttctgcc      5340
ggcgagccga tggcggaaag cagaaagacg acctggtaga aacctgcatt cggttaaaca      5400
ccacgcacgt tgccatgcag cgtacgaaga aggccaagaa cggccgcctg gtgacggtat      5460
ccgagggtga agccttgatt agccgctaca agatcgtaaa gagcgaaacc gggcggccgg      5520
agtacatcga gatcgagcta gctgattgga tgtaccgcga gatcacagaa ggcaagaacc      5580
cggacgtgct gacggttcac cccgattact ttttgatcga tcccggcatc ggccgttttc      5640
tctaccgcct ggcacgccgc gccgcaggca aggcagaagc cagatggttg ttcaagacga      5700
tctacgaacg cagtggcagc gccggagagt tcaagaagtt ctgtttcacc gtgcgcaagc      5760
tgatcgggtc aaatgacctg ccggagtacg atttgaagga ggaggcgggg caggctggcc      5820
cgatcctagt catgcgctac cgcaacctga tcgaggcgca agcatccgcc ggttcctaat      5880
gtacggagca gatgctaggg caaattgccc tagcagggga aaaaggtcga aaaggtctct      5940
ttcctgtgga tagcacgtac attgggaacc caaagccgta cattgggaac cggaacccgt      6000
acattgggaa cccaaagccg tacattggga accggtcaca catgtaagtg actgatataa      6060
aagagaaaaa aggcgatttt ccgcctaaa actctttaaa acttattaaa actcttaaaa      6120
cccgcctggc ctgtgcataa ctgtctggcc agcgcacagc cgaagagctg caaaaagcgc      6180
ctacccttcg gtcgctgcgc tccctacgcc ccgccgcttc gcgtcggcct atcgcggccg      6240
ctggccgctc aaaaatggct ggcctacggc caggcaatct accagggcgc ggacaagccg      6300
cgccgtcgcc actcgaccgc cggcgcccac atcaaggcac cctgcctcgc gcgtttcggt      6360
gatgacggtg aaaacctctg acacatgcag ctcccggaga cggtcacagc ttgtctgtaa      6420
gcggatgccg ggagcagaca gcccgtcag ggcgcgtcag cgggtgttgg cgggtgtcgg      6480
ggcgcagcca tgacccagtc acgtagcgat agcggagtgt atactggctt aactatgcgg      6540
catcagagca gattgtactg agagtgcacc atatgcggtg tgaaataccg cacagatgcg      6600
taaggagaaa ataccgcatc aggcgctctt ccgcttcctc gctcactgac tcgctgcgct      6660
cggtcgttcg gctgcggcga gcggtatcag ctcactcaaa ggcggtaata cggttatcca      6720
cagaatcagg ggataacgca ggaaagaaca tgtgagcaaa aggccagcaa aaggccagga      6780
accgtaaaaa ggccgcgttg ctggcgtttt tccataggct ccgcccccct gacgagcatc      6840
acaaaaatcg acgctcaagt cagaggtggc gaaacccgac aggactataa agataccagg      6900
cgtttccccc tggaagctcc ctcgtgcgct ctcctgttcc gaccctgccg cttaccggat      6960
acctgtccgc ctttctccct tcgggaagcg tggcgctttc tcatagctca cgctgtaggt      7020
atctcagttc ggtgtaggtc gttcgctcca agctgggctg tgtgcacgaa ccccccgttc      7080
agcccgaccg ctgcgcctta tccggtaact atcgtcttga gtccaacccg gtaagacacg      7140
acttatcgcc actggcagca gccactggta acaggattag cagagcgagg tatgtaggcg      7200
gtgctacaga gttcttgaag tggtggccta actacggcta cactagaagg acagtatttg      7260
```

-continued

```
gtatctgcgc tctgctgaag ccagttacct tcggaaaaag agttggtagc tcttgatccg    7320
gcaaacaaac caccgctggt agcggtggtt tttttgtttg caagcagcag attacgcgca    7380
gaaaaaaagg atctcaagaa gatcctttga tcttttctac ggggtctgac gctcagtgga    7440
acgaaaactc acgttaaggg attttggtca tgcattctag gtactaaaac aattcatcca    7500
gtaaaatata atattttatt ttctcccaat caggcttgat ccccagtaag tcaaaaaata    7560
gctcgacata ctgttcttcc ccgatatcct ccctgatcga ccggacgcag aaggcaatgt    7620
cataccactt gtccgccctg ccgcttctcc caagatcaat aaagccactt actttgccat    7680
ctttcacaaa gatgttgctg tctcccaggt cgccgtggga aaagacaagt tcctcttcgg    7740
gcttttccgt ctttaaaaaa tcatacagct cgcgcggatc tttaaatgga gtgtcttctt    7800
cccagttttc gcaatccaca tcggccagat cgttattcag taagtaatcc aattcggcta    7860
agcggctgtc taagctattc gtatagggac aatccgatat gtcgatggag tgaaagagcc    7920
tgatgcactc cgcatacagc tcgataatct tttcagggct ttgttcatct tcatactctt    7980
ccgagcaaag gacgccatcg gcctcactca tgagcagatt gctccagcca tcatgccgtt    8040
caaagtgcag gacctttgga acaggcagct ttccttccag ccatagcatc atgtcctttt    8100
cccgttccac atcataggtg gtccctttat accggctgtc cgtcattttt aaatataggt    8160
tttcattttc tcccaccagc ttatatacct tagcaggaga cattccttcc gtatctttta    8220
cgcagcggta ttttttcgatc agttttttca attccggtga tattctcatt ttagccattt    8280
attatttcct tcctcttttc tacagtattt aaagataccc caagaagcta attataacaa    8340
gacgaactcc aattcactgt tccttgcatt ctaaaacctt aaataccaga aaacagcttt    8400
ttcaaagttg ttttcaaagt tggcgtataa catagtatcg acggagccga tttttgaaacc   8460 gcggtgatca caggcagcaa cgctctgtca tcgttacaat caacatgcta ccctccgcga    8520
gatcatccgt gtttcaaacc cggcagctta gttgccgttc ttccgaatag catcggtaac    8580
atgagcaaag tctgccgcct tacaacggct ctcccgctga cgccgtcccg gactgatggg    8640
ctgcctgtat cgagtggtga ttttgtgccg agctgccggt cggggagctg ttggctggct    8700
ggtggcagga tatattgtgg tgtaaacaaa ttgacgctta gacaacttaa taacacattg    8760
cggacgtttt taatgtactg aattaacgcc gaattaattc ctaggccacc atgttgggcc    8820
cggcgcgcca agcttgcatg cctgcaggtc aacatggtgg agcacgacac tctcgtctac    8880
tccaagaata tcaaagatac agtctcagaa gaccagaggg ctattgagac ttttcaacaa    8940
agggtaatat cgggaaacct cctcggattc cattgcccag ctatctgtca cttcatcgaa    9000
aggacagtag aaaaggaaga tggcttctac aaatgccatc attgcgataa aggaaaggct    9060
atcgttcaag atgcctctac cgacagtggt cccaaagatg accccccacc cacgaggaac    9120
atcgtggaaa aagaagacgt tccaaccacg tcttcaaagc aagtggattg atgtgatggt    9180
caacatggtg gagcacgaca ctctcgtcta ctccaagaat atcaaagata cagtctcaga    9240
agaccagagg gctattgaga cttttcaaca aagggtaata tcgggaaacc tcctcggatt    9300
ccattgccca gctatctgtc acttcatcga aggacagta gaaaaggaag atggcttcta    9360
caaatgccat cattgcgata aaggaaaggc tatcgttcaa gatgcctcta ccgacagtgg    9420
tcccaaagat ggacccccac ccacgaggaa catcgtggaa aaagaagacg ttccaaccac    9480
gtcttcaaag caagtggatt gatgtgatat ctccactgac gtaagggatg acgcacaatc    9540
ccactatcct tcgcaagacc cttcctctat ataaggaagt tcatttcatt tggagagg      9598
```

<210> SEQ ID NO 44
<211> LENGTH: 10139
<212> TYPE: DNA
<213> ORGANISM: Artificial
<220> FEATURE:
<223> OTHER INFORMATION: synthetic oligonucleotide

<400> SEQUENCE: 44

```
ataaaacatt gcacctatgg tgttgccctg gctggggtat gtcagtgatc gcagtagaat        60
gtactaattg acaagttgga gaatacggta gaacgtcctt atccaacaca gcctttatcc       120
ctctccctga cgaggttttt gtcagtgtaa tatttctttt tgaactatcc agcttagtac       180
cgtacgggaa agtgactggt gtgcttatct ttgaaatgtt actttgggtt tcggttcttt       240
aggttagtaa gaaagcactt gtcttctcat acaaaggaaa acctgagacg tatcgcttac       300
gaaagtagca atgaaagaaa ggtggtggtt ttaatcgcta ccgcaaaaac gatggggtcg       360
ttttaattaa cttctcctac gcaagcgtct aaacggacgt tggggttttg ctagtttctt       420
tagagaaaac tagctaagtc tttaatgtta tcattagaga tggcataaat ataatacttg       480
tgtctgctga taagatcatt ttaatttgga cgattagact tgttgaacta caggttactg       540
aatcacttgc gctaatcaac atgggagata tgtacgatga atcatttgac aagtcgggcg       600
gtcctgctga cttgatggac gattcttggg tggaatcagt ttcgtggaaa gatctgttga       660
agaagttaca cagcataaaa tttgcactac agtctggtag agatgagatc actgggttac       720
tagcggcact gaatagacag tgtccttatt caccatatga gcagtttcca gataagaagg       780
tgtatttcct tttagactca cgggctaaca gtgctcttgg tgtgattcag aacgcttcag       840
cgttcaagag acgagctgat gagaagaatg cagtggcggg tgttacaaat attcctgcga       900
atccaaacac aacggttacg acgaaccaag ggagtactac tactaccaag gcgaacactg       960
gctcgacttt ggaagaagac ttgtacactt attacaaatt cgatgatgcc tctacagctt      1020
tccacaaatc tctaacttcg ttagagaaca tggagttgaa gagttattac cgaaggaact      1080
ttgagaaagt attcgggatt aagtttggtg gagcagctgc tagttcatct gcaccgcctc      1140
cagcgagtgg aggtccgata cgtcctaatc cctaggggatt taaggacgtg aactctgttg      1200
agatctctgt gaaattcaga gggtgggtga taccatattc actgatgcca ttagcgacat      1260
ctaaataggg ctaattgtga ctaatttgag ggaatttcct ttaccattga cgtcagtgtc      1320
gttggtagca tttgagtttc ggagcatctt gttctggggt ttcacactat ctttagagaa      1380
agtgttaagt taattaagtt atcttaatta agagcataat tatactgatt tgtctctcgt      1440
tgatagagtc tatcattctg ttactaaaaa tttgacaact cggtttgctg acctactggt      1500
tactgtatca cttacccgag ttaacgagtc tagaaacgtg tgaaagaaac aattgaggtt      1560
ttagagctag aaatagcaag ttaaaataag gctagtccgt tatcaacttg aaaaagtggc      1620
accgagtcgg tgctcccgcg gccaccatgt ctataaatat aagagaccct cttatagtaa      1680
gcagagttgt tggagacgtt cttgatccgt ttaatagatc aatcactcta aaggttactt      1740
atggccaaag agaggtgact aatggcttgg atctaaggcc ttctcaggtt caaaacaagc      1800
caagagttga gattggtgga gaagacctca ggaacttcta tactttggtt atggtggatc      1860
cagatgttcc aagtcctagc aaccctcacc tccgagaata tctccattgg ttggtgactg      1920
atatccctgc tacaactgga acaacctttg gcaatgagat tgtgtgttac gaaaatccaa      1980
gtcccactgc aggaattcat cgtgtcgtgt ttatattgtt tcgacagctt ggcaggcaaa      2040
cagtgtatgc accagggtgg cgccagaact tcaacactcg cgagtttgct gagatctaca      2100
```

-continued

```
atctcggcct tcccgtggcc gcagttttct acaattgtca gagggagagt ggctgcggag    2160
gaagaagact ttagagtgcc gggcatgtcc cgaagacatt aaactacggt tctttaagta    2220
gatccgtgtc tgaagtttta ggttcaattt aaacctacga gattgacatt ctcgactgat    2280
cttgattgat cggtaagtct tttgtaattt aattttcttt ttgattttat tttaaattgt    2340
tatctgtttc tgtgtataga ctgtttgaga tcggcgtttg gccgactcat tgtcttacca    2400
taggggaacg gactttgttt gtgttgttat tttatttgta ttttattaaa attctcaacg    2460
atctgaaaaa gcctcgcggc taagagattg ttgggggtg agtaagtact tttaaagtga    2520
tgatggttac aaaggcaaaa ggggtaaaac ccctcgccta cgtaagcgtt attacgcccg    2580
tctgtactta tatcagtaca ctgacgagtc cctaaaggac gaaacgggag aacgctagcc    2640
accaccacca ccaccacgtg tgaattacag gtgaccagct cgaatttccc cgatcgttca    2700
aacatttggc aataaagttt cttaagattg aatcctgttg ccggtcttgc gatgattatc    2760
atataatttc tgttgaatta cgttaagcat gtaataatta acatgtaatg catgacgtta    2820
tttatgagat gggtttttat gattagagtc ccgcaattat acatttaata cgcgatagaa    2880
aacaaaatat agcgcgcaaa ctaggataaa ttatcgcgcg cggtgtcatc tatgttacta    2940
gatcgggaat taaactatca gtgtttgaca ggatatattg gcgggtaaac ctaagagaaa    3000
agagcgttta ttagaataac ggatatttaa aagggcgtga aaaggtttat ccgttcgtcc    3060
atttgtatgt gcatgccaac cacagggttc ccctcgggat caaagtactt tgatccaacc    3120
cctccgctgc tatagtgcag tcggcttctg acgttcagtg cagccgtctt ctgaaaacga    3180
catgtcgcac aagtcctaag ttacgcgaca ggctgccgcc ctgccctttt cctggcgttt    3240
tcttgtcgcg tgttttagtc gcataaagta gaatacttgc gactagaacc ggagacatta    3300
cgccatgaac aagagcgccg ccgctggcct gctgggctat cccgcgtca gcaccgacga    3360 ccaggacttg accaaccaac gggccgaact gcacgcggcc ggctgcacca agctgttttc    3420
cgagaagatc accggcacca ggcgcgaccg cccggagctg gccaggatgc ttgaccacct    3480
acgccctggc gacgttgtga cagtgaccag gctagaccgc ctggcccgca gcacccgcga    3540
cctactggac attgccgagc gcatccagga ggccggcgcg ggcctgcgta gcctggcaga    3600
gccgtgggcc gacaccacca cgccggccgg ccgcatggtg ttgaccgtgt cgccggcat    3660 tgccgagttc gagcgttccc taatcatcga ccgcacccgg agcgggcgcg aggccgccaa    3720
ggcccgaggc gtgaagtttg gcccccgccc taccctcacc ccggcacaga tcgcgcacgc    3780
ccgcgagctg atcgaccagg aaggccgcac cgtgaaagag gcggctgcac tgcttggcgt    3840
gcatcgctcg accctgtacc gcgcacttga gcgcagcgag gaagtgacgc ccaccgaggc    3900
caggcggcgc ggtgccttcc gtgaggacgc attgaccgag gccgacgccc tggcggccgc    3960
cgagaatgaa cgccaagagg aacaagcatg aaaccgcacc aggacggcca ggacgaaccg    4020
tttttcatta ccgaagagat cgaggcggag atgatcgcgg ccgggtacgt gttcgagccg    4080
cccgcgcacg tctcaaccgt gcggctgcat gaaatcctgg ccggtttgtc tgatgccaag    4140
ctggcggcct ggccggccag cttggccgct gaagaaaccg agcgccgccg tctaaaaagg    4200
tgatgtgtat ttgagtaaaa cagcttgcgt catgcggtcg ctgcgtatat gatgcgatga    4260
gtaaataaac aaatacgcaa ggggaacgca tgaaggttat cgctgtactt aaccagaaag    4320
gcgggtcagg caagacgacc atcgcaaccc atctagcccg cgccctgcaa ctcgccgggg    4380
ccgatgttct gttagtcgat tccgatcccc agggcagtgc ccgcgattgg gcggccgtgc    4440
gggaagatca accgctaacc gttgtcggca tcgaccgccc gacgattgac cgcgacgtga    4500
```

-continued

```
aggccatcgg ccggcgcgac ttcgtagtga tcgacggagc gccccaggcg gcggacttgg   4560
ctgtgtccgc gatcaaggca gccgacttcg tgctgattcc ggtgcagcca agcccttacg   4620
acatatgggc caccgccgac ctggtggagc tggttaagca gcgcattgag gtcacggatg   4680
gaaggctaca agcggccttt gtcgtgtcgc gggcgatcaa aggcacgcgc atcggcggtg   4740
aggttgccga ggcgctggcc gggtacgagc tgcccattct tgagtcccgt atcacgcagc   4800
gcgtgagcta cccaggcact gccgccgccg gcacaaccgt tcttgaatca gaacccgagg   4860
gcgacgctgc ccgcgaggtc caggcgctgg ccgctgaaat taaatcaaaa ctcatttgag   4920
ttaatgaggt aaagagaaaa tgagcaaaag cacaaacacg ctaagtgccg gccgtccgag   4980
cgcacgcagc agcaaggctg caacgttggc cagcctggca gacacgccag ccatgaagcg   5040
ggtcaacttt cagttgccgg cggaggatca caccaagctg aagatgtacg cggtacgcca   5100
aggcaagacc attaccgagc tgctatctga atacatcgcg cagctaccag agtaaatgag   5160
caaatgaata aatgagtaga tgaattttag cggctaaagg aggcggcatg gaaaatcaag   5220
aacaaccagg caccgacgcc gtggaatgcc ccatgtgtgg aggaacgggc ggttggccag   5280
gcgtaagcgg ctgggttgtc tgccggccct gcaatggcac tggaacccc aagcccgagg   5340 aatcggcgtg acggtcgcaa accatccggc ccggtacaaa tcggcgcggc gctgggtgat   5400
gacctggtgg agaagttgaa ggccgcgcag gccgcccagc ggcaacgcat cgaggcagaa   5460
gcacgccccg gtgaatcgtg gcaagcggcc gctgatcgaa tccgcaaaga atcccggcaa   5520
ccgccggcag ccggtgcgcc gtcgattagg aagccgccca agggcgacga gcaaccagat   5580
tttttcgttc cgatgctcta tgacgtgggc acccgcgata gtcgcagcat catggacgtg   5640
gccgttttcc gtctgtcgaa gcgtgaccga cgagctggcg aggtgatccg ctacgagctt   5700
ccagacgggc acgtagaggt ttccgcaggg ccggccggca tggccagtgt gtgggattac   5760
gacctggtac tgatggcggt ttcccatcta accgaatcca tgaaccgata ccgggaaggg   5820
aagggagaca agcccggccg cgtgttccgt ccacacgttg cggacgtact caagttctgc   5880
cggcgagccg atggcggaaa gcagaaagac gacctggtag aaacctgcat tcggttaaac   5940
accacgcacg ttgccatgca gcgtacgaag aaggccaaga acggccgcct ggtgacggta   6000
tccgagggtg aagccttgat tagccgctac aagatcgtaa agagcgaaac cgggcggccg   6060
gagtacatcg agatcgagct agctgattgg atgtaccgcg agatcacaga aggcaagaac   6120
ccggacgtgc tgacggttca ccccgattac tttttgatcg atcccggcat cggccgtttt   6180
ctctaccgcc tggcacgccg cgccgcaggc aaggcagaag ccagatggtt gttcaagacg   6240
atctacgaac gcagtggcag cgccggagag ttcaagaagt tctgtttcac cgtgcgcaag   6300
ctgatcgggt caaatgacct gccggagtac gatttgaagg aggaggcggg gcaggctggc   6360
ccgatcctag tcatgcgcta ccgcaacctg atcgagggcg aagcatccgc cggttcctaa   6420
tgtacggagc agatgctagg gcaaattgcc ctagcagggg aaaaaggtcg aaaaggtctc   6480
tttcctgtgg atagcacgta cattgggaac ccaaagccgt acattgggaa ccggaacccg   6540
tacattggga acccaaagcc gtacattggg aaccggtcac acatgtaagt gactgatata   6600
aaagagaaaa aaggcgattt ttccgcctaa aactctttaa aacttattaa aactcttaaa   6660
acccgcctgg cctgtgcata actgtctggc cagcgcacag ccgaagagct gcaaaaagcg   6720
cctacccttc ggtcgctgcg ctccctacgc ccgccgcttc gcgtcggcc tatcgcggcc   6780 gctggccgct caaaaatggc tggcctacgg ccaggcaatc taccagggcg cggacaagcc   6840
```

-continued

```
gcgccgtcgc cactcgaccg ccggcgccca catcaaggca ccctgcctcg cgcgtttcgg      6900
tgatgacggt gaaaacctct gacacatgca gctcccggag acggtcacag cttgtctgta      6960
agcggatgcc gggagcagac aagcccgtca gggcgcgtca gcgggtgttg gcgggtgtcg      7020
gggcgcagcc atgacccagt cacgtagcga tagcggagtg tatactggct taactatgcg      7080
gcatcagagc agattgtact gagagtgcac catatgcggt gtgaaatacc gcacagatgc      7140
gtaaggagaa aataccgcat caggcgctct tccgcttcct cgctcactga ctcgctgcgc      7200
tcggtcgttc ggctgcggcg agcggtatca gctcactcaa aggcggtaat acggttatcc      7260
acagaatcag gggataacgc aggaaagaac atgtgagcaa aaggccagca aaaggccagg      7320
aaccgtaaaa aggccgcgtt gctggcgttt ttccataggc tccgcccccc tgacgagcat      7380
cacaaaaatc gacgctcaag tcagaggtgg cgaaacccga caggactata aagataccag      7440
gcgtttcccc ctggaagctc cctcgtgcgc tctcctgttc cgaccctgcc gcttaccgga      7500
tacctgtccg cctttctccc ttcgggaagc gtggcgcttt ctcatagctc acgctgtagg      7560
tatctcagtt cggtgtaggt cgttcgctcc aagctgggct gtgtgcacga accccccgtt      7620
cagcccgacc gctgcgcctt atccggtaac tatcgtcttg agtccaaccc ggtaagacac      7680
gacttatcgc cactggcagc agccactggt aacaggatta gcagagcgag gtatgtaggc      7740
ggtgctacag agttcttgaa gtggtggcct aactacggct acactagaag gacagtattt      7800
ggtatctgcg ctctgctgaa gccagttacc ttcggaaaaa gagttggtag ctcttgatcc      7860
ggcaaacaaa ccaccgctgg tagcggtggt ttttttgttt gcaagcagca gattacgcgc      7920
agaaaaaaag gatctcaaga agatcctttg atcttttcta cggggtctga cgctcagtgg      7980
aacgaaaact cacgttaagg gattttggtc atgcattcta ggtactaaaa caattcatcc      8040
agtaaaatat aatattttat tttctcccaa tcaggcttga tccccagtaa gtcaaaaaat      8100
agctcgacat actgttcttc cccgatatcc tccctgatcg accggacgca gaaggcaatg      8160
tcataccact tgtccgccct gccgcttctc ccaagatcaa taaagccact tactttgcca      8220
tctttcacaa agatgttgct gtctcccagg tcgccgtggg aaaagacaag ttcctcttcg      8280
ggcttttccg tctttaaaaa atcatacagc tcgcgcggat ctttaaatgg agtgtcttct      8340
tcccagtttt cgcaatccac atcggccaga tcgttattca gtaagtaatc caattcggct      8400
aagcggctgt ctaagctatt cgtataggga caatccgata tgtcgatgga gtgaaagagc      8460
ctgatgcact ccgcatacag ctcgataatc ttttcagggc tttgttcatc ttcatactct      8520
tccgagcaaa ggacgccatc ggcctcactc atgagcagat tgctccagcc atcatgccgt      8580
tcaaagtgca ggacctttgg aacaggcagc tttccttcca gccatagcat catgtccttt      8640
tcccgttcca catcataggt ggtcccttta taccggctgt ccgtcatttt taaatatagg      8700
ttttcatttt ctcccaccag cttatatacc ttagcaggag acattccttc cgtatctttt      8760
acgcagcggt atttttcgat cagttttttc aattccggtg atattctcat tttagccatt      8820
tattatttcc ttcctctttt ctacagtatt taaagatacc ccaagaagct aattataaca      8880
agacgaactc caattcactg ttccttgcat tctaaaacct taaataccag aaaacagctt      8940
tttcaaagtt gttttcaaag ttggcgtata acatagtatc gacggagccg attttgaaac      9000
cgcggtgatc acaggcagca acgctctgtc atcgttacaa tcaacatgct accctccgcg      9060
agatcatccg tgtttcaaac ccggcagctt agttgccgtt cttccgaata gcatcggtaa      9120
catgagcaaa gtctgccgcc ttacaacggc tctcccgctg acgccgtccc ggactgatgg      9180
gctgcctgta tcgagtggtg attttgtgcc gagctgccgg tcggggagct gttggctggc      9240
```

-continued

```
tggtggcagg atatattgtg gtgtaaacaa attgacgctt agacaactta ataacacatt      9300
gcggacgttt ttaatgtact gaattaacgc cgaattaatt cctaggccac catgttgggc      9360
ccggcgcgcc aagcttgcat gcctgcaggt caacatggtg gagcacgaca ctctcgtcta      9420
ctccaagaat atcaaagata cagtctcaga agaccagagg gctattgaga cttttcaaca      9480
aagggtaata tcgggaaacc tcctcggatt ccattgccca gctatctgtc acttcatcga      9540
aaggacagta gaaaaggaag atggcttcta caaatgccat cattgcgata aaggaaaggc      9600
tatcgttcaa gatgcctcta ccgacagtgg tcccaaagat ggacccccac ccacgaggaa      9660
catcgtggaa aaagaagacg ttccaaccac gtcttcaaag caagtggatt gatgtgatgg      9720
tcaacatggt ggagcacgac actctcgtct actccaagaa tatcaaagat acagtctcag      9780
aagaccagag ggctattgag acttttcaac aaagggtaat atcgggaaac ctcctcggat      9840
tccattgccc agctatctgt cacttcatcg aaaggacagt agaaaaggaa gatggcttct      9900
acaaatgcca tcattgcgat aaaggaaagg ctatcgttca agatgcctct accgacagtg      9960
gtcccaaaga tggacccca cccacgagga acatcgtgga aaaagaagac gttccaacca     10020
cgtcttcaaa gcaagtggat tgatgtgata tctccactga cgtaagggat gacgcacaat     10080
cccactatcc ttcgcaagac ccttcctcta tataaggaag ttcatttcat ttggagagg      10139
```

<210> SEQ ID NO 45
<211> LENGTH: 10130
<212> TYPE: DNA
<213> ORGANISM: Artificial
<220> FEATURE:
<223> OTHER INFORMATION: synthetic oligonucleotide

<400> SEQUENCE: 45

```
ataaaacatt gcacctatgg tgttgccctg gctggggtat gtcagtgatc gcagtagaat        60
gtactaattg acaagttgga gaatacggta gaacgtcctt atccaacaca gcctttatcc       120
ctctccctga cgaggttttt gtcagtgtaa tatttctttt tgaactatcc agcttagtac       180
cgtacgggaa agtgactggt gtgcttatct ttgaaatgtt actttgggtt tcggttcttt       240
aggttagtaa gaaagcactt gtcttctcat acaaaggaaa acctgagacg tatcgcttac       300
gaaagtagca atgaaagaaa ggtggtggtt ttaatcgcta ccgcaaaaac gatggggtcg       360
ttttaattaa cttctcctac gcaagcgtct aaacggacgt tggggttttg ctagtttctt       420
tagagaaaac tagctaagtc tttaatgtta tcattagaga tggcataaat ataatacttg       480
tgtctgctga taagatcatt ttaatttgga cgattagact tgttgaacta caggttactg       540
aatcacttgc gctaatcaac atgggagata tgtacgatga atcatttgac aagtcgggcg       600
gtcctgctga cttgatggac gattcttggg tggaatcagt ttcgtggaaa gatctgttga       660
agaagttaca cagcataaaa tttgcactac agtctggtag agatgagatc actgggttac       720
tagcggcact gaatagacag tgtccttatt caccatatga gcagtttcca gataagaagg       780
tgtatttcct tttagactca cgggctaaca gtgctcttgg tgtgattcag aacgcttcag       840
cgttcaagag acgagctgat gagaagaatg cagtggcggg tgttacaaat attcctgcga       900
atccaaacac aacggttacg acgaaccaag ggagtactac tactaccaag gcgaacactg       960
gctcgacttt ggaagaagac ttgtacactt attacaaatt cgatgatgcc tctacagctt      1020
tccacaaatc tctaacttcg ttagagaaca tggagttgaa gagttattac cgaaggaact      1080
ttgagaaagt attcgggatt aagtttggtg gagcagctgc tagttcatct gcaccgcctc      1140
```

-continued

```
cagcgagtgg aggtccgata cgtcctaatc cctagggatt taaggacgtg aactctgttg      1200
agatctctgt gaaattcaga gggtgggtga taccatattc actgatgcca ttagcgacat      1260
ctaaataggg ctaattgtga ctaatttgag ggaatttcct ttaccattga cgtcagtgtc      1320
gttggtagca tttgagtttc ggagcatctt gttctggggt ttcacactat ctttagagaa      1380
agtgttaagt taattaagtt atcttaatta agagcataat tatactgatt tgtctctcgt      1440
tgatagagtc tatcattctg ttactaaaaa tttgacaact cggtttgctg acctactggt      1500
tactgtatca cttacccgag ttaacgagtc tagaaacgtg tgaaagaaac aattgaggtt      1560
ttagagctag aaatagcaag ttaaaataag gctagtccgt tatcaacttg aaaaagtggc      1620
accgagtcgg tgctccctag tctataaata taagagaccc tcttatagta agcagagttg      1680
ttggagacgt tcttgatccg tttaatagat caatcactct aaaggttact tatggccaaa      1740
gagaggtgac taatggcttg gatctaaggc cttctcaggt tcaaacaag ccaagagttg      1800 agattggtgg agaagacctc aggaacttct atactttggt tatggtggat ccagatgttc      1860
caagtcctag caaccctcac ctccgagaat atctccattg gttggtgact gatatccctg      1920
ctacaactgg aacaaccttt ggcaatgaga ttgtgtgtta cgaaaatcca agtcccactg      1980
caggaattca tcgtgtcgtg tttatattgt ttcgacagct tggcaggcaa acagtgtatg      2040
caccagggtg gcgccagaac ttcaacactc gcgagtttgc tgagatctac aatctcggcc      2100
ttcccgtggc cgcagttttc tacaattgtc agagggagag tggctgcgga ggaagaagac      2160
tttagagtgc cgggcatgtc ccgaagacat aaaactacgg ttctttaagt agatccgtgt      2220
ctgaagtttt aggttcaatt taaacctacg agattgacat tctcgactga tcttgattga      2280
tcggtaagtc ttttgtaatt taattttctt tttgatttta ttttaaattg ttatctgttt      2340
ctgtgtatag actgtttgag atcggcgttt ggccgactca ttgtcttacc ataggggaac      2400
ggactttgtt tgtgttgtta ttttatttgt attttattaa aattctcaac gatctgaaaa      2460
agcctcgcgg ctaagagatt gttgggggggt gagtaagtac ttttaaagtg atgatggtta      2520
caaaggcaaa aggggtaaaa cccctcgcct acgtaagcgt tattacgccc gtctgtactt      2580
atatcagtac actgacgagt ccctaaagga cgaaacggga gaacgctagc caccaccacc      2640
accaccacgt gtgaattaca ggtgaccagc tcgaatttcc ccgatcgttc aaacatttgg      2700
caataaagtt tcttaagatt gaatcctgtt gccggtcttg cgatgattat catataattt      2760
ctgttgaatt acgttaagca tgtaataatt aacatgtaat gcatgacgtt atttatgaga      2820
tgggttttta tgattagagt cccgcaatta tacatttaat acgcgataga aaacaaaata      2880
tagcgcgcaa actaggataa attatcgcgc gcggtgtcat ctatgttact agatcgggaa      2940
ttaaactatc agtgtttgac aggatatatt ggcgggtaaa cctaagagaa aagagcgttt      3000
attagaataa cggatattta aaagggcgtg aaaaggttta tccgttcgtc catttgtatg      3060
tgcatgccaa ccacagggtt cccctcggga tcaaagtact ttgatccaac ccctccgctg      3120
ctatagtgca gtcggcttct gacgttcagt gcagccgtct tctgaaaacg acatgtcgca      3180
caagtcctaa gttacgcgac aggctgccgc cctgcccttt tcctggcgtt ttcttgtcgc      3240
gtgttttagt cgcataaagt agaatacttg cgactagaac cggagacatt acgccatgaa      3300
caagagcgcc gccgctggcc tgctgggcta tgcccgcgtc agcaccgacg accaggactt      3360
gaccaaccaa cgggccgaac tgcacgcggc cggctgcacc aagctgtttt ccgagaagat      3420
caccggcacc aggcgcgacc gcccggagct ggccaggatg cttgaccacc tacgccctgg      3480
cgacgttgtg acagtgacca ggctagaccg cctggcccgc agcacccgcg acctactgga      3540
```

-continued

```
cattgccgag cgcatccagg aggccggcgc gggcctgcgt agcctggcag agccgtgggc   3600
cgacaccacc acgccggccg gccgcatggt gttgaccgtg ttcgccggca ttgccgagtt   3660
cgagcgttcc ctaatcatcg accgcacccg gagcgggcgc gaggccgcca aggcccgagg   3720
cgtgaagttt ggcccccgcc ctaccctcac cccggcacag atcgcgcacg cccgcgagct   3780
gatcgaccag gaaggccgca ccgtgaaaga ggcggctgca ctgcttggcg tgcatcgctc   3840
gaccctgtac cgcgcacttg agcgcagcga ggaagtgacg cccaccgagg ccaggcggcg   3900
cggtgccttc cgtgaggacg cattgaccga ggccgacgcc ctggcggccg ccgagaatga   3960
acgccaagag gaacaagcat gaaaccgcac caggacggcc aggacgaacc gtttttcatt   4020
accgaagaga tcgaggcgga gatgatcgcg gccgggtacg tgttcgagcc gcccgcgcac   4080
gtctcaaccg tgcggctgca tgaaatcctg gccggtttgt ctgatgccaa gctggcggcc   4140
tggccggcca gcttggccgc tgaagaaacc gagcgccgcc gtctaaaaag gtgatgtgta   4200
tttgagtaaa acagcttgcg tcatgcggtc gctgcgtata tgatgcgatg agtaaataaa   4260
caaatacgca aggggaacgc atgaaggtta tcgctgtact taaccagaaa ggcgggtcag   4320
gcaagacgac catcgcaacc catctagccc gcgccctgca actcgccggg gccgatgttc   4380
tgttagtcga ttccgatccc cagggcagtg cccgcgattg ggcggccgtg cgggaagatc   4440
aaccgctaac cgttgtcggc atcgaccgcc cgacgattga ccgcgacgtg aaggccatcg   4500
gccggcgcga cttcgtagtg atcgacggag cgccccaggc ggcggacttg gctgtgtccg   4560
cgatcaaggc agccgacttc gtgctgattc cggtgcagcc aagcccttac gacatatggg   4620
ccaccgccga cctggtggag ctggttaagc agcgcattga ggtcacggat ggaaggctac   4680
aagcggcctt tgtcgtgtcg cgggcgatca aaggcacgcg catcggcggt gaggttgccg   4740
aggcgctggc cgggtacgag ctgcccattc ttgagtcccg tatcacgcag cgcgtgagct   4800
acccaggcac tgccgccgcc ggcacaaccg ttcttgaatc agaacccgag ggcgacgctg   4860
cccgcgaggt ccaggcgctg gccgctgaaa ttaaatcaaa actcatttga gttaatgagg   4920
taaagagaaa atgagcaaaa gcacaaacac gctaagtgcc ggccgtccga gcgcacgcag   4980
cagcaaggct gcaacgttgg ccagcctggc agacacgcca gccatgaagc gggtcaactt   5040
tcagttgccg gcggaggatc acaccaagct gaagatgtac gcggtacgcc aaggcaagac   5100
cattaccgag ctgctatctg aatacatcgc gcagctacca gagtaaatga gcaaatgaat   5160
aaatgagtag atgaatttta gcggctaaag gaggcggcat ggaaaatcaa gaacaaccag   5220
gcaccgacgc cgtggaatgc cccatgtgtg gaggaacggg cggttggcca ggcgtaagcg   5280
gctgggttgt ctgccggccc tgcaatggca ctggaacccc caagcccgag gaatcggcgt   5340
gacggtcgca aaccatccgg cccggtacaa atcggcgcgg cgctgggtga tgacctggtg   5400
gagaagttga aggccgcgca ggccgcccag cggcaacgca tcgaggcaga agcacgcccc   5460
ggtgaatcgt ggcaagcggc cgctgatcga atccgcaaag aatcccggca accgccggca   5520
gccggtgcgc cgtcgattag gaagccgccc aagggcgacg agcaaccaga ttttttcgtt   5580
ccgatgctct atgacgtggg cacccgcgat agtcgcagca tcatggacgt ggccgttttc   5640
cgtctgtcga agcgtgaccg acgagctggc gaggtgatcc gctacgagct tccagacggg   5700
cacgtagagg tttccgcagg gccggccggc atggccagtg tgtgggatta cgacctggta   5760
ctgatggcgg tttcccatct aaccgaatcc atgaaccgat accgggaagg gaagggagac   5820
aagcccggcc gcgtgttccg tccacacgtt gcggacgtac tcaagttctg ccggcgagcc   5880
```

```
gatggcggaa agcagaaaga cgacctggta gaaacctgca ttcggttaaa caccacgcac    5940
gttgccatgc agcgtacgaa gaaggccaag aacggccgcc tggtgacggt atccgagggt    6000
gaagccttga ttagccgcta caagatcgta aagagcgaaa ccgggcggcc ggagtacatc    6060
gagatcgagc tagctgattg gatgtaccgc gagatcacag aaggcaagaa cccggacgtg    6120
ctgacggttc accccgatta cttttttgatc gatcccggca tcggccgttt tctctaccgc    6180
ctggcacgcc gcgccgcagg caaggcagaa gccagatggt tgttcaagac gatctacgaa    6240
cgcagtggca gcgccggaga gttcaagaag ttctgtttca ccgtgcgcaa gctgatcggg    6300
tcaaatgacc tgccggagta cgatttgaag gaggaggcgg ggcaggctgg cccgatccta    6360
gtcatgcgct accgcaacct gatcgagggc gaagcatccg ccggttccta atgtacggag    6420
cagatgctag ggcaaattgc cctagcaggg gaaaaaggtc gaaaaggtct ctttcctgtg    6480
gatagcacgt acattgggaa cccaaagccg tacattggga accggaaccc gtacattggg    6540
aacccaaagc cgtacattgg gaaccggtca cacatgtaag tgactgatat aaaagagaaa    6600
aaaggcgatt tttccgccta aaactcttta aaacttatta aaactcttaa aacccgcctg    6660
gcctgtgcat aactgtctgg ccagcgcaca gccgaagagc tgcaaaaagc gcctaccctt    6720
cggtcgctgc gctccctacg ccccgccgct tcgcgtcggc ctatcgcggc cgctggccgc    6780
tcaaaaatgg ctggcctacg gccaggcaat ctaccagggc gcggacaagc gcgccgtcg     6840 ccactcgacc gccggcgccc acatcaaggc accctgcctc gcgcgtttcg gtgatgacgg    6900
tgaaaacctc tgacacatgc agctcccgga cacggtcaca gcttgtctgt aagcggatgc    6960
cgggagcaga caagcccgtc agggcgcgtc agcgggtgtt ggcgggtgtc ggggcgcagc    7020
catgacccag tcacgtagcg atagcggagt gtatactggc ttaactatgc ggcatcagag    7080
cagattgtac tgagagtgca ccatatgcgg tgtgaaatac cgcacagatg cgtaaggaga    7140
aaataccgca tcaggcgctc ttccgcttcc tcgctcactg actcgctgcg ctcggtcgtt    7200
cggctgcggc gagcggtatc agctcactca aaggcggtaa tacggttatc cacagaatca    7260
ggggataacg caggaaagaa catgtgagca aaaggccagc aaaaggccag gaaccgtaaa    7320
aaggccgcgt tgctggcgtt tttccatagg ctccgccccc ctgacgagca tcacaaaaat    7380
cgacgctcaa gtcagaggtg gcgaaacccg acaggactat aaagatacca ggcgtttccc    7440
cctggaagct ccctcgtgcg ctctcctgtt ccgaccctgc cgcttaccgg atacctgtcc    7500
gcctttctcc cttcgggaag cgtggcgctt tctcatagct cacgctgtag gtatctcagt    7560
tcggtgtagg tcgttcgctc caagctgggc tgtgtgcacg aacccccgt tcagcccgac      7620 cgctgcgcct tatccggtaa ctatcgtctt gagtccaacc cggtaagaca cgacttatcg    7680
ccactggcag cagccactgg taacaggatt agcagagcga ggtatgtagg cggtgctaca    7740
gagttcttga agtggtggcc taactacggc tacactagaa ggacagtatt tggtatctgc    7800
gctctgctga agccagttac cttcggaaaa agagttggta gctcttgatc cggcaaacaa    7860
accaccgctg gtagcggtgg tttttttgtt tgcaagcagc agattacgcg cagaaaaaaa    7920
ggatctcaag aagatccttt gatctttct acggggtctg acgctcagtg gaacgaaaac      7980
tcacgttaag ggattttggt catgcattct aggtactaaa acaattcatc cagtaaaata    8040
taatatttta ttttctccca atcaggcttg atccccagta agtcaaaaaa tagctcgaca    8100
tactgttctt ccccgatatc ctccctgatc gaccggacgc agaaggcaat gtcataccac    8160
ttgtccgccc tgccgcttct cccaagatca ataaagccac ttactttgcc atctttcaca    8220
aagatgttgc tgtctcccag gtcgccgtgg gaaaagacaa gttcctcttc gggcttttcc    8280
```

```
gtctttaaaa aatcatacag ctcgcgcgga tctttaaatg gagtgtcttc ttcccagttt      8340
tcgcaatcca catcggccag atcgttattc agtaagtaat ccaattcggc taagcggctg      8400
tctaagctat tcgtataggg acaatccgat atgtcgatgg agtgaaagag cctgatgcac      8460
tccgcataca gctcgataat cttttcaggg ctttgttcat cttcatactc ttccgagcaa      8520
aggacgccat cggcctcact catgagcaga ttgctccagc catcatgccg ttcaaagtgc      8580
aggacctttg gaacaggcag ctttccttcc agccatagca tcatgtcctt ttcccgttcc      8640
acatcatagg tggtcccttt ataccggctg tccgtcattt ttaaatatag gttttcattt      8700
tctcccacca gctatatac cttagcagga gacattcctt ccgtatcttt tacgcagcgg       8760
tatttttcga tcagtttttt caattccggt gatattctca ttttagccat ttattatttc      8820
cttcctcttt tctacagtat ttaaagatac cccaagaagc taattataac aagacgaact      8880
ccaattcact gttccttgca ttctaaaacc ttaaatacca gaaaacagct ttttcaaagt       8940
tgttttcaaa gttggcgtat aacatagtat cgacggagcc gattttgaaa ccgcggtgat      9000
cacaggcagc aacgctctgt catcgttaca atcaacatgc taccctccgc gagatcatcc      9060
gtgtttcaaa cccggcagct tagttgccgt tcttccgaat agcatcggta acatgagcaa      9120
agtctgccgc cttacaacgg ctctcccgct gacgccgtcc cggactgatg ggctgcctgt       9180
atcgagtggt gattttgtgc cgagctgccg gtcggggagc tgttggctgg ctggtggcag       9240
gatatattgt ggtgtaaaca aattgacgct tagacaactt aataacacat tgcggacgtt      9300
tttaatgtac tgaattaacg ccgaattaat tcctaggcca ccatgttggg cccggcgcgc      9360
caagcttgca tgcctgcagg tcaacatggt ggagcacgac actctcgtct actccaagaa      9420
tatcaaagat acagtctcag aagaccagag ggctattgag acttttcaac aaagggtaat      9480
atcgggaaac ctcctcggat tccattgccc agctatctgt cacttcatcg aaaggacagt      9540
agaaaaggaa gatggcttct acaaatgcca tcattgcgat aaaggaaagg ctatcgttca      9600
agatgcctct accgacagtg gtcccaaaga tggaccccca cccacgagga acatcgtgga      9660
aaaagaagac gttccaacca cgtcttcaaa gcaagtggat tgatgtgatg gtcaacatgg      9720
tggagcacga cactctcgtc tactccaaga atatcaaaga tacagtctca gaagaccaga      9780
gggctattga acttttcaa caaagggtaa tatcgggaaa cctcctcgga ttccattgcc      9840
cagctatctg tcacttcatc gaaaggacag tagaaaagga agatggcttc tacaaatgcc      9900
atcattgcga taaaggaaag gctatcgttc aagatgcctc taccgacagt ggtcccaaag      9960 atggacccccc acccacgagg aacatcgtgg aaaaagaaga cgttccaacc acgtcttcaa    10020
agcaagtgga ttgatgtgat atctccactg acgtaaggga tgacgcacaa tcccactatc    10080
cttcgcaaga cccttcctct atataaggaa gttcatttca tttggagagg               10130
```

<210> SEQ ID NO 46
<211> LENGTH: 9704
<212> TYPE: DNA
<213> ORGANISM: Artificial
<220> FEATURE:
<223> OTHER INFORMATION: synthetic oligonucleotide

<400> SEQUENCE: 46

```
ataaaacatt gcacctatgg tgttgccctg gctggggtat gtcagtgatc gcagtagaat        60
gtactaattg acaagttgga gaatacggta gaacgtcctt atccaacaca gcctttatcc       120
ctctccctga cgaggttttt gtcagtgtaa tatttctttt tgaactatcc agcttagtac       180
```

-continued

```
cgtacgggaa agtgactggt gtgcttatct ttgaaatgtt actttgggtt tcggttcttt      240
aggttagtaa gaaagcactt gtcttctcat acaaaggaaa acctgagacg tatcgcttac      300
gaaagtagca atgaaagaaa ggtggtggtt ttaatcgcta ccgcaaaaac gatggggtcg      360
ttttaattaa cttctcctac gcaagcgtct aaacggacgt tggggttttg ctagtttctt      420
tagagaaaac tagctaagtc tttaatgtta tcattagaga tggcataaat ataatacttg      480
tgtctgctga taagatcatt ttaatttgga cgattagact tgttgaacta caggttactg      540
aatcacttgc gctaatcaac atgggagata tgtacgatga atcatttgac aagtcgggcg      600
gtcctgctga cttgatggac gattcttggg tggaatcagt ttcgtggaaa gatctgttga      660
agaagttaca cagcataaaa tttgcactac agtctggtag agatgagatc actgggttac      720
tagcggcact gaatagacag tgtccttatt caccatatga gcagtttcca gataagaagg      780
tgtatttcct tttagactca cgggctaaca gtgctcttgg tgtgattcag aacgcttcag      840
cgttcaagag acgagctgat gagaagaatg cagtggcggg tgttacaaat attcctgcga      900
atccaaacac aacggttacg acgaaccaag ggagtactac tactaccaag gcgaacactg      960
gctcgacttt ggaagaagac ttgtacactt attacaaatt cgatgatgcc tctacagctt      1020
tccacaaatc tctaacttcg ttagagaaca tggagttgaa gagttattac cgaaggaact      1080
ttgagaaagt attcgggatt aagtttggtg gagcagctgc tagttcatct gcaccgcctc      1140
cagcgagtgg aggtccgata cgtcctaatc cctagggatt taaggacgtg aactctgttg      1200
agatctctgt gaaattcaga gggtgggtga taccatattc actgatgcca ttagcgacat      1260
ctaaataggg ctaattgtga ctaatttgag ggaatttcct ttaccattga cgtcagtgtc      1320
gttggtagca tttgagtttc ggagcatctt gttctggggt ttcacactat ctttagagaa      1380
agtgttaagt taattaagtt atcttaatta agagcataat tatactgatt tgtctctcgt      1440
tgatagagtc tatcattctg ttactaaaaa tttgacaact cggtttgctg acctactggt      1500
tactgtatca cttacccgag ttaacgagtc tagaaacgtg tgaaagaaac aattgaggtt      1560
ttagagctag aaatagcaag ttaaaataag gctagtccgt tatcaacttg aaaaagtggc      1620
accgagtcgg tgctccctag tctataaata taagagaccc tcttatagta agcagagttg      1680
ttggagacgt tcttgatccg tttaatagat caatcactct aaaggttact tatggccaaa      1740
gtgccgggca tgtcccgaag acattaaact acggttcttt aagtagatcc gtgtctgaag      1800
ttttaggttc aatttaaacc tacgagattg acattctcga ctgatcttga ttgatcggta      1860
agtcttttgt aatttaattt tcttttttgat tttattttaa attgttatct gtttctgtgt      1920
atagactgtt tgagatcggc gtttggccga ctcattgtct taccataggg gaacggactt      1980
tgtttgtgtt gttattttat ttgtatttta ttaaaattct caacgatctg aaaaagcctc      2040
gcggctaaga gattgttggg gggtgagtaa gtacttttaa agtgatgatg gttacaaagg      2100
caaaaggggg aaaacccctc gcctacgtaa gcgttattac gcccgtctgt acttatatca      2160
gtacactgac gagtccctaa aggacgaaac gggagaacgc tagccaccac caccaccacc      2220
acgtgtgaat tacaggtgac cagctcgaat ttccccgatc gttcaaacat ttggcaataa      2280
agtttcttaa gattgaatcc tgttgccggt cttgcgatga ttatcatata atttctgttg      2340
aattacgtta agcatgtaat aattaacatg taatgcatga cgttatttat gagatgggtt      2400
tttatgatta gagtcccgca attatacatt taatacgcga tagaaaacaa aatatagcgc      2460
gcaaactagg ataaattatc gcgcgcggtg tcatctatgt tactagatcg ggaattaaac      2520
tatcagtgtt tgacaggata tattggcggg taaacctaag agaaaagagc gtttattaga      2580
```

-continued

```
ataacggata tttaaaaggg cgtgaaaagg tttatccgtt cgtccatttg tatgtgcatg   2640
ccaaccacag ggttcccctc gggatcaaag tactttgatc caacccctcc gctgctatag   2700
tgcagtcggc ttctgacgtt cagtgcagcc gtcttctgaa aacgacatgt cgcacaagtc   2760
ctaagttacg cgacaggctg ccgccctgcc cttttcctgg cgttttcttg tcgcgtgttt   2820
tagtcgcata aagtagaata cttgcgacta gaaccggaga cattacgcca tgaacaagag   2880
cgccgccgct ggcctgctgg gctatgcccg cgtcagcacc gacgaccagg acttgaccaa   2940
ccaacgggcc gaactgcacg cggccggctg caccaagctg ttttccgaga agatcaccgg   3000
caccaggcgc gaccgcccgg agctggccag gatgcttgac cacctacgcc ctggcgacgt   3060
tgtgacagtg accaggctag accgcctggc ccgcagcacc cgcgacctac tggacattgc   3120
cgagcgcatc caggaggccg gcgcgggcct gcgtagcctg gcagagccgt gggccgacac   3180
caccacgccg gccggccgca tggtgttgac cgtgttcgcc ggcattgccg agttcgagcg   3240
ttccctaatc atcgaccgca cccggagcgg gcgcgaggcc gccaaggccc gaggcgtgaa   3300
gtttggcccc cgccctaccc tcaccccggc acagatcgcg cacgcccgcg agctgatcga   3360
ccaggaaggc cgcaccgtga aagaggcggc tgcactgctt ggcgtgcatc gctcgaccct   3420
gtaccgcgca cttgagcgca gcgaggaagt gacgcccacc gaggccaggc ggcgcggtgc   3480
cttccgtgag gacgcattga ccgaggccga cgccctggcg gccgccgaga atgaacgcca   3540
agaggaacaa gcatgaaacc gcaccaggac ggccaggacg aaccgttttt cattaccgaa   3600
gagatcgagg cggagatgat cgcggccggg tacgtgttcg agccgcccgc gcacgtctca   3660
accgtgcggc tgcatgaaat cctggccggt ttgtctgatg ccaagctggc ggcctggccg   3720
gccagcttgg ccgctgaaga aaccgagcgc cgccgtctaa aaaggtgatg tgtatttgag   3780
taaaacagct tgcgtcatgc ggtcgctgcg tatatgatgc gatgagtaaa taaacaaata   3840
cgcaagggga acgcatgaag gttatcgctg tacttaacca gaaaggcggg tcaggcaaga   3900
cgaccatcgc aacccatcta gcccgcgccc tgcaactcgc cggggccgat gttctgttag   3960
tcgattccga tccccagggc agtgcccgcg attgggcggc cgtgcgggaa gatcaaccgc   4020
taaccgttgt cggcatcgac cgcccgacga ttgaccgcga cgtgaaggcc atcggccggc   4080
gcgacttcgt agtgatcgac ggagcgcccc aggcggcgga cttggctgtg tccgcgatca   4140
aggcagccga cttcgtgctg attccggtgc agccaagccc ttacgacata tgggccaccg   4200
ccgacctggt ggagctggtt aagcagcgca ttgaggtcac ggatggaagg ctacaagcgg   4260
cctttgtcgt gtcgcgggcg atcaaaggca cgcgcatcgg cggtgaggtt gccgaggcgc   4320
tggccgggta cgagctgccc attcttgagt cccgtatcac gcagcgcgtg agctacccag   4380
gcactgccgc cgccggcaca accgttcttg aatcagaacc cgagggcgac gctgcccgcg   4440
aggtccaggc gctggccgct gaaattaaat caaaactcat ttgagttaat gaggtaaaga   4500
gaaaatgagc aaaagcacaa acacgctaag tgccggccgt ccgagcgcac gcagcagcaa   4560
ggctgcaacg ttggccagcc tggcagacac gccagccatg aagcgggtca actttcagtt   4620
gccggcggag gatcacacca agctgaagat gtacgcggta cgccaaggca agaccattac   4680
cgagctgcta tctgaataca tcgcgcagct accagagtaa atgagcaaat gaataaatga   4740
gtagatgaat tttagcggct aaaggaggcg catggaaaa tcaagaacaa ccaggcaccg   4800
acgccgtgga atgccccatg tgtggaggaa cgggcggttg gccaggcgta agcggctggg   4860
ttgtctgccg gccctgcaat ggcactggaa cccccaagcc cgaggaatcg gcgtgacggt   4920
```

-continued

```
cgcaaaccat ccggcccggt acaaatcggc gcggcgctgg gtgatgacct ggtggagaag    4980
ttgaaggccg cgcaggccgc ccagcggcaa cgcatcgagg cagaagcacg ccccggtgaa    5040
tcgtggcaag cggccgctga tcgaatccgc aaagaatccc ggcaaccgcc ggcagccggt    5100
gcgccgtcga ttaggaagcc gcccaagggc gacgagcaac cagatttttt cgttccgatg    5160
ctctatgacg tgggcacccg cgatagtcgc agcatcatgg acgtggccgt tttccgtctg    5220
tcgaagcgtg accacgagc tggcgaggtg atccgctacg agcttccaga cgggcacgta    5280
gaggtttccg cagggccggc cggcatggcc agtgtgtggg attacgacct ggtactgatg    5340
gcggtttccc atctaaccga atccatgaac cgataccggg aagggaaggg agacaagccc    5400
ggccgcgtgt tccgtccaca cgttgcggac gtactcaagt tctgccggcg agccgatggc    5460
ggaaagcaga aagacgacct ggtagaaacc tgcattcggt taaacaccac gcacgttgcc    5520
atgcagcgta cgaagaaggc caagaacggc cgcctggtga cggtatccga gggtgaagcc    5580
ttgattagcc gctacaagat cgtaaagagc gaaaccgggc ggccggagta catcgagatc    5640
gagctagctg attggatgta ccgcgagatc acagaaggca agaacccgga cgtgctgacg    5700
gttcaccccg attacttttt gatcgatccc ggcatcggcc gttttctcta ccgcctggca    5760
cgccgcgccg caggcaaggc agaagccaga tggttgttca agacgatcta cgaacgcagt    5820
ggcagcgccg gagagttcaa gaagttctgt ttcaccgtgc gcaagctgat cgggtcaaat    5880
gacctgccgg agtacgattt gaaggaggag gcggggcagg ctggcccgat cctagtcatg    5940
cgctaccgca acctgatcga gggcgaagca tccgccggtt cctaatgtac ggagcagatg    6000
ctagggcaaa ttgccctagc aggggaaaaa ggtcgaaaag gtctctttcc tgtggatagc    6060
acgtacattg ggaacccaaa gccgtacatt gggaaccgga acccgtacat tgggaaccca    6120
aagccgtaca ttgggaaccg gtcacacatg taagtgactg atataaaaga gaaaaaaggc    6180
gatttttccg cctaaaactc tttaaaactt attaaaactc ttaaaacccg cctggcctgt    6240
gcataactgt ctggccagcg cacagccgaa gagctgcaaa aagcgcctac ccttcggtcg    6300
ctgcgctccc tacgcccgc cgcttcgcgt cggcctatcg cggccgctgg ccgctcaaaa    6360
atggctggcc tacggccagg caatctacca gggcgcggac aagccgcgcc gtcgccactc    6420
gaccgccggc gcccacatca aggcaccctg cctcgcgcgt ttcggtgatg acggtgaaaa    6480
cctctgacac atgcagctcc cggagacggt cacagcttgt ctgtaagcgg atgccgggag    6540
cagacaagcc cgtcagggcg cgtcagcggg tgttggcggg tgtcggggcg cagccatgac    6600
ccagtcacgt agcgatagcg gagtgtatac tggcttaact atgcggcatc agagcagatt    6660
gtactgagag tgcaccatat gcggtgtgaa ataccgcaca gatgcgtaag gagaaaatac    6720
cgcatcaggc gctcttccgc ttcctcgctc actgactcgc tgcgctcggt cgttcggctg    6780
cggcgagcgg tatcagctca ctcaaaggcg gtaatacggt tatccacaga atcaggggat    6840
aacgcaggaa agaacatgtg agcaaaaggc cagcaaaagg ccaggaaccg taaaaaggcc    6900
gcgttgctgg cgtttttcca taggctccgc ccccctgacg agcatcacaa aaatcgacgc    6960
tcaagtcaga ggtggcgaaa cccgacagga ctataaagat accaggcgtt cccccctgga    7020
agctccctcg tgcgctctcc tgttccgacc ctgccgctta ccggatacct gtccgccttt    7080
ctcccttcgg gaagcgtggc gctttctcat agctcacgct gtaggtatct cagttcggtg    7140
taggtcgttc gctccaagct gggctgtgtg cacgaacccc ccgttcagcc cgaccgctgc    7200
gccttatccg gtaactatcg tcttgagtcc aacccggtaa gacacgactt atcgccactg    7260
gcagcagcca ctggtaacag gattagcaga gcgaggtatg taggcggtgc tacagagttc    7320
```

-continued

```
ttgaagtggt ggcctaacta cggctacact agaaggacag tatttggtat ctgcgctctg    7380
ctgaagccag ttaccttcgg aaaaagagtt ggtagctctt gatccggcaa acaaaccacc    7440
gctggtagcg gtggtttttt tgtttgcaag cagcagatta cgcgcagaaa aaaaggatct    7500
caagaagatc ctttgatctt ttctacgggg tctgacgctc agtggaacga aaactcacgt    7560
taagggattt tggtcatgca ttctaggtac taaaacaatt catccagtaa aatataatat    7620
tttattttct cccaatcagg cttgatcccc agtaagtcaa aaaatagctc gacatactgt    7680
tcttccccga tatcctccct gatcgaccgg acgcagaagg caatgtcata ccacttgtcc    7740
gccctgccgc ttctcccaag atcaataaag ccacttactt tgccatcttt cacaaagatg    7800
ttgctgtctc ccaggtcgcc gtgggaaaag acaagttcct cttcgggctt ttccgtcttt    7860
aaaaaatcat acagctcgcg cggatcttta aatggagtgt cttcttccca gttttcgcaa    7920
tccacatcgg ccagatcgtt attcagtaag taatccaatt cggctaagcg gctgtctaag    7980
ctattcgtat agggacaatc cgatatgtcg atggagtgaa agagcctgat gcactccgca    8040
tacagctcga taatcttttc agggctttgt tcatcttcat actcttccga gcaaaggacg    8100
ccatcggcct cactcatgag cagattgctc cagccatcat gccgttcaaa gtgcaggacc    8160
tttggaacag gcagctttcc ttccagccat agcatcatgt ccttttcccg ttccacatca    8220
taggtggtcc ctttataccg gctgtccgtc atttttaaat ataggttttc attttctccc    8280
accagcttat ataccttagc aggagacatt ccttccgtat cttttacgca gcggtatttt    8340
tcgatcagtt ttttcaattc cggtgatatt ctcattttag ccatattatta tttccttcct    8400 cttttctaca gtatttaaag ataccccaag aagctaatta taacaagacg aactccaatt    8460
cactgttcct tgcattctaa aaccttaaat accagaaaac agcttttca aagttgtttt    8520 caaagttggc gtataacata gtatcgacgg agccgatttt gaaaccgcgg tgatcacagg    8580
cagcaacgct ctgtcatcgt tacaatcaac atgctaccct ccgcgagatc atccgtgttt    8640
caaacccggc agcttagttg ccgttcttcc gaatagcatc ggtaacatga gcaaagtctg    8700
ccgccttaca acggctctcc cgctgacgcc gtcccggact gatgggctgc ctgtatcgag    8760
tggtgatttt gtgccgagct gccggtcggg gagctgttgg ctggctggtg gcaggatata    8820
ttgtggtgta aacaaattga cgcttagaca acttaataac acattgcgga cgtttttaat    8880
gtactgaatt aacgccgaat taattcctag gccaccatgt tgggcccggc gcgccaagct    8940
tgcatgcctg caggtcaaca tggtggagca cgacactctc gtctactcca agaatatcaa    9000
agatacagtc tcagaagacc agagggctat tgagactttt caacaaaggg taatatcggg    9060
aaacctcctc ggattccatt gcccagctat ctgtcacttc atcgaaagga cagtagaaaa    9120
ggaagatggc ttctacaaat gccatcattg cgataaagga aaggctatcg ttcaagatgc    9180
ctctaccgac agtggtccca aagatggacc cccacccacg aggaacatcg tggaaaaaga    9240
agacgttcca accacgtctt caaagcaagt ggattgatgt gatggtcaac atggtggagc    9300
acgacactct cgtctactcc aagaatatca aagatacagt ctcagaagac cagagggcta    9360
ttgagacttt tcaacaaagg gtaatatcgg gaaacctcct cggattccat tgcccagcta    9420
tctgtcactt catcgaaagg acagtagaaa aggaagatgc cttctacaaa tgccatcatt    9480
gcgataaagg aaaggctatc gttcaagatg cctctaccga cagtggtccc aaagatggac    9540
ccccacccac gaggaacatc gtggaaaaag aagacgttcc aaccacgtct tcaaagcaag    9600
tggattgatg tgatatctcc actgacgtaa gggatgacgc acaatcccac tatccttcgc    9660
```

-continued

```
aagacccttc ctctatataa ggaagttcat ttcatttgga gagg                    9704
```

```
<210> SEQ ID NO 47
<211> LENGTH: 1060
<212> TYPE: DNA
<213> ORGANISM: Nicotiana benthamiana

<400> SEQUENCE: 47
ttccagccct ttctttcctt accaggttag tcatcacctg aaaatattca tattccatgt      60
ccaaaattac ctcactaaat tcccttgcat tttctatcaa attttaacca tttattgaat     120
gtaactacaa atatggggtt gggatttttaa ttcattctaa ccagtattag gaaagtgtga    180
tctccaaatt ctttagctac cttttctttt ttaatcttga tcaagttttg tcacatatgt     240
tttgatatgt aggtgaaggt atggaattcc aaagtgatct aacaagagag atctctccac     300
aaaggaaact aggaagagga aagattgaga tcaaacggat cgaaacaca acgaatcgtc      360 aagttacttt ctgtaagaga cgcaatggtt tgctcaaaaa ggcctatgaa ttatctgtgc     420
tctgtgatgc tgaggttgct ttgattgtct tctcaagcag aggcagactc tatgagtatg     480
ccaacaacag gtacaaatat taataaaagt cttgaaaata gaaaaacttg aaagtttttaa     540 tcttatatat cttttgatgt caagtttttca tctttgaaag gtcctcccct ttcttcatca     600
tttctcattt ctttgcaatt ttacttgtct tcttttaaaa ggggaactaa ttaattgttt     660
tgtgtttgct taggaagatc tgaactgcca aagaacaatt acaattacta tactatattg     720
ttgtgaagtt ttttagactt tgagtttttt ttttctatca aataatgact ttcctttcct     780 tttttttcgtt aatggtttttg tttgtttcct tcaatttgct ctattttggg gtagtttctc     840
ttttttatga tcccattttc gttaattgac ttgtagatat atagatctgt ttgttgtaag     900
aaagagtaga aatttaggaa gaagtactct atcagaactc tgagatcagc atactacttt     960
cttcctccat tgctgctaag ttttttctct ctctctctct cctctttctc tctctcaaag    1020
atcaagcaag aaagctgtca gttctaattc gtccatttgt                         1060
```

```
<210> SEQ ID NO 48
<211> LENGTH: 1060
<212> TYPE: DNA
<213> ORGANISM: Nicotiana benthamiana

<400> SEQUENCE: 48
ttccagccct ttctttcctt accaggttag tcatcacctg aaaatattca tattccatgt      60
ccaaaattac ctcactaaat tcccttgcat tttctatcaa attttaacca tttattgaat     120
gtaactacaa atatggggtt gggatttttaa ttcattctaa ccagtattag gaaagtgtga    180
tctccaaatt ctttagctac cttttctttt ttaatcttga tcaagttttg tcacatatgt     240
tttgatatgt aggtgaaggt atggaattcc aaagtgatct aacaagagag atctctccac     300
aaaggaaact aggaagagga aagattgaga tcaaacggat cgaaacaca acgaatcgtc      360 aagttacttt ctgtaagaga cgcaatggtt tgctcaaaaa ggcctatgaa ttatctgtgc     420
tctgtgatgc tgaggttgct ttgattgtct tctcaagcag aggcagactc tatgagtatg     480
ccaacaacag gtacaaatat taataaaagt cttgaaaata gaaaaacttg aaagtttttaa     540 tcttatatat cttttgatgt caagtttttca tctttgaaag gtcctcccct ttcttcatca     600
tttctcattt ctttgcaatt ttacttgtct tcttttaaaa ggggaactaa ttaattgttt     660
tgtgtttgct taggaagatc tgaactgcca aagaacaatt acaattacta tactatattg     720
ttgtgaagtt ttttagactt tgagtttttt ttttctatca aataatgact ttcctttcct     780
```

-continued

```
ttttttcgtt aatggttttg tttgtttcct tcaatttgct ctattttggg gtagtttctc      840
ttttttatga tcccattttc gttaattgac ttgtagatat atagatctgt ttgttgtaag      900
aaagagtaga aatttaggaa gaagtactct atcagaactc tgagatcagc atactacttt      960
cttcctccat tgctgctaag ttttttctct ctctctctct cctctttctc tctctcaaag     1020
atcaagcaag aaagctgtca gttctaattc gtccatttgt                           1060
```

```
<210> SEQ ID NO 49
<211> LENGTH: 77
<212> TYPE: DNA
<213> ORGANISM: Artificial
<220> FEATURE:
<223> OTHER INFORMATION: synthetic oligonucleotide

<400> SEQUENCE: 49
aacaaagcac cagtggtcta gtggtagaat agtaccctgc cacggtacag acccgggttc       60
gattcccggc tggtgca                                                      77
```

```
<210> SEQ ID NO 50
<211> LENGTH: 23
<212> TYPE: DNA
<213> ORGANISM: Artificial
<220> FEATURE:
<223> OTHER INFORMATION: synthetic oligonucleotide

<400> SEQUENCE: 50
tcgcggccgg gtacgtgttg agc                                               23
```

```
<210> SEQ ID NO 51
<211> LENGTH: 24
<212> TYPE: DNA
<213> ORGANISM: Artificial
<220> FEATURE:
<223> OTHER INFORMATION: synthetic oligonucleotide

<400> SEQUENCE: 51
aaggaggttg acagaatgcc aaat                                              24
```

```
<210> SEQ ID NO 52
<211> LENGTH: 32
<212> TYPE: DNA
<213> ORGANISM: Artificial
<220> FEATURE:
<223> OTHER INFORMATION: synthetic oligonucleotide

<400> SEQUENCE: 52
tcacctgcta gtctaaagtc ttcttcctcc gc                                     32
```

```
<210> SEQ ID NO 53
<211> LENGTH: 35
<212> TYPE: DNA
<213> ORGANISM: Artificial
<220> FEATURE:
<223> OTHER INFORMATION: synthetic oligonucleotide

<400> SEQUENCE: 53
acacctgcaa cgccaaaaca aagcaccagt ggtct                                  35
```

```
<210> SEQ ID NO 54
<211> LENGTH: 30
<212> TYPE: DNA
<213> ORGANISM: Artificial
<220> FEATURE:
```

<223> OTHER INFORMATION: synthetic oligonucleotide

<400> SEQUENCE: 54
tcacctgcta gtcacttgca ccagccggga                                    30

<210> SEQ ID NO 55
<211> LENGTH: 32
<212> TYPE: DNA
<213> ORGANISM: Artificial
<220> FEATURE:
<223> OTHER INFORMATION: synthetic oligonucleotide

<400> SEQUENCE: 55
tcacctgcta gtctaaagtc ttcttcctcc gc                                 32

<210> SEQ ID NO 56
<211> LENGTH: 60
<212> TYPE: DNA
<213> ORGANISM: Artificial
<220> FEATURE:
<223> OTHER INFORMATION: synthetic oligonucleotide

<400> SEQUENCE: 56
acgtctcgca ggcacctgca acggtgcttg gtagtagcga ctccatggtt ttagagctag  60

<210> SEQ ID NO 57
<211> LENGTH: 30
<212> TYPE: DNA
<213> ORGANISM: Artificial
<220> FEATURE:
<223> OTHER INFORMATION: synthetic oligonucleotide

<400> SEQUENCE: 57
tcacctgcta gtcctgtgca ccagccggga                                    30

<210> SEQ ID NO 58
<211> LENGTH: 30
<212> TYPE: DNA
<213> ORGANISM: Artificial
<220> FEATURE:
<223> OTHER INFORMATION: synthetic oligonucleotide

<400> SEQUENCE: 58
tcacctgcta gtcctgtgca ccagccggga                                    30

<210> SEQ ID NO 59
<211> LENGTH: 10272
<212> TYPE: DNA
<213> ORGANISM: Artificial
<220> FEATURE:
<223> OTHER INFORMATION: synthetic oligonucleotide)

<400> SEQUENCE: 59
ggggagctgt tggctggctg gtggcaggat atattgtggt gtaaacaaat tgacgcttag  60
acaacttaat aacacattgc ggacgttttt aatgtactga attaacgccg aattaattcc  120
taggccacca tgttgggccc ggcgcgccaa gcttgcatgc ctgcaggtca acatggtgga  180
gcacgacact ctcgtctact ccaagaatat caaagataca gtctcagaag accagagggc  240
tattgagact tttcaacaaa gggtaatatc gggaaacctc ctcggattcc attgcccagc  300
tatctgtcac ttcatcgaaa ggacagtaga aaaggaagat ggcttctaca aatgccatca  360
ttgcgataaa ggaaaggcta tcgttcaaga tgcctctacc gacagtggtc ccaaagatgg  420
acccccaccc acgaggaaca tcgtggaaaa agaagacgtt ccaaccacgt cttcaaagca  480

```
agtggattga tgtgatggtc aacatggtgg agcacgacac tctcgtctac tccaagaata      540
tcaaagatac agtctcagaa gaccagaggg ctattgagac ttttcaacaa agggtaatat      600
cgggaaacct cctcggattc cattgcccag ctatctgtca cttcatcgaa aggacagtag      660
aaaaggaaga tggcttctac aaatgccatc attgcgataa aggaaaggct atcgttcaag      720
atgcctctac cgacagtggt cccaaagatg gacccccacc cacgaggaac atcgtggaaa      780
aagaagacgt tccaaccacg tcttcaaagc aagtggattg atgtgatatc tccactgacg      840
taagggatga cgcacaatcc cactatcctt cgcaagaccc ttcctctata taaggaagtt      900
catttcattt ggagaggata aaacattgca cctatggtgt tgccctggct ggggtatgtc      960
agtgatcgca gtagaatgta ctaattgaca agttggagaa tacggtagaa cgtccttatc     1020
caacacagcc tttatccctc tccctgacga ggttttttgtc agtgtaatat ttcttttttga    1080 actatccagc ttagtaccgt acgggaaagt gactggtgtg cttatctttg aaatgttact     1140
ttgggtttcg gttctttagg ttagtaagaa agcacttgtc ttctcataca aaggaaaacc     1200
tgagacgtat cgcttacgaa agtagcaatg aaagaaaggt ggtggtttta atcgctaccg     1260
caaaaacgat ggggtcgttt taattaactt ctcctacgca agcgtctaaa cggacgttgg     1320
ggttttgcta gtttctttag agaaaactag ctaagtcttt aatgttatca ttagagatgg     1380
cataaatata atacttgtgt ctgctgataa gatcatttta atttggacga ttagacttgt     1440
tgaactacag gttactgaat cacttgcgct aatcaacatg ggagatatgt acgatgaatc     1500
atttgacaag tcgggcggtc ctgctgactt gatggacgat tcttgggtgg aatcagtttc     1560
gtggaaagat ctgttgaaga agttacacag cataaaattt gcactacagt ctggtagaga     1620
tgagatcact gggttactag cggcactgaa tagacagtgt ccttattcac catatgagca     1680
gtttccagat aagaaggtgt atttcctttt agactcacgg gctaacagtg ctcttggtgt     1740
gattcagaac gcttcagcgt tcaagagacg agctgatgag aagaatgcag tggcgggtgt     1800
tacaaatatt cctgcgaatc caaacacaac ggttacgacg aaccaaggga gtactactac     1860
taccaaggcg aacactggct cgactttgga agaagacttg tacacttatt acaaattcga     1920
tgatgcctct acagctttcc acaaatctct aacttcgtta gagaacatgg agttgaagag     1980
ttattaccga aggaactttg agaaagtatt cgggattaag tttggtggag cagctgctag     2040
ttcatctgca ccgcctccag cgagtggagg tccgatacgt cctaatccct agggatttaa     2100
ggacgtgaac tctgttgaga tctctgtgaa attcagaggg tgggtgatac catattcact     2160
gatgccatta gcgacatcta aatagggcta attgtgacta atttgaggga atttcctttta    2220 ccattgacgt cagtgtcgtt ggtagcattt gagtttcgga gcatcttgtt ctggggtttc     2280
acactatctt tagagaaagt gttaagttaa ttaagttatc ttaattaaga gcataattat     2340
actgatttgt ctctcgttga tagagtctat cattctgtta ctaaaaattt gacaactcgg     2400
tttgctgacc tactggttac tgtatcactt acccgagtta acgagtctag aaacgtgtga     2460
aagaaacaat tgaggtttta gagctagaaa tagcaagtta aaataaggct agtccgttat     2520
caacttgaaa aagtggcacc gagtcggtgc tccctagtct ataaatataa gagaccctct     2580
tatagtaagc agagttgttg gagacgttct tgatccgttt aatagatcaa tcactctaaa     2640
ggttacttat ggccaaaaca aagcaccagt ggtctagtgg tagaatagta ccctgccacg     2700
gtacagaccc gggttcgatt cccggctggt gcagtgcttg gtagtagcga ctccatggtt     2760
ttagagctag aaatagcaag ttaaaataag gctagtccgt tatcaacttg aaaaagtggc     2820
```

-continued

```
accgagtcgg tgctccctag tctataaata taagagaccc tcttatagta agcagagttg    2880
ttggagacgt tcttgatccg tttaatagat caatcactct aaaggttact tatggccaaa    2940
acaaagcacc agtggtctag tggtagaata gtaccctgcc acggtacaga cccgggttcg    3000
attcccggct ggtgcacagg ttgattgtct tctcaagcag gttttagagc tagaaatagc    3060
aagttaaaat aaggctagtc cgttatcaac ttgaaaaagt ggcaccgagt cggtgctccc    3120
tagtctataa atataagaga ccctcttata gtaagcagag ttgttggaga cgttcttgat    3180
ccgtttaata gatcaatcac tctaaaggtt acttatggcc aaagtgccgg gcatgtcccg    3240
aagacattaa actacggttc tttaagtaga tccgtgtctg aagtttttagg ttcaatttaa    3300 acctacgaga ttgacattct cgactgatct tgattgatcg gtaagtcttt tgtaatttaa    3360
ttttcttttt gattttattt taaattgtta tctgtttctg tgtatagact gtttgagatc    3420
ggcgtttggc cgactcattg tcttaccata ggggaacgga ctttgtttgt gttgttattt    3480
tatttgtatt ttattaaaat tctcaacgat ctgaaaaagc ctcgcggcta agagattgtt    3540 gggggtgag taagtacttt taaagtgatg atggttacaa aggcaaaagg ggtaaaaccc    3600
ctcgcctacg taagcgttat tacgcccgtc tgtacttata tcagtacact gacgagtccc    3660
taaaggacga aacgggagaa cgctagccac caccaccacc accacgtgtg aattacaggt    3720
gaccagctcg aatttccccg atcgttcaaa catttggcaa taaagtttct taagattgaa    3780
tcctgttgcc ggtcttgcga tgattatcat ataatttctg ttgaattacg ttaagcatgt    3840
aataattaac atgtaatgca tgacgttatt tatgagatgg gtttttatga ttagagtccc    3900
gcaattatac atttaatacg cgatagaaaa caaaatatag cgcgcaaact aggataaatt    3960
atcgcgcgcg gtgtcatcta tgttactaga tcgggaatta aactatcagt gtttgacagg    4020
atatattggc gggtaaacct aagagaaaag agcgtttatt agaataatcg gatatttaaa    4080
agggcgtgaa aagtttatc cgttcgtcca tttgtatgtg catgccaacc acagggttcc    4140
cctcgggatc aaagtacttt gatccaaccc ctccgctgct atagtgcagt cggcttctga    4200
cgttcagtgc agccgtcttc tgaaaacgac atgtcgcaca agtcctaagt tacgcgacag    4260
gctgccgccc tgcccttttc ctggcgtttt cttgtcgcgt gttttagtcg cataaagtag    4320
aatacttgcg actagaaccg gagacattac gccatgaaca agagcgccgc cgctggcctg    4380
ctgggctatg cccgcgtcag caccgacgac caggacttga ccaaccaacg ggccgaactg    4440
cacgcggccg gctgcaccaa gctgttttcc gagaagatca ccggcaccag gcgcgaccgc    4500
ccggagctgg ccaggatgct tgaccaccta cgccctggcg acgttgtgac agtgaccagg    4560
ctagaccgcc tggcccgcag cacccgcgac ctactggaca ttgccgagcg catccaggag    4620
gccggcgcgg gcctgcgtag cctggcagag ccgtgggccg acaccaccac gccggccggc    4680
cgcatggtgt tgaccgtgtt cgccggcatt gccgagttcg agcgttccct aatcatcgac    4740
cgcaccccga gcgggcgcga ggccgccaag gcccgaggcg tgaagtttgg ccccgccct    4800 accctcaccc cggcacagat cgcgcacgcc cgcgagctga tcgaccagga aggccgcacc    4860
gtgaaagagg cggctgcact gcttggcgtg catcgctcga ccctgtaccg cgcacttgag    4920
cgcagcgagg aagtgacgcc caccgaggcc aggcggcgcg tgccttccg tgaggacgca    4980 ttgaccgagg ccgacgccct ggcggccgcc gagaatgaac gccaagagga acaagcatga    5040
aaccgcacca ggacggccag gacgaaccgt ttttcattac cgaagagatc gaggcggaga    5100
tgatcgcggc cgggtacgtg ttcgagccgc ccgcgcacgt ctcaaccgtg cggctgcatg    5160
aaatcctggc cggtttgtct gatgccaagc tggcggcctg gccggccagc ttggccgctg    5220
```

-continued

```
aagaaaccga gcgccgccgt ctaaaaaggt gatgtgtatt tgagtaaaac agcttgcgtc   5280
atgcggtcgc tgcgtatatg atgcgatgag taaataaaca aatacgcaag gggaacgcat   5340
gaaggttatc gctgtactta accagaaagg cgggtcaggc aagacgacca tcgcaaccca   5400
tctagcccgc gccctgcaac tcgccggggc cgatgttctg ttagtcgatt ccgatcccca   5460
gggcagtgcc cgcgattggg cggccgtgcg ggaagatcaa ccgctaaccg ttgtcggcat   5520
cgaccgcccg acgattgacc gcgacgtgaa ggccatcggc cggcgcgact tcgtagtgat   5580
cgacggagcg ccccaggcgg cggacttggc tgtgtccgcg atcaaggcag ccgacttcgt   5640
gctgattccg gtgcagccaa gcccttacga catatgggcc accgccgacc tggtggagct   5700
ggttaagcag cgcattgagg tcacggatgg aaggctacaa gcggcctttg tcgtgtcgcg   5760
ggcgatcaaa ggcacgcgca tcggcggtga ggttgccgag gcgctggccg ggtacgagct   5820
gcccattctt gagtcccgta tcacgcagcg cgtgagctac ccaggcactg ccgccgccgg   5880
cacaaccgtt cttgaatcag aacccgaggg cgacgctgcc cgcgaggtcc aggcgctggc   5940
cgctgaaatt aaatcaaaac tcatttgagt taatgaggta aagagaaaat gagcaaaagc   6000
acaaacacgc taagtgccgg ccgtccgagc gcacgcagca gcaaggctgc aacgttggcc   6060
agcctggcag acacgccagc catgaagcgg gtcaactttc agttgccggc ggaggatcac   6120
accaagctga agatgtacgc ggtacgccaa ggcaagacca ttaccgagct gctatctgaa   6180
tacatcgcgc agctaccaga gtaaatgagc aaatgaataa atgagtagat gaattttagc   6240
ggctaaagga ggcggcatgg aaaatcaaga acaaccaggc accgacgccg tggaatgccc   6300
catgtgtgga ggaacgggcg gttggccagg cgtaagcggc tgggttgcct gccggccctg   6360
caatggcact ggaaccccca agcccgagga atcggcgtga gcggtcgcaa accatccggc   6420
ccggtacaaa tcggcgcggc gctgggtgat gacctggtgg agaagttgaa ggccgcgcag   6480
gccgcccagc ggcaacgcat cgaggcagaa gcacgccccg gtgaatcgtg caagcggcc    6540 gctgatcgaa tccgcaaaga tcccggcaa ccgccggcag ccggtgcgcc gtcgattagg    6600
aagccgccca agggcgacga gcaaccagat tttttcgttc cgatgctcta tgacgtgggc   6660
acccgcgata gtcgcagcat catggacgtg gccgttttcc gtctgtcgaa gcgtgaccga   6720
cgagctggcg aggtgatccg ctacgagctt ccagacgggc acgtagaggt ttccgcaggg   6780
ccggccggca tggccagtgt gtgggattac gacctggtac tgatggcggt ttcccatcta   6840
accgaatcca tgaaccgata ccgggaaggg aagggagaca gccccggccg cgtgttccgt   6900
ccacacgttg cggacgtact caagttctgc cggcgagccg atggcggaaa gcagaaagac   6960
gacctggtag aaacctgcat tcggttaaac accacgcacg ttgccatgca gcgtacgaag   7020
aaggccaaga acggccgcct ggtgacggta tccgagggtg aagccttgat tagccgctac   7080
aagatcgtaa agagcgaaac cgggcggccg gagtacatcg atatcgagct agctgattgg   7140
atgtaccgcg agatcacaga aggcaagaac ccggacgtgc tgacggttca ccccgattac   7200
tttttgatcg atcccggcat cggccgtttt ctctaccgcc tggcacgccg cgccgcaggc   7260
aaggcagaag ccagatggtt gttcaagacg atctacgaac gcagtggcag cgccggagag   7320
ttcaagaagt tctgtttcac cgtgcgcaag ctgatcgggt caaatgacct gccggagtac   7380
gatttgaagg aggaggcggg gcaggctggc ccgatcctag tcatgcgcta ccgcaacctg   7440
atcgagggcg aagcatccgc cggttcctaa tgtacggagc agatgctagg gcaaattgcc   7500
ctagcagggg aaaaaggtcg aaaaggtctc tttcctgtgg atagcacgta cattgggaac   7560
```

-continued

```
ccaaagccgt acattgggaa ccggaacccg tacattggga acccaaagcc gtacattggg   7620
aaccggtcac acatgtaagt gactgatata aaagagaaaa aaggcgattt ttccgcctaa   7680
aactctttaa aacttattaa aactcttaaa acccgcctgg cctgtgcata actgtctggc   7740
cagcgcacag ccgaagagct gcaaaaagcg cctacccttc ggtcgctgcg ctccctacgc   7800
cccgccgctt cgcgtcggcc tatcgcggcc gctggccgct caaaaatggc tggcctacgg   7860
ccaggcaatc taccagggcg cggacaagcc gcgccgtcgc cactcgaccg ccggcgccca   7920
catcaaggca ccctgcctcg cgcgtttcgg tgatgacggt gaaaacctct gacacatgca   7980
gctcccggag acggtcacag cttgtctgta agcggatgcc gggagcagac aagcccgtca   8040
gggcgcgtca gcgggtgttg gcgggtgtcg gggcgcagcc atgacccagt cacgtagcga   8100
tagcggagtg tatactggct taactatgcg gcatcagagc agattgtact gagagtgcac   8160
catatgcggt gtgaaatacc gcacagatgc gtaaggagaa aataccgcat caggcgctct   8220
tccgcttcct cgctcactga ctcgctgcgc tcggtcgttc ggctgcggcg agcggtatca   8280
gctcactcaa aggcggtaat acggttatcc acagaatcag gggataacgc aggaaagaac   8340
atgtgagcaa aaggccagca aaaggccagg aaccgtaaaa aggccgcgtt gctggcgttt   8400
ttccataggc tccgccccc tgacgagcat cacaaaaatc gacgctcaag tcagaggtgg   8460
cgaaacccga caggactata aagataccag gcgtttcccc ctggaagctc cctcgtgcgc   8520
tctcctgttc cgaccctgcc gcttaccgga tacctgtccg cctttctccc ttcgggaagc   8580
gtggcgcttt ctcatagctc acgctgtagg tatctcagtt cggtgtaggt cgttcgctcc   8640
aagctgggct gtgtgcacga accccccgtt cagcccgacc gctgcgcctt atccggtaac   8700
tatcgtcttg agtccaaccc ggtaagacac gacttatcgc cactggcagc agccactggt   8760
aacaggatta gcagagcgag gtatgtaggc ggtgctacag agttcttgaa gtggtggcct   8820
aactacggct acactagaag gacagtattt ggtatctgcg ctctgctgaa gccagttacc   8880
ttcggaaaaa gagttggtag ctcttgatcc ggcaaacaaa ccaccgctgg tagcggtggt   8940
ttttttgttt gcaagcagca gattacgcgc agaaaaaaag gatctcaaga agatcctttg   9000
atcttttcta cggggtctga cgctcagtgg aacgaaaact cacgttaagg gattttggtc   9060
atgcattcta ggtactaaaa caattcatcc agtaaaatat aatattttat tttctcccaa   9120
tcaggcttga tccccagtaa gtcaaaaaat agctcgacat actgttcttc cccgatatcc   9180
tccctgatcg accggacgca gaaggcaatg tcataccact tgtccgccct gccgcttctc   9240
ccaagatcaa taaagccact tactttgcca tctttcacaa agatgttgct gtctcccagg   9300
tcgccgtggg aaaagacaag ttcctcttcg gcttttccg tctttaaaaa atcatacagc   9360
tcgcgcggat ctttaaatgg agtgtcttct tcccagtttt cgcaatccac atcggccaga   9420
tcgttattca gtaagtaatc caattcggct aagcggctgt ctaagctatt cgtataggga   9480
caatccgata tgtcgatgga gtgaaagagc ctgatgcact ccgcatacag ctcgataatc   9540
ttttcagggc tttgttcatc ttcatactct tccgagcaaa ggacgccatc ggcctcactc   9600
atgagcagat tgctccagcc atcatgccgt tcaaagtgca ggacctttgg aacaggcagc   9660
tttccttcca gccatagcat catgtccttt tcccgttcca catcataggt ggtcccttta   9720
taccggctgt ccgtcatttt taaatatagg ttttcatttt ctcccaccag cttatatacc   9780
ttagcaggag acattccttc cgtatctttt acgcagcggt attttcgat cagtttttc    9840 aattccggtg atattctcat tttagccatt tattatttcc ttcctctttt ctacagtatt   9900
taaagatacc ccaagaagct aattataaca agacgaactc caattcactg ttccttgcat   9960
```

```
tctaaaacct taaataccag aaaacagctt tttcaaagtt gttttcaaag ttggcgtata    10020
acatagtatc gacggagccg attttgaaac cgcggtgatc acaggcagca acgctctgtc    10080
atcgttacaa tcaacatgct accctccgcg agatcatccg tgtttcaaac ccggcagctt    10140
agttgccgtt cttccgaata gcatcggtaa catgagcaaa gtctgccgcc ttacaacggc    10200
tctcccgctg acgccgtccc ggactgatgg gctgcctgta tcgagtggtg attttgtgcc    10260
gagctgccgg tc                                                        10272
```

```
<210> SEQ ID NO 60
<211> LENGTH: 64
<212> TYPE: DNA
<213> ORGANISM: Artificial
<220> FEATURE:
<223> OTHER INFORMATION: synthetic oligonucleotide

<400> SEQUENCE: 60
tcacctgcta gtgcacgctc gaacacgtac ccggccgcga ttggccataa gtaaccttta      60
gagt                                                                     64
```

```
<210> SEQ ID NO 61
<211> LENGTH: 64
<212> TYPE: DNA
<213> ORGANISM: Artificial
<220> FEATURE:
<223> OTHER INFORMATION: synthetic oligonucleotide

<400> SEQUENCE: 61
tcacctgcta gtcctggctc gaacacgtac ccggccgcga ttggccataa gtaaccttta      60
gagt                                                                     64
```

```
<210> SEQ ID NO 62
<211> LENGTH: 40
<212> TYPE: DNA
<213> ORGANISM: Artificial
<220> FEATURE:
<223> OTHER INFORMATION: synthetic oligonucleotide

<400> SEQUENCE: 62
tcacctgcta gtgcacttgg ccataagtaa cctttagagt                              40
```

```
<210> SEQ ID NO 63
<211> LENGTH: 40
<212> TYPE: DNA
<213> ORGANISM: Artificial
<220> FEATURE:
<223> OTHER INFORMATION: synthetic oligonucleotide

<400> SEQUENCE: 63
tcacctgcta gtcctgttgg ccataagtaa cctttagagt                              40
```

```
<210> SEQ ID NO 64
<211> LENGTH: 64
<212> TYPE: DNA
<213> ORGANISM: Artificial
<220> FEATURE:
<223> OTHER INFORMATION: synthetic oligonucleotide

<400> SEQUENCE: 64
tcacctgcta gtgcacattt ggcattctgt caacctcctt ttggccataa gtaaccttta      60
gagt                                                                     64
```

```
<210> SEQ ID NO 65
<211> LENGTH: 64
<212> TYPE: DNA
<213> ORGANISM: Artificial
<220> FEATURE:
<223> OTHER INFORMATION: synthetic oligonucleotide

<400> SEQUENCE: 65
tcacctgcta gtcctgattt ggcattctgt caacctcctt ttggccataa gtaacctta       60 gagt                                                                    64

<210> SEQ ID NO 66
<211> LENGTH: 10164
<212> TYPE: DNA
<213> ORGANISM: Artificial
<220> FEATURE:
<223> OTHER INFORMATION: synthetic oligonucleotide

<400> SEQUENCE: 66
ggggagctgt tggctggctg gtggcaggat atattgtggt gtaaacaaat tgacgcttag       60
acaacttaat aacacattgc ggacgttttt aatgtactga attaacgccg aattaattcc      120
taggccacca tgttgggccc ggcgcgccaa gcttgcatgc ctgcaggtca acatggtgga      180
gcacgacact ctcgtctact ccaagaatat caaagataca gtctcagaag accagagggc      240
tattgagact tttcaacaaa gggtaatatc gggaaacctc ctcggattcc attgcccagc      300
tatctgtcac ttcatcgaaa ggacagtaga aaaggaagat ggcttctaca aatgccatca      360
ttgcgataaa ggaaaggcta tcgttcaaga tgcctctacc gacagtggtc ccaaagatgg      420
acccccaccc acgaggaaca tcgtggaaaa agaagacgtt ccaaccacgt cttcaaagca      480
agtggattga tgtgatggtc aacatggtgg agcacgacac tctcgtctac tccaagaata      540
tcaaagatac agtctcagaa gaccagaggg ctattgagac ttttcaacaa agggtaatat      600
cgggaaacct cctcggattc cattgcccag ctatctgtca cttcatcgaa aggacagtag      660
aaaaggaaga tggcttctac aaatgccatc attgcgataa aggaaaggct atcgttcaag      720
atgcctctac cgacagtggt cccaaagatg gacccccacc cacgaggaac atcgtggaaa      780
aagaagacgt tccaaccacg tcttcaaagc aagtggattg atgtgatatc tccactgacg      840
taagggatga cgcacaatcc cactatcctt cgcaagaccc ttcctctata taaggaagtt      900
catttcattt ggagaggata aacattgca cctatggtgt tgccctggct ggggtatgtc      960
agtgatcgca gtagaatgta ctaattgaca agttggagaa tacggtagaa cgtccttatc     1020
caacacagcc tttatccctc tccctgacga ggttttttgtc agtgtaatat ttctttttga     1080
actatccagc ttagtaccgt acgggaaagt gactggtgtg cttatctttg aaatgttact     1140
ttgggtttcg gttctttagg ttagtaagaa agcacttgtc ttctcataca aaggaaaacc     1200
tgagacgtat cgcttacgaa agtagcaatg aaagaaaggt ggtggtttta atcgctaccg     1260
caaaaacgat ggggtcgttt taattaactt ctcctacgca agcgtctaaa cggacgttgg     1320
ggttttgcta gtttctttag agaaaactag ctaagtcttt aatgttatca ttagagatgg     1380
cataaatata atacttgtgt ctgctgataa gatcatttta atttggacga ttagacttgt     1440
tgaactacag gttactgaat cacttgcgct aatcaacatg ggagatatgt acgatgaatc     1500
atttgacaag tcgggcggtc ctgctgactt gatggacgat tcttgggtgg aatcagtttc     1560
gtggaaagat ctgttgaaga agttacacag cataaaattt gcactacagt ctggtagaga     1620
tgagatcact gggttactag cggcactgaa tagacagtgt ccttattcac catatgagca     1680
```

-continued

```
gtttccagat aagaaggtgt atttcctttt agactcacgg gctaacagtg ctcttggtgt   1740
gattcagaac gcttcagcgt tcaagagacg agctgatgag aagaatgcag tggcgggtgt   1800
tacaaatatt cctgcgaatc caaacacaac ggttacgacg aaccaaggga gtactactac   1860
taccaaggcg aacactggct cgactttgga agaagacttg tacacttatt acaaattcga   1920
tgatgcctct acagctttcc acaaatctct aacttcgtta gagaacatgg agttgaagag   1980
ttattaccga aggaactttg agaaagtatt cgggattaag tttggtggag cagctgctag   2040
ttcatctgca ccgcctccag cgagtggagg tccgatacgt cctaatccct agggatttaa   2100
ggacgtgaac tctgttgaga tctctgtgaa attcagaggg tgggtgatac catattcact   2160
gatgccatta gcgacatcta aatagggcta attgtgacta atttgaggga atttccttta   2220
ccattgacgt cagtgtcgtt ggtagcattt gagtttcgga gcatcttgtt ctggggtttc   2280
acactatctt tagagaaagt gttaagttaa ttaagttatc ttaattaaga gcataattat   2340
actgatttgt ctctcgttga tagagtctat cattctgtta ctaaaaattt gacaactcgg   2400
tttgctgacc tactggttac tgtatcactt acccgagtta acgagtctag aaacgtgtga   2460
aagaaacaat tgaggtttta gagctagaaa tagcaagtta aaataaggct agtccgttat   2520
caacttgaaa aagtggcacc gagtcggtgc tccctagtct ataaatataa gagaccctct   2580
tatagtaagc agagttgttg gagacgttct tgatccgttt aatagatcaa tcactctaaa   2640
ggttacttat ggccaatcgc ggccgggtac gtgttgagcg tgcttggtag tagcgactcc   2700
atggttttag agctagaaat agcaagttaa aataaggcta gtccgttatc aacttgaaaa   2760
agtggcaccg agtcggtgct ccctagtcta taaatataag agaccctctt atagtaagca   2820
gagttgttgg agacgttctt gatccgttta atagatcaat cactctaaag gttacttatg   2880
gccaatcgcg gccgggtacg tgttgagcca ggttgattgt cttctcaagc aggttttaga   2940
gctagaaata gcaagttaaa ataaggctag tccgttatca acttgaaaaa gtggcaccga   3000
gtcggtgctc cctagtctat aaatataaga gaccctctta gtaagcag agttgttgga   3060 gacgttcttg atccgtttaa tagatcaatc actctaaagg ttacttatgg ccaaagtgcc   3120
gggcatgtcc cgaagacatt aaactacggt tctttaagta gatccgtgtc tgaagtttta   3180
ggttcaattt aaacctacga gattgacatt ctcgactgat cttgattgat cggtaagtct   3240
tttgtaattt aattttcttt ttgattttat tttaaattgt tatctgtttc tgtgtataga   3300
ctgtttgaga tcggcgtttg gccgactcat tgtcttacca taggggaacg gactttgttt   3360
gtgttgttat tttatttgta ttttattaaa attctcaacg atctgaaaaa gcctcgcggc   3420
taagagattg ttggggggtg agtaagtact tttaaagtga tgatggttac aaaggcaaaa   3480
ggggtaaaac ccctcgccta cgtaagcgtt attacgcccg tctgtactta tatcagtaca   3540
ctgacgagtc cctaaaggac gaaacgggag aacgctagcc accaccacca ccaccacgtg   3600
tgaattacag gtgaccagct cgaatttccc cgatcgttca aacatttggc aataaagttt   3660
cttaagattg aatcctgttg ccggtcttgc gatgattatc atataatttc tgttgaatta   3720
cgttaagcat gtaataatta acatgtaatg catgacgtta tttatgagat gggtttttat   3780
gattagagtc ccgcaattat acatttaata cgcgatagaa acaaaatat agcgcgcaaa   3840 ctaggataaa ttatcgcgcg cggtgtcatc tatgttacta gatcgggaat taaactatca   3900
gtgtttgaca ggatatattg gcgggtaaac ctaagagaaa agagcgttta ttagaataat   3960 cggatatttta aaaggggcgtg aaaaggttta tccgttcgtc catttgtatg tgcatgccaa   4020
```

-continued

```
ccacagggtt cccctcggga tcaaagtact ttgatccaac ccctccgctg ctatagtgca    4080
gtcggcttct gacgttcagt gcagccgtct tctgaaaacg acatgtcgca caagtcctaa    4140
gttacgcgac aggctgccgc cctgcccttt tcctggcgtt ttcttgtcgc gtgttttagt    4200
cgcataaagt agaatacttg cgactagaac cggagacatt acgccatgaa caagagcgcc    4260
gccgctggcc tgctgggcta tgcccgcgtc agcaccgacg accaggactt gaccaaccaa    4320
cgggccgaac tgcacgcggc cggctgcacc aagctgtttt ccgagaagat caccggcacc    4380
aggcgcgacc gcccggagct ggccaggatg cttgaccacc tacgccctgg cgacgttgtg    4440
acagtgacca ggctagaccg cctggcccgc agcacccgcg acctactgga cattgccgag    4500
cgcatccagg aggccggcgc gggcctgcgt agcctggcag agccgtgggc cgacaccacc    4560
acgccggccg gccgcatggt gttgaccgtg ttcgccggca ttgccgagtt cgagcgttcc    4620
ctaatcatcg accgcacccg gagcgggcgc gaggccgcca aggcccgagg cgtgaagttt    4680
ggccccccgc ctaccctcac cccggcacag atcgcgcacg cccgcgagct gatcgaccag    4740
gaaggccgca ccgtgaaaga ggcggctgca ctgcttggct tgcatcgctc gaccctgtac    4800
cgcgcacttg agcgcagcga ggaagtgacg cccaccgagg ccaggcggcg cggtgccttc    4860
cgtgaggacg cattgaccga ggccgacgcc ctggcggccg ccgagaatga acgccaagag    4920
gaacaagcat gaaaccgcac caggacggcc aggacgaacc gttttcatt accgaagaga    4980 tcgaggcgga gatgatcgcg gccgggtacg tgttcgagcc gcccgcgcac gtctcaaccg    5040
tgcggctgca tgaaatcctg gccggtttgt ctgatgccaa gctggcggcc tggccggcca    5100
gcttggccgc tgaagaaacc gagcgccgcc gtctaaaaag gtgatgtgta tttgagtaaa    5160
acagcttgcg tcatgcggtc gctgcgtata tgatgcgatg agtaaataaa caaatacgca    5220
aggggaacgc atgaaggtta tcgctgtact taaccagaaa ggcgggtcag gcaagacgac    5280
catcgcaacc catctagccc gcgccctgca actcgccggg gccgatgttc tgttagtcga    5340
ttccgatccc cagggcagtg cccgcgattg ggcggccgtg cgggaagatc aaccgctaac    5400
cgttgtcggc atcgaccgcc cgacgattga ccgcgacgtg aaggccatcg gccggcgcga    5460
cttcgtagtg atcgacggag cgccccaggc ggcggacttg gctgtgtccg cgatcaaggc    5520
agccgacttc gtgctgattc cggtgcagcc aagcccttac gacatatggg ccaccgccga    5580
cctggtggag ctggttaagc agcgcattga ggtcacggat ggaaggctac aagcggcctt    5640
tgtcgtgtcg cgggcgatca aaggcacgcg catcggcggt gaggttgccg aggcgctggc    5700
cgggtacgag ctgcccattc ttgagtcccg tatcacgcag cgcgtgagct acccaggcac    5760
tgccgccgcc ggcacaaccg ttcttgaatc agaacccgag ggcgacgctg cccgcgaggt    5820
ccaggcgctg gccgctgaaa ttaaatcaaa actcatttga gttaatgagg taaagagaaa    5880
atgagcaaaa gcacaaacac gctaagtgcc ggccgtccga gcgcacgcag cagcaaggct    5940
gcaacgttgg ccagcctggc agacacgcca gccatgaagc gggtcaactt tcagttgccg    6000
gcggaggatc acaccaagct gaagatgtac gcggtacgcc aaggcaagac cattaccgag    6060
ctgctatctg aatacatcgc gcagctacca gagtaaatga gcaaatgaat aaatgagtag    6120
atgaatttta gcggctaaag gaggcggcat ggaaaatcaa gaacaaccag gcaccgacgc    6180
cgtggaatgc cccatgtgtg gaggaacggg cggttggcca ggcgtaagcg gctgggttgc    6240
ctgccggccc tgcaatggca ctggaacccc caagcccgag gaatcggcgt gagcggtcgc    6300
aaaccatccg gcccggtaca aatcggcgcg gcgctgggtg atgacctggt ggagaagttg    6360
aaggccgcgc aggccgccca gcggcaacgc atcgaggcag aagcacgccc cggtgaatcg    6420
```

-continued

```
tggcaagcgg ccgctgatcg aatccgcaaa gaatcccggc aaccgccggc agccggtgcg    6480
ccgtcgatta ggaagccgcc caagggcgac gagcaaccag attttttcgt tccgatgctc    6540
tatgacgtgg gcacccgcga tagtcgcagc atcatggacg tggccgtttt ccgtctgtcg    6600
aagcgtgacc gacgagctgg cgaggtgatc cgctacgagc ttccagacgg gcacgtagag    6660
gtttccgcag ggccggccgg catggccagt gtgtgggatt acgacctggt actgatggcg    6720
gtttcccatc taaccgaatc catgaaccga taccgggaag ggaagggaga caagcccggc    6780
cgcgtgttcc gtccacacgt tgcggacgta ctcaagttct gccggcgagc cgatggcgga    6840
aagcagaaag acgacctggt agaaacctgc attcggttaa acaccacgca cgttgccatg    6900
cagcgtacga agaaggccaa gaacggccgc ctggtgacgg tatccgaggg tgaagccttg    6960
attagccgct acaagatcgt aaagagcgaa accgggcggc cggagtacat cgagatcgag    7020
ctagctgatt ggatgtaccg cgagatcaca gaaggcaaga acccggacgt gctgacggtt    7080 cacccccgatt actttttgat cgatcccggc atcggccgtt ttctctaccg cctggcacgc    7140
cgcgccgcag gcaaggcaga agccagatgg ttgttcaaga cgatctacga acgcagtggc    7200
agcgccggag agttcaagaa gttctgtttc accgtgcgca agctgatcgg gtcaaatgac    7260
ctgccggagt acgatttgaa ggaggaggcg gggcaggctg gcccgatcct agtcatgcgc    7320
taccgcaacc tgatcgaggg cgaagcatcc gccggttcct aatgtacgga gcagatgcta    7380
gggcaaattg ccctagcagg ggaaaaaggt cgaaaaggtc tctttcctgt ggatagcacg    7440
tacattggga acccaaagcc gtacattggg aaccggaacc cgtacattgg gaacccaaag    7500
ccgtacattg ggaaccggtc acacatgtaa gtgactgata taaaagagaa aaaaggcgat    7560
ttttccgcct aaaactcttt aaaacttatt aaaactctta aaacccgcct ggcctgtgca    7620
taactgtctg gccagcgcac agccgaagag ctgcaaaaag cgcctaccct tcggtcgctg    7680
cgctccctac gccccgccgc ttcgcgtcgg cctatcgcgg ccgctggccg ctcaaaaatg    7740
gctggcctac ggccaggcaa tctaccaggg cgcggacaag ccgcgccgtc gccactcgac    7800
cgccggcgcc cacatcaagg caccctgcct cgcgcgtttc ggtgatgacg gtgaaaacct    7860
ctgacacatg cagctcccgg agacggtcac agcttgtctg taagcggatg ccgggagcag    7920
acaagcccgt cagggcgcgt cagcgggtgt tggcgggtgt cggggcgcag ccatgaccca    7980
gtcacgtagc gatagcggag tgtatactgg cttaactatg cggcatcaga gcagattgta    8040
ctgagagtgc accatatgcg gtgtgaaata ccgcacagat gcgtaaggag aaaataccgc    8100
atcaggcgct cttccgcttc ctcgctcact gactcgctgc gctcggtcgt tcggctgcgg    8160
cgagcggtat cagctcactc aaaggcggta atacggttat ccacagaatc aggggataac    8220
gcaggaaaga acatgtgagc aaaaggccag caaaaggcca ggaaccgtaa aaaggccgcg    8280
ttgctggcgt ttttccatag gctccgcccc cctgacgagc atcacaaaaa tcgacgctca    8340
agtcagaggt ggcgaaaccc gacaggacta taaagatacc aggcgtttcc ccctggaagc    8400
tccctcgtgc gctctcctgt tccgaccctg ccgcttaccg gatacctgtc cgcctttctc    8460
ccttcgggaa gcgtggcgct ttctcatagc tcacgctgta ggtatctcag ttcggtgtag    8520
gtcgttcgct ccaagctggg ctgtgtgcac gaaccccccg ttcagcccga ccgctgcgcc    8580
ttatccggta actatcgtct tgagtccaac ccggtaagac acgacttatc gccactggca    8640
gcagccactg gtaacaggat tagcagagcg aggtatgtag gcggtgctac agagttcttg    8700
aagtggtggc ctaactacgg ctacactaga aggacagtat ttggtatctg cgctctgctg    8760
```

-continued

```
aagccagtta ccttcggaaa aagagttggt agctcttgat ccggcaaaca aaccaccgct    8820
ggtagcggtg gttttttttgt ttgcaagcag cagattacgc gcagaaaaaa aggatctcaa    8880
gaagatcctt tgatctttttc tacggggtct gacgctcagt ggaacgaaaa ctcacgttaa    8940 gggatttttgg tcatgcattc taggtactaa aacaattcat ccagtaaaat ataatatttt    9000
attttctccc aatcaggctt gatccccagt aagtcaaaaa atagctcgac atactgttct    9060
tccccgatat cctccctgat cgaccggacg cagaaggcaa tgtcatacca cttgtccgcc    9120
ctgccgcttc tcccaagatc aataaagcca cttactttgc catctttcac aaagatgttg    9180
ctgtctccca ggtcgccgtg ggaaaagaca agttcctctt cgggcttttc cgtctttaaa    9240
aaatcataca gctcgcgcgg atctttaaat ggagtgtctt cttcccagtt ttcgcaatcc    9300
acatcggcca gatcgttatt cagtaagtaa tccaattcgg ctaagcggct gtctaagcta    9360
ttcgtatagg gacaatccga tatgtcgatg gagtgaaaga gcctgatgca ctccgcatac    9420
agctcgataa tctttttcagg gctttgttca tcttcatact cttccgagca aaggacgcca    9480
tcggcctcac tcatgagcag attgctccag ccatcatgcc gttcaaagtg caggaccttt    9540
ggaacaggca gctttccttc cagccatagc atcatgtcct tttcccgttc cacatcatag    9600
gtggtccctt tataccggct gtccgtcatt tttaaatata ggttttcatt ttctcccacc    9660
agcttatata ccttagcagg agacattcct tccgtatctt ttacgcagcg gtatttttcg    9720
atcagttttt tcaattccgg tgatattctc attttagcca tttattatttt ccttcctcttt    9780 ttctacagta tttaaagata ccccaagaag ctaattataa caagacgaac tccaattcac    9840
tgttccttgc attctaaaac cttaaatacc agaaaacagc tttttcaaag ttgttttcaa    9900
agttggcgta taacatagta tcgacggagc cgattttgaa accgcggtga tcacaggcag    9960
caacgctctg tcatcgttac aatcaacatg ctaccctccg cgagatcatc cgtgtttcaa   10020
acccggcagc ttagttgccg ttcttccgaa tagcatcggt aacatgagca aagtctgccg   10080
ccttacaacg gctctcccgc tgacgccgtc ccggactgat gggctgcctg tatcgagtgg   10140
tgattttgtg ccgagctgcc ggtc                                          10164
```

<210> SEQ ID NO 67
<211> LENGTH: 10118
<212> TYPE: DNA
<213> ORGANISM: Artificial
<220> FEATURE:
<223> OTHER INFORMATION: synthetic oligonucleotide

<400> SEQUENCE: 67

```
ggggagctgt tggctggctg gtggcaggat atattgtggt gtaaacaaat tgacgcttag      60
acaacttaat aacacattgc ggacgttttt aatgtactga attaacgccg aattaattcc     120
taggccacca tgttgggccc ggcgcgccaa gcttgcatgc ctgcaggtca acatggtgga     180
gcacgacact ctcgtctact ccaagaatat caaagataca gtctcagaag accagagggc     240
tattgagact tttcaacaaa gggtaatatc gggaaacctc ctcggattcc attgcccagc     300
tatctgtcac ttcatcgaaa ggacagtaga aaggaagat ggcttctaca aatgccatca     360
ttgcgataaa ggaaaggcta tcgttcaaga tgcctctacc gacagtggtc ccaaagatgg     420
acccccaccc acgaggaaca tcgtggaaaa agaagacgtt ccaaccacgt cttcaaagca     480
agtggattga tgtgatggtc aacatggtgg agcacgacac tctcgtctac tccaagaata     540
tcaaagatac agtctcagaa gaccagaggg ctattgagac ttttcaacaa agggtaatat     600
cgggaaacct cctcggattc cattgcccag ctatctgtca cttcatcgaa aggacagtag     660
```

-continued

```
aaaaggaaga tggcttctac aaatgccatc attgcgataa aggaaaggct atcgttcaag        720
atgcctctac cgacagtggt cccaaagatg gacccccacc cacgaggaac atcgtggaaa        780
aagaagacgt tccaaccacg tcttcaaagc aagtggattg atgtgatatc tccactgacg        840
taagggatga cgcacaatcc cactatcctt cgcaagaccc ttcctctata taaggaagtt        900
catttcattt ggagaggata aaacattgca cctatggtgt tgccctggct ggggtatgtc        960
agtgatcgca gtagaatgta ctaattgaca agttggagaa tacggtagaa cgtccttatc       1020
caacacagcc tttatccctc tccctgacga ggttttttgtc agtgtaatat ttcttttttga     1080 actatccagc ttagtaccgt acgggaaagt gactggtgtg cttatctttg aaatgttact       1140
ttgggtttcg gttctttagg ttagtaagaa agcacttgtc ttctcataca aaggaaaacc       1200
tgagacgtat cgcttacgaa agtagcaatg aaagaaaggt ggtggtttta atcgctaccg       1260
caaaaacgat ggggtcgttt taattaactt ctcctacgca agcgtctaaa cggacgttgg       1320
ggttttgcta gtttctttag agaaaactag ctaagtcttt aatgttatca ttagagatgg       1380
cataaatata atacttgtgt ctgctgataa gatcatttta atttggacga ttagacttgt       1440
tgaactacag gttactgaat cacttgcgct aatcaacatg ggagatatgt acgatgaatc       1500
atttgacaag tcgggcggtc ctgctgactt gatggacgat tcttgggtgg aatcagtttc       1560
gtggaaagat ctgttgaaga agttacacag cataaaattt gcactacagt ctggtagaga       1620
tgagatcact gggttactag cggcactgaa tagacagtgt ccttattcac catatgagca       1680
gtttccagat aagaaggtgt atttcctttt agactcacgg gctaacagtg ctcttggtgt       1740
gattcagaac gcttcagcgt tcaagagacg agctgatgag aagaatgcag tggcgggtgt       1800
tacaaatatt cctgcgaatc caaacacaac ggttacgacg aaccaaggga gtactactac       1860
taccaaggcg aacactggct cgactttgga agaagacttg tacacttatt acaaattcga       1920
tgatgcctct acagctttcc acaaatctct aacttcgtta gagaacatgg agttgaagag       1980
ttattaccga aggaactttg agaaagtatt cgggattaag tttggtggag cagctgctag       2040
ttcatctgca ccgcctccag cgagtggagg tccgatacgt cctaatccct agggatttaa       2100
ggacgtgaac tctgttgaga tctctgtgaa attcagaggg tgggtgatac catattcact       2160
gatgccatta gcgacatcta aatagggcta attgtgacta atttgaggga atttccttta       2220
ccattgacgt cagtgtcgtt ggtagcattt gagtttcgga gcatcttgtt ctggggtttc       2280
acactatctt tagagaaagt gttaagttaa ttaagttatc ttaattaaga gcataattat       2340
actgatttgt ctctcgttga tagagtctat cattctgtta ctaaaaattt gacaactcgg       2400
tttgctgacc tactggttac tgtatcactt acccgagtta acgagtctag aaacgtgtga       2460
aagaaacaat tgaggtttta gagctagaaa tagcaagtta aaataaggct agtccgttat       2520
caacttgaaa aagtggcacc gagtcggtgc tccctagtct ataaatataa gagaccctct       2580
tatagtaagc agagttgttg gagacgttct tgatccgttt aatagatcaa tcactctaaa       2640
ggttacttat ggccaagtgc ttggtagtag cgactccatg gttttagagc tagaaatagc       2700
aagttaaaat aaggctagtc cgttatcaac ttgaaaaagt ggcaccgagt cggtgctccc       2760
tagtctataa atataagaga ccctcttata gtaagcagag ttgttggaga cgttcttgat       2820
ccgtttaata gatcaatcac tctaaaggtt acttatggcc aacaggttga ttgtcttctc       2880
aagcaggttt tagagctaga aatagcaagt taaaataagg ctagtccgtt atcaacttga       2940
aaaagtggca ccgagtcggt gctccctagt ctataaatat aagagaccct cttatagtaa      3000
```

-continued

```
gcagagttgt tggagacgtt cttgatccgt ttaatagatc aatcactcta aaggttactt   3060
atggccaaag tgccgggcat gtcccgaaga cattaaacta cggttcttta agtagatccg   3120
tgtctgaagt tttaggttca atttaaacct acgagattga cattctcgac tgatcttgat   3180
tgatcggtaa gtcttttgta atttaatttt ctttttgatt ttattttaaa ttgttatctg   3240
tttctgtgta tagactgttt gagatcggcg tttggccgac tcattgtctt accatagggg   3300
aacggacttt gtttgtgttg ttattttatt tgtattttat taaaattctc aacgatctga   3360
aaaagcctcg cggctaagag attgttgggg ggtgagtaag tacttttaaa gtgatgatgg   3420
ttacaaaggc aaaaggggta aaacccctcg cctacgtaag cgttattacg cccgtctgta   3480
cttatatcag tacactgacg agtccctaaa ggacgaaacg ggagaacgct agccaccacc   3540
accaccacca cgtgtgaatt acaggtgacc agctcgaatt tccccgatcg ttcaaacatt   3600
tggcaataaa gtttcttaag attgaatcct gttgccggtc ttgcgatgat tatcatataa   3660
tttctgttga attacgttaa gcatgtaata attaacatgt aatgcatgac gttatttatg   3720
agatgggttt ttatgattag agtcccgcaa ttatacattt aatacgcgat agaaaacaaa   3780
atatagcgcg caaactagga taaattatcg cgcgcggtgt catctatgtt actagatcgg   3840
gaattaaact atcagtgttt gacaggatat attggcgggt aaacctaaga gaaaagagcg   3900
tttattagaa taatcggata tttaaaaggg cgtgaaaagg tttatccgtt cgtccatttg   3960
tatgtgcatg ccaaccacag ggttcccctc gggatcaaag tactttgatc caacccctcc   4020
gctgctatag tgcagtcggc ttctgacgtt cagtgcagcc gtcttctgaa aacgacatgt   4080
cgcacaagtc ctaagttacg cgacaggctg ccgccctgcc cttttcctgg cgttttcttg   4140
tcgcgtgttt tagtcgcata aagtagaata cttgcgacta gaaccggaga cattacgcca   4200
tgaacaagag cgccgccgct ggcctgctgg gctatgcccg cgtcagcacc gacgaccagg   4260
acttgaccaa ccaacgggcc gaactgcacg cggccggctg caccaagctg ttttccgaga   4320
agatcaccgg caccaggcgc gaccgcccgg agctggccag gatgcttgac cacctacgcc   4380
ctggcgacgt tgtgacagtg accaggctag accgcctggc ccgcagcacc cgcgacctac   4440
tggacattgc cgagcgcatc caggaggccg gcgcgggcct gcgtagcctg gcagagccgt   4500
gggccgacac caccacgccg gccggccgca tggtgttgac cgtgttcgcc ggcattgccg   4560
agttcgagcg ttccctaatc atcgaccgca cccggagcgg cgcgcgaggcc gccaaggccc   4620 gaggcgtgaa gtttggcccc cgccctaccc tcacccccggc acagatcgcg cacgcccgcg   4680
agctgatcga ccaggaaggc cgcaccgtga aagaggcggc tgcactgctt ggcgtgcatc   4740
gctcgaccct gtaccgcgca cttgagcgca gcgaggaagt gacgcccacc gaggccaggc   4800
ggcgcggtgc cttccgtgag gacgcattga ccgaggccga cgccctggcg gccgccgaga   4860
atgaacgcca agaggaacaa gcatgaaacc gcaccaggac ggccaggacg aaccgttttt   4920
cattaccgaa gagatcgagg cggagatgat cgcggccggg tacgtgttcg agccgccgc   4980 gcacgtctca accgtgcggc tgcatgaaat cctggccggt ttgtctgatg ccaagctggc   5040
ggcctggccg gccagcttgg ccgctgaaga aaccgagcgc cgccgtctaa aaaggtgatg   5100
tgtatttgag taaaacagct tgcgtcatgc ggtcgctgcg tatatgatgc gatgagtaaa   5160
taaacaaata cgcaagggga acgcatgaag gttatcgctg tacttaacca gaaaggcggg   5220
tcaggcaaga cgaccatcgc aacccatcta gcccgcgccc tgcaactcgc cggggccgat   5280
gttctgttag tcgattccga tccccagggc agtgcccgcg attgggcggc cgtgcgggaa   5340
gatcaaccgc taaccgttgt cggcatcgac cgcccgacga ttgaccgcga cgtgaaggcc   5400
```

-continued

```
atcggccggc gcgacttcgt agtgatcgac ggagcgcccc aggcggcgga cttggctgtg    5460
tccgcgatca aggcagccga cttcgtgctg attccggtgc agccaagccc ttacgacata    5520
tgggccaccg ccgacctggt ggagctggtt aagcagcgca ttgaggtcac ggatggaagg    5580
ctacaagcgg cctttgtcgt gtcgcgggcg atcaaaggca cgcgcatcgg cggtgaggtt    5640
gccgaggcgc tggccgggta cgagctgccc attcttgagt cccgtatcac gcagcgcgtg    5700
agctacccag gcactgccgc cgccggcaca accgttcttg aatcagaacc cgagggcgac    5760
gctgcccgcg aggtccaggc gctggccgct gaaattaaat caaaactcat ttgagttaat    5820
gaggtaaaga gaaaatgagc aaaagcacaa acacgctaag tgccggccgt ccgagcgcac    5880
gcagcagcaa ggctgcaacg ttggccagcc tggcagacac gccagccatg aagcgggtca    5940
actttcagtt gccggcggag gatcacacca agctgaagat gtacgcggta cgccaaggca    6000
agaccattac cgagctgcta tctgaataca tcgcgcagct accagagtaa atgagcaaat    6060
gaataaatga gtagatgaat tttagcggct aaaggaggcg gcatggaaaa tcaagaacaa    6120
ccaggcaccg acgccgtgga atgccccatg tgtggaggaa cgggcggttg gccaggcgta    6180
agcggctggg ttgcctgccg gccctgcaat ggcactggaa cccccaagcc cgaggaatcg    6240
gcgtgagcgg tcgcaaacca tccggcccgg tacaaatcgg cgcggcgctg ggtgatgacc    6300
tggtggagaa gttgaaggcc gcgcaggccg cccagcggca acgcatcgag gcagaagcac    6360
gccccggtga atcgtggcaa gcggccgctg atcgaatccg caaagaatcc cggcaaccgc    6420
cggcagccgg tgcgccgtcg attaggaagc cgcccaaggg cgacgagcaa ccagattttt    6480
tcgttccgat gctctatgac gtgggcaccc gcgatagtcg cagcatcatg gacgtggccg    6540
ttttccgtct gtcgaagcgt gaccgacgag ctggcgaggt gatccgctac gagcttccag    6600
acgggcacgt agaggtttcc gcagggccgg ccggcatggc cagtgtgtgg gattacgacc    6660
tggtactgat ggcggtttcc catctaaccg aatccatgaa ccgataccgg gaagggaagg    6720
gagacaagcc cggccgcgtg ttccgtccac acgttgcgga cgtactcaag ttctgccggc    6780
gagccgatgg cggaaagcag aaagacgacc tggtagaaac ctgcattcgg ttaaacacca    6840
cgcacgttgc catgcagcgt acgaagaagg ccaagaacgg ccgcctggtg acggtatccg    6900
agggtgaagc cttgattagc cgctacaaga tcgtaaagag cgaaaccggg cggccggagt    6960
acatcgagat cgagctagct gattggatgt accgcgagat cacagaaggc aagaacccgg    7020
acgtgctgac ggttcacccc gattactttt tgatcgatcc cggcatcggc cgttttctct    7080
accgcctggc acgccgcgcc gcaggcaagg cagaagccag atggttgttc aagacgatct    7140
acgaacgcag tggcagcgcc ggagagttca agaagttctg tttcaccgtg cgcaagctga    7200
tcgggtcaaa tgacctgccg gagtacgatt tgaaggagga ggcggggcag ctggcccga    7260 tcctagtcat gcgctaccgc aacctgatcg agggcgaagc atccgccggt tcctaatgta    7320
cggagcagat gctagggcaa attgccctag caggggaaaa aggtcgaaaa ggtctctttc    7380
ctgtggatag cacgtacatt gggaacccaa agccgtacat tgggaaccgg aacccgtaca    7440
ttgggaaccc aaagccgtac attgggaacc ggtcacacat gtaagtgact gatataaaag    7500
agaaaaaagg cgattttttcc gcctaaaact ctttaaaact tattaaaact cttaaaaccc    7560
gcctggcctg tgcataactg tctggccagc gcacagccga agagctgcaa aaagcgccta    7620
cccttcggtc gctgcgctcc ctacgccccg ccgcttcgcg tcggcctatc gcggccgctg    7680
gccgctcaaa aatggctggc ctacggccag gcaatctacc agggcgcgga caagccgcgc    7740
```

-continued

```
cgtcgccact cgaccgccgg cgcccacatc aaggcaccct gcctcgcgcg tttcggtgat    7800
gacggtgaaa acctctgaca catgcagctc ccggagacgg tcacagcttg tctgtaagcg    7860
gatgccggga gcagacaagc ccgtcagggc gcgtcagcgg gtgttggcgg gtgtcggggc    7920
gcagccatga cccagtcacg tagcgatagc ggagtgtata ctggcttaac tatgcggcat    7980
cagagcagat tgtactgaga gtgcaccata tgcggtgtga aataccgcac agatgcgtaa    8040
ggagaaaata ccgcatcagg cgctcttccg cttcctcgct cactgactcg ctgcgctcgg    8100
tcgttcggct gcggcgagcg gtatcagctc actcaaaggc ggtaatacgg ttatccacag    8160
aatcagggga taacgcagga aagaacatgt gagcaaaagg ccagcaaaag gccaggaacc    8220
gtaaaaaggc cgcgttgctg gcgtttttcc ataggctccg cccccctgac gagcatcaca    8280
aaaatcgacg ctcaagtcag aggtggcgaa acccgacagg actataaaga taccaggcgt    8340
ttccccctgg aagctccctc gtgcgctctc ctgttccgac cctgccgctt accggatacc    8400
tgtccgcctt tctcccttcg ggaagcgtgg cgctttctca tagctcacgc tgtaggtatc    8460
tcagttcggt gtaggtcgtt cgctccaagc tgggctgtgt gcacgaaccc cccgttcagc    8520
ccgaccgctg cgccttatcc ggtaactatc gtcttgagtc caacccggta agacacgact    8580
tatcgccact ggcagcagcc actggtaaca ggattagcag agcgaggtat gtaggcggtg    8640
ctacagagtt cttgaagtgg tggcctaact acggctacac tagaaggaca gtatttggta    8700
tctgcgctct gctgaagcca gttaccttcg gaaaaagagt tggtagctct tgatccggca    8760
aacaaaccac cgctggtagc ggtggttttt ttgtttgcaa gcagcagatt acgcgcagaa    8820
aaaaaggatc tcaagaagat cctttgatct tttctacggg gtctgacgct cagtggaacg    8880
aaaactcacg ttaagggatt ttggtcatgc attctaggta ctaaaacaat tcatccagta    8940
aaatataata ttttatttc tcccaatcag gcttgatccc cagtaagtca aaaaatagct    9000
cgacatactg ttcttcccg atatcctccc tgatcgaccg gacgcagaag gcaatgtcat    9060
accacttgtc cgccctgccg cttctcccaa gatcaataaa gccacttact ttgccatctt    9120
tcacaaagat gttgctgtct cccaggtcgc cgtgggaaaa gacaagttcc tcttcgggct    9180
tttccgtctt taaaaaatca tacagctcgc gcggatcttt aaatggagtg tcttcttccc    9240
agttttcgca atccacatcg gccagatcgt tattcagtaa gtaatccaat tcggctaagc    9300
ggctgtctaa gctattcgta tagggacaat ccgatatgtc gatggagtga aagagcctga    9360
tgcactccgc atacagctcg ataatctttt cagggctttg ttcatcttca tactcttccg    9420
agcaaaggac gccatcggcc tcactcatga gcagattgct ccagccatca tgccgttcaa    9480
agtgcaggac ctttggaaca ggcagctttc cttccagcca tagcatcatg tccttttccc    9540
gttccacatc ataggtggtc cctttatacc ggctgtccgt cattttaaa tataggtttt    9600 cattttctcc caccagctta tataccttag caggagacat tccttccgta tcttttacgc    9660
agcggtattt ttcgatcagt tttttcaatt ccggtgatat tctcatttta gccatttatt    9720
atttccttcc tcttttctac agtatttaaa gataccccaa gaagctaatt ataacaagac    9780
gaactccaat tcactgttcc ttgcattcta aaaccttaaa taccagaaaa cagctttttc    9840
aaagttgttt tcaaagttgg cgtataacat agtatcgacg gagccgattt tgaaaccgcg    9900
gtgatcacag gcagcaacgc tctgtcatcg ttacaatcaa catgctaccc tccgcgagat    9960
catccgtgtt tcaaacccgg cagcttagtt gccgttcttc cgaatagcat cggtaacatg   10020
agcaaagtct gccgccttac aacggctctc ccgctgacgc cgtcccggac tgatgggctg   10080
cctgtatcga gtggtgattt tgtgccgagc tgccggtc                          10118
```

-continued

```
<210> SEQ ID NO 68
<211> LENGTH: 10164
<212> TYPE: DNA
<213> ORGANISM: Artificial
<220> FEATURE:
<223> OTHER INFORMATION: synthetic oligonucleotide

<400> SEQUENCE: 68 gggggagctgt tggctggctg gtggcaggat atattgtggt gtaaacaaat tgacgcttag      60
acaacttaat aacacattgc ggacgttttt aatgtactga attaacgccg aattaattcc     120
taggccacca tgttgggccc ggcgcgccaa gcttgcatgc ctgcaggtca acatggtgga     180
gcacgacact ctcgtctact ccaagaatat caaagataca gtctcagaag accagagggc     240
tattgagact tttcaacaaa gggtaatatc gggaaacctc ctcggattcc attgcccagc     300
tatctgtcac ttcatcgaaa ggacagtaga aaaggaagat ggcttctaca aatgccatca     360
ttgcgataaa ggaaaggcta tcgttcaaga tgcctctacc gacagtggtc ccaaagatgg     420
acccccaccc acgaggaaca tcgtggaaaa agaagacgtt ccaaccacgt cttcaaagca     480
agtggattga tgtgatggtc aacatggtgg agcacgacac tctcgtctac tccaagaata     540
tcaaagatac agtctcagaa gaccagaggg ctattgagac ttttcaacaa agggtaatat     600
cgggaaacct cctcggattc cattgcccag ctatctgtca cttcatcgaa aggacagtag     660
aaaaggaaga tggcttctac aaatgccatc attgcgataa aggaaaggct atcgttcaag     720
atgcctctac cgacagtggt cccaaagatg accccccacc cacgaggaac atcgtggaaa     780
aagaagacgt tccaaccacg tcttcaaagc aagtggattg atgtgatatc tccactgacg     840
taagggatga cgcacaatcc cactatcctt cgcaagaccc ttcctctata taaggaagtt     900
catttcattt ggagaggata aaacattgca cctatggtgt tgccctggct ggggtatgtc     960
agtgatcgca gtagaatgta ctaattgaca agttggagaa tacggtagaa cgtccttatc    1020
caacacagcc tttatccctc tccctgacga ggttttttgtc agtgtaatat ttctttttga    1080
actatccagc ttagtaccgt acgggaaagt gactggtgtg cttatctttg aaatgttact    1140
ttgggtttcg gttctttagg ttagtaagaa agcacttgtc ttctcataca aaggaaaacc    1200
tgagacgtat cgcttacgaa agtagcaatg aaagaaaggt ggtggtttta atcgctaccg    1260
caaaaacgat ggggtcgttt taattaactt ctcctacgca agcgtctaaa cggacgttgg    1320
ggttttgcta gtttctttag agaaaactag ctaagtcttt aatgttatca ttagagatgg    1380
cataaatata atacttgtgt ctgctgataa gatcatttta atttggacga ttagacttgt    1440
tgaactacag gttactgaat cacttgcgct aatcaacatg ggagatatgt acgatgaatc    1500
atttgacaag tcgggcggtc ctgctgactt gatggacgat tcttgggtgg aatcagtttc    1560
gtggaaagat ctgttgaaga agttacacag cataaaattt gcactacagt ctggtagaga    1620
tgagatcact gggttactag cggcactgaa tagacagtgt ccttattcac catatgagca    1680
gtttccagat aagaaggtgt atttcctttt agactcacgg gctaacagtg ctcttggtgt    1740
gattcagaac gcttcagcgt tcaagagacg agctgatgag aagaatgcag tggcgggtgt    1800
tacaaatatt cctgcgaatc caaacacaac ggttacgacg aaccaaggga gtactactac    1860
taccaaggcg aacactggct cgactttgga agaagacttg tacacttatt acaaattcga    1920
tgatgcctct acagctttcc acaaatctct aacttcgtta gagaacatgg agttgaagag    1980
ttattaccga aggaactttg agaaagtatt cgggattaag tttggtggag cagctgctag    2040
```

-continued

```
ttcatctgca ccgcctccag cgagtggagg tccgatacgt cctaatccct agggatttaa    2100
ggacgtgaac tctgttgaga tctctgtgaa attcagaggg tgggtgatac catattcact    2160
gatgccatta gcgacatcta aatagggcta attgtgacta atttgaggga atttccttta    2220
ccattgacgt cagtgtcgtt ggtagcattt gagtttcgga gcatcttgtt ctggggtttc    2280
acactatctt tagagaaagt gttaagttaa ttaagttatc ttaattaaga gcataattat    2340
actgatttgt ctctcgttga tagagtctat cattctgtta ctaaaaattt gacaactcgg    2400
tttgctgacc tactggttac tgtatcactt acccgagtta acgagtctag aaacgtgtga    2460
aagaaacaat tgaggtttta gagctagaaa tagcaagtta aaataaggct agtccgttat    2520
caacttgaaa aagtggcacc gagtcggtgc tccctagtct ataaatataa gagaccctct    2580
tatagtaagc agagttgttg gagacgttct tgatccgttt aatagatcaa tcactctaaa    2640
ggttacttat ggccaaaagg aggttgacag aatgccaaat gtgcttggta gtagcgactc    2700
catggtttta gagctagaaa tagcaagtta aaataaggct agtccgttat caacttgaaa    2760
aagtggcacc gagtcggtgc tccctagtct ataaatataa gagaccctct tatagtaagc    2820
agagttgttg gagacgttct tgatccgttt aatagatcaa tcactctaaa ggttacttat    2880
ggccaaaagg aggttgacag aatgccaaat caggttgatt gtcttctcaa gcaggtttta    2940
gagctagaaa tagcaagtta aaataaggct agtccgttat caacttgaaa aagtggcacc    3000
gagtcggtgc tccctagtct ataaatataa gagaccctct tatagtaagc agagttgttg    3060
gagacgttct tgatccgttt aatagatcaa tcactctaaa ggttacttat ggccaaagtg    3120
ccgggcatgt cccgaagaca ttaaactacg gttctttaag tagatccgtg tctgaagttt    3180
taggttcaat ttaaacctac gagattgaca ttctcgactg atcttgattg atcggtaagt    3240
cttttgtaat ttaattttct ttttgatttt attttaaatt gttatctgtt tctgtgtata    3300
gactgtttga gatcggcgtt tggccgactc attgtcttac catagggaa cggactttgt     3360 ttgtgttgtt attttatttg tattttatta aaattctcaa cgatctgaaa aagcctcgcg    3420
gctaagagat tgttgggggg tgagtaagta cttttaaagt gatgatggtt acaaaggcaa    3480
aaggggtaaa acccctcgcc tacgtaagcg ttattacgcc cgtctgtact tatatcagta    3540
cactgacgag tccctaaagg acgaaacggg agaacgctag ccaccaccac caccaccacg    3600
tgtgaattac aggtgaccag ctcgaatttc cccgatcgtt caaacatttg gcaataaagt    3660
ttcttaagat tgaatcctgt tgccggtctt gcgatgatta tcatataatt tctgttgaat    3720
tacgttaagc atgtaataat taacatgtaa tgcatgacgt tatttatgag atgggttttt    3780
atgattagag tcccgcaatt atacatttaa tacgcgatag aaaacaaaat atagcgcgca    3840
aactaggata aattatcgcg cgcggtgtca tctatgttac tagatcggga attaaactat    3900
cagtgtttga caggatatat tggcgggtaa acctaagaga aaagagcgtt tattagaata    3960
acggatattt aaaagggcgt gaaaaggttt atccgttcgt ccatttgtat gtgcatgcca    4020
accacagggt tcccctcggg atcaaagtac tttgatccaa cccctccgct gctatagtgc    4080
agtcggcttc tgacgttcag tgcagccgtc ttctgaaaac gacatgtcgc acaagtccta    4140
agttacgcga caggctgccg ccctgccctt ttcctggcgt tttcttgtcg cgtgttttag    4200
tcgcataaag tagaatactt gcgactagaa ccggagacat tacgccatga acaagagcgc    4260
cgccgctggc ctgctgggct atgcccgcgt cagcaccgac gaccaggact tgaccaacca    4320
acgggccgaa ctgcacgcgg ccggctgcac caagctgttt tccgagaaga tcaccggcac    4380
caggcgcgac cgcccggagc tggccaggat gcttgaccac ctacgccctg gcgacgttgt    4440
```

```
gacagtgacc aggctagacc gcctggcccg cagcacccgc gacctactgg acattgccga    4500
gcgcatccag gaggccggcg cgggcctgcg tagcctggca gagccgtggg ccgacaccac    4560
cacgccggcc ggccgcatgg tgttgaccgt gttcgccggc attgccgagt tcgagcgttc    4620
cctaatcatc gaccgcaccc ggagcgggcg cgaggccgcc aaggcccgag gcgtgaagtt    4680
tggcccccgc cctaccctca ccccggcaca gatcgcgcac gcccgcgagc tgatcgacca    4740
ggaaggccgc accgtgaaag aggcggctgc actgcttggc gtgcatcgct cgaccctgta    4800
ccgcgcactt gagcgcagcg aggaagtgac gcccaccgag gccaggcggc gcggtgcctt    4860
ccgtgaggac gcattgaccg aggccgacgc cctggcggcc gccgagaatg aacgccaaga    4920
ggaacaagca tgaaaccgca ccaggacggc caggacgaac cgtttttcat taccgaagag    4980
atcgaggcgg agatgatcgc ggccgggtac gtgttcgagc cgcccgcgca cgtctcaacc    5040
gtgcggctgc atgaaatcct ggccggtttg tctgatgcca agctggcggc ctggccggcc    5100
agcttggccg ctgaagaaac cgagcgccgc cgtctaaaaa ggtgatgtgt atttgagtaa    5160
aacagcttgc gtcatgcggt cgctgcgtat atgatgcgat gagtaaataa acaaatacgc    5220
aaggggaacg catgaaggtt atcgctgtac ttaaccagaa aggcgggtca ggcaagacga    5280
ccatcgcaac ccatctagcc cgcgccctgc aactcgccgg ggccgatgtt ctgttagtcg    5340
attccgatcc ccagggcagt gcccgcgatt gggcggccgt gcgggaagat caaccgctaa    5400
ccgttgtcgg catcgaccgc ccgacgattg accgcgacgt gaaggccatc ggccggcgcg    5460
acttcgtagt gatcgacgga gcgccccagg cggcggactt ggctgtgtcc gcgatcaagg    5520
cagccgactt cgtgctgatt ccggtgcagc caagccctta cgacatatgg gccaccgccg    5580
acctggtgga gctggttaag cagcgcattg aggtcacgga tggaaggcta caagcggcct    5640
ttgtcgtgtc gcgggcgatc aaaggcacgc gcatcggcgg tgaggttgcc gaggcgctgg    5700
ccgggtacga gctgcccatt cttgagtccc gtatcacgca gcgcgtgagc tacccaggca    5760
ctgccgccgc cggcacaacc gttcttgaat cagaacccga gggcgacgct gcccgcgagg    5820
tccaggcgct ggccgctgaa attaaatcaa aactcatttg agttaatgag gtaaagagaa    5880
aatgagcaaa agcacaaaca cgctaagtgc cggccgtccg agcgcacgca gcagcaaggc    5940
tgcaacgttg gccagcctgg cagacacgcc agccatgaag cgggtcaact ttcagttgcc    6000
ggcggaggat cacaccaagc tgaagatgta cgcggtacgc caaggcaaga ccattaccga    6060
gctgctatct gaatacatcg cgcagctacc agagtaaatg agcaaatgaa taaatgagta    6120
gatgaatttt agcggctaaa ggaggcggca tggaaaatca agaacaacca ggcaccgacg    6180
ccgtggaatg ccccatgtgt ggaggaacgg gcggttggcc aggcgtaagc ggctgggttg    6240
tctgccggcc ctgcaatggc actggaaccc ccaagcccga ggaatcggcg tgacggtcgc    6300
aaaccatccg gcccggtaca aatcggcgcg gcgctgggtg atgacctggt ggagaagttg    6360
aaggccgcgc aggccgccca gcggcaacgc atcgaggcag aagcacgccc cggtgaatcg    6420
tggcaagcgg ccgctgatcg aatccgcaaa gaatcccggc aaccgccggc agccggtgcg    6480
ccgtcgatta ggaagccgcc caagggcgac gagcaaccag attttttcgt tccgatgctc    6540
tatgacgtgg gcacccgcga tagtcgcagc atcatggacg tggccgtttt ccgtctgtcg    6600
aagcgtgacc gacgagctgg cgaggtgatc cgctacgagc ttccagacgg gcacgtagag    6660
gtttccgcag gccggccggc catggccagt gtgtgggatt acgacctggt actgatggcc    6720
gtttcccatc taaccgaatc catgaaccga taccgggaag ggaagggaga caagcccggc    6780
```

-continued

```
cgcgtgttcc gtccacacgt tgcggacgta ctcaagttct gccggcgagc cgatggcgga     6840
aagcagaaag acgacctggt agaaacctgc attcggttaa acaccacgca cgttgccatg     6900
cagcgtacga agaaggccaa gaacggccgc ctggtgacgg tatccgaggg tgaagccttg     6960
attagccgct acaagatcgt aaagagcgaa accgggcggc cggagtacat cgagatcgag     7020
ctagctgatt ggatgtaccg cgagatcaca gaaggcaaga acccggacgt gctgacggtt     7080
caccccgatt actttttgat cgatcccggc atcggccgtt ttctctaccg cctggcacgc     7140
cgcgccgcag gcaaggcaga agccagatgg ttgttcaaga cgatctacga acgcagtggc     7200
agcgccggag agttcaagaa gttctgtttc accgtgcgca agctgatcgg gtcaaatgac     7260
ctgccggagt acgatttgaa ggaggaggcg gggcaggctg gcccgatcct agtcatgcgc     7320
taccgcaacc tgatcgaggg cgaagcatcc gccggttcct aatgtacgga gcagatgcta     7380
gggcaaattg ccctagcagg ggaaaaaggt cgaaaaggtc tctttcctgt ggatagcacg     7440
tacattggga acccaaagcc gtacattggg aaccggaacc cgtacattgg gaacccaaag     7500
ccgtacattg ggaaccggtc acacatgtaa gtgactgata taaaagagaa aaaaggcgat     7560 tttttccgcct aaaactcttt aaaacttatt aaaactctta aaacccgcct ggcctgtgca     7620
taactgtctg gccagcgcac agccgaagag ctgcaaaaag cgcctaccct tcggtcgctg     7680
cgctccctac gccccgccgc ttcgcgtcgg cctatcgcgg ccgctggccg ctcaaaaatg     7740
gctggcctac ggccaggcaa tctaccaggg cgcggacaag ccgcgccgtc gccactcgac     7800
cgccggcgcc cacatcaagg caccctgcct cgcgcgtttc ggtgatgacg gtgaaaacct     7860
ctgacacatg cagctcccgg agacggtcac agcttgtctg taagcggatg ccgggagcag     7920
acaagcccgt cagggcgcgt cagcgggtgt tggcgggtgt cggggcgcag ccatgaccca     7980
gtcacgtagc gatagcggag tgtatactgg cttaactatg cggcatcaga gcagattgta     8040
ctgagagtgc accatatgcg gtgtgaaata ccgcacagat gcgtaaggag aaaataccgc     8100
atcaggcgct cttccgcttc ctcgctcact gactcgctgc gctcggtcgt tcggctgcgg     8160
cgagcggtat cagctcactc aaaggcggta atacggttat ccacagaatc aggggataac     8220
gcaggaaaga acatgtgagc aaaaggccag caaaaggcca ggaaccgtaa aaaggccgcg     8280
ttgctggcgt ttttccatag gctccgcccc cctgacgagc atcacaaaaa tcgacgctca     8340
agtcagaggt ggcgaaaccc gacaggacta taaagatacc aggcgtttcc ccctggaagc     8400
tccctcgtgc gctctcctgt tccgaccctg ccgcttaccg gatacctgtc cgcctttctc     8460
ccttcgggaa gcgtggcgct ttctcatagc tcacgctgta ggtatctcag ttcggtgtag     8520
gtcgttcgct ccaagctggg ctgtgtgcac gaaccccccg ttcagcccga ccgctgcgcc     8580
ttatccggta actatcgtct tgagtccaac ccggtaagac acgacttatc gccactggca     8640
gcagccactg gtaacaggat tagcagagcg aggtatgtag gcggtgctac agagttcttg     8700
aagtggtggc ctaactacgg ctacactaga aggacagtat ttggtatctg cgctctgctg     8760
aagccagtta ccttcggaaa aagagttggt agctcttgat ccggcaaaca aaccaccgct     8820
ggtagcggtg gtttttttgt ttgcaagcag cagattacgc gcagaaaaaa aggatctcaa     8880
gaagatcctt tgatcttttc tacggggtct gacgctcagt ggaacgaaaa ctcacgttaa     8940
gggattttgg tcatgcattc taggtactaa aacaattcat ccagtaaaat ataatatttt     9000
attttctccc aatcaggctt gatccccagt aagtcaaaaa atagctcgac atactgttct     9060
tccccgatat cctccctgat cgaccggacg cagaaggcaa tgtcatacca cttgtccgcc     9120
ctgccgcttc tcccaagatc aataaagcca cttactttgc catctttcac aaagatgttg     9180
```

```
ctgtctccca ggtcgccgtg ggaaaagaca agttcctctt cgggcttttc cgtctttaaa    9240
aaatcataca gctcgcgcgg atctttaaat ggagtgtctt cttcccagtt ttcgcaatcc    9300
acatcggcca gatcgttatt cagtaagtaa tccaattcgg ctaagcggct gtctaagcta    9360
ttcgtatagg gacaatccga tatgtcgatg gagtgaaaga gcctgatgca ctccgcatac    9420
agctcgataa tcttttcagg gctttgttca tcttcatact cttccgagca aaggacgcca    9480
tcggcctcac tcatgagcag attgctccag ccatcatgcc gttcaaagtg caggaccttt    9540
ggaacaggca gctttccttc cagccatagc atcatgtcct tttcccgttc cacatcatag    9600
gtggtccctt tataccggct gtccgtcatt tttaaatata ggttttcatt ttctcccacc    9660
agcttatata ccttagcagg agacattcct tccgtatctt ttacgcagcg gtatttttcg    9720
atcagttttt tcaattccgg tgatattctc attttagcca tttattattt ccttcctctt    9780
ttctacagta tttaaagata ccccaagaag ctaattataa caagacgaac tccaattcac    9840
tgttccttgc attctaaaac cttaaatacc agaaaacagc tttttcaaag ttgtttttcaa    9900 agttggcgta taacatagta tcgacggagc cgattttgaa accgcggtga tcacaggcag    9960
caacgctctg tcatcgttac aatcaacatg ctaccctccg cgagatcatc cgtgtttcaa   10020
acccggcagc ttagttgccg ttcttccgaa tagcatcggt aacatgagca aagtctgccg   10080
ccttacaacg gctctcccgc tgacgccgtc ccggactgat gggctgcctg tatcgagtgg   10140
tgattttgtg ccgagctgcc ggtc                                          10164

<210> SEQ ID NO 69
<211> LENGTH: 20
<212> TYPE: DNA
<213> ORGANISM: Nicotiana benthamiana

<400> SEQUENCE: 69
ggacctcatg attcagatcc                                                  20

<210> SEQ ID NO 70
<211> LENGTH: 833
<212> TYPE: DNA
<213> ORGANISM: Nicotiana benthamiana

<400> SEQUENCE: 70
ccatccagtt cgaaaccttc gaaatggctg cgtcgagatc agtgctcagg tatgttaaac      60
agaaaactct agctgaatag tgatttctgt aaatttccaa attttccata taattgcacc     120
tcagttcatc aatgtttact tccctttata agtactacct tcgacacata gtgatgagag     180
cctagttttt cagtttaaat tagagctgtt agttcctcag attttttaaca ttttaaaatc     240 ttggtgactc tccgtatgct gcagaatcac aactatgccg ttgaccctga atctcttccg     300
gaaggtgtag aggtgactca tgtaaatttg aatgatggaa gttgtgctgg tcttgcctcc     360
tctaaaatga agctaatgtc acttcaatac catcccgaag catctccagg acctcatgat     420
tcagatcctg gtaaacatat actgactcga tcttctcgac acaaaaaacg tcggccaatt     480
tgttcattgg gtgtcgttag ctgttaactt ttaaacaaat atagctgtac atatgaggat     540
ttacgaaaac aattaagtac aatctggaga ataatgattt cacatggtca atcatttcta     600
caaaagaaag tttctgaaca actactttag ttttgattaa tcccaagtta ggattctgct     660
gtctaattca attaagaaat ctactttatt tccagctggt cttgtgttca tgatcactct     720
catatttcaa tttccatctg aacttttgag acaaatagaa tgataaaaga gtcaaaaaat     780
```

-continued

```
tcataaggta aaccatgatt tgcttgcatc tgagtgcagc tacttgaatc aag          833

<210> SEQ ID NO 71
<211> LENGTH: 15190
<212> TYPE: DNA
<213> ORGANISM: Artificial
<220> FEATURE:
<223> OTHER INFORMATION: synthetic construct

<400> SEQUENCE: 71
ggccgctaat acgactcact atagggagag ccgccaccat gagctcagag actggcccag           60
tggctgtgga ccccacattg agacggcgga tcgagcccca tgagtttgag gtattcttcg          120
atccgagaga gctccgcaag gagacctgcc tgctttacga aattaattgg gggggccggc          180
actccatttg gcgacataca tcacagaaca ctaacaagca cgtcgaagtc aacttcatcg          240
agaagttcac gacagaaaga tatttctgtc cgaacacaag gtgcagcatt acctggtttc          300
tcagctggag cccatgcggc gaatgtagta gggccatcac tgaattcctg tcaaggtatc          360
cccacgtcac tctgtttatt tacatcgcaa ggctgtacca ccacgctgac ccccgcaatc          420
gacaaggcct gcgggatttg atctcttcag gtgtgactat ccaaattatg actgagcagg          480
agtcaggata ctgctggaga aactttgtga attatagccc gagtaatgaa gcccactggc          540
ctaggtatcc ccatctgtgg gtacgactgt acgttcttga actgtactgc atcatactgg          600
gcctgcctcc ttgtctcaac attctgagaa ggaagcagcc acagctgaca ttctttacca          660
tcgctcttca gtcttgtcat taccagcgac tgcccccaca cattctctgg gccaccgggt          720
tgaaaagcgg cagcgagact cccgggacct cagagtccgc cacacccgaa agtgataaaa          780
agtattctat tggtttagcc atcggcacta attccgttgg atgggctgtc ataaccgatg          840
aatacaaagt accttcaaag aaatttaagg tgttggggaa cacagaccgt cattcgatta          900
aaaagaatct tatcggtgcc ctcctattcg atagtggcga aacggcagag gcgactcgcc          960
tgaaacgaac cgctcggaga aggtatacac gtcgcaagaa ccgaatatgt tacttacaag         1020 aaattttag caatgagatg gccaaagttg acgattcttt ctttcaccgt ttggaagagt         1080
ccttccttgt cgaagaggac aagaaacatg aacggcaccc catctttgga aacatagtag         1140
atgaggtggc atatcatgaa aagtacccaa cgatttatca cctcagaaaa aagctagttg         1200
actcaactga taaagcggac ctgaggttaa tctacttggc tcttgcccat atgataaagt         1260
tccgtgggca ctttctcatt gagggtgatc taaatccgga caactcggat gtcgacaaac         1320
tgttcatcca gttagtacaa acctataatc agttgtttga agagaaccct ataaatgcaa         1380
gtggcgtgga tgcgaaggct attcttagcg cccgcctctc taaatcccga cggctagaaa         1440
acctgatcgc acaattaccc ggagagaaga aaaatgggtt gttcggtaac cttatagcgc         1500
tctcactagg cctgacacca aattttaagt cgaacttcga cttagctgaa gatgccaaat         1560
tgcagcttag taaggacacg tacgatgacg atctcgacaa tctactggca caaattggag         1620
atcagtatgc ggacttattt ttggctgcca aaaaccttag cgatgcaatc ctcctatctg         1680
acatactgag agttaatact gagattacca aggcgccgtt atccgcttca atgatcaaaa         1740
ggtacgatga acatcaccaa gacttgacac ttctcaaggc cctagtccgt cagcaactgc         1800
ctgagaaata taaggaaata ttctttgatc agtcgaaaaa cgggtacgca ggttatattg         1860
acggcggagc gagtcaagag gaattctaca gtttatcaa acccatatta gagaagatgg         1920
atgggacgga agagttgctt gtaaaactca atcgcgaaga tctactgcga aagcagcgga         1980
ctttcgacaa cggtagcatt ccacatcaaa tccacttagg cgaattgcat gctatactta         2040
```

-continued

```
gaaggcagga ggatttttat ccgttcctca aagacaatcg tgaaaagatt gagaaaatcc   2100
taacctttcg cataccttac tatgtgggac ccctggcccg agggaactct cggttcgcat   2160
ggatgacaag aaagtccgaa gaaacgatta ctccatggaa ttttgaggaa gttgtcgata   2220
aaggtgcgtc agctcaatcg ttcatcgaga ggatgaccaa ctttgacaag aatttaccga   2280
acgaaaaagt attgcctaag cacagtttac tttacgagta tttcacagtg tacaatgaac   2340
tcacgaaagt taagtatgtc actgagggca tgcgtaaacc cgcctttcta agcggagaac   2400
agaagaaagc aatagtagat ctgttattca agaccaaccg caaagtgaca gttaagcaat   2460
tgaaagagga ctactttaag aaaattgaat gcttcgattc tgtcgagatc tccggggtag   2520
aagatcgatt taatgcgtca cttggtacgt atcatgacct cctaaagata attaaagata   2580
aggacttcct ggataacgaa gagaatgaag atatcttaga agatatagtg ttgactctta   2640
ccctctttga agatcgggaa atgattgagg aaagactaaa aacatacgct cacctgttcg   2700
acgataaggt tatgaaacag ttaaagaggc gtcgctatac gggctgggga cgattgtcgc   2760
ggaaacttat caacgggata agagacaagc aaagtggtaa aactattctc gattttctaa   2820
agagcgacgg cttcgccaat aggaacttta tgcagctgat ccatgatgac tctttaacct   2880
tcaaagagga tatacaaaag gcacaggttt ccggacaagg ggactcattg cacgaacata   2940
ttgcgaatct tgctggttcg ccagccatca aaaaggcat actccagaca gtcaaagtag   3000
tggatgagct agttaaggtc atgggacgtc acaaaccgga aaacattgta atcgagatgg   3060
cacgcgaaaa tcaaacgact cagaaggggc aaaaaaacag tcgagagcgg atgaagagaa   3120
tagaagaggg tattaaagaa ctgggcagcc agatcttaaa ggagcatcct gtggaaaata   3180
cccaattgca gaacgagaaa ctttacctct attacctaca aaatggaagg gacatgtatg   3240
ttgatcagga actggacata aaccgtttat ctgattacga cgtcgatcac attgtaccc   3300 aatccttttt gaaggacgat tcaatcgaca ataaagtgct tacacgctcg gataagaacc   3360
gagggaaaag tgacaatgtt ccaagcgagg aagtcgtaaa gaaaatgaag aactattggc   3420
ggcagctcct aaatgcgaaa ctgataacgc aaagaaagtt cgataactta actaaagctg   3480
agaggggtgg cttgtctgaa cttgacaagg ccggatttat taaacgtcag ctcgtggaaa   3540
cccgccaaat cacaaagcat gttgcacaga tactagattc ccgaatgaat acgaaatacg   3600
acgagaacga taagctgatt cgggaagtca aagtaatcac tttaaagtca aaattggtgt   3660
cggacttcag aaaggatttt caattctata aagttaggga gataaataac taccaccatg   3720
cgcacgacgc ttatcttaat gccgtcgtag ggaccgcact cattaagaaa tacccgaagc   3780
tagaaagtga gtttgtgtat ggtgattaca agtttatga cgtccgtaag atgatcgcga   3840
aaagcgaaca ggagatagg caaggctacag ccaaatactt cttttattct aacattatga   3900 atttcttaa dacggaaatc actctggcaa acggagagat acgcaaacga cctttaattg   3960
aaaccaatgg ggagacaggt gaaatcgtat gggataaggg ccgggacttc gcgacggtga   4020
gaaaagtttt gtccatgccc caagtcaaca tagtaaagaa aactgaggtg cagaccggag   4080
ggttttcaaa ggaatcgatt cttccaaaaa ggaatagtga taagctcatc gctcgtaaaa   4140
aggactggga cccgaaaaag tacggtggct cgatagccc tacagttgcc tattctgtcc   4200
tagtagtggc aaaagttgag aagggaaaat ccaagaaact gaagtcagtc aaagaattat   4260
tggggataac gattatggag cgctcgtctt ttgaaaagaa ccccatcgac ttccttgagg   4320
cgaaaggtta caaggaagta aaaaaggatc tcataattaa actaccaaag tatagtctgt   4380
```

-continued

```
ttgagttaga aaatggccga aaacggatgt tggctagcgc cggagagctt caaaagggga    4440
acgaactcgc actaccgtct aaatacgtga atttcctgta tttagcgtcc cattacgaga    4500
agttgaaagg ttcacctgaa gataacgaac agaagcaact ttttgttgag cagcacaaac    4560
attatctcga cgaaatcata gagcaaattt cggaattcag taagagagtc atcctagctg    4620
atgccaatct ggacaaagta ttaagcgcat acaacaagca cagggataaa cccatacgtg    4680
agcaggcgga aaatattatc catttgttta ctcttaccaa cctcggcgct ccagccgcat    4740
tcaagtattt tgacacaacg atagatcgca aacgatacac ttctaccaag gaggtgctag    4800
acgcgacact gattcaccaa tccatcacgg gattatatga aactcggata gatttgtcac    4860
agcttggggg tgactctggt ggttctacta atctgtcaga tattattgaa aaggagaccg    4920
gtaagcaact ggttatccag gaatccatcc tcatgctccc agaggaggtg gaagaagtca    4980
ttgggaacaa gccggaaagc gatatactcg tgcacaccgc ctacgacgag agcaccgacg    5040
agaatgtcat gcttctgact agcgacgccc ctgaatacaa gccttgggct ctggtcatac    5100
aggatagcaa cggtgagaac aagattaaga tgctctctgg tggttctccc aagaagaaga    5160
ggaaagtcta accggtcatc atcaccatca ccattgagtt taaacctcga gatatgaaga    5220
tgaagatgaa atatttggtg tgtcaaataa aaagcttgtg tgcttaagtt tgtgtttttt    5280
tcttggcttg ttgtgttatg aatttgtggc tttttctaat attaaatgaa tgtaagatca    5340
cattataatg aataaacaaa tgtttctata atccattgtg aatgttttgt tggatctctt    5400
ctgcagcata taactactgt atgtgctatg gtatggacta tggaatatga ttaaagataa    5460
ggagctccgg tgacgacggc cgcgactagt tttacgtacg ttaattaacc cggcgagctt    5520
tgggtacgtc acgtggctcg agcgcgtagt cctcggtaat atcgcagaac aaaagtacct    5580
gatatcgagt gtacttcaag tcacaccggc gagtgtggca ctggccgtcg ttttacaacg    5640
tcgtgactgg gaaaaccctg gcgttaccca acttaatcgc cttgcagcac atccccttt    5700 cgccagctgg cgtaatagcg aagaggcccg caccgatcgc ccttcccaac agttgcgcag    5760
cctgaatggc gaatgctaga gcagcttgag cttggatcag attgtcgttt cccgccttca    5820
gtttaaacta tcagtgtttg acaggatata ttggcgggta aacctaagag aaaagagcgt    5880
ttattagaat aatcggatat ttaaaagggc gtgaaaaggt ttatccgttc gtccatttgt    5940
atgtgcatgc caaccacagg gttcccctcg ggatcaaagt actttgatcc aaccctccg    6000 ctgctatagt gcagtcggct tctgacgttc agtgcagccg tcttctgaaa cgacatgtc    6060 gcacaagtcc taagttacgc gacaggctgc cgccctgccc ttttcctggc gttttcttgt    6120
cgcgtgtttt agtcgcataa agtagaatac ttgcgactag aaccggagac attacgccat    6180
gaacaagagc gccgccgctg gcctgctggg ctatgcccgc gtcagcaccg acgaccagga    6240
cttgaccaac caacgggccg aactgcacgc ggccggctgc accaagctgt tttccgagaa    6300
gatcaccggc accaggcgcg accgcccgga gctggccagg atgcttgacc acctacgccc    6360
tggcgacgtt gtgacagtga ccaggctaga ccgcctggcc cgcagcaccc gcgacctact    6420
ggacattgcc gagcgcatcc aggaggccgg cgcgggcctg cgtagcctgg cagagccgtg    6480
ggccgacacc accacgccgg ccggccgcat ggtgttgacc gtgttcgccg gcattgccga    6540
gttcgagcgt tccctaatca tcgaccgcac ccggagcggg cgcgaggccg ccaaggcccg    6600
aggcgtgaag tttggccccc gccctaccct caccccggca cagatcgcgc acgcccgcga    6660
gctgatcgac caggaaggcc gcaccgtgaa agaggcggct gcactgcttg gcgtgcatcg    6720
ctcgaccctg taccgcgcac ttgagcgcag cgaggaagtg acgcccaccg aggccaggcg    6780
```

```
gcgcggtgcc ttccgtgagg acgcattgac cgaggccgac gccctggcgg ccgccgagaa    6840
tgaacgccaa gaggaacaag catgaaaccg caccaggacg gccaggacga accgtttttc    6900
attaccgaag agatcgaggc ggagatgatc gcggccgggt acgtgttcga gccgcccgcg    6960
cacgtctcaa ccgtgcggct gcatgaaatc ctggccggtt tgtctgatgc caagctggcg    7020
gcctggccgg ccagcttggc cgctgaagaa accgagcgcc gccgtctaaa aaggtgatgt    7080
gtatttgagt aaaacagctt gcgtcatgcg gtcgctgcgt atatgatgcg atgagtaaat    7140
aaacaaatac gcaaggggaa cgcatgaagg ttatcgctgt acttaaccag aaaggcgggt    7200
caggcaagac gaccatcgca acccatctag cccgcgccct gcaactcgcc ggggccgatg    7260
ttctgttagt cgattccgat ccccagggca gtgcccgcga ttgggcggcc gtgcgggaag    7320
atcaaccgct aaccgttgtc ggcatcgacc gcccgacgat tgaccgcgac gtgaaggcca    7380
tcggccggcg cgacttcgta gtgatcgacg gagcgcccca ggcggcggac ttggctgtgt    7440
ccgcgatcaa ggcagccgac ttcgtgctga ttccggtgca gccaagccct tacgacatat    7500
gggccaccgc cgacctggtg gagctggtta agcagcgcat tgaggtcacg gatggaaggc    7560
tacaagcggc ctttgtcgtg tcgcgggcga tcaaaggcac gcgcatcggc ggtgaggttg    7620
ccgaggcgct ggccgggtac gagctgccca ttcttgagtc ccgtatcacg cagcgcgtga    7680
gctacccagg cactgccgcc gccggcacaa ccgttcttga atcagaaccc gagggcgacg    7740
ctgcccgcga ggtccaggcg ctggccgctg aaattaaatc aaaactcatt tgagttaatg    7800
aggtaaagag aaaatgagca aaagcacaaa cacgctaagt gccggccgtc cgagcgcacg    7860
cagcagcaag gctgcaacgt tggccagcct ggcagacacg ccagccatga agcgggtcaa    7920
ctttcagttg ccggcggagg atcacaccaa gctgaagatg tacgcggtac gccaaggcaa    7980
gaccattacc gagctgctat ctgaatacat cgcgcagcta ccagagtaaa tgagcaaatg    8040
aataaatgag tagatgaatt ttagcggcta aaggaggcgg catggaaaat caagaacaac    8100
caggcaccga cgccgtggaa tgccccatgt gtggaggaac gggcggttgg ccaggcgtaa    8160
gcggctgggt tgtctgccgg ccctgcaatg gcactggaac ccccaagccc gaggaatcgg    8220
cgtgacggtc gcaaaccatc cggcccggta caaatcggcg cggcgctggg tgatgacctg    8280
gtggagaagt tgaaggccgc gcaggccgcc cagcggcaac gcatcgaggc agaagcacgc    8340
cccggtgaat cgtggcaagc ggccgctgat cgaatccgca aagaatcccg gcaaccgccg    8400
gcagccggtg cgccgtcgat taggaagccg cccaagggcg acgagcaacc agattttttc    8460
gttccgatgc tctatgacgt gggcacccgc gatagtcgca gcatcatgga cgtggccgtt    8520
ttccgtctgt cgaagcgtga ccgacgagct ggcgaggtga tccgctacga gcttccagac    8580
gggcacgtag aggtttccgc agggccggcc ggcatggcca gtgtgtggga ttacgacctg    8640
gtactgatgg cggtttccca tctaaccgaa tccatgaacc gataccggga agggaaggga    8700
gacaagcccg gccgcgtgtt ccgtccacac gttgcggacg tactcaagtt ctgccggcga    8760
gccgatggcg gaaagcagaa agacgacctg gtagaaacct gcattcggtt aaacaccacg    8820
cacgttgcca tgcagcgtac gaagaaggcc aagaacggcc gcctggtgac ggtatccgag    8880
ggtgaagcct tgattagccg ctacaagatc gtaaagagcg aaaccgggcg gccggagtac    8940
atcgagatcg agctagctga ttggatgtac cgcgagatca cagaaggcaa gaacccggac    9000
gtgctgacgg ttcaccccga ttactttttg atcgatcccg gcatcggccg ttttctctac    9060
cgcctggcac gccgcgccgc aggcaaggca gaagccagat ggttgttcaa gacgatctac    9120
```

-continued

```
gaacgcagtg gcagcgccgg agagttcaag aagttctgtt tcaccgtgcg caagctgatc    9180
gggtcaaatg acctgccgga gtacgatttg aaggaggagg cggggcaggc tggcccgatc    9240
ctagtcatgc gctaccgcaa cctgatcgag ggcgaagcat ccgccggttc ctaatgtacg    9300
gagcagatgc tagggcaaat tgccctagca ggggaaaaag gtcgaaaagg tctctttcct    9360
gtggatagca cgtacattgg gaacccaaag ccgtacattg ggaaccggaa cccgtacatt    9420
gggaacccaa agccgtacat tgggaaccgg tcacacatgt aagtgactga tataaaagag    9480
aaaaaaggcg atttttccgc ctaaaactct ttaaaactta ttaaaactct taaaacccgc    9540
ctggcctgtg cataactgtc tggccagcgc acagccgaag agctgcaaaa agcgcctacc    9600
cttcggtcgc tgcgctccct acgccccgcc gcttcgcgtc ggcctatcgc ggccgctggc    9660
cgctcaaaaa tggctggcct acggccaggc aatctaccag ggcgcggaca agccgcgccg    9720
tcgccactcg accgccggcg cccacatcaa ggcaccctgc ctcgcgcgtt tcggtgatga    9780
cggtgaaaac ctctgacaca tgcagctccc ggagacggtc acagcttgtc tgtaagcgga    9840
tgccgggagc agacaagccc gtcagggcgc gtcagcgggt gttggcgggt gtcggggcgc    9900
agccatgacc cagtcacgta gcgatagcgg agtgtatact ggcttaacta tgcggcatca    9960
gagcagattg tactgagagt gcaccatatg cggtgtgaaa taccgcacag atgcgtaagg    10020
agaaaatacc gcatcaggcg ctcttccgct tcctcgctca ctgactcgct gcgctcggtc    10080
gttcggctgc ggcgagcggt atcagctcac tcaaaggcgg taatacggtt atccacagaa    10140
tcaggggata acgcaggaaa gaacatgtga gcaaaaggcc agcaaaaggc caggaaccgt    10200
aaaaaggccg cgttgctggc gttttttccat aggctccgcc cccctgacga gcatcacaaa    10260
aatcgacgct caagtcagag gtggcgaaac ccgacaggac tataaagata ccaggcgttt    10320
ccccctggaa gctccctcgt gcgctctcct gttccgaccc tgccgcttac cggatacctg    10380
tccgcctttc tcccttcggg aagcgtggcg ctttctcata gctcacgctg taggtatctc    10440
agttcggtgt aggtcgttcg ctccaagctg ggctgtgtgc acgaacccc cgttcagccc    10500 gaccgctgcg ccttatccgg taactatcgt cttgagtcca acccggtaag acacgactta    10560
tcgccactgg cagcagccac tggtaacagg attagcagag cgaggtatgt aggcggtgct    10620
acagagttct tgaagtggtg gcctaactac ggctacacta gaaggacagt atttggtatc    10680
tgcgctctgc tgaagccagt taccttcgga aaaagagttg gtagctcttg atccggcaaa    10740
caaaccaccg ctggtagcgg tggttttttt gtttgcaagc agcagattac gcgcagaaaa    10800
aaaggatctc aagaagatcc tttgatcttt tctacggggt ctgacgctca gtggaacgaa    10860
aactcacgtt aagggatttt ggtcatgcat tctaggtact aaaacaattc atccagtaaa    10920
atataatatt ttattttctc ccaatcaggc ttgatcccca gtaagtcaaa aaatagctcg    10980
acatactgtt cttccccgat atcctccctg atcgaccgga cgcagaaggc aatgtcatac    11040
cacttgtccg ccctgccgct tctcccaaga tcaataaagc cacttacttt gccatctttc    11100
acaaagatgt tgctgtctcc caggtcgccg tgggaaaaga caagttcctc ttcgggcttt    11160
tccgtcttta aaaaatcata cagctcgcgc ggatctttaa atggagtgtc ttcttcccag    11220
ttttcgcaat ccacatcggc cagatcgtta ttcagtaagt aatccaattc ggctaagcgg    11280
ctgtctaagc tattcgtata gggacaatcc gatatgtcga tggagtgaaa gagcctgatg    11340
cactccgcat acagctcgat aatcttttca gggctttgtt catcttcata ctcttccgag    11400
caaaggacgc catcggcctc actcatgagc agattgctcc agccatcatg ccgttcaaag    11460
tgcaggacct ttggaacagg cagctttcct tccagccata gcatcatgtc ctttttcccgt    11520
```

```
tccacatcat aggtggtccc tttataccgg ctgtccgtca tttttaaata taggttttca   11580
ttttctccca ccagcttata taccttagca ggagacattc cttccgtatc ttttacgcag   11640 cggtatttt cgatcagttt tttcaattcc ggtgatattc tcattttagc catttattat   11700
ttccttcctc ttttctacag tatttaaaga taccccaaga agctaattat aacaagacga   11760
actccaattc actgttcctt gcattctaaa accttaaata ccagaaaaca gcttttcaa   11820 agttgtttc aaagttggcg tataacatag tatcgacgga gccgattttg aaaccgcggt   11880
gatcacaggc agcaacgctc tgtcatcgtt acaatcaaca tgctaccctc cgcgagatca   11940
tccgtgtttc aaacccggca gcttagttgc cgttcttccg aatagcatcg gtaacatgag   12000
caaagtctgc cgccttacaa cggctctccc gctgacgccg tcccggactg atgggctgcc   12060
tgtatcgagt ggtgatttg tgccgagctg ccggtcgggg agctgttggc tggctggtgg   12120
caggatatat tgtggtgtaa acaaattgac gcttagacaa cttaataaca cattgcggac   12180
gtttttaatg tactgaatta acgccgaatt aattcggggg atctggattt tagtactgga   12240
ttttggtttt aggaattaga aattttattg atagaagtat tttacaaata caaatacata   12300
ctaagggttt cttatatgct caacacatga gcgaaaccct ataggaaccc taattccctt   12360
atctgggaac tactcacaca ttattatgga gaaactcgag cttgtcgatc gactctagct   12420
agaggatcga tccgaacccc agagtcccgc tcagaagaac tcgtcaagaa ggcgatagaa   12480
ggcgatgcgc tgcgaatcgg gagcggcgat accgtaaagc acgaggaagc ggtcagccca   12540
ttcgccgcca agctcttcag caatatcacg ggtagccaac gctatgtcct gatagcggtc   12600
cgccacaccc agccggccac agtcgatgaa tccagaaaag cggccatttt ccaccatgat   12660
attcggcaag caggcatcgc catgtgtcac gacgagatcc tcgccgtcgg gcatgcgcgc   12720
cttgagcctg gcgaacagtt cggctggcgc gagcccctga tgctcttcgt ccagatcatc   12780
ctgatcgaca gaccggctt ccatccgagt acgtgctcgc tcgatgcgat gtttcgcttg   12840
gtggtcgaat gggcaggtag ccggatcaag cgtatgcagc cgccgcattg catcagccat   12900
gatggatact ttctcggcag gagcaaggtg agatgacagg agatcctgcc ccggcacttc   12960
gcccaatagc agccagtccc ttcccgcttc agtgacaacg tcgagcacag ctgcgcaagg   13020
aacgcccgtc gtggccagcc acgatagccg cgctgcctcg tcctggagtt cattcagggc   13080
accggacagg tcggtcttga caaaaagaac cgggcgcccc tgcgctgaca gccggaacac   13140
ggcggcatca gagcagccga ttgtctgttg tgcccagtca tagccgaata gcctctccac   13200
ccaagcggcc ggagaacctg cgtgcaatcc atcttgttca atccccatgg tcgatcgaca   13260
gatctgcgaa agctcgagag agatagattt gtagagagag actggtgatt tcagcgtgtc   13320
ctctccaaat gaaatgaact tccttatata gaggaagggt cttgcgaagg atagtgggat   13380
tgtgcgtcat cccttacgtc agtggagata tcacatcaat ccacttgctt tgaagacgtg   13440
gttggaacgt cttctttttc cacgatgctc ctcgtgggtg ggggtccatc tttgggacca   13500
ctgtcggcag aggcatcttg aacgatagcc tttcctttat cgcaatgatg gcatttgtag   13560
gtgccacctt cctttctac tgtccttttg atgaagtgac agatagctgg gcaatggaat   13620
ccgaggaggt ttcccgatat tacccttgt tgaaaagtct caatagccct ttggtcttct   13680
gagactgtat ctttgatatt cttggagtag acgagagtgt cgtgctccac catgttcaca   13740
tcaatccact tgctttgaag acgtggttgg aacgtcttct ttttccacga tgctcctcgt   13800 gggtggggt ccatctttgg gaccactgtc ggcagaggca tcttgaacga tagcctttcc   13860
```

-continued

```
tttatcgcaa tgatggcatt tgtaggtgcc accttccttt tctactgtcc ttttgatgaa    13920
gtgacagata gctgggcaat ggaatccgag gaggtttccc gatattaccc tttgttgaaa    13980
agtctcaata gccctttggt cttctgagac tgtatctttg atattcttgg agtagacgag    14040
agtgtcgtgc tccaccatgt tggcaagctg ctctagccaa tacgcaaacc gcctctcccc    14100
gcgcgttggc cgattcatta atgcagctgg cacgacaggt ttcccgactg gaaagcgggc    14160
agtgagcgca acgcaattaa tgtgagttag ctcactcatt aggcacccca ggctttacac    14220
tttatgcttc cggctcgtat gttgtgtgga attgtgagcg gataacaatt tcacacagga    14280
aacagctatg acatgattac gaattcgagc tcggtacccg gggatcggcg cgccagattt    14340
gccttttcaa tttcagaaag aatgctaacc cacagatggt tagagaggct tacgcagcag    14400
gtatcatcaa gacgatctac ccgagcaata atctccagga aatcaaatac cttcccaaga    14460
aggttaaaga tgcagtcaaa agattcagga ctaactgcat caagaacaca gagaaagata    14520
tatttctcaa gatcagaagt actattccag tatggacgat tcaaggcttg cttcacaaac    14580
caaggcaagt aatagagatt ggagtctcta aaaaggtagt tcccactgaa tcaaaggcca    14640
tggagtcaaa gattcaaata gaggacctaa cagaactcgc cgtaaagact ggcgaacagt    14700
tcatacagag tctcttacga ctcaatgaca agaagaaaat cttcgtcaac atggtggagc    14760
acgacacact tgtctactcc aaaaatatca aagatacagt ctcagaagac caaagggcaa    14820
ttgagacttt caacaaaggg taatatccg gaaacctcct cggattccat tgcccagcta    14880
tctgtcactt tattgtgaag atagtggaaa aggaaggtgg ctcctacaaa tgccatcatt    14940
gcgataaagg aaaggccatc gttgaagatg cctctgccga cagtggtccc aaagatggac    15000
ccccacccac gaggagcatc gtggaaaaag aagacgttcc aaccacgtct tcaaagcaag    15060
tggattgatg tgatatctcc actgacgtaa gggatgacgc acaatcccac tatccttcgc    15120
aagacccttc ctctatataa ggaagttcat ttcatttgga gagaacacgg gggactcctg    15180
caggatccgc                                                          15190
```

<210> SEQ ID NO 72
<211> LENGTH: 10130
<212> TYPE: DNA
<213> ORGANISM: Artificial
<220> FEATURE:
<223> OTHER INFORMATION: synthetic construct

<400> SEQUENCE: 72

```
ggggagctgt tggctggctg gtggcaggat atattgtggt gtaaacaaat tgacgcttag       60
acaacttaat aacacattgc ggacgttttt aatgtactga attaacgccg aattaattcc      120
taggccacca tgttgggccc ggcgcgccaa gcttgcatgc ctgcaggtca acatggtgga      180
gcacgacact ctcgtctact ccaagaatat caaagataca gtctcagaag accagagggc      240
tattgagact tttcaacaaa gggtaatatc gggaaacctc ctcggattcc attgcccagc      300
tatctgtcac ttcatcgaaa ggacagtaga aaaggaagat ggcttctaca aatgccatca      360
ttgcgataaa ggaaaggcta tcgttcaaga tgcctctacc gacagtggtc ccaaagatgg      420
accccacccc acgaggaaca tcgtggaaaa agaagacgtt ccaaccacgt cttcaaagca      480
agtggattga tgtgatggtc aacatggtgg agcacgacac tctcgtctac tccaagaata      540
tcaaagatac agtctcagaa gaccagaggg ctattgagac ttttcaacaa agggtaatat      600
cgggaaacct cctcggattc cattgcccag ctatctgtca cttcatcgaa aggacagtag      660
aaaaggaaga tggcttctac aaatgccatc attgcgataa aggaaaggct atcgttcaag      720
```

```
atgcctctac cgacagtggt cccaaagatg accccccacc cacgaggaac atcgtggaaa      780
aagaagacgt tccaaccacg tcttcaaagc aagtggattg atgtgatatc tccactgacg      840
taagggatga cgcacaatcc cactatcctt cgcaagaccc ttcctctata taaggaagtt      900
catttcattt ggagaggata aaacattgca cctatggtgt tgccctggct ggggtatgtc      960
agtgatcgca gtagaatgta ctaattgaca agttggagaa tacggtagaa cgtccttatc     1020
caacacagcc tttatccctc tccctgacga ggttttttgtc agtgtaatat ttcttttttga     1080 actatccagc ttagtaccgt acgggaaagt gactggtgtg cttatctttg aaatgttact     1140
ttgggtttcg gttctttagg ttagtaagaa agcacttgtc ttctcataca aaggaaaacc     1200
tgagacgtat cgcttacgaa agtagcaatg aaagaaaggt ggtggtttta atcgctaccg     1260
caaaaacgat ggggtcgttt taattaactt ctcctacgca agcgtctaaa cggacgttgg     1320
ggttttgcta gtttctttag agaaaactag ctaagtcttt aatgttatca ttagagatgg     1380
cataaatata atacttgtgt ctgctgataa gatcatttta atttggacga ttagacttgt     1440
tgaactacag gttactgaat cacttgcgct aatcaacatg ggagatatgt acgatgaatc     1500
atttgacaag tcgggcggtc ctgctgactt gatggacgat tcttgggtgg aatcagtttc     1560
gtggaaagat ctgttgaaga agttacacag cataaaattt gcactacagt ctggtagaga     1620
tgagatcact gggttactag cggcactgaa tagacagtgt ccttattcac catatgagca     1680
gtttccagat aagaaggtgt atttcctttt agactcacgg gctaacagtg ctcttggtgt     1740
gattcagaac gcttcagcgt tcaagagacg agctgatgag aagaatgcag tggcgggtgt     1800
tacaaatatt cctgcgaatc caaacacaac ggttacgacg aaccaaggga gtactactac     1860
taccaaggcg aacactggct cgactttgga agaagacttg tacacttatt acaaaattcga     1920 tgatgcctct acagctttcc acaaatctct aacttcgtta gagaacatgg agttgaagag     1980
ttattaccga aggaactttg agaaagtatt cgggattaag tttggtggag cagctgctag     2040
ttcatctgca ccgcctccag cgagtggagg tccgatacgt cctaatccct agggatttaa     2100
ggacgtgaac tctgttgaga tctctgtgaa attcagaggg tgggtgatac catattcact     2160
gatgccatta gcgacatcta aatagggcta attgtgacta atttgaggga atttcctttta     2220 ccattgacgt cagtgtcgtt ggtagcattt gagtttcgga gcatcttgtt ctggggtttc     2280
acactatctt tagagaaagt gttaagttaa ttaagttatc ttaattaaga gcataattat     2340
actgatttgt ctctcgttga tagagtctat cattctgtta ctaaaaattt gacaactcgg     2400
tttgctgacc tactggttac tgtatcactt acccgagtta acgagtctag aaacggacct     2460
catgattcag atccgtttta gagctagaaa tagcaagtta aaataaggct agtccgttat     2520
caacttgaaa aagtggcacc gagtcggtgc tccctagtct ataaatataa gagaccctct     2580
tatagtaagc agagttgttg gagacgttct tgatccgttt aatagatcaa tcactctaaa     2640
ggttacttat ggccaaagag aggtgactaa tggcttggat ctaaggcctt ctcaggttca     2700
aaacaagcca agagttgaga ttggtggaga agacctcagg aacttctata ctttggttat     2760
ggtggatcca gatgttccaa gtcctagcaa ccctcacctc cgagaatatc tccattggtt     2820
ggtgactgat atccctgcta caactggaac aacctttggc aatgagattg tgtgttacga     2880
aaatccaagt cccactgcag gaattcatcg tgtcgtgttt atattgtttc gacagcttgg     2940
caggcaaaca gtgtatgcac cagggtggcg ccagaacttc aacactcgcg agtttgctga     3000
gatctacaat ctcggccttc ccgtggccgc agttttctac aattgtcaga gggagagtgg     3060
```

-continued

```
ctgcggagga agaagacttt agagtgccgg gcatgtcccg aagacattaa actacggttc      3120
tttaagtaga tccgtgtctg aagttttagg ttcaatttaa acctacgaga ttgacattct      3180
cgactgatct tgattgatcg gtaagtcttt tgtaatttaa ttttcttttt gattttattt      3240
taaattgtta tctgtttctg tgtatagact gtttgagatc ggcgtttggc cgactcattg      3300
tcttaccata ggggaacgga ctttgtttgt gttgttattt tatttgtatt ttattaaaat      3360
tctcaacgat ctgaaaaagc ctcgcggcta agagattgtt gggggtgag taagtacttt       3420 taaagtgatg atggttacaa aggcaaaagg ggtaaaaccc ctcgcctacg taagcgttat      3480
tacgcccgtc tgtacttata tcagtacact gacgagtccc taaaggacga aacgggagaa      3540
cgctagccac caccaccacc accacgtgtg aattacaggt gaccagctcg aatttccccg      3600
atcgttcaaa catttggcaa taaagtttct taagattgaa tcctgttgcc ggtcttgcga      3660
tgattatcat ataatttctg ttgaattacg ttaagcatgt aataattaac atgtaatgca      3720
tgacgttatt tatgagatgg gttttttatga ttagagtccc gcaattatac atttaatacg     3780
cgatagaaaa caaaatatag cgcgcaaact aggataaatt atcgcgcgcg gtgtcatcta      3840
tgttactaga tcgggaatta aactatcagt gtttgacagg atatattggc gggtaaacct      3900
aagagaaaag agcgtttatt agaataacgg atatttaaaa gggcgtgaaa aggtttatcc      3960
gttcgtccat ttgtatgtgc atgccaacca cagggttccc ctcgggatca aagtactttg      4020
atccaacccc tccgctgcta tagtgcagtc ggcttctgac gttcagtgca gccgtcttct      4080
gaaaacgaca tgtcgcacaa gtcctaagtt acgcgacagg ctgccgccct gccctttttcc     4140 tggcgttttc ttgtcgcgtg ttttagtcgc ataaagtaga atacttgcga ctagaaccgg      4200
agacattacg ccatgaacaa gagcgccgcc gctggcctgc tgggctatgc ccgcgtcagc      4260
accgacgacc aggacttgac caaccaacgg gccgaactgc acgcggccgg ctgcaccaag      4320 ctgtttttccg agaagatcac cggcaccagg cgcgaccgcc cggagctggc caggatgctt     4380
gaccacctac gccctggcga cgttgtgaca gtgaccaggc tagaccgcct ggccccgcagc     4440 acccgcgacc tactggacat tgccgagcgc atccaggagg ccggcgcggg cctgcgtagc      4500
ctggcagagc cgtgggccga caccaccacg ccggccggcc gcatggtgtt gaccgtgttc      4560
gccggcattg ccgagttcga gcgttcccta atcatcgacc gcacccggag cgggcgcgag      4620
gccgccaagg cccgaggcgt gaagtttggc ccccgcccta ccctcacccc ggcacagatc      4680
gcgcacgccc gcgagctgat cgaccaggaa ggccgcaccg tgaaagaggc ggctgcactg      4740
cttggcgtgc atcgctcgac cctgtaccgc gcacttgagc gcagcgagga agtgacgccc      4800
accgaggcca ggcggcgcgg tgccttccgt gaggacgcat tgaccgaggc cgacgccctg      4860
gcggccgccg agaatgaacg ccaagaggaa caagcatgaa accgcaccag gacggccagg      4920
acgaaccgtt tttcattacc gaagagatcg aggcggagat gatcgcggcc gggtacgtgt      4980
tcgagccgcc cgcgcacgtc tcaaccgtgc ggctgcatga aatcctggcc ggtttgtctg      5040
atgccaagct ggcggcctgg ccggccagct tggccgctga agaaaccgag cgccgccgtc      5100
taaaaaggtg atgtgtattt gagtaaaaca gcttgcgtca tgcggtcgct gcgtatatga      5160
tgcgatgagt aaataaacaa atacgcaagg ggaacgcatg aaggttatcg ctgtacttaa      5220
ccagaaaggc gggtcaggca agacgaccat cgcaacccat ctagcccgcg ccctgcaact      5280
cgccggggcc gatgttctgt tagtcgattc cgatcccca ggcagtgccc gcgattgggc       5340
ggccgtgcgg gaagatcaac cgctaaccgt tgtcggcatc gaccgcccga cgattgaccg      5400
cgacgtgaag gccatcggcc ggcgcgactt cgtagtgatc gacggagcgc cccaggcggc      5460
```

-continued

```
ggacttggct gtgtccgcga tcaaggcagc cgacttcgtg ctgattccgg tgcagccaag   5520
cccttacgac atatgggcca ccgccgacct ggtggagctg gttaagcagc gcattgaggt   5580
cacggatgga aggctacaag cggcctttgt cgtgtcgcgg gcgatcaaag gcacgcgcat   5640
cggcggtgag gttgccgagg cgctggccgg gtacgagctg cccattcttg agtcccgtat   5700
cacgcagcgc gtgagctacc caggcactgc cgccgccggc acaaccgttc ttgaatcaga   5760
acccgagggc gacgctgccc gcgaggtcca ggcgctggcc gctgaaatta aatcaaaact   5820
catttgagtt aatgaggtaa agagaaaatg agcaaaagca caaacacgct aagtgccggc   5880
cgtccgagcg cacgcagcag caaggctgca acgttggcca gcctggcaga cacgccagcc   5940
atgaagcggg tcaactttca gttgccggcg gaggatcaca ccaagctgaa gatgtacgcg   6000
gtacgccaag gcaagaccat taccgagctg ctatctgaat acatcgcgca gctaccagag   6060
taaatgagca aatgaataaa tgagtagatg aattttagcg gctaaaggag gcggcatgga   6120
aaatcaagaa caaccaggca ccgacgccgt ggaatgcccc atgtgtggag gaacgggcgg   6180
ttggccaggc gtaagcggct gggttgtctg ccggccctgc aatggcactg gaacccccaa   6240
gcccgaggaa tcggcgtgac ggtcgcaaac catccggccc ggtacaaatc ggcgcggcgc   6300
tgggtgatga cctggtggag aagttgaagg ccgcgcaggc cgcccagcgg caacgcatcg   6360
aggcagaagc acgccccggt gaatcgtggc aagcggccgc tgatcgaatc cgcaaagaat   6420
cccggcaacc gccggcagcc ggtgcgccgt cgattaggaa gccgcccaag ggcgacgagc   6480
aaccagattt tttcgttccg atgctctatg acgtgggcac ccgcgatagt cgcagcatca   6540
tggacgtggc cgtttttccgt ctgtcgaagc gtgaccgacg agctggcgag gtgatccgct   6600
acgagcttcc agacgggcac gtagaggttt ccgcagggcc ggccggcatg gccagtgtgt   6660
gggattacga cctggtactg atggcggttt cccatctaac cgaatccatg aaccgatacc   6720
gggaagggaa gggagacaag cccggccgcg tgttccgtcc acacgttgcg gacgtactca   6780
agttctgccg gcgagccgat ggcggaaagc agaaagacga cctggtagaa acctgcattc   6840
ggttaaacac cacgcacgtt gccatgcagc gtacgaagaa ggccaagaac ggccgcctgg   6900
tgacggtatc cgagggtgaa gccttgatta gccgctacaa gatcgtaaag agcgaaaccg   6960
ggcggccgga gtacatcgag atcgagctag ctgattggat gtaccgcgag atcacagaag   7020
gcaagaaccc ggacgtgctg acggttcacc ccgattactt tttgatcgat cccggcatcg   7080
gccgttttct ctaccgcctg gcacgccgcg ccgcaggcaa ggcagaagcc agatggttgt   7140
tcaagacgat ctacgaacgc agtggcagcg ccggagagtt caagaagttc tgtttcaccg   7200
tgcgcaagct gatcgggtca aatgacctgc cggagtacga tttgaaggag gaggcggggc   7260
aggctggccc gatcctagtc atgcgctacc gcaacctgat cgaggcgaa gcatccgccg   7320 gttcctaatg tacggagcag atgctagggc aaattgccct agcaggggaa aaaggtcgaa   7380
aaggtctctt tcctgtggat agcacgtaca ttgggaaccc aaagccgtac attgggaacc   7440
ggaacccgta cattgggaac ccaaagccgt acattgggaa ccggtcacac atgtaagtga   7500
ctgatataaa agagaaaaaa ggcgattttt ccgcctaaaa ctctttaaaa cttattaaaa   7560
ctcttaaaac ccgcctggcc tgtgcataac tgtctggcca gcgcacagcc gaagagctgc   7620
aaaaagcgcc taccccttcgg tcgctgcgct ccctacgccc cgccgcttcg cgtcggccta   7680
tcgcggccgc tggccgctca aaaatggctg gcctacggcc aggcaatcta ccagggcgcg   7740
gacaagccgc gccgtcgcca ctcgaccgcc ggcgcccaca tcaaggcacc ctgcctcgcg   7800
```

-continued

```
cgtttcggtg atgacggtga aaacctctga cacatgcagc tcccggagac ggtcacagct    7860
tgtctgtaag cggatgccgg gagcagacaa gcccgtcagg gcgcgtcagc gggtgttggc    7920
gggtgtcggg gcgcagccat gacccagtca cgtagcgata gcggagtgta tactggctta    7980
actatgcggc atcagagcag attgtactga gagtgcacca tatgcggtgt gaaataccgc    8040
acagatgcgt aaggagaaaa taccgcatca ggcgctcttc cgcttcctcg ctcactgact    8100
cgctgcgctc ggtcgttcgg ctgcggcgag cggtatcagc tcactcaaag gcggtaatac    8160
ggttatccac agaatcaggg gataacgcag gaaagaacat gtgagcaaaa ggccagcaaa    8220
aggccaggaa ccgtaaaaag gccgcgttgc tggcgttttt ccataggctc cgcccccctg    8280
acgagcatca caaaaatcga cgctcaagtc agaggtggcg aaacccgaca ggactataaa    8340
gataccaggc gtttccccct ggaagctccc tcgtgcgctc tcctgttccg accctgccgc    8400
ttaccggata cctgtccgcc tttctccctt cgggaagcgt ggcgctttct catagctcac    8460
gctgtaggta tctcagttcg gtgtaggtcg ttcgctccaa gctgggctgt gtgcacgaac    8520
cccccgttca gcccgaccgc tgcgccttat ccggtaacta tcgtcttgag tccaacccgg    8580
taagacacga cttatcgcca ctggcagcag ccactggtaa caggattagc agagcgaggt    8640
atgtaggcgg tgctacagag ttcttgaagt ggtggcctaa ctacggctac actagaagga    8700
cagtatttgg tatctgcgct ctgctgaagc cagttacctt cggaaaaaga gttggtagct    8760
cttgatccgg caaacaaacc accgctggta gcggtggttt ttttgtttgc aagcagcaga    8820
ttacgcgcag aaaaaaagga tctcaagaag atcctttgat cttttctacg gggtctgacg    8880
ctcagtggaa cgaaaactca cgttaaggga ttttggtcat gcattctagg tactaaaaca    8940
attcatccag taaaatataa tattttattt tctcccaatc aggcttgatc cccagtaagt    9000
caaaaaatag ctcgacatac tgttcttccc cgatatcctc cctgatcgac cggacgcaga    9060
aggcaatgtc ataccacttg tccgccctgc cgcttctccc aagatcaata aagccactta    9120
ctttgccatc tttcacaaag atgttgctgt ctcccaggtc gccgtgggaa aagacaagtt    9180
cctcttcggg ctttttccgtc tttaaaaaat catacagctc gcgcggatct ttaaatggag    9240
tgtcttcttc ccagttttcg caatccacat cggccagatc gttattcagt aagtaatcca    9300
attcggctaa gcggctgtct aagctattcg tatagggaca atccgatatg tcgatggagt    9360
gaaagagcct gatgcactcc gcatacagct cgataatctt ttcagggctt tgttcatctt    9420
catactcttc cgagcaaagg acgccatcgg cctcactcat gagcagattg ctccagccat    9480
catgccgttc aaagtgcagg acctttggaa caggcagctt tccttccagc catagcatca    9540
tgtccttttc ccgttccaca tcataggtgg tcccttata ccggctgtcc gtcattttta    9600
aatataggtt ttcattttct cccaccagct tatatacctt agcaggagac attccttccg    9660
tatcttttac gcagcggtat ttttcgatca gttttttcaa ttccggtgat attctcattt    9720
tagccattta ttatttcctt cctctttct acagtattta aagatacccc aagaagctaa    9780
ttataacaag acgaactcca attcactgtt ccttgcattc taaaacctta aataccagaa    9840
aacagctttt tcaaagttgt tttcaaagtt ggcgtataac atagtatcga cggagccgat    9900
tttgaaaccg cggtgatcac aggcagcaac gctctgtcat cgttacaatc aacatgctac    9960
cctccgcgag atcatccgtg tttcaaaccc ggcagcttag ttgccgttct tccgaatagc    10020
atcggtaaca tgagcaaagt ctgccgcctt acaacggctc tcccgctgac gccgtcccgg    10080
actgatgggc tgcctgtatc gagtggtgat tttgtgccga gctgccggtc                10130
```

-continued

<210> SEQ ID NO 73
<211> LENGTH: 25
<212> TYPE: DNA
<213> ORGANISM: Nicotiana benthamiana

<400> SEQUENCE: 73
tttggtagta gcgactccat ggggc                                                       25

<210> SEQ ID NO 74
<211> LENGTH: 26
<212> TYPE: DNA
<213> ORGANISM: Artificial
<220> FEATURE:
<223> OTHER INFORMATION: synthetic construct

<400> SEQUENCE: 74
tttggtagta gcgactccca tggggc                                                      26

<210> SEQ ID NO 75
<211> LENGTH: 24
<212> TYPE: DNA
<213> ORGANISM: Artificial
<220> FEATURE:
<223> OTHER INFORMATION: synthetic construct

<400> SEQUENCE: 75
tttggtagta gcgactcatg gggc                                                        24

<210> SEQ ID NO 76
<211> LENGTH: 22
<212> TYPE: DNA
<213> ORGANISM: Artificial
<220> FEATURE:
<223> OTHER INFORMATION: synthetic construct

<400> SEQUENCE: 76
tttggtagta gcgacatggg gc                                                          22

<210> SEQ ID NO 77
<211> LENGTH: 19
<212> TYPE: DNA
<213> ORGANISM: Artificial
<220> FEATURE:
<223> OTHER INFORMATION: synthetic construct

<400> SEQUENCE: 77
tttggtagta gcatggggc                                                              19

<210> SEQ ID NO 78
<211> LENGTH: 24
<212> TYPE: DNA
<213> ORGANISM: Artificial
<220> FEATURE:
<223> OTHER INFORMATION: synthetic construct

<400> SEQUENCE: 78
tttggtagta gcgactcatg gggc                                                        24

<210> SEQ ID NO 79
<211> LENGTH: 21
<212> TYPE: DNA
<213> ORGANISM: Artificial
<220> FEATURE:
<223> OTHER INFORMATION: synthetic construct

<400> SEQUENCE: 79
tttggtagta gcgaatgggg c                                              21

<210> SEQ ID NO 80
<211> LENGTH: 25
<212> TYPE: DNA
<213> ORGANISM: Nicotiana benthamiana

<400> SEQUENCE: 80
agtgtgaaag aaacaattga gaggt                                          25

<210> SEQ ID NO 81
<211> LENGTH: 26
<212> TYPE: DNA
<213> ORGANISM: Artificial
<220> FEATURE:
<223> OTHER INFORMATION: synthetic construct

<400> SEQUENCE: 81
agtgtgaaag aaacaatttg agaggt                                         26

<210> SEQ ID NO 82
<211> LENGTH: 21
<212> TYPE: DNA
<213> ORGANISM: Artificial
<220> FEATURE:
<223> OTHER INFORMATION: synthetic construct

<400> SEQUENCE: 82
agtgtgaaag aaatgagagg t                                              21

<210> SEQ ID NO 83
<211> LENGTH: 24
<212> TYPE: DNA
<213> ORGANISM: Artificial
<220> FEATURE:
<223> OTHER INFORMATION: synthetic construct

<400> SEQUENCE: 83
agtgtgaaag aaacaatgag aggt                                           24

<210> SEQ ID NO 84
<211> LENGTH: 19
<212> TYPE: DNA
<213> ORGANISM: Artificial
<220> FEATURE:
<223> OTHER INFORMATION: synthetic construct

<400> SEQUENCE: 84
agtgtgaaag atgagaggt                                                 19

<210> SEQ ID NO 85
<211> LENGTH: 22
<212> TYPE: DNA
<213> ORGANISM: Artificial
<220> FEATURE:
<223> OTHER INFORMATION: synthetic construct

<400> SEQUENCE: 85
agtgtgaaag aaactgagag gt                                             22

<210> SEQ ID NO 86
<211> LENGTH: 18
<212> TYPE: DNA
<213> ORGANISM: Artificial
<220> FEATURE:
<223> OTHER INFORMATION: synthetic construct -continued

<400> SEQUENCE: 86
agtgtgaaag tgagaggt                                                                              18

<210> SEQ ID NO 87
<211> LENGTH: 23
<212> TYPE: DNA
<213> ORGANISM: Artificial
<220> FEATURE:
<223> OTHER INFORMATION: synthetic construct

<400> SEQUENCE: 87
tttggtagta gcgactatgg ggc                                                                        23

<210> SEQ ID NO 88
<211> LENGTH: 19
<212> TYPE: DNA
<213> ORGANISM: Artificial
<220> FEATURE:
<223> OTHER INFORMATION: synthetic construct

<400> SEQUENCE: 88
tttggtagta gcgtggggc                                                                             19

<210> SEQ ID NO 89
<211> LENGTH: 24
<212> TYPE: DNA
<213> ORGANISM: Artificial
<220> FEATURE:
<223> OTHER INFORMATION: synthetic construct

<400> SEQUENCE: 89
agtgtgaaag aaacaatgag aggt                                                                       24

<210> SEQ ID NO 90
<211> LENGTH: 20
<212> TYPE: DNA
<213> ORGANISM: Artificial
<220> FEATURE:
<223> OTHER INFORMATION: synthetic construct

<400> SEQUENCE: 90
agtgtgaaag aatgagaggt                                                                            20

<210> SEQ ID NO 91
<211> LENGTH: 26
<212> TYPE: DNA
<213> ORGANISM: Artificial
<220> FEATURE:
<223> OTHER INFORMATION: synthetic construct

<400> SEQUENCE: 91
agtgtgaaag aaacaattag agaggt                                                                     26

<210> SEQ ID NO 92
<211> LENGTH: 19
<212> TYPE: DNA
<213> ORGANISM: Artificial
<220> FEATURE:
<223> OTHER INFORMATION: synthetic construct

<400> SEQUENCE: 92
agtgtgaaag aagagaggt                                                                             19

<210> SEQ ID NO 93

-continued

```
<211> LENGTH: 19
<212> TYPE: DNA
<213> ORGANISM: Artificial
<220> FEATURE:
<223> OTHER INFORMATION: synthetic construct

<400> SEQUENCE: 93
agtgtgaaag aagagaggt                                                        19

<210> SEQ ID NO 94
<211> LENGTH: 21
<212> TYPE: DNA
<213> ORGANISM: Artificial
<220> FEATURE:
<223> OTHER INFORMATION: synthetic construct

<400> SEQUENCE: 94
agtgtgaaag aaacgagagg t                                                     21

<210> SEQ ID NO 95
<211> LENGTH: 12
<212> TYPE: DNA
<213> ORGANISM: Artificial
<220> FEATURE:
<223> OTHER INFORMATION: synthetic construct

<400> SEQUENCE: 95
agtgtgagag gt                                                               12

<210> SEQ ID NO 96
<211> LENGTH: 18
<212> TYPE: DNA
<213> ORGANISM: Artificial
<220> FEATURE:
<223> OTHER INFORMATION: synthetic construct

<400> SEQUENCE: 96
agtgtgaaag agagaggt                                                         18

<210> SEQ ID NO 97
<211> LENGTH: 4104
<212> TYPE: DNA
<213> ORGANISM: Streptococcus pyogenes

<400> SEQUENCE: 97
atggataaga aatactcaat aggcttagat atcggcacaa atagcgtcgg atgggcggtg      60
atcactgatg attataaggt tccgtctaaa aagttcaagg ttctgggaaa tacagaccgc     120
cacagtatca aaaaaaatct tatagggggct cttttatttg gcagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagcatg aacgtcatcc tattttttgga     360 aatatagtag atgaagttgc ttatcatgag aaatatccaa ctatctatca tctgcgaaaa     420
aaattggcag attctactga taaagcggat ttgcgcttaa tctatttggc cttagcgcat     480
atgattaagt ttcgtggtca ttttttgatt gagggagatt aaatcctga taatagtgat     540 gtggacaaac tatttatcca gttggtacaa atctacaatc aattatttga agaaaaccct     600
attaacgcaa gtagagtaga tgctaaagcg attctttctg cacgattgag taaatcaaga     660
cgattagaaa atctcattgc tcagctcccc ggtgagaaga gaaatggctt gtttgggaat     720
ctcattgctt tgtcattggg attgacccct aattttaaat caaattttga tttggcagaa     780
```

-continued

```
gatgctaaat tacagctttc aaaagatact tacgatgatg atttagataa tttattggcg      840
caaattggag atcaatatgc tgatttgttt ttggcagcta agaatttatc agatgctatt      900
ttactttcag atatcctaag agtaaatagt gaaataacta aggctcccct atcagcttca      960
atgattaagc gctacgatga acatcatcaa gacttgactc ttttaaaagc tttagttcga     1020
caacaacttc cagaaaagta taaagaaatc tttttgatc aatcaaaaaa cggatatgca      1080
ggttatattg atgggggagc tagccaagaa gaattttata aatttatcaa accaatttta     1140
gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat     1260
gctattttga gaagacaaga agactttat ccatttttaa aagacaatcg tgagaagatt      1320
gaaaaaatct tgacttttcg aattccttat tatgttggtc cattggcgcg tggcaatagt     1380
cgttttgcat ggatgactcg gaagtctgaa gaaacaatta ccccatggaa ttttgaagaa     1440
gttgtcgata aaggtgcttc agctcaatca tttattgaac gcatgacaaa ctttgataaa     1500
aatcttccaa atgaaaaagt actaccaaaa catagtttgc tttatgagta ttttacggtt     1560
tataacgaat tgacaaaggt caaatatgtt actgagggaa tgcgaaaacc agcatttctt     1620
tcaggtgaac agaagaaagc cattgttgat ttactcttca aaacaaatcg aaaagtaacc     1680
gttaagcaat taaaagaaga ttatttcaaa aaaatagaat gttttgatag tgttgaaatt     1740
tcaggagttg aagatagatt taatgcttca ttaggcgcct accatgattt gctaaaaatt     1800
attaaagata aagatttttt ggataatgaa gaaaatgaag atatcttaga ggatattgtt     1860
ttaacattga ccttatttga agatagggg atgattgagg aaagacttaa aacatatgct       1920
cacctctttg atgataaggt gatgaaacag cttaaacgtc gccgttatac tggttgggga     1980
cgtttgtctc gaaaattgat taatggtatt agggataagc aatctggcaa aacaatatta     2040
gattttttga aatcagatgg ttttgccaat cgcaatttta tgcagctgat ccatgatgat     2100
agtttgacat ttaagaaga tattcaaaaa gcacaggtgt ctggacaagg ccatagttta      2160
catgaacaga ttgctaactt agctggcagt cctgctatta aaaaaggtat tttacagact     2220
gtaaaaattg ttgatgaact ggtcaaagta atggggcata agccagaaaa tatcgttatt     2280
gaaatggcac gtgaaaatca gacaactcaa aagggccaga aaaattcgcg agagcgtatg     2340
aaacgaatcg aagaaggtat caagaatta ggaagtcaga ttcttaaaga gcatcctgtt      2400
gaaaatactc aattgcaaaa tgaaaagctc tatctctatt atctacaaaa tggaagagac     2460
atgtatgtgg accaagaatt agatattaat cgtttaagtg attatgatgt cgatcacatt     2520
gttccacaaa gtttcattaa agacgattca atagacaata aggtactaac gcgttctgat     2580
aaaaatcgtg taaatcgga taacgttcca agtgaagaag tagtcaaaaa gatgaaaaac     2640
tattggagac aacttctaaa cgccaagtta atcactcaac gtaagtttga taatttaacg     2700
aaagctgaac gtggaggttt gagtgaactt gataaagctg gttttatcaa acgccaattg     2760
gttgaaactc gccaaatcac taagcatgtg gcacaaattt tggatagtcg catgaatact     2820
aaatacgatg aaaatgataa acttattcga gaggttaaag tgattacctt aaaatctaaa     2880
ttagtttctg acttccgaaa agatttccaa ttctataaag tacgtgagat taacaattac     2940
catcatgccc atgatgcgta tctaaatgcc gtcgttggaa ctgctttgat taagaaatat     3000
ccaaaacttg aatcggagtt tgtctatggt gattataaag tttatgatgt tcgtaaaatg     3060
attgctaagt ctgagcaaga aataggcaaa gcaaccgcaa aatatttctt ttactctaat     3120
```

-continued

```
atcatgaact tcttcaaaac agaaattaca cttgcaaatg gagagattcg caaacgccct     3180
ctaatcgaaa ctaatgggga aactggagaa attgtctggg ataaagggcg agattttgcc     3240
acagtgcgca aagtattgtc catgccccaa gtcaatattg tcaagaaaac agaagtacag     3300
acaggcggat tctccaagga gtcaatttta ccaaaaagaa attcggacaa gcttattgct     3360
cgtaaaaaag actgggatcc aaaaaaatat ggtggttttg atagtccaac ggtagcttat     3420
tcagtcctag tggttgctaa ggtggaaaaa gggaaatcga agaagttaaa atccgttaaa     3480
gagttactag ggatcacaat tatggaaaga agttcctttg aaaaaaatcc gattgacttt     3540
ttagaagcta aaggatataa ggaagttaaa aaagacttaa tcattaaact acctaaatat     3600
agtctttttg agttagaaaa cggtcgtaaa cggatgctgg ctagtgccgg agaattacaa     3660
aaaggaaatg agctggctct gccaagcaaa tatgtgaatt ttttatattt agctagtcat     3720
tatgaaaagt tgaagggtag tccagaagat aacgaacaaa aacaattgtt tgtggagcag     3780
cataagcatt atttagatga gattattgag caaatcagtg aattttctaa gcgtgttatt     3840
ttagcagatg ccaatttaga taaagttctt agtgcatata caaacatag agacaaacca      3900 atacgtgaac aagcagaaaa tattattcat ttatttacgt tgacgaatct tggagctccc     3960
gctgctttta aatattttga tacaacaatt gatcgtaaac gatatacgtc tacaaaagaa     4020
gttttagatg ccactcttat ccatcaatcc atcactggtc tttatgaaac acgcattgat     4080
ttgagtcagc taggaggtga ctga                                            4104
```

```
<210> SEQ ID NO 98
<211> LENGTH: 1368
<212> TYPE: PRT
<213> ORGANISM: Streptococcus pyogenes

<400> SEQUENCE: 98

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
```

-continued

```
              195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
    610                 615                 620
```

-continued

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035
```

-continued

```
Tyr Ser  Asn Ile Met Asn Phe  Phe Lys Thr Glu Ile  Thr Leu Ala
    1040             1045             1050

Asn Gly  Glu Ile Arg Lys Arg  Pro Leu Ile Glu Thr  Asn Gly Glu
    1055             1060             1065

Thr Gly  Glu Ile Val Trp Asp  Lys Gly Arg Asp Phe  Ala Thr Val
    1070             1075             1080

Arg Lys  Val Leu Ser Met Pro  Gln Val Asn Ile Val  Lys Lys Thr
    1085             1090             1095

Glu Val  Gln Thr Gly Gly Phe  Ser Lys Glu Ser Ile  Leu Pro Lys
    1100             1105             1110

Arg Asn  Ser Asp Lys Leu Ile  Ala Arg Lys Lys Asp  Trp Asp Pro
    1115             1120             1125

Lys Lys  Tyr Gly Gly Phe Asp  Ser Pro Thr Val Ala  Tyr Ser Val
    1130             1135             1140

Leu Val  Val Ala Lys Val Glu  Lys Gly Lys Ser Lys  Lys Leu Lys
    1145             1150             1155

Ser Val  Lys Glu Leu Leu Gly  Ile Thr Ile Met Glu  Arg Ser Ser
    1160             1165             1170

Phe Glu  Lys Asn Pro Ile Asp  Phe Leu Glu Ala Lys  Gly Tyr Lys
    1175             1180             1185

Glu Val  Lys Lys Asp Leu Ile  Ile Lys Leu Pro Lys  Tyr Ser Leu
    1190             1195             1200

Phe Glu  Leu Glu Asn Gly Arg  Lys Arg Met Leu Ala  Ser Ala Gly
    1205             1210             1215

Glu Leu  Gln Lys Gly Asn Glu  Leu Ala Leu Pro Ser  Lys Tyr Val
    1220             1225             1230

Asn Phe  Leu Tyr Leu Ala Ser  His Tyr Glu Lys Leu  Lys Gly Ser
    1235             1240             1245

Pro Glu  Asp Asn Glu Gln Lys  Gln Leu Phe Val Glu  Gln His Lys
    1250             1255             1260

His Tyr  Leu Asp Glu Ile Ile  Glu Gln Ile Ser Glu  Phe Ser Lys
    1265             1270             1275

Arg Val  Ile Leu Ala Asp Ala  Asn Leu Asp Lys Val  Leu Ser Ala
    1280             1285             1290

Tyr Asn  Lys His Arg Asp Lys  Pro Ile Arg Glu Gln  Ala Glu Asn
    1295             1300             1305

Ile Ile  His Leu Phe Thr Leu  Thr Asn Leu Gly Ala  Pro Ala Ala
    1310             1315             1320

Phe Lys  Tyr Phe Asp Thr Thr  Ile Asp Arg Lys Arg  Tyr Thr Ser
    1325             1330             1335

Thr Lys  Glu Val Leu Asp Ala  Thr Leu Ile His Gln  Ser Ile Thr
    1340             1345             1350

Gly Leu  Tyr Glu Thr Arg Ile  Asp Leu Ser Gln Leu  Gly Gly Asp
    1355             1360             1365
```